(12) United States Patent
Klein et al.

(10) Patent No.: US 7,517,876 B2
(45) Date of Patent: Apr. 14, 2009

(54) ANTI-INFECTIVE AGENTS

(75) Inventors: Larry L. Klein, Lake Forest, IL (US); Peggy P. Huang, Lake Bluff, IL (US); John T. Randolph, Libertyville, IL (US); Douglas K. Hutchinson, Antioch, IL (US); Ming C. Yeung, Grayslake, IL (US); Charles A. Flentge, Salem, WI (US)

(73) Assignee: Abbott Laboratories, Abbott Park, IL (US)

( * ) Notice: Subject to any disclaimer, the term of this patent is extended or adjusted under 35 U.S.C. 154(b) by 7 days.

(21) Appl. No.: 11/363,377

(22) Filed: Feb. 27, 2006

(65) Prior Publication Data

US 2006/0287300 A1 Dec. 21, 2006

Related U.S. Application Data

(60) Provisional application No. 60/656,767, filed on Feb. 25, 2005.

(51) Int. Cl.
*C07D 285/26* (2006.01)
*A61K 31/549* (2006.01)

(52) U.S. Cl. ............................ 514/223.2; 544/12
(58) Field of Classification Search .................. 544/12; 514/223.2
See application file for complete search history.

(56) References Cited

U.S. PATENT DOCUMENTS

| 5,459,138 | A  | 10/1995 | Pirotte et al. | 514/223.8 |
| 6,348,587 | B1 | 2/2002 | Schinazi et al. | 536/25.3 |
| 7,378,414 | B2 | 5/2008 | Hutchinson et al. | 514/223.2 |

FOREIGN PATENT DOCUMENTS

| EP | 1162196 | A1 | 12/2001 |
| WO | WO0132153 | A2 | 5/2001 |
| WO | WO0132153 | A3 | 5/2001 |
| WO | WO0160315 | A2 | 8/2001 |
| WO | WO0160315 | A3 | 8/2001 |
| WO | WO0190121 | A2 | 11/2001 |
| WO | WO0190121 | A3 | 11/2001 |
| WO | WO0204425 | A2 | 1/2002 |
| WO | WO0204425 | A3 | 1/2002 |
| WO | WO02098424 | A1 | 12/2002 |
| WO | WO2004058150 | A2 | 7/2004 |
| WO | WO2004058150 | A3 | 7/2004 |
| WO | WO2005019191 | A2 | 3/2005 |
| WO | WO2005019191 | A3 | 3/2005 |
| WO | WO2006093801 | A1 | 9/2006 |

OTHER PUBLICATIONS

Wolff Manfred E. "Burger's Medicinal Chemistry, 5ed, Part 1" John Wiley & Sons, 1995, pp. 975-977.*
Banker, G.S. et al, "Modern Paharmaceutices, 3ed." Marcel Dekker, New York, 1996, pp. 451 and 596.*
K.J. Blight et al., *Efficient Initiation of HCV RNA Replication in Cell Culture*, Science 290:1972-4 (2000).
A. Goldfarb, *New Compounds. Derivatives of 2,5-Diaminobenzenesulfonamide*, J. Amer. Chem. Soc. 65(4):738-9 (1943).
M. Ikeda et al., *Selectable Subgenomic and Genome-Length Dicistronic RNAs Derived from an Infectious Molecular Clone of the HCV-N Strain of Hepatitis C Virus Replicate Efficiently in cultured Huh7 Cells*, J. Virol. 76(6):2997-3006 (2002).
J.F. Morrison et al., *Approaches to the Study and Analysis of the Inhibition of Enzymes by Slow- and Tight-Binding Inhibitors*, Comm. Mol. Cell. Biophys. 2:347-68 (1985).

* cited by examiner

*Primary Examiner*—Kahsay T Habte
(74) *Attorney, Agent, or Firm*—Paul D. Yasger; Michael J. Ward; Lydia N. Nenow

(57) ABSTRACT

Compounds having the formula

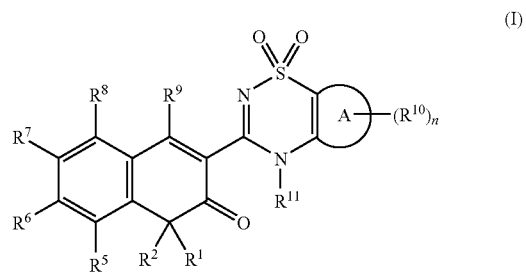

(I)

are hepatitis C (HCV) polymerase inhibitors. Also disclosed are compositions and methods for inhibiting hepatitis C (HCV) polymerase, processes for making the compounds, and synthetic intermediates employed in the processes.

19 Claims, No Drawings

ANTI-INFECTIVE AGENTS

This application claims priority from U.S. Provisional Patent Application Ser. No. 60/656,767, filed Feb. 25, 2005, which is incorporated herein by reference.

TECHNICAL FIELD

The present invention relates to novel anti-infective agents. Specifically, the present invention relates to compounds, compositions, a method for inhibiting hepatitis C virus (HCV) polymerase, a method for inhibiting HCV viral replication, and a method for treating or preventing HCV infection, and processes for making the compounds, and synthetic intermediates employed in the processes.

BACKGROUND OF THE INVENTION

Infection with hepatitis C virus (HCV) is a major cause of human liver disease throughout the world. More than 85% of all infected individuals become chronically infected. Chronic HCV infection accounts for 30% of all cirrhosis, end-stage liver disease, and liver cancer in the United States. The CDC estimates that the number of deaths due to HCV will increase to 38,000/year by the year 2010.

While initial therapy consisted of interferon alone, the combination of interferon alpha-2b with ribavirin for either 24 or 48 weeks is currently the most efficacious approved therapy for the treatment of chronic HCV infection. However, there are many adverse side effects associated with this therapy (flu-like symptoms, leukopenia, thrombocytopenia, and depression from interferon, as well as anemia induced by ribavirin). Furthermore, this therapy is less effective against infections caused by HCV genotype 1 which constitutes about 75% of all HCV infections.

Based on the foregoing, there exists a significant need to identify compounds with the ability to inhibit HCV. The present invention provides novel anti-infective agents which are HCV polymerase inhibitors.

SUMMARY OF THE INVENTION

In its principle embodiment, the present invention provides a compound of formula (I)

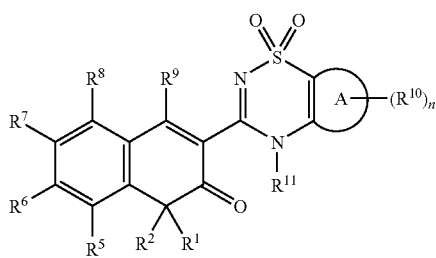

(I)

or a pharmaceutically acceptable salt form, stereoisomer, tautomer, pro drug, salt of a prodrug, or combination thereof, wherein:

A is a monocyclic or bicyclic ring selected from the group consisting of aryl, cycloalkyl, cycloalkenyl, heteroaryl and heterocycle;

$R^1$ is —$OR_A$, —O-alkyl-C(O)Y, —$NR_AR_B$, —$N(R_C)$(—N($R_C$)($R_A$)), —$N(R_B)L^1C(O)Y$ or —$N(R_B)S(O)_2Z$;

X at each occurrence, is independently selected from the group consisting of $R_A$, —$OR_A$ and —$NR_AR_B$;

$L^1$ is a bond or lower alkyl;

Y at each occurrence is independently selected from the group consisting of $R_A$, —$OR_A$, —$NR_AR_B$, —O-alkyl-$OR_A$, —O-alkyl-$NR_AR_B$, —$N(R_C)$-alkyl-$NR_AR_B$, —$(CR^3R^4)$—N($R_C$)C(O)X; —$(CR^3R^4)$—$NR_AR_B$; and heterocycle;

Z at each occurrence is independently selected from the group consisting of $R_A$, —$OR_A$, —$NR_AR_B$, -alkyl-$OR_A$, -alkyl-$NR_AR_B$, -alkyl-$N(R_C)C(O)X$, -alkyl-O-alkyl-$OR_A$, -alkyl-O-alkyl-$NR_AR_B$ and -alkyl-$N(R_C)$-alkyl-$NR_AR_B$;

$R^3$ and $R^4$, at each occurrence, are independently selected from the group consisting of hydrogen, alkyl, alkenyl and arylalkyl wherein the aryl moiety of the arylalkyl is substituted with 0, 1, 2, 3, 4 or 5 substituents independently selected from the group consisting of alkyl, alkenyl, alkynyl, formyl, halo, nitro, cyano, alkoxy, —OH, —OC(O)(alkyl), —SH, —S(alkyl), —S(O)alkyl, —$S(O)_2$(alkyl), —$NH_2$, —N(H)(alkyl), —$N(alkyl)_2$, —C(O)alkyl, —C(O)OH, —C(O)(—Oalkyl), —$C(O)NH_2$, —C(O)N(H)(alkyl), —$C(O)N(alkyl)_2$ and haloalkyl;

$R_A$ at each occurrence, is independently selected from the group consisting of hydrogen, alkyl, alkenyl, haloalkyl, haloalkenyl, $R_a$ and -alkyl$R_a$;

$R_B$ at each occurrence, is independently selected from the group consisting of hydrogen, alkyl, haloalkyl, $R_a$, -alkylyl$R_a$, —OH, alkoxy, hydroxyalkyl, alkoxyalkyl, —$OR_a$, and —O-alkyl$R_a$;

$R_C$ at each occurrence, is independently selected from the group consisting of hydrogen and lower alkyl;

$R_a$ at each occurrence, is independently selected from the group consisting of cycloalkyl, cycloalkenyl, heterocycle, aryl and heteroaryl; wherein each $R_a$ at each occurrence is independently substituted with 0, 1, 2, 3, 4 or 5 substituents independently selected from the group consisting of alkyl, alkenyl, alkynyl, formyl, halo, nitro, cyano, alkoxy, —OH, —O-alkyl-$R_b$, —OC(O)(alkyl), —SH, —S(alkyl), —S(O)alkyl, —$S(O)_2$(alkyl), —$NH_2$, —N(H)(alkyl), —$N(alkyl)_2$, —C(O)alkyl, —C(O)OH, —C(O)(—Oalkyl), —$C(O)NH_2$, —C(O)N(H)(alkyl), —$C(O)N(alkyl)_2$, haloalkyl, $R_b$ and -alkyl-$R_b$;

$R_b$ at each occurrence is independently selected from the group consisting of cycloalkyl, cycloalkenyl, heterocycle, aryl and heteroaryl; wherein each $R_b$ at each occurrence is independently substituted with 0, 1, 2, 3, 4 or 5 substituents independently selected from the group consisting of alkyl, alkenyl, alkynyl, formyl, halo, nitro, cyano, alkoxy, —OH, —OC(O)(alkyl), —SH, —S(alkyl), —S(O)alkyl, —$S(O)_2$(alkyl), —$NH_2$, —N(H)(alkyl), —$N(alkyl)_2$, —C(O)alkyl, —C(O)OH, —C(O)(—Oalkyl), —$C(O)NH_2$, —C(O)N(H)(alkyl), —$C(O)N(alkyl)_2$ and haloalkyl;

$R^2$ is selected from the group consisting of hydrogen, alkyl, alkenyl, alkynyl, $R_a$, -alkyl-$R_a$, -alkenyl-$R_a$, -alkynyl-$R_a$, haloalkyl, hydroxyalkyl, formylalkyl, cyanoalkyl, -alkyl-$OR_A$, and -alkyl-$NR_AR_B$;

$R_5$, $R^6$, $R^7$ and $R^8$ are each independently selected from the group consisting of hydrogen, alkyl, alkenyl, alkynyl, cyano, formyl, halo, nitro, —$OR_A$, —$OC(O)R_A$, —$OC(O)OR_A$, —$OC(O)NR_AR_B$, —$OS(O)_2R_A$, —$SR_A$, —$S(O)R_A$, —$S(O)_2R_A$, —$S(O)_2(OR_A)$, —$S(O)_2NR_AR_B$, —$NR_AR_B$, —$N(R_C)C(O)R_A$, —$N(R_C)C(O)NR_AR_B$, —$N(R_C)C(O)OR_A$, —$N(R_C)S(O)_2R_A$, —$N(R_C)S(O)_2NR_AR_B$, —$N(R_C)S(O)_2N(R_C)C(O)OR_A$, —$C(O)R_A$, —$C(O)OR_A$, —$C(O)NR_AR_B$, haloalkyl, cyanoalkyl, -alkyl$OR_A$, -alkyl-$OC(O)R_A$, -alkyl-$OC(O)OR_A$, -alkyl-$OC(O)NR_AR_B$, -alkyl-$OS(O)_2R_A$, -alkyl-$SR_A$, -alkyl-$S(O)R_A$, -alkyl-$S(O)_2R_A$, -alkyl-$S(O)_2(OR_A)$, -alkyl-$S(O)_2NR_AR_B$, -alkyl-$NR_AR_B$, -alkyl-$N(R_C)C(O)R_A$, -alkyl-$N(R_C)$ C(O)NR$_A$R$_B$, -alkyl-N(R$_C$)C(O)OR$_A$, -alkyl-N(R$_C$)S(O)$_2$R$_A$, -alkyl-N(R$_C$)S(O)$_2$NR$_A$R$_B$, -alkyl-N(R$_C$)S(O)$_2$N(R$_C$)C(O)OR$_A$, -alkyl-C(O)R$_A$, -alkyl-C(O)(OR$_A$) and -alkyl-C(O)NR$_A$R$_B$;

R$^9$ is —OR$_A$, —SR$_A$, —NR$_A$R$_B$, —N(R$_C$)C(O)R$_A$, —N(R$_C$)C(O)OR$_A$, —N(R$_C$)S(O)$_2$R$_A$ or —N(R$_C$)S(O)$_2$NR$_A$R$_B$;

n is 0, 1, 2, 3 or 4;

R$^{10}$ at each occurrence is independently selected from the group consisting of alkyl, alkenyl, alkynyl, cyano, formyl, nitro, halo, R$_a$, —OR$_A$, —OC(O)X, —OS(O)$_2$R$_A$, —O-alkyl-G$^1$, —SR$_A$, —S(O)R$_A$, —S(O)$_2$X, —NR$_A$R$_B$, —N(R$_B$)C(O)X, —N(R$_B$)C(O)(-alkyl-G$^1$), —N(R$_B$)S(O)$_2$X, —N(R$_B$)S(O)$_2$(-alkyl-G$^1$), —C(O)X, —C(O)N(R$_B$)(-alkyl-G$^1$), haloalkyl, cyanoalkyl, nitroalkyl, -alkyl-R$_a$, —N(-alkyl-C(O)X)(S(O)$_2$X) and -alkyl-G$^1$;

G$^1$ is selected from the group consisting of —OR$_A$, —NR$_A$R$_B$, —N(R$_C$)(—NR$_A$R$_B$), —N(R$_C$)S(O)$_2$X, —N(R$_C$)C(O)X, —C(O)X, —OC(O)X and —S(O)$_2$X; and R$^{11}$ is selected from the group consisting of hydrogen, alkyl, alkenyl and arylalkyl; wherein the aryl moiety of the arylalkyl is substituted with 0, 1, 2, 3, 4 or 5 substituents selected from the group consisting of alkyl, alkenyl, alkynyl, formyl, halo, nitro, cyano, haloalkyl, —OH, alkoxy, —OC(O)(alkyl), —NH$_2$, —N(H)(alkyl), —N(alkyl)$_2$, —C(O)OH, —C(O)(—Oalkyl), —C(O)alkyl, —C(O)NH$_2$, —C(O)N(H)(alkyl) and —C(O)N(alkyl)$_2$.

In another embodiment, the present invention provides a pharmaceutical compound of Formula (I)

or a pharmaceutically acceptable salt form, stereoisomer, tautomer, prodrug, salt of a prodrug, or combination thereof, wherein:

A is a monocyclic or bicyclic ring selected from the group consisting of aryl, cycloalkyl, cycloalkenyl, heteroaryl and heterocycle;

R$^1$ is —OR$_A$, —O-alkyl-C(O)Y, —NR$_A$R$_B$, —N(R$_C$)(—N(R$_C$)(R$_A$)), —N(R$_B$)L$^1$(O)Y or —N(R$_B$)S(O)$_2$Z;

X at each occurrence, is independently selected from the group consisting of R$_A$, —OR$_A$ and —NR$_A$R$_B$;

L$^1$ is a bond or lower alkyl;

Y at each occurrence is independently selected from the group consisting of R$_A$, —OR$_A$, —NR$_A$R$_B$, —O-alkyl-OR$_A$, —O-alkyl-NR$_A$R$_B$, —N(R$_C$)-alkyl-NR$_A$R$_B$, —(CR$^3$R$^4$)—N(R$_C$)C(O)X; —(CR$^3$R$^4$)—NR$_A$R$_B$; and 2-oxo-4-substituted oxazolidines, and in particular 2-oxo-4-(R)-phenyl-oxazolidine;

Z at each occurrence is independently selected from the group consisting of R$_A$, —OR$_A$, —NR$_A$R$_B$, -alkyl-OR$_A$, -alkyl-NR$_A$R$_B$, -alkyl-N(R$_C$)C(O)X, -alkyl-O-alkyl-OR$_A$, -alkyl-O-alkyl-NR$_A$R$_B$ and -alkyl-N(R$_C$)-alkyl-NR$_A$R$_B$;

R$^3$ and R$^4$, at each occurrence, are independently selected from the group consisting of hydrogen, alkyl, alkenyl and arylalkyl wherein the aryl moiety of the arylalkyl is substituted with 0, 1, 2, 3, 4 or 5 substituents independently selected from the group consisting of alkyl, alkenyl, alkynyl, formyl, halo, nitro, cyano, alkoxy, —OH, —OC(O)(alkyl), —SH, —S(alkyl), —S(O)alkyl, —S(O)$_2$(alkyl), —NH$_2$, —N(H)(alkyl), —N(alkyl)$_2$, —C(O)alkyl, —C(O)OH, —C(O)(—Oalkyl), —C(O)NH$_2$, —C(O)N(H)(alkyl), —C(O)N(alkyl)$_2$ and haloalkyl;

R$_A$ at each occurrence, is independently selected from the group consisting of hydrogen, alkyl, alkenyl, haloalkyl, haloalkenyl, R$_a$ and -alkylR$_a$;

R$_B$ at each occurrence, is independently selected from the group consisting of hydrogen, alkyl, haloalkyl, R$_a$, -alkylR$_a$, —OH, alkoxy, hydroxyalkyl, alkoxyalkyl, —OR$_a$, and —O-alkylR$_a$;

R$_C$ at each occurrence, is independently selected from the group consisting of hydrogen and lower alkyl;

R$_a$ at each occurrence, is independently selected from the group consisting of cycloalkyl, cycloalkenyl, heterocycle, aryl and heteroaryl; wherein each R$_a$ at each occurrence is independently substituted with 0, 1, 2, 3, 4 or 5 substituents independently selected from the group consisting of alkyl, alkenyl, alkynyl, formyl, halo, nitro, cyano, alkoxy, —OH, —O-alkyl-R$_b$, —OC(O)(alkyl), —SH, —S(alkyl), —S(O)alkyl, —S(O)$_2$(alkyl), —NH$_2$, —N(H)(alkyl), —N(alkyl)$_2$, —C(O)alkyl, —C(O)OH, —C(O)(—Oalkyl), —C(O)NH$_2$, —C(O)N(H)(alkyl), —C(O)N(alkyl)$_2$, haloalkyl, R$_b$ and -alkyl-R$_b$;

R$_b$ at each occurrence, is independently selected from the group consisting of cycloalkyl, cycloalkenyl, heterocycle, aryl and heteroaryl; wherein each R$_b$ at each occurrence is independently substituted with 0, 1, 2, 3, 4 or 5 substituents independently selected from the group consisting of alkyl, alkenyl, alkynyl, formyl, halo, nitro, cyano, alkoxy, —OH, —OC(O)(alkyl), —SH, —S(alkyl), —S(O)alkyl, —S(O)$_2$(alkyl), —NH$_2$, —N(H)(alkyl), —N(alkyl)$_2$, —C(O)alkyl, —C(O)OH, —C(O)(—Oalkyl), —C(O)NH$_2$, —C(O)N(H)(alkyl), —C(O)N(alkyl)$_2$ and haloalkyl;

R$^2$ is selected from the group consisting of hydrogen, alkyl, alkenyl, alkynyl, R$_a$, -alkyl-R$_a$, -alkenyl-R$_a$, -alkynyl-R$_a$, haloalkyl, hydroxyalkyl, formylalkyl, cyanoalkyl, -alkyl-OR$_A$, and -alkyl-NR$_A$R$_B$;

R$^5$, R$^6$, R$_7$ and R$^8$ are each independently selected from the group consisting of hydrogen, alkyl, alkenyl, alkynyl, cyano, formyl, halo, nitro, —OR$_A$, —OC(O)R$_A$, —OC(O)OR$_A$, —OC(O)NR$_A$R$_B$, —OS(O)$_2$R$_A$, —SR$_A$, —S(O)R$_A$, —S(O)$_2$R$_A$, —S(O)$_2$(OR$_A$), —S(O)$_2$NR$_A$R$_B$, —NR$_A$R$_B$, —N(R$_C$)C(O)R$_A$, —N(R$_C$)C(O)NR$_A$R$_B$, —N(R$_C$)C(O)OR$_A$, —N(R$_C$)S(O)$_2$R$_A$, —N(R$_C$)S(O)$_2$NR$_A$R$_B$, —N(R$_C$)S(O)$_2$N(R$_C$)C(O)OR$_A$, —C(O)R$_A$, —C(O)OR$_A$, —C(O)NR$_A$R$_B$, haloalkyl, cyanoalkyl, -alkylOR$_A$, -alkyl-OC(O)R$_A$, -alkyl-OC(O)OR$_A$, -alkyl-OC(O)NR$_A$R$_B$, -alkyl-OS(O)$_2$R$_A$, -alkyl-SR$_A$, -alkyl-S(O)R$_A$, -alkyl-S(O)$_2$R$_A$, -alkyl-S(O)$_2$(OR$_A$), -alkyl-S(O)$_2$NR$_A$R$_B$, -alkyl-NR$_A$R$_B$, -alkyl-N(R$_C$)C(O)R$_A$, -alkyl-N(R$_C$)C(O)NR$_A$R$_B$, -alkyl-N(R$_C$)C(O)OR$_A$, -alkyl-N(R$_C$)S(O)$_2$R$_A$, -alkyl-N(R$_C$)S(O)$_2$NR$_A$R$_B$, -alkyl-N(R$_C$)S(O)$_2$N(R$_C$)C(O)OR$_A$, -alkyl-C(O)R$_A$, -alkyl-C(O)(OR$_A$) and -alkyl-C(O)NR$_A$R$_B$;

R$^9$ is —OR$_A$, —SR$_A$, —NR$_A$R$_B$, —N(R$_C$)C(O)R$_A$, —N(R$_C$)C(O)OR$_A$, —N(R$_C$)S(O)$_2$R$_A$ or —N(R$_C$)S(O)$_2$NR$_A$R$_B$;

n is 0, 1, 2, 3 or 4;

R$^{10}$ at each occurrence is independently selected from the group consisting of alkyl, alkenyl, alkynyl, cyano, formyl, nitro, halo, R$_a$, —OR$_A$, —OC(O)X, —OS(O)$_2$R$_A$, —O-alkyl-G$^1$, —SR$_A$, —S(O)R$_A$, —S(O)$_2$X, —NR$_A$R$_B$, —N(R$_B$)C(O)X, —N(R$_B$)C(O)(-alkyl-G$^1$), —N(R$_B$)S(O)$_2$X, —N(R$_B$)S(O)$_2$(-alkyl-G$^1$), —C(O)X, —C(O)N(R$_B$)(-alkyl-G$^1$), haloalkyl, cyanoalkyl, nitroalkyl, -alkyl-R$_a$, —N(-alkyl-C(O)X)(S(O)$_2$X) and -alkyl-G$^1$;

G$^1$ is selected from the group consisting of —OR$_A$, —NR$_A$R$_B$, —N(R$_C$)(—NR$_A$R$_B$), —N(R$_C$)S(O)$_2$X, —N(R$_C$)C(O)X, —C(O)X, —OC(O)X and —S(O)$_2$X; and R$^{11}$ is selected from the group consisting of hydrogen, alkyl, alkenyl and arylalkyl; wherein the aryl moiety of the arylalkyl is substituted with 0, 1, 2, 3, 4 or 5 substituents selected from the group consisting of alkyl, alkenyl, alkynyl, formyl, halo, nitro, cyano, haloalkyl, —OH, alkoxy, —OC —(O)(alkyl), —NH$_2$, —N(H)(alkyl), —N(alkyl)$_2$, —C(O)OH, —C(O)(—Oalkyl), —C(O)alkyl, —C(O)NH$_2$, —C(O)N(H)(alkyl) and —C(O)N(alkyl)$_2$.

In another embodiment, the present invention provides a pharmaceutical composition comprising a therapeutically effective amount of a compound or combination of compounds of the present invention, or a pharmaceutically acceptable salt form, prodrug, salt of a prodrug, stereoisomer, tautomer, or combination thereof, in combination with a pharmaceutically acceptable carrier.

In yet another embodiment, the present invention provides a method of inhibiting the replication of an RNA-containing virus comprising contacting said virus with a therapeutically effective amount of a compound or a combination of compounds of the present invention, or a pharmaceutically acceptable salt, pro drug, salt of a pro drug, stereoisomer, tautomer, or combination thereof. Particularly, this invention is directed to methods of inhibiting the replication of hepatitis C virus.

In still another embodiment, the present invention provides a method of treating or preventing infection caused by an RNA-containing virus comprising administering to a patient in need of such treatment a therapeutically effective amount of a compound or combination of compounds of the present invention, or a pharmaceutically acceptable salt form, prodrug, salt of a prodrug, stereoisomer, or tautomer, or combination thereof. Particularly, this invention is directed to methods of treating or preventing infection caused by hepatitis C virus.

Yet another embodiment of the present invention provides the use of a compound or combination of compounds of the present invention, or a therapeutically acceptable salt form, prodrug, salt of a prodrug, stereoisomer or tautomer, or combination thereof, as defined hereinafter, in the preparation of a medicament for the treatment or prevention of infection caused by RNA-containing virus, specifically hepatitis C virus (HCV).

DETAILED DESCRIPTION OF THE INVENTION

As used in the present specification the following terms have the meanings indicated:

As used herein, the singular forms "a", "an", and "the" include plural reference unless the context clearly dictates otherwise.

The term "alkenyl," as used herein, refers to a straight or branched chain group of 2, 3, 4, 5, 6, 7, or 8 carbon atoms containing at least one carbon-carbon double bond. Examples of alkenyl groups include alkyl, prop-2-enyl, 2-methyl-prop-2-enyl, 3-methylbut-2-enyl, 4-ethylpenta-2,4-dienyl, vinyl, and the like.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, refers to an alkyl group, as defined herein, wherein one, two or three hydrogen atoms are replaced by alkoxy, as defined herein. Representative examples of alkoxyalkyl include, but not limited to, 2,2-dimethoxyethyl, methoxymethyl and methoxyethyl.

The term "alkyl," as used herein, refers to a group derived from a straight or branched chain saturated hydrocarbon containing 1, 2, 3, 4, 5, 6, 7, 8, 9, or 10 carbon atoms. Examples of alkyl groups include propyl, butyl, methyl, ethyl, isobutyl, 2-methylbutyl, 3-methylbutyl, 3,3-dimethylbutyl, tert-butyl, 5,5-dimethylhexyl, 3-methylpentyl, and the like.

The term "$C_1$-$C_6$ alkyl" or "lower alkyl" as used herein, refers to a group derived from a straight or branched chain saturated hydrocarbon containing 1, 2, 3, 4, 5, 6 carbon atoms. Examples of alkyl groups include propyl, butyl, methyl, ethyl, isobutyl, 2-methylbutyl, 3-methylbutyl, 3,3-dimethylbutyl, tert-butyl, 3-methylpentyl, and the like.

The term "alkynyl," as used herein, refers to a straight or branched chain hydrocarbon of 2, 3, 4, 5, or 6 carbon atoms containing at least one carbon-carbon triple bond. Examples of alkynyl groups include ethynyl, 2-methyl-3-butynyl, 3-pentynyl, and the like.

The term "aryl," as used herein, refers to a phenyl group, or a bicyclic hydrocarbon fused ring systems wherein one or more of the rings is a phenyl group. Bicyclic fused ring systems have a phenyl group fused to a monocyclic cycloalkenyl group, as defined herein, a monocyclic cycloalkyl group, as defined herein, or another phenyl group. Examples of aryl groups include indanyl, indenyl, naphthyl (naphthalenyl), phenyl, tetrahydronaphthyl, and the like. The aryl groups of the present invention can be substituted or unsubstituted, and can be connected to the parent molecular moiety through any substitutable carbon atom of the group.

The term "arylalkyl" as used herein, refers to an aryl group, as defined herein, appendended to the parent molecular moiety through an alkyl group, as defined herein. Example of arylalky include, but not limited to, benzyl (phenylmethyl).

The term "cyano" as used herein, refers to —CN.

The term "cyanoalkyl" as used herein, refers to a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkenyl," as used herein, refers to a non-aromatic, partially unsaturated, monocyclic or bicyclic ring system, having 3, 4, 5, 6, 7, 8, 9, 10, 11, 12, 13, or 14 carbon atoms and zero heteroatom. The three-, four- or five-membered ring have one double bond. The six-membered ring has one or two double bonds. The seven and eight-membered rings have one, two, or three double bonds. The bicyclic fused ring systems have a monocyclic cycloalkenyl group fused to a monocyclic cycloalkyl group, as defined herein, or a second monocyclic cycloalkenyl group, as defined herein. The monocyclic examples of cycloalkenyl groups include cyclohexenyl, octahydronaphthalenyl, norbornylenyl, and the like. The cycloalkenyl groups of the present invention can be unsubstituted or substituted, and are attached to the parent molecular moiety through any substitutable carbon atom of the group.

The term "cycloalkyl," as used herein, refers to a saturated monocyclic, or bicyclic fused ring system having 3, 4, 5, 6, 7, 8, 9, 10, 11, 12, 13, or 14 carbon atoms and zero heteroatom. The bicyclic fused ring systems have a monocyclic cycloalkyl group fused to a second mocyclic cycloalkyl group, as defined herein. The cycloalkyl groups of the present invention can be unsubstituted or substituted, and are attached to the parent molecular moiety through any substitutable carbon atom of the group. Examples of cycloalkyl groups include cyclopropyl, cyclobutyl, cyclopentyl, cyclohexyl, cycloheptyl, bicyclo[3.1.1]heptyl, 6,6-dimethylbcyclo[3.1.1]heptyl, adamantyl, and the like.

The term "$C_3$-$C_6$ cycloalkyl" as used herein, refers to cyclopropyl, cyclobutyl, cyclopentyl and cyclohexyl.

The term "formyl," as used herein, refers to —CHO.

The term "formylalkyl" as used herein, refers to a formyl group, as defined herein, appendended to the parent molecular moiety through an alkyl group, as defined herein.

The terms "halo," and "halogen," as used herein, refer to F, Cl, Br, and I.

The term "haloalkenyl" as used herein, refers to an alkenyl group as defined herein, in which one, two, three, four, five or six hydrogen atoms are replaced by halogen.

The term "haloalkyl" as used herein, refers to an alkyl group as defined herein, in which one, two, three, four, five or six hydrogen atoms are replaced by halogen. Examples of haloalkyl include, but not limited to, chloromethyl and trifluoromethyl.

The term "heteroaryl" as used herein, refers to an aromatic five- or six-membered ring where at least one atom is selected from the group consisting of N, O, and S, and the remaining atoms are carbon. The term "heteroaryl" also includes bicyclic fused ring systems where a heteroaryl ring is fused to a phenyl group, a monocyclic cycloalkyl group, as defined herein, a monocyclic heterocycle group, as defined herein, or an additional monocyclic heteroaryl group. Examples of heteroaryl groups include benzimidazolyl, benzothienyl, benzothien-3-yl, benzoxadiazolyl, furanyl (furyl), furan-2-yl, imidazolyl, imidazo[1,5,-a]pyridin-3-yl, indazolyl, indolyl, isoindolyl, isoxazolyl, isoquinolinyl, isothiazolyl, oxadiazolyl, oxadiazolyl, oxazolyl, thiazolyl, 1,3-thiazol-2-yl, thienopyridinyl, thienyl, triazolyl, thiadiazolyl, pyridinyl (pyridyl), pyridazinyl, pyrimidinyl, pyrazinyl, pyrazolyl, pyrrolyl, quinolinyl, triazinyl, and the like. The heteroaryl groups of the present invention can be unsubstituted or substituted and are connected to the parent molecular moiety through any substitutable carbon or nitrogen atom of the groups. In addition, The nitrogen heteroatoms can be optionally quaternized or oxidized to the N-oxide. Also, the nitrogen containing rings can be optionally N-protected.

The term "heterocycle" as used herein, refers to cyclic, non-aromatic, saturated or partially unsaturated, three, four, five-, six-, or seven-membered rings containing at least one atom selected from the group consisting of oxygen, nitrogen, and sulfur. The term "heterocycle" also includes bicyclic fused ring systems where a heterocycle ring is fused to a phenyl group, a monocyclic cycloalkenyl group, as defined herein, a monocyclic cycloalkyl group, as defined herein, or an additional monocyclic heterocycle group. The heterocycle groups of the invention can be unsubstituted or substituted and are connected to the parent molecular moiety through any substitutable carbon or nitrogen atom in the group. Examples of heterocycle groups include azetidinyl, 4,5-dihydro-1,3-oxazol-2-yl, dihydroindolyl, dihydropyridinyl, 1,3-dioxanyl, 1,4-dioxanyl, 1,3-dioxolan-2-yl, 1,1-dioxidoisothiazolidin-2-yl, isoindolinyl, morpholin-4-yl, piperazinyl, pyrrolidinyl, tetrahydropyridinyl, piperidinyl, thiomorpholinyl, tetrahydropyranyl, and the like. For "Y" of "$R^1$" in Formula (I), heterocycles of particular interest include 2-oxo-oxazolidines, more preferred heterocycles include 2-oxo-4-substituted-oxazolidines, and most preferred include 2-oxo-4-(R)-phenyl-oxazolidine. In addition, The nitrogen heteroatoms in heterocylces can be optionally quaternized or oxidized to the N-oxide. Also, the nitrogen containing heterocyclic rings can be optionally N-protected.

The term "hydroxy" as used herein, refers to an —OH group.

The term "hydroxyalkyl" as used herein, refers to a alkyl group, as defined herein, wherein one, two, three or four hydrogen atoms are replaced with hydroxy, as defined herein. Representative examples of hydroxyalkyl include, but are not limited to, hydroxymethyl, 2-hydroxyethyl, 3-hydroxypropyl, and 2-ethyl-4-hydroxyheptyl.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in T. H. Greene and P. G. M. Wuts, *Protective Groups in Organic Synthesis*, 3rd edition, John Wiley & Sons, New York (1999). N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; sulfenyl groups such as phenylsulfanyl, triphenylmethylsulfanyl, and the like; sulfinyl groups such as p-methylphenylsulfinyl, t-butylsulfinyl, and the like; carbamate forming groups such as benzyloxycarbonyl, p-chlorobenzyloxycarbonyl, p-methoxybenzyoxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitro-phenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, p-methoxybenzyl, triphenylmethyl, benzyloxymethyl and the like; p-methoxyphenyl and the like; and silyl groups such as trimethylsilyl and the like. Preferred N-protecting groups include formyl, acetyl, benzoyl, pivaloyl, t-butylacetyl, phenylsulfonyl, benzyl, t-butyloxycarbonyl (Boc) and benzyloxycarbonyl (Cbz).

The term "nitro," as used herein, refers to —$NO_2$.

The term "nitroalkyl" as used herein, refers to a nitro group, as defined herein, appendende to the parent molecular moiety througn an alkyl group, as defined herein.

In a first embodiment the present invention provides a compound of formula (I)

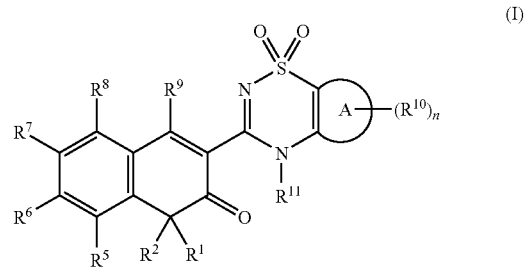

or a pharmaceutically acceptable salt form, stereoisomer, tautomer, prodrug, salt of a prodrug, or combination thereof, wherein:

A is a monocyclic or bicyclic ring selected from the group consisting of aryl, cycloalkyl, cycloalkenyl, heteroaryl and heterocycle;

$R^1$ is —$OR_A$, —O-alkyl-C(O)Y, —$NR_AR_B$, —$N(R_C)$(—N($R_C$)($R_A$)), —$N(R_B)L^1C(O)Y$ or —$N(R_B)S(O)_2Z$;

X at each occurrence, is independently selected from the group consisting of $R_A$, —$OR_A$ and —$NR_AR_B$;

$L^1$ is a bond or lower alkyl;

Y at each occurrence is independently selected from the group consisting of $R_A$, —$OR_A$, —$NR_AR_B$, —O-alkyl-$OR_A$, —O-alkyl-$NR_AR_B$, —$N(R_C)$-alkyl-$NR_AR_B$, —$(CR^3R^4)$—N$(R_C)C(O)X$ and —$(CR^3R^4)$—$NR_AR_B$;

Z at each occurrence is independently selected from the group consisting of $R_A$, —$OR_A$, —$NR_AR_B$, -alkyl-$OR_A$, -alkyl-$NR_AR_B$, -alkyl-$N(R_C)C(O)X$, -alkyl-O-alkyl-$OR_A$, -alkyl-O-alkyl-$NR_AR_B$ and -alkyl-$N(R_C)$-alkyl-$NR_AR_B$;

$R^3$ and $R^4$, at each occurrence, are independently selected from the group consisting of hydrogen, alkyl, alkenyl and arylalkyl wherein the aryl moiety of the arylalkyl is substituted with 0, 1, 2, 3, 4 or 5 substituents independently selected from the group consisting of alkyl, alkenyl, alkynyl, formyl, halo, nitro, cyano, alkoxy, —OH, —OC(O)(alkyl), —SH, —S(alkyl), —S(O)alkyl, —S(O)$_2$(alkyl), —NH$_2$, —N(H)(alkyl), —N(alkyl)$_2$, —C(O)alkyl, —C(O)OH, —C(O)(—Oalkyl), —C(O)NH$_2$, —C(O)N(H)(alkyl), —C(O)N(alkyl)$_2$ and haloalkyl;

$R_A$ at each occurrence, is independently selected from the group consisting of hydrogen, alkyl, alkenyl, haloalkyl, haloalkenyl, $R_a$ and -alkyl$R_a$;

$R_B$ at each occurrence is independently selected from the group consisting of hydrogen, alkyl, haloalkyl, $R_a$, -alkyl$R_a$, —OH, alkoxy, hydroxyalkyl, alkoxyalkyl, —$OR_a$, and —O-alkyl$R_a$;

$R_C$ at each occurrence, is independently selected from the group consisting of hydrogen and lower alkyl;

$R_a$ at each occurrence, is independently selected from the group consisting of cycloalkyl, cycloalkenyl, heterocycle, aryl and heteroaryl; wherein each $R_a$ at each occurrence is independently substituted with 0, 1, 2, 3, 4 or 5 substituents independently selected from the group consisting of alkyl, alkenyl, alkynyl, formyl, halo, nitro, cyano, alkoxy, —OH, —O-alkyl-$R_b$, —OC(O)(alkyl), —SH, —S(alkyl), —S(O)alkyl, —S(O)$_2$(alkyl), —NH$_2$, —N(H)(alkyl), —N(alkyl)$_2$, —C(O)alkyl, —C(O)OH, —C(O)(—Oalkyl), —C(O)NH$_2$, —C(O)N(H)(alkyl), —C(O)N(alkyl)$_2$, haloalkyl, $R_b$ and -alkyl-$R_b$;

$R_b$ at each occurrence is independently selected from the group consisting of cycloalkyl, cycloalkenyl, heterocycle, aryl and heteroaryl; wherein each $R_b$ at each occurrence is independently substituted with 0, 1, 2, 3, 4 or 5 substituents independently selected from the group consisting of alkyl, alkenyl, alkynyl, formyl, halo, nitro, cyano, alkoxy, —OH, —OC(O)(alkyl), —SH, —S(alkyl), —S(O)alkyl, —S(O)$_2$(alkyl), —NH$_2$, —N(H)(alkyl), —N(alkyl)$_2$, —C(O)alkyl, —C(O)OH, —C(O)(—Oalkyl), —C(O)NH$_2$, —C(O)N(H)(alkyl), —C(O)N(alkyl)$_2$ and haloalkyl;

$R^2$ is selected from the group consisting of hydrogen, alkyl, alkenyl, alkynyl, $R_a$, -alkyl-$R_a$, -alkenyl-$R_a$, -alkynyl-$R_a$, haloalkyl, hydroxyalkyl, formylalkyl, cyanoalkyl, -alkyl-$OR_A$, and -alkyl-$NR_AR_B$;

$R^5$, $R^6$, $R^7$ and $R^8$ are each independently selected from the group consisting of hydrogen, alkyl, alkenyl, alkynyl, cyano, formyl, halo, nitro, —$OR_A$, —$OC(O)R_A$, —$OC(O)OR_A$, —$OC(O)NR_AR_B$, —$OS(O)_2R_A$, —$SR_A$, —$S(O)R_A$, —$S(O)_2R_A$, —$S(O)_2(OR_A)$, —$S(O)_2NR_AR_B$, —$NR_AR_B$, —$N(R_C)C(O)R_A$, —$N(R_C)C(O)NR_AR_B$, —$N(R_C)C(O)OR_A$, —$N(R_C)S(O)_2R_A$, —$N(R_C)S(O)_2NR_AR_B$, —$N(R_C)S(O)_2N(R_C)C(O)OR_A$, —$C(O)R_A$, —$C(O)OR_A$, —$C(O)NR_AR_B$, haloalkyl, cyanoalkyl, -alkyl$OR_A$, -alkyl-$OC(O)R_A$, -alkyl-$OC(O)OR_A$, -alkyl-$OC(O)NR_AR_B$, -alkyl-$OS(O)_2R_A$, -alkyl-$SR_A$, -alkyl-$S(O)R_A$, -alkyl-$S(O)_2R_A$, -alkyl-$S(O)_2(OR_A)$, -alkyl-$S(O)_2NR_AR_B$, -alkyl-$NR_AR_B$, -alkyl-$N(R_C)C(O)R_A$, -alkyl-$N(R_C)C(O)NR_AR_B$, -alkyl-$N(R_C)C(O)OR_A$, -alkyl-$N(R_C)S(O)_2R_A$, -alkyl-$N(R_C)S(O)_2NR_AR_B$, -alkyl-$N(R_C)S(O)_2N(R_C)C(O)OR_A$, -alkyl-$C(O)R_A$, -alkyl-$C(O)(OR_A)$ and -alkyl-$C(O)NR_AR_B$;

$R^9$ is —$OR_A$, —$SR_A$, —$NR_AR_B$, —$N(R_C)C(O)R_A$, —$N(R_C)C(O)OR_A$, —$N(R_C)S(O)_2R_A$ or —$N(R_C)S(O)_2NR_AR_B$;

n is 0, 1, 2, 3 or 4;

$R^{10}$ at each occurrence is independently selected from the group consisting of alkyl, alkenyl, alkynyl, cyano, formyl, nitro, halo, $R_a$, —$OR_A$, —$OC(O)X$, —$OS(O)_2R_A$, —O-alkyl-$G^1$, —$SR_A$, —$S(O)R_A$, —$S(O)_2X$, —$NR_AR_B$, —$N(R_B)C(O)X$, —$N(R_B)C(O)(-alkyl-G^1)$, —$N(R_B)S(O)_2X$, —$N(R_B)S(O)_2(-alkyl-G^1)$, —$C(O)X$, —$C(O)N(R_B)(-alkyl-G^1)$, haloalkyl, cyanoalkyl, nitroalkyl, -alkyl-$R_a$, —N(-alkyl-C(O)X)(S(O)$_2$X) and -alkyl-$G^1$;

$G^1$ is selected from the group consisting of —$OR_A$, —$NR_AR_B$, —$N(R_C)(—NR_AR_B)$, —$N(R_C)S(O)_2X$, —$N(R_C)C(O)X$, —$C(O)X$, —$OC(O)X$ and —$S(O)_2X$; and $R^{11}$ is selected from the group consisting of hydrogen, alkyl, alkenyl and arylalkyl; wherein the aryl moiety of the arylalkyl is substituted with 0, 1, 2, 3, 4 or 5 substituents selected from the group consisting of alkyl, alkenyl, alkynyl, formyl, halo, nitro, cyano, haloalkyl, —OH, alkoxy, —OC(O)(alkyl), —NH$_2$, —N(H)(alkyl), —N(alkyl)$_2$, —C(O)OH, —C(O)(—Oalkyl), —C(O)alkyl, —C(O)NH$_2$, —C(O)N(H)(alkyl) and —C(O)N(alkyl)$_2$.

For example, the first embodiment of the present invention provides a compound of formula (I) wherein A is a monocyclic ring selected from the group consisting of aryl, cycloalkyl, cycloalkenyl, heteroaryl and heterocycle. Specifically, the first embodiment of the present invention provides a compound of formula (I) wherein A is a monocyclic ring selected from the group consisting of aryl and heteroaryl. Examples of the monocyclic ring represented by A include, but not limited to, phenyl, pyridyl, thienyl and furanyl.

For example, the first embodiment of the present invention provides a compound of formula (I) wherein $R^{11}$ is selected from the group consisting of hydrogen and $C_1$-$C_6$ alkyl.

For example, the first embodiment of the present invention provides a compound of formula (I) wherein $R^1$ is —$OR_A$ wherein $R_A$ is selected from the group consisting of hydrogen, alkyl and -alkyl-$R_a$, and $R_a$ is as defined in formula (I). Specifically, $R^1$ is —$OR_A$ wherein $R_A$ is selected from the group consisting of hydrogen, $C_1$-$C_6$ alkyl and -methyl-$R_a$; wherein $R_a$ is aryl, unsubstituted or substituted with substituents as defined in formula (I). Examples of $R^1$ include, but not limited to, —OH, —O-methyl, and —O-methyl-phenyl, wherein the phenyl moiety of —O-methyl-phenyl is unsubstituted or substituted with substituents as defined in formula (I).

For example, the first embodiment of the present invention provides a compound of formula (I) wherein $R^1$ is —O-alkyl-C(O)Y wherein Y is selected from the group consisting of —$OR_A$ and —$NR_AR_B$, and wherein $R_A$ and $R_B$ are each independently selected from the group consisting of hydrogen and alkyl. Specifically, $R^1$ is —O—($C_1$-$C_6$ alkyl)-C(O)$OR_A$ or —O—($C_1$-$C_6$ alkyl)-C(O)$NR_AR_B$, wherein $R_A$ and $R_B$ are each independently selected from the group consisting of hydrogen and $C_1$-$C_6$ alkyl. More specifically, $R^1$ is —O-(methyl)-C(O)$OR_A$ or —O-(methyl)-C(O)$NR_AR_B$ wherein $R_A$ and $R_B$ are each independently selected from the group consisting of hydrogen and methyl.

For example, the first embodiment of the present invention provides a compound of formula (I) wherein $R^1$ is —$NR_AR_B$ wherein $R_A$ is selected from the group consisting of hydrogen and alkyl, and $R_B$ is selected from the group consisting of hydrogen, alkyl, -alkyl$R_a$, —OH and alkoxy, and $R_a$ is as defined in formula (I). Specifically, $R^1$ is —$NR_AR_B$ wherein $R_A$ is selected from the group consisting of hydrogen and alkyl, and $R_B$ is selected from the group consisting of hydrogen, alkyl, -alkyl$R_a$, —OH, and alkoxy, and $R_a$ is selected from the group consisting of aryl, $C_3$-$C_6$ cycloalkyl and heteroaryl and each $R_a$ is independently unsubstituted or substituted with substituents as defined in formula (I). More specifically, $R^1$ is —$NR_A R_B$, wherein $R_A$ is selected from the group consisting of hydrogen and $C_1$-$C_6$ alkyl, and $R_B$ is selected from the group consisting of hydrogen, $C_1$-$C_6$ alkyl, —($C_1$-$C_3$ alkyl)-$R_a$, —OH and $C_1$-$C_6$ alkoxy, and wherein $R_a$ is selected from the group consisting of phenyl, naphthyl, cyclopropyl, furanyl, thienyl, thiazolyl, pyridyl, benzothienyl, benzofuranyl and imidazo[1,5,a]pyridyl and each $R_a$ is independently unsubstituted or substituted with substituents as defined in formula (I). Even more specifically, $R^1$ is —$NR_A R_B$ wherein $R_A$ is selected from the group consisting of hydrogen and methyl, and $R_B$ is selected from the group consisting of hydrogen, isobutyl, -methyl-$R_a$, —OH, methoxy, ethoxy and tert-butoxy, wherein $R_a$ is selected from the group consisting of phenyl, naphthyl, cyclopropyl, furanyl, thienyl, thiazolyl, pyridyl, benzothienyl, benzofuranyl and imidazo[1,5,a]pyridyl, and each $R_a$ is independently unsubstituted or substituted with substituents as defined in formula (I), examples of such substituents include, but are not limited to, methyl, vinyl, methoxy, —OH, —OC(O)(methyl), nitro, cyano, trifluoromethyl, —$NH_2$, acetyl, phenyl, and phenylmethoxy.

For example, the first embodiment of the present invention provides a compound of formula (I) wherein $R^1$ is —N($R_B$)$L^1$(O)Y wherein $L^1$ is a bond or alkyl, $R_B$ is selected from the group consisting of hydrogen, —OH, -alkyl$R_a$ and alkoxy wherein $R_a$ is unsubstituted or substituted aryl with substituents as defined in formula (I), and Y is selected from the group consisting of $R_A$, —$NR_A R_B$, $OR_A$, —O-alkyl-$OR_A$, $CR^3R^4$—N($R_C$)C(O)X, and —$CR^3R^4$—$NR_A R_B$ wherein $R_A$, $R_B$, $R_C$, $R^3$, $R^4$ and X are as defined in formula (I). Specifically, $R^1$ is —N($R_B$)$L^1$C(O)Y wherein $L^1$ is a bond or $C_1$-$C_2$ alkyl, $R_B$ is selected from the group consisting of hydrogen, —OH, -methyl-aryl and alkoxy, and Y is selected from the group consisting of $C_1$-$C_6$ alkyl, haloalkyl, aryl, —$NR_A R_B$, —O($C_1$-$C_6$ alkyl), —O(-methyl-aryl), —O—($C_1$-$C_6$ alkyl)-O($C_1$-$C_6$ alkyl), —$CH_2$—N(H)C(O)$R_A$, —$CH_2$—N(H)C(O)$OR_A$ and —$CH_2$—$NR_A R_B$, wherein $R_A$ and $R_B$ are independently selected from the group consisting of hydrogen and $C_1$-$C_6$ alkyl and wherein the aryl and the aryl moieties of -methyl-aryl and —O(-methyl-aryl) are independently unsubstituted or substituted with substituents as defined in formula (I). More specifically, $R_1$ is —N($R_B$)$L^1$C(O)Y wherein $L^1$ is a bond or methyl, $R_B$ is selected from the group consisting of hydrogen, —OH, -benzyl and methoxy, and Y is selected from the group consisting of methyl, chloromethyl, phenyl, —$NH_2$, —N(H)(tert-butyl), —O(methyl), —O(ethyl), —O(benzyl), —O-ethyl-O(methyl), —$CH_2$N(H)C(O)(methyl), —$CH_2$N(H)C(O)(—O-tert-butyl) and —$CH_2$—$NH_2$, wherein the phenyl and phenyl moieties of benzyl and —O(benzyl) are each independently unsubstituted or substituted with substituents as defined in formula (I).

For example, the first embodiment of the present invention provides a compound of formula (I) wherein $R_1$ is —N($R_B$)S(O)$_2$Z wherein $R_B$ is hydrogen or alkyl, and Z is selected from the group consisting of $R_A$, -alkyl-$NR_A R_B$, -alkyl-$OR_A$-alkyl-N($R_C$)-alkyl-$NR_A R_B$ and -alkyl-N($R_C$)C(O)X wherein $R_A$, $R_B$, $R_C$ and X are as defined in formula (I). Specifically, $R_1$ is —N(H)S(O)$_2$Z wherein Z is selected from the group consisting of $C_1$-$C_6$ alkyl, aryl, —($C_1$-$C_2$ alkyl)-heterocycle, —($C_1$-$C_2$ alkyl)-O($C_1$-$C_6$ alkyl), —($C_1$-$C_6$ alkyl)-N($C_1$-$C_6$ alkyl)-($C_1$-$C_6$ alkyl)-N(H)($C_1$-$C_6$ alkyl), —($C_1$-$C_6$ alkyl)-N($C_1$-$C_6$ alkyl)C(O)($C_1$-$C_6$ alkyl), and —($C_1$-$C_2$ alkyl)-$NR_A R_B$, wherein $R_A$ is hydrogen, $C_1$-$C_2$ alkyl or —($C_1$-$C_2$ alkyl)-aryl, and $R_B$ is $C_1$-$C_6$ alkyl, —($C_1$-$C_2$ alkyl)-aryl, —($C_1$-$C_2$ alkyl)-heterocycle, alkoxy or alkoxyalkyl; and the aryl, the heterocycle moiety of —($C_1$-$C_2$ alkyl)-heterocycle and the aryl moieties of —($C_1$-$C_2$ alkyl)-aryl are independently unsubstituted or substituted with substituents as defined in formula (I). More specifically, $R_1$ is —N(H)S(O)$_2$Z wherein Z is selected from the group consisting of methyl, phenyl, morpholinylmethyl-, morpholinylethyl-, -ethyl-O-methyl, -ethyl-N(methyl)-ethyl-N(H)(methyl), -ethyl-N(methyl)C(O)(methyl), and -ethyl-$NR_A R_B$, wherein $R_A$ is hydrogen, methyl, ethyl or benzyl, and $R_B$ is methyl, ethyl, benzyl, (1,3-dioxolan-2-yl)methyl-, methoxy, methoxyethyl or 2,2-dimethoxyethyl; wherein the phenyl and the phenyl moiety of benzyl are independently unsubstituted or substituted with substituents as defined in formula (I), representative examples of substituents on the phenyl and the phenyl moiety of benzyl include, but not limited to, methyl, vinyl, halo, nitro, cyano, methoxy, —OH, —OC(O)(methyl), —$NH_2$, —C(O)(methyl), —C(O)OH, —C(O)(—O-methyl) and trifluoromethyl.

For example, the first embodiment of the present invention provides a compound of formula (I) wherein $R^2$ is selected from the group consisting of alkyl, alkenyl, -alkyl-$R_a$, and -alkenyl-$R_a$ wherein $R_a$ is as defined in formula (I). Specifically, $R^2$ is selected from the group consisting of alkyl, alkenyl, -alkyl-$R_a$, and -alkenyl-$R_a$ wherein $R_a$ is aryl, unsubstituted or substituted with substituents as defined in formula (I). More specifically, $R^2$ is selected from the group consisting of $C_1$-$C_6$ alky, $C_2$-$C_6$ alkenyl, —($C_1$-$C_3$ alkyl)-aryl and —($C_3$ alkenyl)-aryl wherein the aryl moieties of —($C_1$-$C_3$ alkyl)-aryl and —($C_3$ alkenyl)-aryl are independently unsubstituted or substituted with substituents as defined in formula (I). More specifically, $R^2$ is selected from the group consisting of propyl, butyl, isobutyl, 3,3-dimethylbutyl, 3-methylbutyl, allyl, 2-methylprop-2-enyl, 3-methylbut-2-enyl, phenylmethyl and 3-phenylprop-2-enyl; wherein the phenyl moieties of phenylmethyl and 3-phenylprop-2-enyl are independently unsubstituted or substituted with the substituents as defined in formula (I). Even more specifically, $R^2$ is selected from the group consisting of propyl, butyl, isobutyl, 3,3-dimethylbutyl, 3-methylbutyl, allyl, 2-methylprop-2-enyl, 3-methylbut-2-enyl, phenylmethyl and 3-phenylprop-2-enyl; wherein the phenyl moieties of phenylmethyl and 3-phenylprop-2-enyl are independently substituted with 0, 1, 2 or 3 substituents selected from the group consisting of methyl, vinyl, halo, nitro, cyano, methoxy, —OH, —OC(O)(methyl), —$NH_2$, —C(O)(methyl), —C(O)OH, —C(O)(—O-methyl) and trifluoromethyl.

For example, the first embodiment of the present invention provides a compound of formula (I) wherein $R^5$, $R^6$, $R^7$ and $R^8$ are each independently selected from the group consisting of hydrogen, alkyl, alkenyl, halo and haloalkyl. Specifically, $R^5$, $R^6$, $R^1$ and $R^8$ are each independently selected from the group consisting of hydrogen, $C_1$-$C_6$ alkyl, halo and haloalkyl. More specifically, $R^5$, $R^6$, $R^7$ and $R^8$ are each independently selected from the group consisting of hydrogen, methyl, ethyl, halo and trifluoromethyl.

For example, the first embodiment of the present invention provides a compound of formula (I) wherein $R^9$ is —$OR_A$ wherein $R_A$ is hydrogen.

For example, the first embodiment of the present invention provides a compound of formula (I) wherein $R^{10}$ at each occurrence is independently selected from the group consisting of —N($R_B$)S(O)$_2$X and —N(-alkyl-C(O)X)(S(O)$_2$X) wherein $R_B$ and X are as defined in formula (I). Specifically, $R^{10}$ at each occurrence is independently selected from the group consisting of —$N(R_B)S(O)_2X$ and —$N(\text{-alkyl-}C(O)X)(S(O)_2X)$ wherein $R_B$ is hydrogen or $C_1$-$C_6$ alkyl and X is $C_1$-$C_6$ alkyl. More specifically, $R^{10}$ at each occurrence is independently selected from the group consisting of —$N(R_B)S(O)_2X$ and —$N(\text{-alkyl-}C(O)X)(S(O)_2X)$ wherein $R_B$ is hydrogen and X is methyl or ethyl.

It is understood that the present invention encompasses all combinations of the above embodiments, specific and more specific embodiments described hereinabove.

Accordingly, one embodiment of the present invention provides a compound of formula (I) wherein $R^9$ is $OR_A$ wherein $R_A$ is hydrogen; A is a monocyclic ring selected from the group consisting of aryl, cycloalkyl, cycloalkenyl, heteroaryl and heterocycle; and $R^1$, $R^2$, $R^5$, $R^6$, $R^7$, $R^8$, $R^{10}$, $R^{11}$ and n are as defined in formula (I).

Another embodiment of the present invention provides a compound of formula (I) wherein $R^9$ is $OR_A$ wherein $R_A$ is hydrogen; A is a monocyclic ring selected from the group consisting of phenyl, pyridyl, thienyl and furanyl; and $R^1$, $R^2$, $R^5$, $R^6$, $R^7$, $R^8$, $R^{10}$, $R^{11}$ and n are as defined in formula (I).

Another embodiment of the present invention provides a compound of formula (I) wherein $R^9$ is $OR_A$ wherein $R_A$ is hydrogen; A is a monocyclic ring selected from the group consisting of aryl, cycloalkyl, cycloalkenyl, heteroaryl and heterocycle; $R^{11}$ is hydrogen; and $R^1$, $R^2$, $R^5$, $R^6$, $R^7$, $R^8$, $R^{10}$ and n are as defined in formula (I).

Another embodiment of the present invention provides a compound of formula (I) wherein $R^9$ is $OR_A$ wherein $R_A$ is hydrogen; A is a monocyclic ring selected from the group consisting of aryl, cycloalkyl, cycloalkenyl, heteroaryl and heterocycle; $R^{11}$ is hydrogen; n is 1 and $R^{10}$ is —$N(R_B)S(O)_2X$; and $R_B$, X, $R^1$, $R^2$, $R^5$, $R^6$, $R^7$, and $R^8$ are as defined in formula (I).

Another embodiment of the present invention provides a compound of formula (I) wherein $R^2$ is selected from the group consisting of alkyl, alkenyl, -alkyl-$R_a$, and -alkenyl-$R_a$; $R^9$ is $OR_A$ wherein $R_A$ is hydrogen; and $R^1$, $R^5$, $R^6$, $R^7$, $R^8$, $R^{10}$, $R^{11}$, $R_a$, A and n are as defined in formula (I).

Another embodiment of the present invention provides a compound of formula (I) wherein $R^2$ is selected from the group consisting of alkyl, alkenyl, -alkyl-$R_a$, and -alkenyl-$R_a$; $R^9$ is $OR_A$ wherein $R_A$ is hydrogen; $R^{11}$ is hydrogen; and $R^1$, $R^5$, $R^6$, $R^7$, $R^8$, $R^{10}$, $R_a$, A and n are as defined in formula (I).

Another embodiment of the present invention provides a compound of formula (I) wherein $R^2$ is selected from the group consisting of alkyl, alkenyl -alkyl-$R_a$ and -alkenyl-$R_a$; $R^9$ is $OR_A$ wherein $R_A$ is hydrogen; $R^{11}$ is hydrogen; $R^1$ is —$OR_A$ wherein $R_A$ is as defined in formula (I); and $R_a$, $R^5$, $R^6$, $R^7$, $R^8$, $R^{10}$, A and n are as defined in formula (I).

Another embodiment of the present invention provides a compound of formula (I) wherein $R^2$ is selected from the group consisting of alkyl, alkenyl -alkyl-$R_a$ and -alkenyl-$R_a$; $R^9$ is $OR_A$ wherein $R_A$ is hydrogen; $R^{11}$ is hydrogen; $R^1$ is —$NR_AR_B$ wherein $R_A$ and $R_B$ are as defined in formula (I); and $R_a$, $R^5$, $R^6$, $R^7$, $R^8$, $R^{10}$, A and n are as defined in formula (I).

Another embodiment of the present invention provides a compound of formula (I) wherein $R^2$ is selected from the group consisting of alkyl, alkenyl -alkyl-$R_a$ and -alkenyl-$R_a$; $R^9$ is $OR_A$ wherein $R_A$ is hydrogen; $R^{11}$ is hydrogen; $R^1$ is —O-alkyl-C(O)Y; and Y, $R_a$, $R^5$, $R^6$, $R^7$, $R^8$, $R^{10}$, A and n are as defined in formula (I).

Another embodiment of the present invention provides a compound of formula (I) wherein $R^2$ is selected from the group consisting of alkyl, alkenyl -alkyl-$R_a$ and -alkenyl-$R_a$; $R^9$ is $OR_A$ wherein $R_A$ is hydrogen; $R^{11}$ is hydrogen; $R^1$ is —$N(R_B)L^1(O)Y$; and $L^1$, $R_B$, Y, $R_a$, $R^5$, $R^6$, $R^7$, $R^8$, $R^{10}$, A and n are as defined in formula (I).

Another embodiment of the present invention provides a compound of formula (I) wherein $R^2$ is selected from the group consisting of alkyl, alkenyl -alkyl-$R_a$ and -alkenyl-$R_a$; $R^9$ is $OR_A$ wherein $R_A$ is hydrogen; $R^{11}$ is hydrogen; $R^1$ is —$N(R_B)L^1S(O)_2Z$; and $R_B$, Z, $R_a$, $R^5$, $R^6$, $R^7$, $R^8$, $R^{10}$, A and n are as defined in formula (I).

Another embodiment of the present invention provides a compound of formula (I) wherein $R^2$ is selected from the group consisting of alkyl, alkenyl -alkyl-$R_a$ and -alkenyl-$R_a$; $R^9$ is $OR_A$ wherein $R_A$ is hydrogen; $R^{11}$ is hydrogen; $R^1$ is —$NR_AR_B$ wherein $R_A$ is selected from the group consisting of hydrogen and alkyl, and $R_B$ is selected from the group consisting of hydrogen, alkyl, -alkyl$R_a$, —OH and alkoxy; and $R_a$, $R^5$, $R^6$, $R^7$, $R^8$, $R^{10}$, A and n are as defined in formula (I).

Another embodiment of the present invention provides a compound of formula (I) wherein $R^2$ is selected from the group consisting of alkyl, alkenyl -alkyl-$R_a$ and -alkenyl-$R_a$ wherein $R_a$ is aryl, unsubstituted or substituted with substituents as defined in formula (I); $R^9$ is $OR_A$ wherein $R_A$ is hydrogen, $R^1$ is —$NR_AR_B$ wherein $R_A$ is selected from the group consisting of hydrogen and alkyl, and $R_B$ is selected from the group consisting of hydrogen, alkyl, -alkyl$R_a$, —OH and alkoxy, wherein $R_a$ is selected from the group consisting of aryl, $C_3$-$C_6$ cycloalkyl and heteroaryl wherein each $R_a$ is independently unsubstituted or substituted with substituents as defined in formula (I); $R^{11}$ is hydrogen; and $R^5$, $R^6$, $R^7$, $R^8$, $R^{10}$, A and n are as defined in formula (I).

Another embodiment of the present invention provides a compound of formula (I) wherein $R^2$ is selected from the group consisting of alkyl, alkenyl -alkyl-$R_a$ and -alkenyl-$R_a$ wherein $R_a$ is aryl, unsubstituted or substituted with substituents as defined in formula (I); $R^9$ is $OR_A$ wherein $R_A$ is hydrogen; $R^1$ is —$NR_AR_B$ wherein $R_A$ is selected from the group consisting of hydrogen and alkyl, and $R_B$ is selected from the group consisting of hydrogen, alkyl, -alkyl$R_a$, —OH and alkoxy wherein $R_a$ is selected from the group consisting of aryl, $C_3$-$C_6$ cycloalkyl and heteroaryl wherein each $R_a$ is independently unsubstituted or substituted with substituents as defined in formula (I); $R^{11}$ is hydrogen, n is 1; $R^{10}$ is —$N(R_B)SO_2X$ or —$N(\text{-alkyl-}C(O)X)(S(O)_2X)$ and $R^5$, $R^6$, $R^1$, $R^8$, $R_B$, X and A are as defined in formula (I).

Another embodiment of the present invention provides a compound of formula (I) wherein $R^2$ is selected from the group consisting of alkyl, alkenyl -alkyl-$R_a$ and -alkenyl-$R_a$ wherein $R_a$ is aryl, unsubstituted or substituted with substituents as defined in formula (I); $R^9$ is $OR_A$ wherein $R_A$ is hydrogen; $R^1$ is —$NR_AR_B$ wherein $R_A$ is selected from the group consisting of hydrogen and alkyl, and $R_B$ is selected from the group consisting of hydrogen, alkyl, -alkyl$R_a$, —OH and alkoxy wherein $R_a$ is selected from the group consisting of aryl, $C_3$-$C_6$ cycloalkyl and heteroaryl wherein each $R_a$ is independently unsubstituted or substituted with substituents as defined in formula (I); $R^1$ is hydrogen, n is 1; $R^{10}$ is —$N(R_B)SO_2X$; and $R^5$, $R^6$, $R^7$, $R^8$, $R_B$, X and A are as defined in formula (I).

Another embodiment of the present invention provides a compound of formula (I) wherein $R^2$ is selected from the group consisting of alkyl, alkenyl -alkyl-$R_a$ and -alkenyl-$R_a$ wherein $R_a$ is aryl, unsubstituted or substituted with substituents as defined in formula (I); $R^9$ is $OR_A$ wherein $R_A$ is hydrogen; $R^1$ is —$NR_AR_B$ wherein $R_A$ is selected from the group consisting of hydrogen and alkyl, and $R_B$ is selected from the group consisting of hydrogen, alkyl, -alkyl$R_a$, —OH and alkoxy wherein $R_a$ is selected from the group consisting of aryl, $C_3$-$C_6$ cycloalkyl and heteroaryl and each $R_a$ is independently unsubstituted or substituted with substituents as defined in formula (I); $R^{11}$ is hydrogen, n is 1; $R^{10}$ is —N(-alkyl-C(O)X)(S(O)$_2$X); and $R^5$, $R^6$, $R^7$, $R^8$, X and A are as defined in formula (I).

Another embodiment of the present invention provides a compound of formula (I) wherein $R^2$ is selected from the group consisting of alkyl, alkenyl -alkyl-$R_a$ and -alkenyl-$R_a$ wherein $R_a$ is aryl, unsubstituted or substituted with substituents as defined in formula (I); $R^9$ is $OR_A$ wherein $R_A$ is hydrogen; $R^1$ is —$NR_AR_B$ wherein $R_A$ is selected from the group consisting of hydrogen and alkyl, and $R_B$ is selected from the group consisting of hydrogen, alkyl, -alkyl$R_a$, —OH and alkoxy wherein $R_a$ is selected from the group consisting of aryl, $C_3$-$C_6$ cycloalkyl and heteroaryl and each $R_a$ is independently unsubstituted or substituted with substituents as defined in formula (I); $R^{11}$ is hydrogen, n is 1; $R^{10}$ is —N($R_B$)SO$_2$X wherein $R_B$ is hydrogen or alkyl and X is alkyl; A is a monocyclic ring selected from the group consisting of aryl and heteroaryl; and $R^5$, $R^6$, $R^7$, and $R^8$ are as defined in formula (I).

Another embodiment of the present invention provides a compound of formula (I) wherein $R^2$ is selected from the group consisting of alkyl, alkenyl -alkyl-$R_a$ and -alkenyl-$R_a$ wherein $R_a$ is aryl, unsubstituted or substituted with substituents as defined in formula (I); $R^9$ is $OR_A$ wherein $R_A$ is hydrogen; $R^1$ is —$NR_AR_B$ wherein $R_A$ is selected from the group consisting of hydrogen and alkyl, and $R_B$ is selected from the group consisting of hydrogen, alkyl, -alkyl$R_a$, —OH and alkoxy wherein $R_a$ is selected from the group consisting of aryl, $C_3$-$C_6$ cycloalkyl and heteroaryl and each $R_a$ is independently unsubstituted or substituted with substituents as defined in formula (I); $R^{11}$ is hydrogen, n is 1; $R^{10}$ is —N($R_B$)SO$_2$X wherein $R_B$ is hydrogen or alkyl and X is alkyl; A is a monocyclic ring selected from the group consisting of aryl and heteroaryl; and $R^5$, $R^6$, $R^7$, and $R^8$ are each independently selected fromt the group consisting of hydrogen, alkyl, alkenyl, alkynyl, cyano, halo, nitro, —$OR_A$, —OC(O)$R_A$, —OC(O)O$R_A$, —OC(O)N$R_AR_B$, —OS(O)$_2R_A$, —S$R_A$, —S(O)$R_A$, —S(O)$_2R_A$, —S(O)$_2$N$R_AR_B$, —N$R_AR_B$, —N($R_C$)C(O)$R_A$, —C(O)$R_A$, —C(O)O$R_A$, —C(O)N$R_AR_B$, haloalkyl, and -alkylO$R_A$, wherein $R_A$, $R_B$ and $R_C$ are each independently selected from the group consisting of hydrogen and alkyl.

Another embodiment of the present invention provides a compound of formula (I) wherein $R^2$ is $C_1$-$C_6$ alkyl, $C_3$-$C_6$ alkenyl, —($C_1$-$C_3$ alkyl)-aryl or —($C_3$ alkenyl)-aryl wherein each of the aryl moieties of —($C_1$-$C_3$ alkyl)-aryl and —($C_3$ alkenyl)-aryl is independently unsubstituted or substituted with the substituents as defined in formula (I); $R^9$ is $OR_A$ wherein $R_A$ is hydrogen; $R^1$ is —$NR_AR_B$ wherein $R_A$ is selected from the group consisting of hydrogen and methyl, and $R_B$ is selected from the group consisting of hydrogen, $C_1$-$C_6$ alkyl, —($C_1$-$C_3$ alkyl)-$R_a$, —OH, and $C_1$-$C_6$ alkoxy, wherein $R_a$ is selected from the group consisting of aryl, $C_3$-$C_6$ cycloalkyl and heteroaryl and each $R_a$ is independently unsubstituted or substituted with substituents as defined in formula (I); $R^{11}$ is hydrogen, n is 1; $R^{10}$ is —N($R_B$)SO$_2$X wherein $R_B$ is hydrogen or $C_1$-$C_6$ alkyl and X is $C_1$-$C_6$ alkyl; A is a monocyclic ring selected from the group consisting of aryl and heteroaryl; and $R^5$, $R^6$, $R^7$, and $R^8$ are each independently selected from the group consisting of hydrogen and $C_1$-$C_6$ alkyl.

Another embodiment of the present invention provides a compound of formula (I) wherein $R^2$ is selected from the group consisting of propyl, butyl, isobutyl, 3,3-dimethylbutyl, 3-methylbutyl, allyl, 2-methylprop-2-enyl, 3-methylbut-2-enyl, phenylmethyl and 3-phenylprop-2-enyl; wherein the phenyl moieties of phenylmethyl and 3-phenylprop-2-enyl are independently unsubstituted or substituted with the substituents as defined in formula (I); $R^9$ is $OR_A$ wherein $R_A$ is hydrogen; $R^1$ is —$NR_AR_B$ wherein $R_A$ is selected from the group consisting of hydrogen and methyl, and $R_B$ is selected from the group consisting of hydrogen, isobutyl, -methyl-$R_a$, —OH, methoxy, ethoxy and tert-butoxy, wherein $R_a$ is selected from the group consisting of phenyl, naphthyl, cyclopropyl, furanyl, thienyl, thiazolyl, pyridyl, benzofuranyl, benzothienyl and imidazo[1,5,a]pyrid-3-yl and each $R_a$ is independently unsubstituted or substituted with substituents as defined in formula (I); $R^{11}$ is hydrogen; n is 1; $R^{10}$ is —N($R_B$)SO$_2$X wherein $R_B$ is hydrogen and X is methyl; A is phenyl; and $R^5$, $R^6$, $R^7$ and $R^8$ are hydrogen.

Another embodiment of the present invention provides a compound of formula (I) wherein $R^2$ is selected from the group consisting of alkyl, alkenyl -alkyl-$R_a$ and -alkenyl-$R_a$ wherein $R_a$ is aryl, unsubstituted or substituted with substituents as defined in formula (I); $R^9$ is $OR_A$ wherein $R_A$ is hydrogen; $R^1$ is —$OR_A$ wherein $R_A$ is selected from the group consisting of hydrogen, alkyl and -alkyl-$R_a$, and $R_a$ is as defined in formula (I); $R^{11}$ is hydrogen, n is 1; $R^{10}$ is —N($R_B$)SO$_2$X wherein $R_B$ is hydrogen or alkyl and X is alkyl; A is a monocyclic ring selected from the group consisting of aryl and heteroaryl; and $R^5$, $R^6$, $R^7$, and $R^8$ are each independently selected fromt the group consisting of hydrogen, alkyl, alkenyl, alkynyl, cyano, halo, nitro, —$OR_A$, —OC(O)$R_A$, —OC(O)O$R_A$, —OC(O)N$R_AR_B$, —OS(O)$_2R_A$, —S$R_A$, —S(O)$R_A$, —S(O)$_2R_A$, —S(O)$_2$N$R_AR_B$, —N$R_AR_B$, —N($R_C$)C(O)$R_A$, —C(O)$R_A$, —C(O)O$R_A$, —C(O)N$R_AR_B$, haloalkyl, and -alkylO$R_A$, wherein $R_A$, $R_B$ and $R_C$ are each independently selected from the group consisting of hydrogen and alkyl.

Another embodiment of the present invention provides a compound of formula (I) wherein $R^2$ is $C_1$-$C_6$ alkyl, $C_3$-$C_6$ alkenyl, —($C_1$-$C_3$ alkyl)-aryl or —($C_3$ alkenyl)-aryl wherein each of the aryl moieties of —($C_1$-$C_3$ alkyl)-aryl and —($C_3$ alkenyl)-aryl is independently unsubstituted or substituted with the substituents as defined in formula (I); $R^9$ is $OR_A$ wherein $R_A$ is hydrogen; $R^1$ is —$OR_A$ wherein $R_A$ is selected from the group consisting of hydrogen, $C_1$-$C_6$ alkyl and -methyl-$R_a$; wherein $R_a$ is aryl, unsubstituted or substituted with substituents as defined in formula (I); $R^{11}$ is hydrogen, n is 1; $R^{10}$ is —N($R_B$)SO$_2$X wherein $R_B$ is hydrogen or $C_1$-$C_6$ alkyl and X is $C_1$-$C_6$ alkyl; A is a monocyclic ring selected from the group consisting of aryl and heteroaryl; and $R^5$, $R^6$, $R^7$, and $R^8$ are each independently selected from the group consisting of hydrogen and $C_1$-$C_6$ alkyl.

Another embodiment of the present invention provides a compound of formula (I) wherein $R^2$ is selected from the group consisting of propyl, butyl, isobutyl, 3,3-dimethylbutyl, 3-methylbutyl, allyl, 2-methylprop-2-enyl, 3-methylbut-2-enyl, phenylmethyl and 3-phenylprop-2-enyl; wherein the phenyl moieties of phenylmethyl and 3-phenylprop-2-enyl are independently unsubstituted or substituted with the substituents as defined in formula (I); $R^9$ is $OR_A$ wherein $R_A$ is hydrogen; $R^1$ is —OH, —O-methyl, or —O-methyl-phenyl, wherein the phenyl moiety of —O-methyl-phenyl is unsubstituted or substituted with substituents as defined in formula (I); $R^{11}$ is hydrogen; n is 1; $R^{10}$ is —N($R_B$)SO$_2$X wherein $R_B$ is hydrogen and X is methyl; A is phenyl; and $R^5$, $R^6$, $R^7$ and $R^8$ are hydrogen.

Another embodiment of the present invention provides a compound of formula (I) wherein $R^2$ is selected from the group consisting of alkyl, alkenyl -alkyl-$R_a$ and -alkenyl-$R_a$ wherein $R_a$ is aryl, unsubstituted or substituted with substituents as defined in formula (I); $R^9$ is $OR_A$ wherein $R_A$ is hydrogen; $R^1$ is —O-alkyl-C(O)Y wherein Y is selected from the group consisting of —$OR_A$ and —$NR_AR_B$, and wherein $R_A$ and $R_B$ are each independently selected from the group consisting of hydrogen and alkyl; $R^{11}$ is hydrogen, n is 1; $R^{10}$ is —N($R_B$)SO$_2$X wherein $R_B$ is hydrogen or alkyl and X is alkyl; A is a monocyclic ring selected from the group consisting of aryl and heteroaryl; and $R^5$, $R^6$, $R^7$, and $R^8$ are each independently selected fromt the group consisting of hydrogen, alkyl, alkenyl, alkynyl, cyano, halo, nitro, —OR$_A$, —OC(O)R$_A$, —OC(O)OR$_A$, —OC(O)NR$_A$R$_B$, —OS(O)$_2$R$_A$, —SR$_A$, —S(O)R$_A$, —S(O)$_2$R$_A$, —S(O)$_2$NR$_A$R$_B$, —NR$_A$R$_B$, —N(R$_C$)C(O)R$_A$, —C(O)R$_A$, —C(O)OR$_A$, —C(O)NR$_A$R$_B$, haloalkyl, and -alkylOR$_A$, wherein R$_A$, R$_B$ and R$_C$ are each independently selected from the group consisting of hydrogen and alkyl.

Another embodiment of the present invention provides a compound of formula (I) wherein $R^2$ is $C_1$-$C_6$ alkyl, $C_3$-$C_6$ alkenyl, —($C_1$-$C_3$ alkyl)-aryl or —($C_3$ alkenyl)-aryl wherein each of the aryl moieties of —($C_1$-$C_3$ alkyl)-aryl and —($C_3$ alkenyl)-aryl is independently unsubstituted or substituted with the substituents as defined in formula (I); $R^9$ is OR$_A$ wherein R$_A$ is hydrogen; $R^1$ is —O—($C_1$-$C_6$ alkyl)-C(O)OR$_A$ or —O—($C_1$-$C_6$ alkyl)-C(O)NR$_A$R$_B$, wherein R$_A$ and R$_B$ are each independently selected from the group consisting of hydrogen and $C_1$-$C_6$ alkyl; $R^{11}$ is hydrogen, n is 1; $R^{10}$ is —N(R$_B$)SO$_2$X wherein R$_B$ is hydrogen or $C_1$-$C_6$ alkyl and X is $C_1$-$C_6$ alkyl; A is a monocyclic ring selected from the group consisting of aryl and heteroaryl; and $R^5$, $R^6$, $R^7$, and $R^8$ are each independently selected from the group consisting of hydrogen and $C_1$-$C_6$ alkyl.

Another embodiment of the present invention provides a compound of formula (I) wherein $R^2$ is selected from the group consisting of propyl, butyl, isobutyl, 3,3-dimethylbutyl, 3-methylbutyl, allyl, 2-methylprop-2-enyl, 3-methylbut-2-enyl, phenylmethyl and 3-phenylprop-2-enyl; wherein the phenyl moieties of phenylmethyl and 3-phenylprop-2-enyl are independently unsubstituted or substituted with the substituents as defined in formula (I); $R^9$ is OR$_A$ wherein R$_A$ is hydrogen; $R^1$ is —O-(methyl)-C(O)OR$_A$ or —O-(methyl)-C(O)NR$_A$R$_B$ wherein R$_A$ and R$_B$ are each independently selected from the group consisting of hydrogen and methyl; $R^{11}$ is hydrogen; n is 1; $R^{10}$ is —N(R$_B$)SO$_2$X wherein R$_B$ is hydrogen and X is methyl; A is phenyl; and $R^5$, $R^6$, $R^7$ and $R^8$ are hydrogen.

Another embodiment of the present invention provides a compound of formula (I) wherein $R^2$ is selected from the group consisting of alkyl, alkenyl -alkyl-R$_a$ and -alkenyl-R$_a$, wherein R$_a$ is aryl, unsubstituted or substituted with substituents as defined in formula (I); $R^9$ is OR$_A$ wherein R$_A$ is hydrogen; $R^1$ is —N(R$_B$)L$^1$(O)Y wherein L$^1$ is a bond or alkyl, R$_B$ is selected from the group consisting of hydrogen, —OH, -alkylR$_a$ and alkoxy wherein R$_a$ is unsubstituted or substituted aryl with substituents as defined in formula (I), and Y is selected from the group consisting of R$_A$, —NR$_A$R$_B$, OR$_A$, —O-alkyl-OR$_A$, CR$^3$R$^4$—N(R$_C$)C(O)X, and —CR$^3$R$^4$—NR$_A$R$_B$ wherein R$_A$, R$_B$, R$_C$, R$^3$, R$^4$ and X are as defined in formula (I); $R^{11}$ is hydrogen, n is 1; $R^{10}$ is —N(R$_B$)SO$_2$X wherein R$_B$ is hydrogen or alkyl and X is alkyl; A is a monocyclic ring selected from the group consisting of aryl and heteroaryl; and $R^5$, $R^6$, $R^7$, and $R^8$ are each independently selected fromt the group consisting of hydrogen, alkyl, alkenyl, alkynyl, cyano, halo, nitro, —OR$_A$, —OC(O)R$_A$, —OC(O)OR$_A$, —OC(O)NR$_A$R$_B$, —OS(O)$_2$R$_A$, —SR$_A$, —S(O)R$_A$, —S(O)$_2$R$_A$, —S(O)$_2$NR$_A$R$_B$, —NR$_A$R$_B$, —N(R$_C$)C(O)R$_A$, —C(O)R$_A$, —C(O)OR$_A$, —C(O)NR$_A$R$_B$, haloalkyl, and -alkylOR$_A$, wherein R$_A$, R$_B$ and R$_C$ are each independently selected from the group consisting of hydrogen and alkyl.

Another embodiment of the present invention provides a compound of formula (I) wherein $R^2$ is $C_1$-$C_6$ alkyl, $C_3$-$C_6$ alkenyl, —($C_1$-$C_3$ alkyl)-aryl or —($C_3$ alkenyl)-aryl wherein each of the aryl moieties of —($C_1$-$C_3$ alkyl)-aryl and —($C_3$ alkenyl)-aryl is independently unsubstituted or substituted with the substituents as defined in formula (I); $R^9$ is OR$_A$ wherein R$_A$ is hydrogen; $R^1$ is —N(R$_B$)L$^1$C(O)Y wherein L$^1$ is a bond or $C_1$-$C_2$ alkyl, R$_B$ is selected from the group consisting of hydrogen, —OH, -methyl-aryl and alkoxy, and Y is selected from the group consisting of $C_1$-$C_6$ alkyl, haloalkyl, aryl, —NR$_A$R$_B$, —O($C_1$-$C_6$ alkyl), —O(-methyl-aryl), —O—($C_1$-$C_6$ alkyl)-O($C_1$-$C_6$ alkyl), —CH$_2$—N(H)C(O)R$_A$, —CH$_2$—N(H)C(O)OR$_A$ and —CH$_2$—NR$_A$R$_B$, wherein R$_A$ and R$_B$ are independently selected from the group consisting of hydrogen and $C_1$-$C_6$ alkyl and wherein the aryl and the aryl moieties of -methyl-aryl and —O(-methyl-aryl) are independently unsubstituted or substituted with substituents as defined in formula (I); $R^{11}$ is hydrogen, n is 1; $R^{10}$ is —N(R$_B$)SO$_2$X wherein R$_B$ is hydrogen or $C_1$-$C_6$ alkyl and X is $C_1$-$C_6$ alkyl; A is a monocyclic ring selected from the group consisting of aryl and heteroaryl; and $R^5$, $R^6$, $R^7$, and $R^8$ are each independently selected from the group consisting of hydrogen and $C_1$-$C_6$ alkyl.

Another embodiment of the present invention provides a compound of formula (I) wherein $R^2$ is selected from the group consisting of propyl, butyl, isobutyl, 3,3-dimethylbutyl, 3-methylbutyl, allyl, 2-methylprop-2-enyl, 3-methylbut-2-enyl, phenylmethyl and 3-phenylprop-2-enyl; wherein the phenyl moieties of phenylmethyl and 3-phenylprop-2-enyl are independently unsubstituted or substituted with the substituents as defined in formula (I); $R^9$ is OR$_A$ wherein R$_A$ is hydrogen; $R^1$ is —N(R$_B$)L$^1$(O)Y wherein L$^1$ is a bond or methyl, R$_B$ is selected from the group consisting of hydrogen, —OH, -benzyl and methoxy, and Y is selected from the group consisting of methyl, chloromethyl, phenyl, —NH$_2$, —N(H)(tert-butyl), —O(methyl), —O(ethyl), —O(benzyl), —O-ethyl-O(methyl), —CH$_2$N(H)C(O)(methyl), —CH$_2$N(H)C(O)(—O-tert-butyl) and —CH$_2$—NH$_2$, wherein the phenyl and the phenyl moieties of benzyl and —O(benzyl) are each independently unsubstituted or substituted with substituents as defined in formula (I); $R^{11}$ is hydrogen; n is 1; $R^{10}$ is —N(R$_B$)SO$_2$X wherein R$_B$ is hydrogen and X is methyl; A is phenyl; and $R^5$, $R^6$, $R^7$ and $R^8$ are hydrogen.

Another embodiment of the present invention provides a compound of formula (I) wherein $R^2$ is selected from the group consisting of alkyl, alkenyl -alkyl-R$_a$ and -alkenyl-R$_a$ wherein R$_a$ is aryl, unsubstituted or substituted with substituents as defined in formula (I); $R^9$ is OR$_A$ wherein R$_A$ is hydrogen; $R^1$ is —N(R$_B$)S(O)$_2$Z wherein R$_B$ is hydrogen or alkyl, and Z is selected from the group consisting of R$_A$, -alkyl-NR$_A$R$_B$, -alkyl-OR$_A$-alkyl-N(R$_C$)-alkyl-NR$_A$R$_B$ and -alkyl-N(R$_C$)C(O)X wherein R$_A$, R$_B$, R$_C$ and X are as defined in formula (I); $R^{11}$ is hydrogen, n is 1; $R^{10}$ is —N(R$_B$)SO$_2$X wherein R$_B$ is hydrogen or alkyl and X is alkyl; A is a monocyclic ring selected from the group consisting of aryl and heteroaryl; and $R^5$, $R^6$, $R^7$, and $R^8$ are each independently selected fromt the group consisting of hydrogen, alkyl, alkenyl, alkynyl, cyano, halo, nitro, —OR$_A$, —OC(O)R$_A$, —OC(O)OR$_A$, —OC(O)NR$_A$R$_B$, —OS(O)$_2$R$_A$, —SR$_A$, —S(O)R$_A$, —S(O)$_2$R$_A$, —S(O)$_2$NR$_A$R$_B$, —NR$_A$R$_B$, —N(R$_C$)C(O)R$_A$, —C(O)R$_A$, —C(O)OR$_A$, —C(O)NR$_A$R$_B$, haloalkyl, and -alkylOR$_A$, wherein R$_A$, R$_B$ and R$_C$ are each independently selected from the group consisting of hydrogen and alkyl.

Another embodiment of the present invention provides a compound of formula (I) wherein $R^2$ is $C_1$-$C_6$ alkyl, $C_3$-$C_6$ alkenyl, —($C_1$-$C_3$ alkyl)-aryl or —($C_3$ alkenyl)-aryl wherein each of the aryl moieties of —($C_1$-$C_3$ alkyl)-aryl and —($C_3$ alkenyl)-aryl is independently unsubstituted or substituted with the substituents as defined in formula (I); $R^9$ is OR$_A$ wherein $R_A$ is hydrogen; $R_1$ is —N(H)S(O)$_2$Z wherein Z is selected from the group consisting of $C_1$-$C_6$ alkyl, aryl, —($C_1$-$C_2$ alkyl)-heterocycle, —($C_1$-$C_2$ alkyl)-O($C_1$-$C_6$ alkyl), —($C_1$-$C_6$ alkyl)-N($C_1$-$C_6$ alkyl)-($C_1$-$C_6$ alkyl), —($C_1$-$C_6$ alkyl)-N($C_1$-$C_6$ alkyl)-N(H)($C_1$-$C_6$ alkyl), —($C_1$-$C_6$ alkyl)-N($C_1$-$C_6$ alkyl)C(O)($C_1$-$C_6$ alkyl), and —($C_1$-$C_2$ alkyl)-NR$_A$R$_B$, wherein R$_A$ is hydrogen, $C_1$-$C_2$ alkyl or —($C_1$-$C_2$ alkyl)-aryl, and R$_B$ is $C_1$-$C_6$ alkyl, —($C_1$-$C_2$ alkyl)-aryl, —($C_1$-$C_2$ alkyl)-heterocycle, alkoxy or alkoxyalkyl; and the aryl, the heterocycle moiety of —($C_1$-$C_2$ alkyl)-heterocycle and the aryl moieties of —($C_1$-$C_2$ alkyl)-aryl are independently unsubstituted or substituted with substituents as defined in formula (I); $R^{11}$ is hydrogen, n is 1; $R^{10}$ is —N(R$_B$)SO$_2$X wherein R$_B$ is hydrogen or $C_1$-$C_6$ alkyl and X is $C_1$-$C_6$ alkyl; A is a monocyclic ring selected from the group consisting of aryl and heteroaryl; and $R^5$, $R^6$, $R^7$, and $R^8$ are each independently selected from the group consisting of hydrogen and $C_1$-$C_6$ alkyl.

Another embodiment of the present invention provides a compound of formula (I) wherein $R^2$ is selected from the group consisting of propyl, butyl, isobutyl, 3,3-dimethylbutyl, 3-methylbutyl, allyl, 2-methylprop-2-enyl, 3-methylbut-2-enyl, phenylmethyl and 3-phenylprop-2-enyl; wherein the phenyl moieties of phenylmethyl and 3-phenylprop-2-enyl are independently unsubstituted or substituted with the substituents as defined in formula (I); $R^9$ is OR$_A$ wherein R$_A$ is hydrogen; $R_1$ is —N(H)S(O)$_2$Z wherein Z is selected from the group consisting of methyl, phenyl, morpholinylmethyl-, morpholinylethyl-, -ethyl-O-methyl, -ethyl-N(methyl)-ethyl-N(H)(methyl), -ethyl-N(methyl)C(O)(methyl), and -ethyl-NR$_A$R$_B$, wherein R$_A$ is hydrogen, methyl, ethyl or benzyl, and R$_B$ is methyl, ethyl, benzyl, (1,3-dioxolan-2-yl)methyl-, methoxy, methoxyethyl or 2,2-dimethoxyethyl; wherein the phenyl and the phenyl moiety of benzyl are independently unsubstituted or substituted with substituents as defined in formula (I); $R^{11}$ is hydrogen; n is 1; $R^{10}$ is —N(R$_B$)SO$_2$X wherein R$_B$ is hydrogen and X is methyl; A is phenyl; and $R^5$, $R^6$, $R^7$ and $R^8$ are hydrogen.

Another aspect of the present invention provides a compound of formula (II)

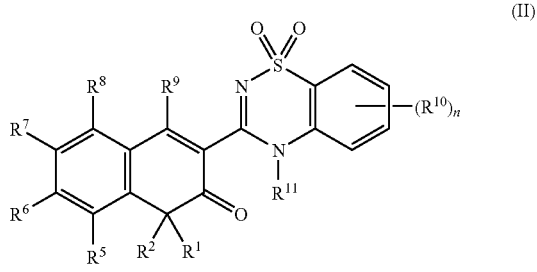

(II)

or a pharmaceutically acceptable salt form, stereoisomer, tautomer, pro drug, salt of a pro drug, or combination thereof, wherein:

$R^1$ is —OR$_A$, —O-alkyl-C(O)Y, —NR$_A$R$_B$, —N(R$_C$)(—N(R$_C$)(R$_A$)), —N(R$_B$)L$^1$(O)Y or —N(R$_B$)S(O)$_2$Z;

X at each occurrence, is independently selected from the group consisting of R$_A$, —OR$_A$ and —NR$_A$R$_B$;

L$^1$ is a bond or lower alkyl;

Y at each occurrence is independently selected from the group consisting of R$_A$, —OR$_A$, —NR$_A$R$_B$, —O-alkyl-OR$_A$, —O-alkyl-NR$_A$R$_B$, —N(R$_C$)-alkyl-NR$_A$R$_B$, —(CR$^3$R$^4$)—N(R$_C$)C(O)X and —(C$^3$R$^4$)—NR$_A$R$_B$;

Z at each occurrence is independently selected from the group consisting of R$_A$, —OR$_A$, —NR$_A$R$_B$, -alkyl-OR$_A$, -alkyl-NR$_A$R$_B$, -alkyl-N(R$_C$)C(O)X, -alkyl-O-alkyl-OR$_A$, -alkyl-O-alkyl-NR$_A$R$_B$ and -alkyl-N(R$_C$)-alkyl-NR$_A$R$_B$;

$R^3$ and $R^4$, at each occurrence, are independently selected from the group consisting of hydrogen, alkyl, alkenyl and arylalkyl wherein the aryl moiety of the arylalkyl is substituted with 0, 1, 2, 3, 4 or 5 substituents independently selected from the group consisting of alkyl, alkenyl, alkynyl, formyl, halo, nitro, cyano, alkoxy, —OH, —OC(O)(alkyl), —SH, —S(alkyl), —S(O)alkyl, —S(O)$_2$(alkyl), —NH$_2$, —N(H)(alkyl), —N(alkyl)$_2$, —C(O)alkyl, —C(O)OH, —C(O)(—Oalkyl), —C(O)NH$_2$, —C(O)N(H)(alkyl), —C(O)N(alkyl)$_2$ and haloalkyl;

R$_A$ at each occurrence, is independently selected from the group consisting of hydrogen, alkyl, alkenyl, haloalkyl, haloalkenyl, R$_a$ and -alkylR$_a$;

R$_B$ at each occurrence, is independently selected from the group consisting of hydrogen, alkyl, haloalkyl, R$_a$, -alkylR$_a$, —OH, alkoxy, hydroxyalkyl, alkoxyalkyl, —OR$_a$, and —O-alkylR$_a$;

R$_C$ at each occurrence, is independently selected from the group consisting of hydrogen and lower alkyl;

R$_a$ at each occurrence, is independently selected from the group consisting of cycloalkyl, cycloalkenyl, heterocycle, aryl and heteroaryl; wherein each R$_a$ at each occurrence is independently substituted with 0, 1, 2, 3, 4 or 5 substituents independently selected from the group consisting of alkyl, alkenyl, alkynyl, formyl, halo, nitro, cyano, alkoxy, —OH, —O-alkyl-R$_a$, —OC(O)(alkyl), —SH, —S(alkyl), —S(O)alkyl, —S(O)$_2$(alkyl), —NH$_2$, —N(H)(alkyl), —N(alkyl)$_2$, —C(O)alkyl, —C(O)OH, —C(O)(—Oalkyl), —C(O)NH$_2$, —C(O)N(H)(alkyl), —C(O)N(alkyl)$_2$, haloalkyl, R$_b$ and -alkyl-R$_b$;

R$_b$ at each occurrence is independently selected from the group consisting of cycloalkyl, cycloalkenyl, heterocycle, aryl and heteroaryl; wherein each R$_b$ at each occurrence is independently substituted with 0, 1, 2, 3, 4 or 5 substituents independently selected from the group consisting of alkyl, alkenyl, alkynyl, formyl, halo, nitro, cyano, alkoxy, —OH, —OC(O)(alkyl), —SH, —S(alkyl), —S(O)alkyl, —S(O)$_2$(alkyl), —NH$_2$, —N(H)(alkyl), —N(alkyl)$_2$, —C(O)alkyl, —C(O)OH, —C(O)(—Oalkyl), —C(O)NH$_2$, —C(O)N(H)(alkyl), —C(O)N(alkyl)$_2$ and haloalkyl;

$R^2$ is selected from the group consisting of hydrogen, alkyl, alkenyl, alkynyl, R$_a$, -alkyl-R$_a$, -alkenyl-R$_a$, -alkynyl-R$_a$, haloalkyl, hydroxyalkyl, formylalkyl, cyanoalkyl, -alkyl-OR$_A$, and -alkyl-NR$_A$R$_B$;

$R^5$, $R^6$, $R^7$ and $R^8$ are each independently selected from the group consisting of hydrogen, alkyl, alkenyl, alkynyl, cyano, formyl, halo, nitro, —OR$_A$, —OC(O)R$_A$, —OC(O)OR$_A$, —OC(O)NR$_A$R$_B$, —OS(O)$_2$R$_A$, —SR$_A$, —S(O)R$_A$, —S(O)$_2$R$_A$, —S(O)$_2$(OR$_A$), —S(O)$_2$NR$_A$R$_B$, —NR$_A$R$_B$, —N(R$_C$)C(O)R$_A$, —N(R$_C$)C(O)NR$_A$R$_B$, —N(R$_C$)C(O)OR$_A$, —N(R$_C$)S(O)$_2$R$_A$, —N(R$_C$)S(O)$_2$NR$_A$R$_B$, —N(R$_C$)S(O)$_2$N(R$_C$)C(O)OR$_A$, —C(O)R$_A$, —C(O)OR$_A$, —C(O)NR$_A$R$_B$, haloalkyl, cyanoalkyl, -alkylOR$_A$, -alkyl-OC(O)R$_A$, -alkyl-OC(O)OR$_A$, -alkyl-OC(O)NR$_A$R$_B$, -alkyl-OS(O)$_2$R$_A$, -alkyl-SR$_A$, -alkyl-S(O)R$_A$, -alkyl-S(O)$_2$R$_A$, -alkyl-S(O)$_2$(OR$_A$), -alkyl-S(O)$_2$NR$_A$R$_B$, -alkyl-NR$_A$R$_B$, -alkyl-N(R$_C$)C(O)R$_A$, -alkyl-N(R$_C$)C(O)NR$_A$R$_B$, -alkyl-N(R$_C$)C(O)OR$_A$, -alkyl-N(R$_C$)S(O)$_2$R$_A$, -alkyl-N(R$_C$)S(O)$_2$NR$_A$R$_B$, -alkyl-N(R$_C$)S(O)$_2$N(R$_C$)C(O)OR$_A$, -alkyl-C(O)R$_A$, -alkyl-C(O)(OR$_A$) and -alkyl-C(O)NR$_A$R$_B$;

$R^9$ is —OR$_A$, —SR$_A$, —NR$_A$R$_B$, —N(R$_C$)C(O)R$_A$, —N(R$_C$)C(O)OR$_A$, —N(R$_C$)S(O)$_2$R$_A$ or —N(R$_C$)S(O)$_2$NR$_A$R$_B$;

n is 0, 1, 2, 3 or 4;

$R^{10}$ at each occurrence is independently selected from the group consisting of alkyl, alkenyl, alkynyl, cyano, formyl, nitro, halo, $R_a$, —$OR_A$, —$OC(O)X$, —$OS(O)_2R_A$, —O-alkyl-$G^1$, —$SR_A$, —$S(O)R_A$, —$S(O)_2X$, —$NR_AR_B$, —$N(R_B)C(O)X$, —$N(R_B)C(O)(-alkyl-G^1)$, —$N(R_B)S(O)_2X$, —$N(R_B)S(O)_2(-alkyl-G^1)$, —$C(O)X$, —$C(O)N(R_B)(-alkyl-G^1)$, haloalkyl, cyanoalkyl, nitroalkyl, -alkyl-$R_a$, —N(-alkyl-C(O)X)(S(O)_2X) and -alkyl-$G^1$;

$G^1$ is selected from the group consisting of —$OR_A$, —$NR_AR_B$, —$N(R_C)(-NR_AR_B)$, —$N(R_C)S(O)_2X$, —$N(R_C)C(O)X$, —$C(O)X$, —$OC(O)X$ and —$S(O)_2X$; and $R^{11}$ is selected from the group consisting of hydrogen, alkyl, alkenyl and arylalkyl; wherein the aryl moiety of the arylalkyl is substituted with 0, 1, 2, 3, 4 or 5 substituents selected from the group consisting of alkyl, alkenyl, alkynyl, formyl, halo, nitro, cyano, haloalkyl, —OH, alkoxy, —OC(O)(alkyl), —$NH_2$, —N(H)(alkyl), —N(alkyl)$_2$, —C(O)OH, —C(O)(—Oalkyl), —C(O)alkyl, —C(O)$NH_2$, —C(O)N(H)(alkyl) and —C(O)N(alkyl)$_2$.

The embodiments, specific and more specific embodiments of the variables: $R^1, R^2, R^5, R^6, R^7, R^8, R^9, R^{10}, R^{11}$ and n in formula (II) are as defined in formula (I). It is understood that the present invention provides compounds of formula (II) that encompasses all combinations of the embodiments, specific and more specific embodiments of the variables: $R^1, R^2, R^5, R^6, R^7, R^8, R^9, R^{10}, R^{11}$ and n described hereinabove.

Accordingly, one embodiment of the invention provides a compound of formula (II) wherein $R^9$ is $OR_A$ and $R_A$ is hydrogen and $R^1, R^2, R^5, R^6, R^7, R^8, R^{10}, R^{11}$ and n are as defined in formula (II). Another embodiment of the present invention provides a compound of formula (II) wherein $R^2$ is selected from the group consisting of alkyl, alkenyl, -alkyl-$R_a$, and -alkenyl-$R_a$; $R^9$ is $OR_A$ wherein $R_A$ is hydrogen; and $R^1, R^5, R^6, R^7, R^8, R^{10}, R^{11}, R_a$, and n are as defined in formula (II).

Another embodiment of the present invention provides a compound of formula (II) wherein $R^2$ is selected from the group consisting of alkyl, alkenyl, -alkyl-$R_a$, and -alkenyl-$R_a$; $R^9$ is $OR_A$ wherein $R_A$ is hydrogen; $R^{11}$ is hydrogen; and $R^1, R^5, R^6, R^7, R^8, R^{10}, R_a$, and n are as defined in formula (II).

Another embodiment of the present invention provides a compound of formula (II) wherein $R^2$ is selected from the group consisting of alkyl, alkenyl -alkyl-$R_a$ and -alkenyl-$R_a$; $R^9$ is $OR_A$ wherein $R_A$ is hydrogen; $R^{11}$ is hydrogen; $R^1$ is —$OR_A$ wherein $R_A$ is as defined in formula (II); and $R_a, R^5, R^6, R^7, R^8, R^{10}$, and n are as defined in formula (II).

Another embodiment of the present invention provides a compound of formula (II) wherein $R^2$ is selected from the group consisting of alkyl, alkenyl -alkyl-$R_a$ and -alkenyl-$R_a$; $R^9$ is $OR_A$ wherein $R_A$ is hydrogen; $R^{11}$ is hydrogen; $R^1$ is —$NR_AR_B$ wherein $R_A$ and $R_B$ are as defined in formula (II); and $R_a, R^5, R^6, R^7, R^8, R^{10}$, and n are as defined in formula (II).

Another embodiment of the present invention provides a compound of formula (II) wherein $R^2$ is selected from the group consisting of alkyl, alkenyl -alkyl-$R_a$ and -alkenyl-$R_a$; $R^9$ is $OR_A$ wherein $R_A$ is hydrogen; $R^{11}$ is hydrogen; $R^1$ is —O-alkyl-C(O)Y; and Y, $R_a, R^5, R^6, R^7, R^8, R^{10}$, and n are as defined in formula (II).

Another embodiment of the present invention provides a compound of formula (II) wherein $R^2$ is selected from the group consisting of alkyl, alkenyl -alkyl-$R_a$ and -alkenyl-$R_a$; $R^9$ is $OR_A$ wherein $R_A$ is hydrogen; $R^{11}$ is hydrogen; $R^1$ is —$N(R_B)L^1(O)Y$; and $L^1, R_B, Y, R_a, R^5, R^6, R^7, R^8, R^{10}$ and n are as defined in formula (II).

Another embodiment of the present invention provides a compound of formula (II) wherein $R^2$ is selected from the group consisting of alkyl, alkenyl -alkyl-$R_a$ and -alkenyl-$R_a$;

$R^9$ is $OR_A$ wherein $R_A$ is hydrogen; $R^{11}$ is hydrogen; $R^1$ is —$N(R_B)L^1S(O)_2 Z$; and $R_B, Z, R_a, R^5, R^6, R^7, R^8, R^{10}$ and n are as defined in formula (II).

Another embodiment of the present invention provides a compound of formula (II) wherein $R^2$ is selected from the group consisting of alkyl, alkenyl -alkyl-$R_a$ and -alkenyl-$R_a$; $R^9$ is $OR_A$ wherein $R_A$ is hydrogen; $R^{11}$ is hydrogen; $R^1$ is —$NR_AR_B$ wherein $R_A$ is selected from the group consisting of hydrogen and alkyl, and $R_B$ is selected from the group consisting of hydrogen, alkyl, -alkyl$R_a$, —OH and alkoxy; and $R_a, R^5, R^6, R^7, R^8, R^{10}$ and n are as defined in formula (II).

Another embodiment of the present invention provides a compound of formula (II) wherein $R^2$ is selected from the group consisting of alkyl, alkenyl -alkyl-$R_a$ and -alkenyl-$R_a$ wherein $R_a$ is aryl, unsubstituted or substituted with substituents as defined in formula (II); $R^9$ is $OR_A$ wherein $R_A$ is hydrogen, $R^1$ is —$NR_AR_B$ wherein $R_A$ is selected from the group consisting of hydrogen and alkyl, and $R_B$ is selected from the group consisting of hydrogen, alkyl, -alkyl$R_a$, —OH and alkoxy, wherein $R_a$ is selected from the group consisting of aryl, $C_3$-$C_6$ cycloalkyl and heteroaryl wherein each $R_a$ is independently unsubstituted or substituted with substituents as defined in formula (II); $R^{11}$ is hydrogen; and $R^5, R^6, R^7, R^8, R^{10}$ and n are as defined in formula (II).

Another embodiment of the present invention provides a compound of formula (II) wherein $R^2$ is selected from the group consisting of alkyl, alkenyl -alkyl-$R_a$ and -alkenyl-$R_a$ wherein $R_a$ is aryl, unsubstituted or substituted with substituents as defined in formula (II); $R^9$ is $OR_A$ wherein $R_A$ is hydrogen; $R^1$ is —$NR_AR_B$ wherein $R_A$ is selected from the group consisting of hydrogen and alkyl, and $R_B$ is selected from the group consisting of hydrogen, alkyl, -alkyl$R_a$, —OH and alkoxy wherein $R_a$ is selected from the group consisting of aryl, $C_3$-$C_6$ cycloalkyl and heteroaryl wherein each $R_a$ is independently unsubstituted or substituted with substituents as defined in formula (II); $R^{11}$ is hydrogen, n is 1; $R^{10}$ is —$N(R_B)SO_2X$ or —N(-alkyl-C(O)X)(S(O)_2X) and $R^5, R^6, R^7, R^8, R_B$, and X are as defined in formula (II).

Another embodiment of the present invention provides a compound of formula (II) wherein $R^2$ is selected from the group consisting of alkyl, alkenyl -alkyl-$R_a$ and -alkenyl-$R_a$ wherein $R_a$ is aryl, unsubstituted or substituted with substituents as defined in formula (II); $R^9$ is $OR_A$ wherein $R_A$ is hydrogen; $R^1$ is —$NR_AR_B$ wherein $R_A$ is selected from the group consisting of hydrogen and alkyl, and $R_B$ is selected from the group consisting of hydrogen, alkyl, -alkyl$R_a$, —OH and alkoxy wherein $R_a$ is selected from the group consisting of aryl, $C_3$-$C_6$ cycloalkyl and heteroaryl wherein each $R_a$ is independently unsubstituted or substituted with substituents as defined in formula (II); $R^{11}$ is hydrogen, n is 1; $R^{10}$ is —$N(R_B)SO_2X$; and $R^5, R^6, R^7, R^8, R_B$ and X are as defined in formula (II).

Another embodiment of the present invention provides a compound of formula (II) wherein $R^2$ is selected from the group consisting of alkyl, alkenyl -alkyl-$R_a$ and -alkenyl-$R_a$ wherein $R_a$ is aryl, unsubstituted or substituted with substituents as defined in formula (II); $R^9$ is $OR_A$ wherein $R_A$ is hydrogen; $R^1$ is —$NR_AR_B$ wherein $R_A$ is selected from the group consisting of hydrogen and alkyl, and $R_B$ is selected from the group consisting of hydrogen, alkyl, -alkyl$R_a$, —OH and alkoxy wherein $R_a$ is selected from the group consisting of aryl, $C_3$-$C_6$ cycloalkyl and heteroaryl and each $R_a$ is independently unsubstituted or substituted with substituents as defined in formula (II); $R^{11}$ is hydrogen, n is 1; $R^{10}$ is —N(-alkyl-C(O)X)(S(O)_2X); and $R^5, R^6, R^7, R^8$, and X are as defined in formula (II).

Another embodiment of the present invention provides a compound of formula (II) wherein $R^2$ is selected from the group consisting of alkyl, alkenyl -alkyl-$R_a$ and -alkenyl-$R_a$ wherein $R_a$ is aryl, unsubstituted or substituted with substituents as defined in formula (II); $R^9$ is $OR_A$ wherein $R_A$ is hydrogen; $R^1$ is —$NR_AR_B$ wherein $R_A$ is selected from the group consisting of hydrogen and alkyl, and $R_B$ is selected from the group consisting of hydrogen, alkyl, -alkyl$R_a$, —OH and alkoxy wherein $R_a$ is selected from the group consisting of aryl, $C_3$-$C_6$ cycloalkyl and heteroaryl and each $R_a$ is independently unsubstituted or substituted with substituents as defined in formula (II); $R^{11}$ is hydrogen, n is 1; $R^{10}$ is —$N(R_B)SO_2X$ wherein $R_B$ is hydrogen or alkyl and X is alkyl; and $R^5$, $R^6$, $R^7$, and $R^8$ are as defined in formula (II).

Another embodiment of the present invention provides a compound of formula (II) wherein $R^2$ is selected from the group consisting of alkyl, alkenyl -alkyl-$R_a$ and -alkenyl-$R_a$ wherein $R_a$ is aryl, unsubstituted or substituted with substituents as defined in formula (II); $R^9$ is $OR_A$ wherein $R_A$ is hydrogen; $R^1$ is —$NR_AR_B$ wherein $R_A$ is selected from the group consisting of hydrogen and alkyl, and $R_B$ is selected from the group consisting of hydrogen, alkyl, -alkyl$R_a$, —OH and alkoxy wherein $R_a$ is selected from the group consisting of aryl, $C_3$-$C_6$ cycloalkyl and heteroaryl and each $R_a$ is independently unsubstituted or substituted with substituents as defined in formula (II); $R^{11}$ is hydrogen, n is 1; $R^{10}$ is —$N(R_B)SO_2X$ wherein $R_B$ is hydrogen or alkyl and X is alkyl; and $R^5$, $R^6$, $R^7$, and $R^8$ are each independently selected from the group consisting of hydrogen, alkyl, alkenyl, alkynyl, cyano, halo, nitro, —$OR_A$, —$OC(O)R_A$, —$OC(O)OR_A$, —$OC(O)NR_AR_B$, —$OS(O)_2R_A$, —$SR_A$, —$S(O)R_A$, —$S(O)_2R_A$, —$S(O)_2NR_AR_B$, —$NR_AR_B$, —$N(R_C)C(O)R_A$, —$C(O)R_A$, —$C(O)OR_A$, —$C(O)NR_AR_B$, haloalkyl, and -alkyl$OR_A$, wherein $R_A$, $R_B$ are each independently selected from the group consisting of hydrogen and alkyl, and $R_C$ is hydrogen or lower alkyl.

Another embodiment of the present invention provides a compound of formula (II) wherein $R^2$ is $C_1$-$C_6$ alkyl, $C_3$-$C_6$ alkenyl, —($C_1$-$C_3$ alkyl)-aryl or —($C_3$ alkenyl)-aryl wherein each of the aryl moieties of —($C_1$-$C_3$ alkyl)-aryl and —($C_3$ alkenyl)-aryl is independently unsubstituted or substituted with the substituents as defined in formula (I); $R^9$ is $OR_A$ wherein $R_A$ is hydrogen; $R^1$ is —$NR_AR_B$ wherein $R_A$ is selected from the group consisting of hydrogen and methyl, and $R_B$ is selected from the group consisting of hydrogen, $C_1$-$C_6$ alkyl, —($C_1$-$C_3$ alkyl)-$R_a$, —OH, and $C_1$-$C_6$ alkoxy, wherein $R_a$ is selected from the group consisting of aryl, $C_3$-$C_6$ cycloalkyl and heteroaryl and each $R_a$ is independently unsubstituted or substituted with substituents as defined in formula (II); $R^{11}$ is hydrogen, n is 1; $R^{10}$ is —$N(R_B)SO_2X$ wherein $R_B$ is hydrogen or $C_1$-$C_6$ alkyl and X is $C_1$-$C_6$ alkyl; and $R^5$, $R^6$, $R^7$, and $R^8$ are each independently selected from the group consisting of hydrogen and $C_1$-$C_6$ alkyl.

Another embodiment of the present invention provides a compound of formula (II) wherein $R^2$ is selected from the group consisting of propyl, butyl, isobutyl, 3,3-dimethylbutyl, 3-methylbutyl, allyl, 2-methylprop-2-enyl, 3-methylbut-2-enyl, phenylmethyl and 3-phenylprop-2-enyl; wherein the phenyl moieties of phenylmethyl and 3-phenylprop-2-enyl are independently unsubstituted or substituted with the substituents as defined in formula (II); $R^9$ is $OR_A$ wherein $R_A$ is hydrogen; $R^1$ is —$NR_AR_B$ wherein $R_A$ is selected from the group consisting of hydrogen and methyl, and $R_B$ is selected from the group consisting of hydrogen, isobutyl, -methyl-$R_a$, —OH, methoxy, ethoxy and tert-butoxy, wherein $R_a$ is selected from the group consisting of phenyl, naphthyl, cyclopropyl, furanyl, thienyl, thiazolyl, pyridyl, benzofuranyl, benzothienyl and imidazo[1,5,a]pyrid-3-yl and each $R_a$ is independently unsubstituted or substituted with substituents as defined in formula (II); $R^{11}$ is hydrogen; n is 1; $R^{10}$ is —$N(R_B)SO_2X$ wherein $R_B$ is hydrogen and X is methyl; and $R^5$, $R^6$, $R^7$ and $R^8$ are hydrogen.

Another embodiment of the present invention provides a compound of formula (II) wherein $R^2$ is selected from the group consisting of alkyl, alkenyl -alkyl-$R_a$ and -alkenyl-$R_a$ wherein $R_a$ is aryl, unsubstituted or substituted with substituents as defined in formula (II); $R^9$ is $OR_A$ wherein $R_A$ is hydrogen; $R^1$ is —$OR_A$ wherein $R_A$ is selected from the group consisting of hydrogen, alkyl and -alkyl-$R_a$, and $R_a$ is as defined in formula (II); $R^{11}$ is hydrogen, n is 1; $R^{10}$ is —$N(R_B)SO_2X$ wherein $R_B$ is hydrogen or alkyl and X is alkyl; and $R^5$, $R^6$, $R^7$, and $R^8$ are each independently selected fromt the group consisting of hydrogen, alkyl, alkenyl, alkynyl, cyano, halo, nitro, —$OR_A$, —$OC(O)R_A$, —$OC(O)OR_A$, —$OC(O)NR_AR_B$, —$OS(O)_2R_A$, —$SR_A$, —$S(O)R_A$, —$S(O)_2R_A$, —$S(O)_2NR_AR_B$, —$NR_AR_B$, —$N(R_C)C(O)R_A$, —$C(O)R_A$, —$C(O)OR_A$, —$C(O)NR_AR_B$, haloalkyl, and -alkyl$OR_A$, wherein $R_A$, $R_B$ are each independently selected from the group consisting of hydrogen and alkyl, and $R_C$ is hydrogen or lower alkyl.

Another embodiment of the present invention provides a compound of formula (II) wherein $R^2$ is $C_1$-$C_6$ alkyl, $C_3$-$C_6$ alkenyl, —($C_1$-$C_3$ alkyl)-aryl or —($C_3$ alkenyl)-aryl wherein each of the aryl moieties of —($C_1$-$C_3$ alkyl)-aryl and —($C_3$ alkenyl)-aryl is independently unsubstituted or substituted with the substituents as defined in formula (II); $R^9$ is $OR_A$ wherein $R_A$ is hydrogen; $R^1$ is —$OR_A$ wherein $R_A$ is selected from the group consisting of hydrogen, $C_1$-$C_6$ alkyl and -methyl-$R_a$; wherein $R_a$ is aryl, unsubstituted or substituted with substituents as defined in formula (II); $R^{11}$ is hydrogen, n is 1; $R^1$ is —$N(R_B)SO_2X$ wherein $R_B$ is hydrogen or $C_1$-$C_6$ alkyl and X is $C_1$-$C_6$ alkyl; and $R^5$, $R^6$, $R^7$, and $R^8$ are each independently selected from the group consisting of hydrogen and $C_1$-$C_6$ alkyl.

Another embodiment of the present invention provides a compound of formula (II) wherein $R^2$ is selected from the group consisting of propyl, butyl, isobutyl, 3,3-dimethylbutyl, 3-methylbutyl, allyl, 2-methylprop-2-enyl, 3-methylbut-2-enyl, phenylmethyl and 3-phenylprop-2-enyl; wherein the phenyl moieties of phenylmethyl and 3-phenylprop-2-enyl are independently unsubstituted or substituted with the substituents as defined in formula (II); $R^9$ is $OR_A$ wherein $R_A$ is hydrogen; $R^1$ is —OH, —O-methyl, or —O-methyl-phenyl, wherein the phenyl moiety of —O-methyl-phenyl is unsubstituted or substituted with substituents as defined in formula (II); $R^{11}$ is hydrogen; n is 1; $R^{10}$ is —$N(R_B)SO_2X$ wherein $R_B$ is hydrogen and X is methyl; and $R^5$, $R^6$, $R^7$ and $R^8$ are hydrogen.

Another embodiment of the present invention provides a compound of formula (II) wherein $R^2$ is selected from the group consisting of alkyl, alkenyl -alkyl-$R_a$ and -alkenyl-$R_a$ wherein $R_a$ is aryl, unsubstituted or substituted with substituents as defined in formula (II); $R^9$ is $OR_A$ wherein $R_A$ is hydrogen; $R^1$ is —O-alkyl-C(O)Y wherein Y is selected from the group consisting of —$OR_A$ and —$NR_AR_B$, and wherein $R_A$ and $R_B$ are each independently selected from the group consisting of hydrogen and alkyl; $R^{11}$ is hydrogen, n is 1; $R^{10}$ is —$N(R_B)SO_2X$ wherein $R_B$ is hydrogen or alkyl and X is alkyl; and $R^5$, $R^6$, $R^7$, and $R^8$ are each independently selected fromt the group consisting of hydrogen, alkyl, alkenyl, alkynyl, cyano, halo, nitro, —$OR_A$, —$OC(O)R_A$, —$OC(O)OR_A$, —$OC(O)NR_AR_B$, —$OS(O)_2R_A$, —$SR_A$, —$S(O)R_A$, —$S(O)_2R_A$, —$S(O)_2NR_AR_B$, —$NR_AR_B$, —$N(R_C)C(O)R_A$, —$C(O)R_A$, —$C(O)OR_A$, —$C(O)NR_AR_B$, haloalkyl, and -alkyl$OR_A$, wherein $R_A$, $R_B$ are each independently selected from the group consisting of hydrogen and alkyl, and $R_C$ is hydrogen or lower alkyl.

Another embodiment of the present invention provides a compound of formula (II) wherein $R^2$ is $C_1$-$C_6$ alkyl, $C_3$-$C_6$ alkenyl, —($C_1$-$C_3$ alkyl)-aryl or —($C_3$ alkenyl)-aryl wherein each of the aryl moieties of —($C_1$-$C_3$ alkyl)-aryl and —($C_3$ alkenyl)-aryl is independently unsubstituted or substituted with the substituents as defined in formula (II); $R^9$ is $OR_A$ wherein $R_A$ is hydrogen; $R^1$ is —O—($C_1$-$C_6$ alkyl)-C(O)$OR_A$ or —O—($C_1$-$C_6$ alkyl)-C(O)$NR_AR_B$, wherein $R_A$ and $R_B$ are each independently selected from the group consisting of hydrogen and $C_1$-$C_6$ alkyl; $R^{11}$ is hydrogen, n is 1; $R^{10}$ is —N($R_B$)$SO_2$X wherein $R_B$ is hydrogen or $C_1$-$C_6$ alkyl and X is $C_1$-$C_6$ alkyl; and $R^5$, $R^6$, $R^7$, and $R^8$ are each independently selected from the group consisting of hydrogen and $C_1$-$C_6$ alkyl.

Another embodiment of the present invention provides a compound of formula (II) wherein $R^2$ is selected from the group consisting of propyl, butyl, isobutyl, 3,3-dimethylbutyl, 3-methylbutyl, allyl, 2-methylprop-2-enyl, 3-methylbut-2-enyl, phenylmethyl and 3-phenylprop-2-enyl; wherein the phenyl moieties of phenylmethyl and 3-phenylprop-2-enyl are independently unsubstituted or substituted with the substituents as defined in formula (II); $R^9$ is $OR_A$ wherein $R_A$ is hydrogen; $R^1$ is —O-(methyl)-C(O)$OR_A$ or —O-(methyl)-C(O)$NR_AR_B$ wherein $R_A$ and $R_B$ are each independently selected from the group consisting of hydrogen and methyl; $R^{11}$ is hydrogen; n is 1; $R^{10}$ is —N($R_B$)$SO_2$X wherein $R_B$ is hydrogen and X is methyl; and $R^5$, $R^6$, $R^7$ and $R^8$ are hydrogen.

Another embodiment of the present invention provides a compound of formula (II) wherein $R^2$ is selected from the group consisting of alkyl, alkenyl -alkyl-$R_a$ and -alkenyl-$R_a$ wherein $R_a$ is aryl, unsubstituted or substituted with substituents as defined in formula (II); $R^9$ is $OR_A$ wherein $R_A$ is hydrogen; $R^1$ is —N($R_B$)$L^1$(O)Y wherein $L^1$ is a bond or alkyl, $R_B$ is selected from the group consisting of hydrogen, —OH, -alkyl$R_a$ and alkoxy wherein $R_a$ is unsubstituted or substituted aryl with substituents as defined in formula (II), and Y is selected from the group consisting of $R_A$, —$NR_AR_B$, $OR_A$, —O-alkyl-$OR_A$, $CR^3R^4$—N($R_C$)C(O)X, and —$CR^3R^4$—$NR_AR_B$ wherein $R_A$, $R_B$, $R_C$, $R^3$, $R^4$ and X are as defined in formula (II); $R^{11}$ is hydrogen, n is 1; $R^{10}$ is —N($R_B$)$SO_2$X wherein $R_B$ is hydrogen or alkyl and X is alkyl; and $R^5$, $R^6$, $R^7$, and $R^8$ are each independently selected fromt the group consisting of hydrogen, alkyl, alkenyl, alkynyl, cyano, halo, nitro, —$OR_A$, —OC(O)$R_A$, —OC(O)$OR_A$, —OC(O)$NR_AR_B$, —OS(O)$_2R_A$, —$SR_A$, —S(O)$R_A$, —S(O)$_2R_A$, —S(O)$_2NR_AR_B$, —$NR_AR_B$, —N($R_C$)C(O)$R_A$, —C(O)$R_A$, —C(O)$OR_A$, —C(O)$NR_AR_B$, haloalkyl, and -alkyl$OR_A$, wherein $R_A$, $R_B$ are each independently selected from the group consisting of hydrogen and alkyl, and $R_C$ is hydrogen or lower alkyl.

Another embodiment of the present invention provides a compound of formula (II) wherein $R^2$ is $C_1$-$C_6$ alkyl, $C_3$-$C_6$ alkenyl, —($C_1$-$C_3$ alkyl)-aryl or —($C_3$ alkenyl)-aryl wherein each of the aryl moieties of —($C_1$-$C_3$ alkyl)-aryl and —($C_3$ alkenyl)-aryl is independently unsubstituted or substituted with the substituents as defined in formula (II); $R^9$ is $OR_A$ wherein $R_A$ is hydrogen; $R^1$ is —N($R_B$)$L^1$(O)Y wherein $L^1$ is a bond or $C_1$-$C_2$ alkyl, $R_B$ is selected from the group consisting of hydrogen, —OH, -methyl-aryl and alkoxy, and Y is selected from the group consisting of $C_1$-$C_6$ alkyl, haloalkyl, aryl, —$NR_AR_B$, —O($C_1$-$C_6$ alkyl), —O(-methyl-aryl), —O—($C_1$-$C_6$ alkyl)-O($C_1$-$C_6$ alkyl), —$CH_2$—N(H)C(O)$R_A$, —$CH_2$—N(H)C(O)$OR_A$ and —$CH_2$—$NR_AR_B$, wherein $R_A$ and $R_B$ are independently selected from the group consisting of hydrogen and $C_1$-$C_6$ alkyl and wherein the aryl and the aryl moieties of -methyl-aryl and —O(-methyl-aryl) are independently unsubstituted or substituted with substituents as defined in formula (II); $R^1$ is hydrogen, n is 1; $R^{10}$ is —N($R_B$)$SO_2$X wherein $R_B$ is hydrogen or $C_1$-$C_6$ alkyl and X is $C_1$-$C_6$ alkyl; and $R^5$, $R^6$, $R^7$, and $R^8$ are each independently selected from the group consisting of hydrogen and $C_1$-$C_6$ alkyl.

Another embodiment of the present invention provides a compound of formula (II) wherein $R^2$ is selected from the group consisting of propyl, butyl, isobutyl, 3,3-dimethylbutyl, 3-methylbutyl, allyl, 2-methylprop-2-enyl, 3-methylbut-2-enyl, phenylmethyl and 3-phenylprop-2-enyl; wherein the phenyl moieties of phenylmethyl and 3-phenylprop-2-enyl are independently unsubstituted or substituted with the substituents as defined in formula (II); $R^9$ is $OR_A$ wherein $R_A$ is hydrogen; $R^1$ is —N($R_B$)$L^1$(O)Y wherein $L^1$ is a bond or methyl, $R_B$ is selected from the group consisting of hydrogen, —OH, -benzyl and methoxy, and Y is selected from the group consisting of methyl, chloromethyl, phenyl, —$NH_2$, —N(H)(tert-butyl), —O(methyl), —O(ethyl), —O(benzyl), —O-ethyl-O(methyl), —$CH_2$N(H)C(O)(methyl), —$CH_2$N(H)C(O)(—O-tert-butyl) and —$CH_2$—$NH_2$, wherein the phenyl and the phenyl moieties of benzyl and —O(benzyl) are each independently unsubstituted or substituted with substituents as defined in formula (II); $R^{11}$ is hydrogen; n is 1; $R^{10}$ is —N($R_B$)$SO_2$X wherein $R_B$ is hydrogen and X is methyl; and $R^5$, $R^6$, $R^7$ and $R^8$ are hydrogen.

Another embodiment of the present invention provides a compound of formula (II) wherein $R^2$ is selected from the group consisting of alkyl, alkenyl-alkyl-$R_a$ and -alkenyl-$R_a$ wherein $R_a$ is aryl, unsubstituted or substituted with substituents as defined in formula (II); $R^9$ is $OR_A$ wherein $R_A$ is hydrogen; $R_1$ is —N($R_B$)S(O)$_2$Z wherein $R_B$ is hydrogen or alkyl, and Z is selected from the group consisting of $R_A$, -alkyl-$NR_AR_B$, -alkyl-$OR_A$-alkyl-N($R_C$)-alkyl-$NR_AR_B$ and -alkyl-N($R_C$)C(O)X wherein $R_A$, $R_B$, $R_C$ and X are as defined in formula (II); $R^{11}$ is hydrogen, n is 1; $R^{10}$ is —N($R_B$)$SO_2$X wherein $R_B$ is hydrogen or alkyl and X is alkyl; and $R^5$, $R^6$, $R^7$, and $R^8$ are each independently selected fromt the group consisting of hydrogen, alkyl, alkenyl, alkynyl, cyano, halo, nitro, —$OR_A$, —OC(O)$R_A$, —OC(O)$OR_A$, —OC(O)$NR_AR_B$, —OS(O)$_2R_A$, —$SR_A$, —S(O)$R_A$, —S(O)$_2R_A$, —S(O)$_2NR_AR_B$, —$NR_AR_B$, —N($R_C$)C(O)$R_A$, —C(O)$R_A$, —C(O)$OR_A$, —C(O)$NR_AR_B$, haloalkyl, and -alkyl$OR_A$, wherein $R_A$, $R_B$ are each independently selected from the group consisting of hydrogen and alkyl, and $R_C$ is hydrogen or alkyl.

Another embodiment of the present invention provides a compound of formula (II) wherein $R^2$ is $C_1$-$C_6$ alkyl, $C_3$-$C_6$ alkenyl, —($C_1$-$C_3$ alkyl)-aryl or —($C_3$ alkenyl)-aryl wherein each of the aryl moieties of —($C_1$-$C_3$ alkyl)-aryl and —($C_3$ alkenyl)-aryl is independently unsubstituted or substituted with the substituents as defined in formula (II); $R^9$ is $OR_A$ wherein $R_A$ is hydrogen; $R^1$ is —N(H)S(O)$_2$Z wherein Z is selected from the group consisting of $C_1$-$C_6$ alkyl, aryl, —($C_1$-$C_2$ alkyl)-heterocycle, —($C_1$-$C_2$ alkyl)-O($C_1$-$C_6$ alkyl), —($C_1$-$C_6$ alkyl)-N($C_1$-$C_6$ alkyl)-($C_1$-$C_6$ alkyl)-N(H)($C_1$-$C_6$ alkyl), —($C_1$-$C_6$ alkyl)-N($C_1$-$C_6$ alkyl)C(O)($C_1$-$C_6$ alkyl), and —($C_1$-$C_2$ alkyl)-$NR_AR_B$, wherein $R_A$ is hydrogen, $C_1$-$C_2$ alkyl or —($C_1$-$C_2$ alkyl)-aryl, and $R_B$ is $C_1$-$C_6$ alkyl, —($C_1$-$C_2$ alkyl)-aryl, —($C_1$-$C_2$ alkyl)-heterocycle, alkoxy or alkoxyalkyl; and the aryl, the heterocycle moiety of —($C_1$-$C_2$ alkyl)-heterocycle and the aryl moieties of —($C_1$-$C_2$ alkyl)-aryl are independently unsubstituted or substituted with substituents as defined in formula (II); $R^{11}$ is hydrogen, n is 1; $R^{10}$ is —N($R_B$)$SO_2$X wherein $R_B$ is hydrogen or $C_1$-$C_6$ alkyl and X is $C_1$-$C_6$ alkyl; and $R^5$, $R^6$, $R^7$, and $R^8$ are each independently selected from the group consisting of hydrogen and $C_1$-$C_6$ alkyl.

Another embodiment of the present invention provides a compound of formula (II) wherein $R^2$ is selected from the group consisting of propyl, butyl, isobutyl, 3,3-dimethylbutyl, 3-methylbutyl, allyl, 2-methylprop-2-enyl, 3-methylbut-2-enyl, phenylmethyl and 3-phenylprop-2-enyl; wherein the phenyl moieties of phenylmethyl and 3-phenylprop-2-enyl are independently unsubstituted or substituted with the substituents as defined in formula (II); $R^9$ is $OR_A$ wherein $R_A$ is hydrogen; $R^1$ is —N(H)S(O)$_2$Z wherein Z is selected from the group consisting of methyl, phenyl, morpholinylmethyl-, morpholinylethyl-, -ethyl-O-methyl, -ethyl-N(methyl)-ethyl-N(H)(methyl), -ethyl-N(methyl)C(O)(methyl), and -ethyl-NR$_A$R$_B$, wherein R$_A$ is hydrogen, methyl, ethyl or benzyl, and R$_B$ is methyl, ethyl, benzyl, (1,3-dioxolan-2-yl)methyl-, methoxy, methoxyethyl or 2,2-dimethoxyethyl; wherein the phenyl and the phenyl moiety of benzyl are independently unsubstituted or substituted with substituents as defined in formula (II); $R^{11}$ is hydrogen; n is 1; $R^{10}$ is —N(R$_B$)SO$_2$X wherein R$_B$ is hydrogen and X is methyl; and $R^5$, $R^6$, $R^7$ and $R^8$ are hydrogen.

Exemplary compounds of the present invention include, but not limited to,

N-[3-(4-butyl-1,4-dihydroxy-3-oxo-3,4-dihydronaphthalen-2-yl)-1,1-dioxido-4H-1,2,4-benzothiadiazin-7-yl]methanesulfonamide;

N-{3-[1,4-dihydroxy-4-(3-methylbutyl)-3-oxo-3,4-dihydronaphthalen-2-yl]-1,1-dioxido-4H-1,2,4-benzothiadiazin-7-yl}methanesulfonamide;

N-{3-[(4S)-1,4-dihydroxy-4-(3-methylbutyl)-3-oxo-3,4-dihydronaphthalen-2-yl]-1,1-dioxido-4H-1,2,4-benzothiadiazin-7-yl}methanesulfonamide;

N-{3-[(4R)-1,4-dihydroxy-4-(3-methylbutyl)-3-oxo-3,4-dihydronaphthalen-2-yl]-1,1-dioxido-4H-1,2,4-benzothiadiazin-7-yl}methanesulfonamide;

N-(3-{1,4-dihydroxy-3-oxo-4-[(2E)-3-phenylprop-2-enyl]-3,4-dihydronaphthalen-2-yl}-1,1-dioxido-4H-1,2,4-benzothiadiazin-7-yl)methanesulfonamide;

N-[3-(4-benzyl-1,4-dihydroxy-3-oxo-3,4-dihydronaphthalen-2-yl)-1,1-dioxido-4H-1,2,4-benzothiadiazin-7-yl]methanesulfonamide;

N-{3-[4-allyl-1-hydroxy-4-(methoxyamino)-3-oxo-3,4-dihydronaphthalen-2-yl]-1,1-dioxido-4H-1,2,4-benzothiadiazin-7-yl}methanesulfonamide;

N-{3-[4-(3,3-dimethylbutyl)-1,4-dihydroxy-3-oxo-3,4-dihydronaphthalen-2-yl]-1,1-dioxido-4H-1,2,4-benzothiadiazin-7-yl}methanesulfonamide;

N-{3-[1-hydroxy-4-(methoxyamino)-3-oxo-4-propyl-3,4-dihydronaphthalen-2-yl]-1,1-dioxido-4H-1,2,4-benzothiadiazin-7-yl}methanesulfonamide;

N-(4-hydroxy-3-{7-[(methylsulfonyl)amino]-1,1-dioxido-4H-1,2,4-benzothiadiazin-3-yl}-2-oxo-1-propyl-1,2-dihydronaphthalen-1-yl)-N-methoxyacetamide;

N-{3-[1-hydroxy-4-methoxy-4-(3-methylbutyl)-3-oxo-3,4-dihydronaphthalen-2-yl]-1,1-dioxido-4H-1,2,4-benzothiadiazin-7-yl}methanesulfonamide;

N-{3-[4-(benzyloxy)-1-hydroxy-4-(3-methylbutyl)-3-oxo-3,4-dihydronaphthalen-2-yl]-1,1-dioxido-4H-1,2,4-benzothiadiazin-7-yl}methanesulfonamide;

N-[3-(4-amino-1-hydroxy-3-oxo-4-propyl-3,4-dihydronaphthalen-2-yl)-1,1-dioxido-4H-1,2,4-benzothiadiazin-7-yl]methanesulfonamide;

N-{3-[1-hydroxy-4-(methoxyamino)-4-(3-methylbut-2-enyl)-3-oxo-3,4-dihydronaphthalen-2-yl]-1,1-dioxido-4H-1,2,4-benzothiadiazin-7-yl}methanesulfonamide;

N-{3-[1-hydroxy-4-(methoxyamino)-4-(3-methylbutyl)-3-oxo-3,4-dihydronaphthalen-2-yl]-1,1-dioxido-4H-1,2,4-benzothiadiazin-7-yl}methanesulfonamide;

N-{3-[4-amino-1-hydroxy-4-(3-methylbutyl)-3-oxo-3,4-dihydronaphthalen-2-yl]-1,1-dioxido-4H-1,2,4-benzothiadiazin-7-yl}methanesulfonamide;

N-{3-[4-[(benzyloxy)amino]-1-hydroxy-4-(3-methylbutyl)-3-oxo-3,4-dihydronaphthalen-2-yl]-1,1-dioxido-4H-1,2,4-benzothiadiazin-7-yl}methanesulfonamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)acetamide;

methyl 4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-ylcarbamate;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)benzamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)methanesulfonamide;

N-{3-[(4R)-1-hydroxy-4-(methoxyamino)-4-(3-methylbutyl)-3-oxo-3,4-dihydronaphthalen-2-yl]-1,1-dioxido-4H-1,2,4-benzothiadiazin-7-yl}methanesulfonamide;

N-{3-[(4S)-1-hydroxy-4-(methoxyamino)-4-(3-methylbutyl)-3-oxo-3,4-dihydronaphthalen-2-yl]-1,1-dioxido-4H-1,2,4-benzothiadiazin-7-yl}methanesulfonamide;

N-hydroxy-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)acetamide;

N-{3-[4-butyl-1-hydroxy-4-(methoxyamino)-3-oxo-3,4-dihydronaphthalen-2-yl]-1,1-dioxido-4H-1,2,4-benzothiadiazin-7-yl}methanesulfonamide;

N-[3-(4-amino-4-butyl-1-hydroxy-3-oxo-3,4-dihydronaphthalen-2-yl)-1,1-dioxido-4H-1,2,4-benzothiadiazin-7-yl]methanesulfonamide;

benzyl 4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-ylcarbamate;

2-methoxyethyl 4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-ylcarbamate;

4-{[(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)amino]sulfonyl}benzoic acid;

N-(1-butyl-4-hydroxy-3-{7-[(methylsulfonyl)amino]-1,1-dioxido-4H-1,2,4-benzothiadiazin-3-yl}-2-oxo-1,2-dihydronaphthalen-1-yl)acetamide;

N-(1-butyl-4-hydroxy-3-{7-[(methylsulfonyl)amino]-1,1-dioxido-4H-1,2,4-benzothiadiazin-3-yl}-2-oxo-1,2-dihydronaphthalen-1-yl)methanesulfonamide;

N-{3-[4-(tert-butoxyamino)-1-hydroxy-3-oxo-4-propyl-3,4-dihydronaphthalen-2-yl]-1,1-dioxido-4H-1,2,4-benzothiadiazin-7-yl}methanesulfonamide;

N-{3-[(4S)-4-amino-1-hydroxy-4-(3-methylbutyl)-3-oxo-3,4-dihydronaphthalen-2-yl]-1,1-dioxido-4H-1,2,4-benzothiadiazin-7-yl}methanesulfonamide;

N-{3-[1-hydroxy-4-(hydroxyamino)-3-oxo-4-propyl-3,4-dihydronaphthalen-2-yl]-1,1-dioxido-4H-1,2,4-benzothiadiazin-7-yl}methanesulfonamide;

N-{3-[1-hydroxy-4-(methoxyamino)-4-(2-methylprop-2-enyl)-3-oxo-3,4-dihydronaphthalen-2-yl]-1,1-dioxido-4H-1,2,4-benzothiadiazin-7-yl}methanesulfonamide;

N-{3-[1-hydroxy-4-isobutyl-4-(methoxyamino)-3-oxo-3,4-dihydronaphthalen-2-yl]-1,1-dioxido-4H-1,2,4-benzothiadiazin-7-yl}methanesulfonamide;

N-{3-[1-hydroxy-4-(hydroxyamino)-4-(3-methylbutyl)-3-oxo-3,4-dihydronaphthalen-2-yl]-1,1-dioxido-4H-1,2,4-benzothiadiazin-7-yl}methanesulfonamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-morpholin-4-ylethanesulfonamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-N-methoxyacetamide;

methyl[(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)oxy]acetate;

2-[(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)oxy]acetamide;

N-((1S)-4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)methanesulfonamide;

N-{3-[(4S)-4-(3,3-dimethylbutyl)-1,4-dihydroxy-3-oxo-3,4-dihydronaphthalen-2-yl]-1,1-dioxido-4H-1,2,4-benzothiadiazin-7-yl}methanesulfonamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-(methylamino)ethanesulfonamide;

tert-butyl 2-[(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)amino]-2-oxoethylcarbamate;

2-amino-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)acetamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-methoxyethanesulfonamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-[(2-methoxyethyl)amino]ethanesulfonamide;

2-(diethylamino)-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)ethanesulfonamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-{methyl[2-(methylamino)ethyl]amino}ethanesulfonamide;

N-{3-[1-hydroxy-4-(isobutylamino)-4-(3-methylbutyl)-3-oxo-3,4-dihydronaphthalen-2-yl]-1,1-dioxido-4H-1,2,4-benzothiadiazin-7-yl}methanesulfonamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-[(2-methoxybenzyl)(methyl)amino]ethanesulfonamide;

ethyl[{3-[1-hydroxy-4-(hydroxyamino)-4-(3-methylbutyl)-3-oxo-3,4-dihydronaphthalen-2-yl]-1,1-dioxido-4H-1,2,4-benzothiadiazin-7-yl}(methylsulfonyl)amino]acetate;

[{3-[1-hydroxy-4-(hydroxyamino)-4-(3-methylbutyl)-3-oxo-3,4-dihydronaphthalen-2-yl]-1,1-dioxido-4H-1,2,4-benzothiadiazin-7-yl}(methylsulfonyl)amino]acetic acid;

2-(acetylamino)-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)acetamide;

2-(dibenzylamino)-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)ethanesulfonamide;

N-{3-[4-{[(tert-butylamino)carbonyl]amino}-1-hydroxy-4-(3-methylbutyl)-3-oxo-3,4-dihydronaphthalen-2-yl]-1,1-dioxido-4H-1,2,4-benzothiadiazin-7-yl}methanesulfonamide;

N-{3-[4-(benzylamino)-1-hydroxy-4-(3-methylbutyl)-3-oxo-3,4-dihydronaphthalen-2-yl]-1,1-dioxido-4H-1,2,4-benzothiadiazin-7-yl}methanesulfonamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-(methoxyamino)ethanesulfonamide;

N-(2-{[(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)amino]sulfonyl}ethyl)-N-methylacetamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-[methoxy(methyl)amino]ethanesulfonamide;

2-[(2,2-dimethoxyethyl)(methyl)amino]-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)ethanesulfonamide;

2-[(1,3-dioxolan-2-ylmethyl)(methyl)amino]-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)ethanesulfonamide;

N-{3-[1-hydroxy-4-[(3-methoxybenzyl)amino]-4-(3-methylbutyl)-3-oxo-3,4-dihydronaphthalen-2-yl]-1,1-dioxido-4H-1,2,4-benzothiadiazin-7-yl}methanesulfonamide;

N-(1-(3,3-dimethylbutyl)-4-hydroxy-3-{7-[(methylsulfonyl)amino]-1,1-dioxido-4H-1,2,4-benzothiadiazin-3-yl}-2-oxo-1,2-dihydronaphthalen-1-yl)acetamide;

N-{3-[4-amino-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-{3-[4-[(cyclopropylmethyl)amino]-1-hydroxy-4-(3-methylbutyl)-3-oxo-3,4-dihydronaphthalen-2-yl]-1,1-dioxido-4H-1,2,4-benzothiadiazin-7-yl}methanesulfonamide;

N-{3-[4-[(aminocarbonyl)amino]-1-hydroxy-4-(3-methylbutyl)-3-oxo-3,4-dihydronaphthalen-2-yl]-1,1-dioxido-4H-1,2,4-benzothiadiazin-7-yl}methanesulfonamide;

N-(1-(3,3-dimethylbutyl)-4-hydroxy-3-{7-[(methylsulfonyl)amino]-1,1-dioxido-4H-1,2,4-benzothiadiazin-3-yl}-2-oxo-1,2-dihydronaphthalen-1-yl)benzamide;

ethyl[(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)amino]acetate;

2-chloro-N-(1-(3,3-dimethylbutyl)-4-hydroxy-3-{7-[(methylsulfonyl)amino]-1,1-dioxido-4H-1,2,4-benzothiadiazin-3-yl}-2-oxo-1,2-dihydronaphthalen-1-yl)acetamide;

N-(1-(3,3-dimethylbutyl)-4-hydroxy-3-{7-[(methylsulfonyl)amino]-1,1-dioxido-4H-1,2,4-benzothiadiazin-3-yl}-2-oxo-1,2-dihydronaphthalen-1-yl)methanesulfonamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2,5-dimethoxybenzenesulfonamide;

N-{3-[4-(benzylamino)-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-(3-{4-(3,3-dimethylbutyl)-1-hydroxy-4-[(3-methoxybenzyl)amino]-3-oxo-3,4-dihydronaphthalen-2-yl}-1,1-dioxido-4H-1,2,4-benzothiadiazin-7-yl)methanesulfonamide;

N-(3-{4-(3,3-dimethylbutyl)-1-hydroxy-4-[(2-methoxybenzyl)amino]-3-oxo-3,4-dihydronaphthalen-2-yl}-1,1-dioxido-4H-1,2,4-benzothiadiazin-7-yl)methanesulfonamide;

N-(3-{4-(3,3-dimethylbutyl)-1-hydroxy-4-[(4-methoxybenzyl)amino]-3-oxo-3,4-dihydronaphthalen-2-yl}-1,1-dioxido-4H-1,2,4-benzothiadiazin-7-yl)methanesulfonamide;

3-{[(1-(3,3-dimethylbutyl)-4-hydroxy-3-{7-[(methylsulfonyl)amino]-1,1-dioxido-4H-1,2,4-benzothiadiazin-3-yl}-2-oxo-1,2-dihydronaphthalen-1-yl)amino]methyl}phenyl acetate;

N-(3-{4-(3,3-dimethylbutyl)-4-[(2-furylmethyl)amino]-1-hydroxy-3-oxo-3,4-dihydronaphthalen-2-yl}-1,1-dioxido-4H-1,2,4-benzothiadiazin-7-yl)methanesulfonamide;

N-{3-[4-[(4-cyanobenzyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-{3-[4-{[4-(benzyloxy)benzyl]amino}-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-{3-[4-[(1-benzothien-3-ylmethyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-((1S)-4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-morpholin-4-ylethanesulfonamide;

N-{3-[(4S)-4-(benzylamino)-1-hydroxy-4-(3-methylbutyl)-3-oxo-3,4-dihydronaphthalen-2-yl]-1,1-dioxido-4H-1,2,4-benzothiadiazin-7-yl}methanesulfonamide;

N-(3-{4-(3,3-dimethylbutyl)-1-hydroxy-4-[(2-naphthylmethyl)amino]-3-oxo-3,4-dihydronaphthalen-2-yl}-1,1-dioxido-4H-1,2,4-benzothiadiazin-7-yl)methanesulfonamide;

N-(3-{4-(3,3-dimethylbutyl)-1-hydroxy-3-oxo-4-[(1,3-thiazol-2-ylmethyl)amino]-3,4-dihydronaphthalen-2-yl}-1,1-dioxido-4H-1,2,4-benzothiadiazin-7-yl)methanesulfonamide;

N-(3-{4-(3,3-dimethylbutyl)-1-hydroxy-4-[(3-nitrobenzyl)amino]-3-oxo-3,4-dihydronaphthalen-2-yl}-1,1-dioxido-4H-1,2,4-benzothiadiazin-7-yl)methanesulfonamide;

N-{3-[4-{[2-(benzyloxy)benzyl]amino}-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-(3-{4-(3,3-dimethylbutyl)-1-hydroxy-3-oxo-4-[(3-vinylbenzyl)amino]-3,4-dihydronaphthalen-2-yl}-1,1-dioxido-4H-1,2,4-benzothiadiazin-7-yl)methanesulfonamide;

N-{3-[4-{[3-(benzyloxy)benzyl]amino}-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-(3-{4-(3,3-dimethylbutyl)-1-hydroxy-4-[(4-hydroxybenzyl)amino]-3-oxo-3,4-dihydronaphthalen-2-yl}-1,1-dioxido-4H-1,2,4-benzothiadiazin-7-yl)methanesulfonamide;

N-((1S)-4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2,5-dimethoxybenzenesulfonamide;

N-(3-{4-(3,3-dimethylbutyl)-1-hydroxy-4-[(2-hydroxybenzyl)amino]-3-oxo-3,4-dihydronaphthalen-2-yl}-1,1-dioxido-4H-1,2,4-benzothiadiazin-7-yl)methanesulfonamide;

N-(3-{4-(3,3-dimethylbutyl)-1-hydroxy-3-oxo-4-[(pyridin-3-ylmethyl)amino]-3,4-dihydronaphthalen-2-yl}-1,1-dioxido-4H-1,2,4-benzothiadiazin-7-yl)methanesulfonamide;

N-{3-[4-[(2,5-dimethoxybenzyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-(3-{4-(3,3-dimethylbutyl)-1-hydroxy-4-[(2-methoxy-5-nitrobenzyl)amino]-3-oxo-3,4-dihydronaphthalen-2-yl}-1,1-dioxido-4H-1,2,4-benzothiadiazin-7-yl)methanesulfonamide;

N-{3-[4-[(1,1'-biphenyl-4-ylmethyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-(3-{4-(3,3-dimethylbutyl)-1-hydroxy-4-[(2-nitrobenzyl)amino]-3-oxo-3,4-dihydronaphthalen-2-yl}-1,1-dioxido-4H-1,2,4-benzothiadiazin-7-yl)methanesulfonamide;

N-(3-{4-(3,3-dimethylbutyl)-1-hydroxy-4-[(4-nitrobenzyl)amino]-3-oxo-3,4-dihydronaphthalen-2-yl}-1,1-dioxido-4H-1,2,4-benzothiadiazin-7-yl)methanesulfonamide;

N-(3-{4-(3,3-dimethylbutyl)-1-hydroxy-3-oxo-4-[(pyridin-2-ylmethyl)amino]-3,4-dihydronaphthalen-2-yl}-1,1-dioxido-4H-1,2,4-benzothiadiazin-7-yl)methanesulfonamide;

N-[3-(4-(3,3-dimethylbutyl)-1-hydroxy-3-oxo-4-{[2-(trifluoromethyl)benzyl]amino}-3,4-dihydronaphthalen-2-yl)-1,1-dioxido-4H-1,2,4-benzothiadiazin-7-yl]methanesulfonamide;

N-{3-[4-[(2,6-dimethylbenzyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-(3-{4-(3,3-dimethylbutyl)-1-hydroxy-4-[(mesitylmethyl)amino]-3-oxo-3,4-dihydronaphthalen-2-yl}-1,1-dioxido-4H-1,2,4-benzothiadiazin-7-yl)methanesulfonamide;

N-[3-(4-(3,3-dimethylbutyl)-1-hydroxy-4-{[(6-methylpyridin-3-yl)methyl]amino}-3-oxo-3,4-dihydronaphthalen-2-yl)-1,1-dioxido-4H-1,2,4-benzothiadiazin-7-yl]methanesulfonamide;

N-[3-(4-(3,3-dimethylbutyl)-1-hydroxy-4-{[(2-methylpyridin-3-yl)methyl]amino}-3-oxo-3,4-dihydronaphthalen-2-yl)-1,1-dioxido-4H-1,2,4-benzothiadiazin-7-yl]methanesulfonamide;

N-[3-(4-(3,3-dimethylbutyl)-1-hydroxy-4-{[(6-methylpyridin-2-yl)methyl]amino}-3-oxo-3,4-dihydronaphthalen-2-yl)-1,1-dioxido-4H-1,2,4-benzothiadiazin-7-yl]methanesulfonamide;

N-{3-[4-[(2-aminobenzyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-(3-{4-(3,3-dimethylbutyl)-1-hydroxy-4-[(imidazo[1,5-a]pyridin-3-ylmethyl)amino]-3-oxo-3,4-dihydronaphthalen-2-yl}-1,1-dioxido-4H-1,2,4-benzothiadiazin-7-yl)methanesulfonamide;

N-{3-[4-[benzyl(methyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-benzyl-N-(1-(3,3-dimethylbutyl)-4-hydroxy-3-{7-[(methylsulfonyl)amino]-1,1-dioxido-4H-1,2,4-benzothiadiazin-3-yl}-2-oxo-1,2-dihydronaphthalen-1-yl)acetamide;

N-[3-(4-(3,3-dimethylbutyl)-1-hydroxy-4-{[(2-methoxypyridin-3-yl)methyl]amino}-3-oxo-3,4-dihydronaphthalen-2-yl)-1,1-dioxido-4H-1,2,4-benzothiadiazin-7-yl]methanesulfonamide; and N-{3-[4-[(3-acetylbenzyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

or a pharmaceutically acceptable salt form, stereoisomer, tautomer, prodrug, salt of a prodrug, or combination thereof.

It will be appreciated by those skilled in the art that the compounds of this invention, exemplified by formula (I) when $R^9$ is —$OR_A$, —$SR_A$ or —$NR_AR_B$ wherein $R_A$ is hydrogen and $R^{11}$ is hydrogen, exist in tautomeric forms. All tautomeric forms of the compounds described herein are intended to be encompassed within the scope of the present invention. Examples of some of the possible tautomer forms of the compounds of this invention include, but are not limited to:

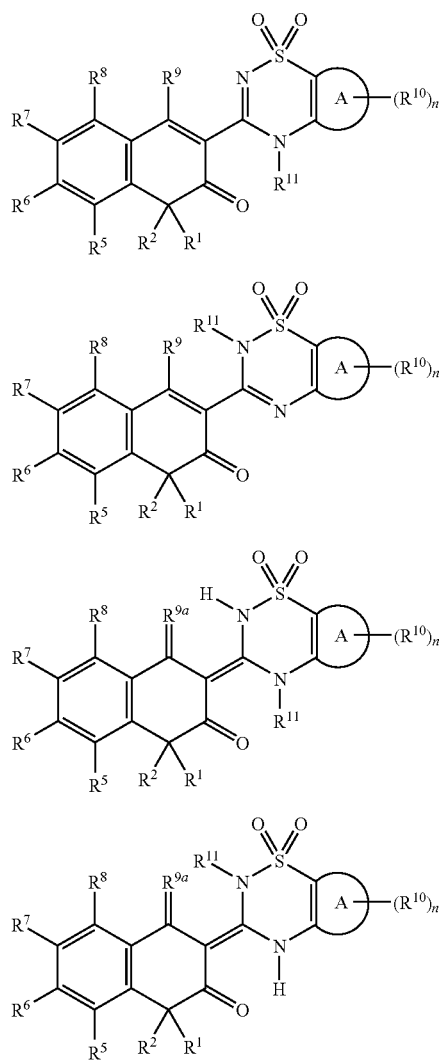

As the drawings within this specification can only represent one possible tautomeric or structural isomeric form, it should be understood that the invention encompasses any tautomeric or structural isomeric form, or mixtures thereof, which possess the ability to inhibit hepatitis C, and is not limited to any one tautomeric or structural isomeric form utilized within the drawings.

As a convention, the compounds exemplified herein have been assigned names based on the structure of the tautomer of formula 1-A. It is to be understood that any reference to such named compounds is intended to encompass all tautomers of the named compounds and any mixture of tautomers of the named compounds.

Compounds of this invention may contain at least one chiral center and may exist as single stereoisomers (e.g. single enantiomer), mixtures of stereoisomers (e.g. any mixture of enantiomers or diastereomers) or racemic mixtures thereof. As a result, all stereoisomers of the compounds of the invention are meant to be included in the invention, including racemic mixtures, mixtures of diastereomers, mixtures of enantiomers, as well as individual optical isomers, including, enantiomers and single diastereomers of the compounds of the invention substantially free from their enantiomers or other diastereomers. By "substantially free" is meant greater than about 80% free of other enantiomers or diastereomers of the compound, more preferably greater than about 90% free of other enantiomers or diastereomers of the compound, even more preferably greater than about 95% free of other enantiomers or diastereomers of the compound, even more highly preferably greater than about 98% free of other enantiomers or diastereomers of the compound and most preferably greater than about 99% free of other enantiomers or diastereomers of the compound. Where the stereochemistry of the chiral centers present in the chemical structures illustrated herein is not specified, the chemical structure is intended to encompass compounds containing either stereoisomer of each chiral center present in the compound.

In addition, compounds comprising the possible geometric isomers of carbon-carbon double bonds and carbon-nitrogen double are also meant to be included in this invention.

Individual stereoisomers of the compounds of this invention can be prepared by any one of a number of methods which are within the knowledge of one of ordinary skill in the art. These methods include stereospecific synthesis from commercially available optically pure (enantiomerically pure) or substantially optically pure starting materials. Alternatively, these compounds may be obtained by resolution/separation of a mixture of stereoisomers, including racemic mixtures, using conventional procedures. Exemplary procedures that may be useful for the resolution/separation of mixtures of stereoisomers include enzymatic resolution, chromatographic separation, crystallization/re-crystallization, and conversion of enantiomers in an enantiomeric mixture to diastereomers followed by separation/resolution of the diastereomers using techniques known in the art, such as recrystallization and or chromatographic resolution, and regeneration of the individual enantiomers. Other useful methods may be found in "*Enantiomers, Racemates, and Resolutions,*" J. Jacques et al., 1981, John Wiley and Sons, New York, N.Y., the disclosure of which is incorporated herein by reference.

Stereospecific synthesis involves the use of appropriate chiral starting materials and synthetic reactions which do not cause racemization or inversion of stereochemistry at the chiral centers. Starting materials of particular stereochemistry are either commercially available or can be made and resolved by techniques known in the art.

Diastereomeric mixtures of compounds resulting from a synthetic reaction can often be separated by chromatographic techniques which are well-known to those of ordinary skill in the art.

Chromatographic resolution of enantiomers can be accomplished on chiral chromatography resins. Chromatography columns containing chiral resins are commercially available. In practice, the racemate is placed in solution and loaded onto the column containing the chiral stationary phase. The enantiomers are then separated by HPLC.

Resolution of enantiomers can also be accomplished by converting the enantiomers in the mixture to diastereomers by reaction with chiral auxiliaries. The resulting diastereomers can then be separated by column chromatography. This technique is especially useful when the compounds to be separated contain a carboxyl, amino or hydroxyl group that will form a salt or covalent bond with the chiral auxiliary. Chirally pure amino acids, organic carboxylic acids or organosulfonic acids are especially useful as chiral auxiliaries. Once the diastereomers have been separated by chromatography, the individual enantiomers can be regenerated. Frequently, the chiral auxiliary can be recovered and used again. Alternatively, the diastereomers can also be separated by crystallization/re-crystallization and the individual enantiomers regenerated therefrom.

Enzymes, such as esterases, phosphatases and lipases, can be useful for resolution of derivatives of the enantiomers in an enantiomeric mixture. For example, an ester derivative of a carboxyl group in the compounds to be separated can be prepared. Certain enzymes will selectively hydrolyze only one of the enantiomers in the mixture. Then the resulting enantiomerically pure acid can be separated from the unhydrolyzed ester.

In addition, solvates and hydrates of the compounds of the invention are meant to be included in this invention.

When any variable (for example $R^3$, $R^4$, $R_A$, $R_B$, $R_C$, $R_a$, $R_b$, $G^1$, X, Y, Z, etc.) occurs more than one time in any substituent or in the compound of the invention or any other formula herein, its definition on each occurrence is independent of its definition at every other occurrence. In addition, combinations of substituents are permissible only if such combinations result in stable compounds. Stable compounds are compounds which can be isolated in a useful degree of purity from a reaction mixture.

The compounds of the present invention can exist as pharmaceutically acceptable salts. The term "pharmaceutically acceptable salt," as used herein, represents acid or base salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting a basic group (for example, a nitrogen containing group) with a suitable acid. Representative acid addition salts include acetates, acrylates, adipates, alginates, aspartates, benzoates, benzenesulfonates, bisulfates, bisulfites, butyrates, camphorates, camphorsulfonates, caproates, caprylates, citrates, chlorobenzoates, digluconates, dinitrobenzoates, formates, fumarates, glutamates, glycerophosphates, hemisulfates, heptanoates, hexanoates, hydrochloride, hydrobromide, hydroiodides, 2-hydroxyethansulfonates, lactates, maleates, mandelates, methoxybenzoates, methylbenzoates, malonates, mesitylenesulfonate, methanesulfonates, naphthylenesulfonates, nicotinates, nitrates, nitrites, 2-naphthalenesulfonates, oxalates, pamoates, pectinates, persulfates, phenylbutyrates, phenylproprionates, phosphates, phthalates, picrates, pivalates, propanesulfonates, propionates, pyrosulfates, salicylates, succinates, sulfonates, tartrate, trichloroacetate, trifluoroacetate, para-toluenesulfonates, and undecanoates. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form pharmaceutically acceptable addition salts include inorganic acids such as hydrochloric, hydrobromic, nitric acid, sulfuric, and phosphoric, and the like, and organic acids such as acetic, fumaric, trifluoroacetic, mandelic, methanesulfonic, pyruvic, oxalic, glycolic, salicylic, oxalic, maleic, succinic, tartaric, aspartic, glutamic, cinnamic and citric.

Basic addition salts can be prepared during the final isolation and purification of the compounds by reacting an acidic group (for example, a carboxy group or an enol) with a suitable base such as the alkoxide, (for example, ethoxide or methoxide and the like) hydroxide, carbonate, or bicarbonate of a metal cation or with ammonia or an organic primary, secondary, or tertiary amine. The cations of pharmaceutically acceptable salts include lithium, sodium, potassium, calcium, copper, manganese, iron, zinc, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of basic addition salts include amino acids such as glycine and arginine, primary, secondary and tertiary amines such as ethylenediamine, ethanolamine, and diethanolamine, and cyclic amines such as dicyclohexylamine, morpholine, piperidine, and piperazine.

The present compounds can also exist as pharmaceutically acceptable prodrugs. The term "pharmaceutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use. "Prodrugs" are considered to be any covalently bonded carriers which release the active parent drug of formula (I) or (II) in vivo metabolically or by solvolysis when such prodrugs is administered to a mammalian subject. Prodrugs of the compounds of formula (I) or (II) can be prepared by modifying functional groups present in the compounds in such a way that the modifications are cleaved, either in routine manipulation or in vivo, to the parent compounds respectively. Examples of such modification include, but not limited to, treatment of a compound of formula (I) or (II), containing an amino, amido or hydroxyl moiety with a suitable derivatising agent, for example, a carboxylic acid halide or acid anhydride, treatment of a compound of formula (I) or(II), containing a carboxyl moiety, to an ester or amide and treatment of a compound of formula (I) or (II), containing a carboxylic acid ester moiety to an enol-ester. Prodrugs include compounds wherein hydroxy, amine, carboxy, or sulfhydryl groups are bonded to any group that, when administered to a mammalian subject, cleaves under physiological conditions to form a free hydroxyl, amino, carboxy, or sulfhydryl group, respectively. Examples of prodrugs include, but are not limited to, acetate, formate, and benzoate derivatives of the hydroxy, carboxy and amine functional groups in the compounds of formula (I) or (II).

Compounds and compositions of the invention are useful for inhibiting the replication of an RNA-containing virus, and more particularly Hepatitis C virus (HCV). In particular, the compounds and compositions of the invention can be used for treating or preventing an an infection caused by an RNA-containing virus, particularly when the RNA-containing virus is Hepatitis C virus (HCV). Typically, such infection can be ameliorated by inhibiting the replication of an RNA-containing virus, specifically when the RNA-containing virus is hepatitis C virus (HCV), in a mammal, preferably by administering a compound or composition of the invention, either alone or in combination with another active agent, for example, as part of a therapeutic regimen.

Accordingly, one aspect of the invention provides a method for inhibiting the replication of an RNA-containing virus, in particularly, Hepatitis C virus (HCV), comprising contacting said virus with a therapeutically effective amount of a compound or combination of compounds of formula (I) or (II), or a pharmaceutically acceptable salt form, tautomer, stereoisomer, prodrug, salt of a prodrug, or combination thereof.

In addition, the invention relates to a method for treating or preventing an infection caused by an RNA-containing virus, in particularly, Hepatitis C virus (HCV), comprising the step of administering a therapeutically effective amount of a compound or combination of compounds of formula (I) or (II), or a pharmaceutically acceptable salt form, tautomer, stereoisomer, prodrug, salt of a prodrug, or combination thereof, to a patient in need of such treatment.

In yet another aspect, the present invention provides the use of a compound or a combination of compounds having formula (I) or (II), or a therapeutically acceptable salt form, stereoisomer, tautomer, prodrug, salt of a prodrug, or combination thereof, to prepare a medicament for the treatment or prevention of an infection caused by an RNA-containing virus, in particularly, Hepatitis C virus (HCV), in a patient.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one or combination of the compounds of the invention can be employed in pure form or, where such forms exist, in pharmaceutically acceptable salt form, prodrug, or salt of a prodrug. Alternatively, the compound can be administered as a pharmaceutical composition containing a therapeutically effective amout of the compound or combination of compounds of interest, or their pharmaceutically acceptable salt form, prodrugs, or salts of the prodrug, in combination with one or more pharmaceutically acceptable carriers.

The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of formula (I) or (II), or pharmaceutically acceptable salts, stereoisomers, tautomers, prodrug, salt of a prodrug thereof, administered to a patient in single or divided doses, can be in amounts from about 0.1 to about 200 mg/kg body weight or preferably from about 0.25 to about 100 mg/kg body weight. Single dose compositions can contain these amounts or submultiples thereof to make up the daily dose.

A "patient" is any individual treated with a compound of the present invention, or a therapeutically acceptable salt form, stereoisomer, tautomer, prodrug, or salt of a prodrug thereof. Patients include humans, as well as other animals such as companion animals (e.g. dogs and cats) and livestock. Patients may be experiencing one or more symptoms of a condition responsive to inhibition of HCV, or may be free of such symptom(s) (i.e. treatment may be prophylactic).

The pharmaceutical compositions comprise a compound or combination of compounds of the invention, or a pharmaceutically acceptable salt, tautomer, stereosisomer, prodrug, salt of a prodrug, or combination thereof, formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier, adjuvants, diluents or vehicles" as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution, ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention can be formulated in a conventional manner using one or more of the aforementioned pharmaceutically acceptable carriers.

The compounds of formula (I) or (II), or a tautomer, stereoisomer, pharmaceutically acceptable salt, prodrug, or salt of a prodrug thereof can be administered orally, parenterally, osmotically (nasal sprays), rectally, vaginally, or topically in unit dosage formulations containing carriers, adjuvants, diluents, vehicles, or combinations thereof. The term "parenteral" includes infusion as well as subcutaneous, intravenous, intramuscular, and intrasternal injection.

Parenterally administered aqueous or oleaginous suspensions of the compounds can be formulated with dispersing, wetting, or suspending agents. The injectable preparation can also be an injectable solution or suspension in a diluent or solvent. Among the acceptable diluents or solvents employed are water, saline, Ringer's solution, buffers, monoglycerides, diglycerides, fatty acids such as oleic acid, and fixed oils such as monoglycerides or diglycerides.

The antiviral effect of parenterally administered compounds can be prolonged by slowing their absorption. One way to slow the absorption of a particular compound is administering injectable depot forms comprising suspensions of crystalline, amorphous, or otherwise water-insoluble forms of the compound. The rate of absorption of the compound is dependent on its rate of dissolution which is, in turn, dependent on its physical state. Another way to slow absorption of a particular compound is administering injectable depot forms comprising the compound as an oleaginous solution or suspension. Yet another way to slow absorption of a particular compound is administering injectable depot forms comprising microcapsule matrices of the compound trapped within liposomes, microemulsions, or biodegradable polymers such as polylactide-polyglycolide, polyorthoesters or polyanhydrides. Depending on the ratio of drug to polymer and the composition of the polymer, the rate of drug release can be controlled.

Transdermal patches can also provide controlled delivery of the compounds. The rate of absorption can be slowed by using rate controlling membranes or by trapping the compound within a polymer matrix or gel. Conversely, absorption enhancers can be used to increase absorption.

Solid dosage forms for oral administration include capsules, tablets, pills, powders, and granules. In these solid dosage forms, the active compound can optionally comprise diluents such as sucrose, lactose, starch, talc, silicic acid, aluminum hydroxide, calcium silicates, polyamide powder, tableting lubricants, and tableting aids such as magnesium stearate or microcrystalline cellulose. Capsules, tablets and pills can also comprise buffering agents, and tablets and pills can be prepared with enteric coatings or other release-controlling coatings. Powders and sprays can also contain excipients such as talc, silicic acid, aluminum hydroxide, calcium silicate, polyamide powder, or mixtures thereof. Sprays can additionally contain customary propellants such as chlorofluorohydrocarbons or substitutes thereof.

Liquid dosage forms for oral administration include emulsions, microemulsions, solutions, suspensions, syrups, and elixirs comprising inert diluents such as water. These compositions can also comprise adjuvants such as wetting, emulsifying, suspending, sweetening, flavoring, and perfuming agents.

Topical dosage forms include ointments, pastes, creams, lotions, gels, powders, solutions, sprays, inhalants, and transdermal patches. The compound is mixed under sterile conditions with a carrier and any needed preservatives or buffers. These dosage forms can also include excipients such as animal and vegetable fats, oils, waxes, paraffins, starch, tragacanth, cellulose derivatives, polyethylene glycols, silicones, bentonites, silicic acid, talc and zinc oxide, or mixtures thereof. Suppositories for rectal or vaginal administration can be prepared by mixing the compounds with a suitable non-irritating excipient such as cocoa butter or polyethylene glycol, each of which is solid at ordinary temperature but fluid in the rectum or vagina. Ophthalmic formulations comprising eye drops, eye ointments, powders, and solutions are also contemplated as being within the scope of this invention.

The compounds of formula (I) or (II), or their pharmaceutically acceptable salts, stereoisomers, tautomers, prodrugs or salt of a prodrug thereof, inhibit HCV polymerase, an RNA dependent RNA polymerase, an enzyme essential for HCV viral replication. Compounds of the present invention can be administered as the sole active pharmaceutical agent, or used in combination with one or more agents to treat or prevent hepatitis C infections or the symptoms associated with HCV infection. Other agents to be administered in combination with a compound or combination of compounds of the invention include therapies for disease caused by HCV infection that suppresses HCV viral replication by direct or indirect mechanisms. These include agents such as host immune modulators (for example, interferon-alpha, pegylated interferon-alpha, interferon-beta, interferon-gamma, CpG oligonucleotides and the like), or antiviral compounds that inhibit host cellular functions such as inosine monophosphate dehydrogenase (for example, ribavirin and the like). Also included are cytokines that modulate immune function. Also included are vaccines comprising HCV antigens or antigen adjuvant combinations directed against HCV. Also included are agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like. Other agents to be administered in combination with a compound of the present invention include any agent or combination of agents that inhibit the replication of HCV by targeting proteins of the viral genome involved in the viral replication. These agents include but are not limited to other inhibitors of HCV RNA dependent RNA polymerase such as, for example, nucleoside type polymerase inhibitors described in WO01 90121(A2), or U.S. Pat. No. 6,348,587B1 or WO0160315 or WO0132153 or non-nucleoside inhibitors such as, for example, benzimidazole polymerase inhibitors described in EP 1162196A1 or WO0204425 or inhibitors of HCV protease such as, for example, peptidomimetic type inhibitors such as BILN2061 and the like or inhibitors of HCV helicase.

Other agents to be administered in combination with a compound of the present invention include any agent or combination of agents that inhibit the replication of other viruses for co-infected individuals. These agent include but are not limited to therapies for disease caused by hepatitis B (HBV) infection such as, for example, adefovir, lamivudine, and tenofovir or therapies for disease caused by human immunodeficiency virus (HIV) infection such as, for example, protease inhibitors: ritonavir, lopinavir, indinavir, nelfinavir, saquinavir, amprenavir, atazanavir, tipranavir, TMC-114, fosamprenavir; reverse transcriptase inhibitors: zidovudine, lamivudine, didanosine, stavudine, tenofovir, zalcitabine, abacavir, efavirenz, nevirapine, delavirdine, TMC-125; integrase inhibitors: L-870812, S-1360, or entry inhibitors: enfuvirtide (T-20), T-1249.

Other agents to be administered in combination with a compound of the present invention include any agent or combination of agents that treat or alleviate symptoms of HCV infection including cirrhosis and inflammation of the liver.

Accordingly, one aspect of the invention is directed to a method for treating or preventing an infection caused by an RNA-containing virus comprising co-administering to a patient in need of such treatment one or more agents selected from the group consisting of a host immune modulator and a second antiviral agent, or a combination thereof, with a therapeutically effective amount of a compound or combination of compounds of formula (I) or (II), or a pharmaceutically acceptable salt, stereoisomer, tautomer, prodrug, salt of a prodrug, or combination thereof. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

Further aspect of the invention is directed to a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound or combination of compounds of formula (I) or (II), or a pharmaceutically acceptable salt, stereoisomer, tautomer, prodrug, salt of a prodrug, or combination thereof.

Yet another aspect of the invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound or a combination of compounds of formula (I) or (II), or a pharmaceutically acceptable salt, stereoisomer, tautomer, prodrug, salt of a prodrug, or combination thereof. An agent that treats patients for disease caused by hepatitis B (HBV) infection may be for example, but not limited thereto, L-deoxythymidine, adefovir, lamivudine or tenfovir, or any combination thereof. Example of the RNA-containing virus includes, but not limited to, hepatitis C virus (HCV).

Another aspect of the invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound or a combination of compounds of formula (I) or (II), or a pharmaceutically acceptable salt, stereoisomer, tautomer, prodrug, salt of a prodrug, or combination thereof. The agent that treats patients for disease caused by human immunodeficiency virus (HIV) infection may include, but is not limited thereto, ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) or T-1249, or any combination thereof. Example of the RNA-containing virus includes, but not limited to, hepatitis C virus (HCV).

In addition, the present invention provides provides the use of a compound or a combination of compounds having formula (I) or (II), or a therapeutically acceptable salt form, stereoisomer, or tautomer, prodrug, salt of a prodrug, or combination thereof, and one or more agents selected from the group consisting of a host immune modulator and a second antiviral agent, or a combination thereof, to prepare a medicament for the treatment of an infection caused by an RNA-containing virus in a patient, particularly hepatitis C virus. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

When used in the above or other treatments, combination of compound or compounds of the invention, together with one or more agents as defined herein above, can be employed in pure form or, where such forms exist, in pharmaceutically acceptable salt form, prodrug, salt of a prodrug, or combination thereof. Alternatively, such combination of therapeutic agents can be administered as a pharmaceutical composition containing a therapeutically effective amout of the compound or combination of compounds of interest, or their pharmaceutically acceptable salt form, prodrugs, or salts of the prodrug, in combination with one or more agents as defined hereinabove, and a pharmaceutically acceptable carriers. Such pharmaceutical compositions can be used for inhibiting the replication of an RNA-containing virus, particularly Hepatitis C virus (HCV), by contacting said virus with said pharmaceutical composition. In addition, such compositions are useful for the treatment or prevention of an infection caused by an RNA-containing virus, particularly Hepatitis C virus (HCV).

Hence, further aspect of the invention is directed to a method of treating or preventing infection caused by an RNA-containing virus, particularly a hepatitis C virus (HCV), comprising administering to a patient in need of such treatment a pharmaceutical composition comprising a compound or combination of compounds of formula (I) or (II), or a pharmaceutically acceptable salt, stereoisomer, or tautomer, prodrug, salt of a prodrug, or combination thereof, one or more agents as defined hereinabove, and a pharmaceutically acceptable carrier.

When administered as a combination, the therapeutic agents can be formulated as separate compositions which are given at the same time or within a predetermined period of time, or the therapeutic agents can be given as a single unit dosage form.

Determination of Biological Activity

HCV Polymerase Inhibition Assay:
Biochemical $IC_{50}$

Either two-fold serial dilutions (fractional inhibition assay) or a narrower range of dilutions spanning the IC50 of the inhibitor (tight binding assay) of the inhibitors were incubated with 20 mM Tris-Cl pH 7.5, 5 mM $MgCl_2$, 50 mM NaCl, 1 mM dithiothreitol, 1 mM ethylene diamine tetraacetic acid (EDTA), 300 µM GTP and 150 to 300 nM NS5B (HCV Strain 1B (J4, Genbank accession number AF054247, or H77, Genbank accession number AF011751)) for 15 minutes at room temperature. The reaction was initiated by the addition of 20 µM CTP, 20 µM ATP, 1 µM 3H-UTP (10 mCi/umol), 150 nM template RNA and 0.4 U/µl RNase inhibitor (RNasin, Promega), and allowed to proceed for 2 to 4 hours at room temperature. Reaction volume was 50 µl. The reaction was terminated by the addition of 1 volume of 4 mM spermine in 10 mM Tris-Cl pH 8.0, 1 mM EDTA. After incubation for at least 15 minutes at room temperature, the precipitated RNA was captured by filtering through a GF/B filter (Millipore) in a 96 well format. The filter plate was washed three times with 200 µl each of 2 mM spermine, 10 mM Tris-Cl pH 8.0, 1 mM EDTA, and 2 times with ethanol. After air drying, 30 µl of Microscint 20 scintillation cocktail (Packard) was added to each well, and the retained cpm were determined by scintillation counting. IC50 values were calculated by a two-variable nonlinear regression equation using an uninhibited control and a fully inhibited control sample to determine the minimum and maximum for the curve. Tight-binding assays were performed on those compounds exhibiting IC50 values less than 0.15 µM in the fractional inhibition assay in order to more precisely measure the IC50 values. Retained cpm were plotted vs. inhibitor concentration and fit to equation 1 using non-linear regression (ref 1) to obtain the IC50 values.

$$\text{Retained } cpm = A/\text{sqrt}\{(IC_{50}+I_t-E_t)^2+4IC_{50}E_t\}-(IC_{50}+I_t-E_t)] \qquad \text{eqn 1.}$$

where $A=V_{max}[S]/2(K_m+[S])$; $I_t$=total inhibitor concentration and $E_t$=total active concentration of enzyme.

Ref. 1: Morrison, J. F. and S. R. Stone. 1985. Approaches to the study and analysis of the inhibition of enzymes by slow- and tight-binding inhibitors. Comments Mol. Cell. Biophys. 2: 347-368.

The sequence of the template RNA used was:

(SEQ ID NO:1)
5' GGGCGAAUUGGGCCCUCUAGAUGCAUGCUCGAGCGGCCGCCAGUGUG

AUGGAUAUCUGCAGAAUUCGCCCUUGGUGGCUCCAUCUUAGCCCUAGUCA

CGGCUAGCUGUGAAAGGUCCGUGAGCCGCUUGACUGCAGAGAGUGCUGAU

ACUGGCCUCUCUGCAGAUCAAGUC-3'.

When tested by the above method, the compounds of the present invention inhibit HCV polymerase 1B with IC50's in the range of 0.002 µM to 500 µM.

Evaluation of the HCV Inhibitors in HCV Replicon: Cell Culture $EC_{50}$

The cell lines and assays were conducted according to the methods described by Ikeda M, Yi M, Li K, Lemon S M., J Virol 2002 March; 76(6):2997-3006, and Blight K. J, Kolykhalov A., Rice C. M., Science 2000 December, 290: 1972-1974) with the following modifications:

RNA Assay

Replicon cells were plated at 3×10³ cells per well in 96-well plate in DMEM medium containing 5% fetal calf serum. At day 1, culture medium was removed and replaced with fresh medium containing eight serial 2-fold dilutions of compound. The final concentration of DMSO in medium was 0.5%. The untreated control culture was treated in an identical manner except no inhibitor was added to the medium. Plates were incubated in a $CO_2$ incubator at 37° C. On Day 4, 100 µL lysis buffer (RTL) (Qiagen) was added to each well after removal of culture medium. RNA was purified according to manufacturer's recommendations (Qiagen RNAeasy) and eluted in 200 µl of water. The HCV RNA level was quantified from a portion (5 µL out of 200 µL) of the purified RNA by real-time RT-PCR method. The primers and probe are derived from specific sequence in the 5'UTR region. RT-PCR reaction was performed at 48° C. for 30 min, followed by 40 cycles set to 95° C., 15 s; 54° C., 30 s; and 72° C., 40 s. The percentage reduction of HCV RNA in the presence of compound was calculated and the 50% inhibitory concentration ($IC_{50}$) was calculated by non-linear regression analysis using the Prism program.

When tested by the above method, the compounds of the present invention inhibit replicon production with EC50's in the range of 0.005 µM to >100 µM.

Cytotoxity Assays

Cytotoxicity assays were performed in replicon cells. Briefly, HCV replicon cells were plated at 3×10³ cells per well in 96-well plate in DMEM medium containing 5% FCS. At day 1, culture medium was removed and replaced with fresh medium containing eight serial 2-fold dilutions of compound. The final concentration of DMSO in medium was 0.5%. All experiments were performed in duplicate. The untreated control culture was treated in an identical manner except no inhibitor was added to the medium. Plates were incubated in a $CO_2$ incubator at 37° C. On day 4, stock solution of the tetrazolium salt, MTT (4 mg/ml in PBS, Sigma cat.# M 2128) was added to each well at 25 µL per well. Plates were further incubated for 4 hours, treated with 20% SDS plus 0.02 N HCl at 50 µL per well to lyse the cells. After an overnight incubation, optical density was measured by reading the plates at 570/650 nm wavelengths. The percent reduction of formazan blue color formed relative to control was calculated and the cytopathic effect was described as a 50% toxicity concentration ($TC_{50}$) was calculated by non-linear regression analysis using the Prism program.

When tested by the above method, the compounds of the present invention exhibited CPE reduction with TC50's in the range of 6.6 µM to >100 µM.

Cell culture assays for agents targeted toward hepatitis C are not yet available because of the inability to produce infectious virus in a sustained cell line. The hepatitis C virus genome encodes a large polyprotein, which after processing produces the necessary functional components to synthesize progeny RNA. Selectable cell lines that produce high and sustained levels of subgenomic HCV RNA (replicons) have been derived from human hepatoma cells (Huh7) as described in the references above. The mechanism of RNA replication in these cell lines is considered to be identical to the replication of full length HCV RNA in infected hepatocytes. The compounds and methods of this invention are inhibitors of HCV RNA replication in the replicon assay systems described above. This forms the basis of the claim for their potential as therapies in treating disease resulting from hepatitis C viral infection.

Synthetic Methods

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. The groups $R^1, R^2, R^3, R^4, R^5, R^6, R^7, R^8, R^9, R^{10}, R^{11}$, A and n are as defined above unless otherwise noted below.

This invention is intended to encompass compounds having formula (I) or (II) when prepared by synthetic processes or by metabolic processes. Preparation of the compounds of the invention by metabolic processes include those occurring in the human or animal body (in vivo) or processes occurring in vitro.

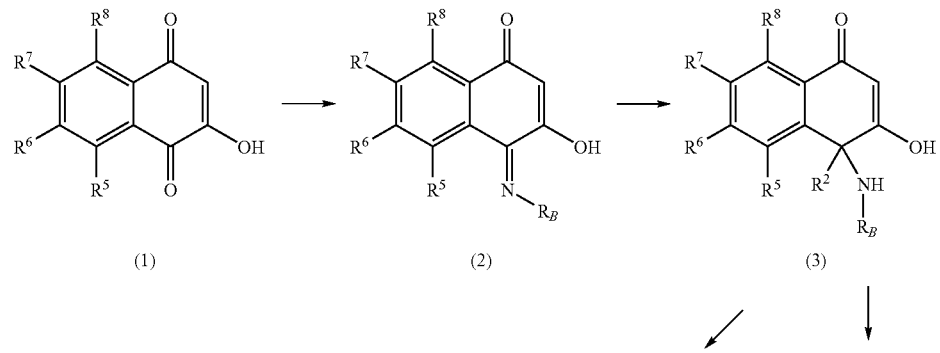

Scheme 1

-continued

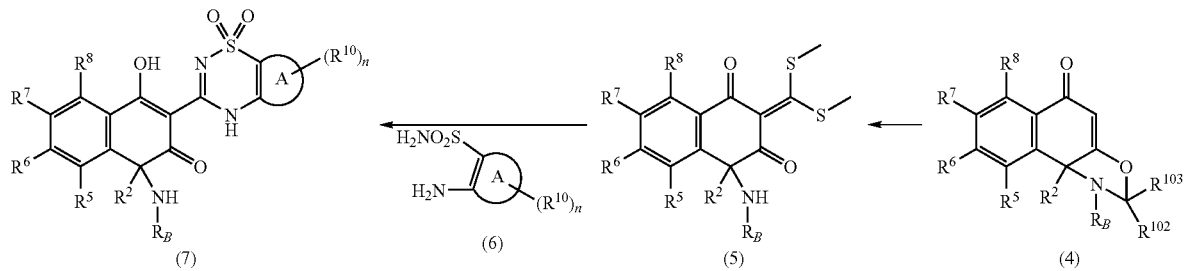

Compounds of formula (6) wherein $R_B$, n, $R^2$, $R^5$, $R^6$, $R^7$, $R^8$ and $R^{10}$ are as defined in formula (I) can be prepared from compounds of formula (1) as outlined in Scheme 1.

2-Hydroxy-1,4-naphthoquinone having formula (1), either purchased or prepared by known methodologies known by one skilled in the art, can be treated with amines having formula $NH_2R_B$ (for example hydroxylamine, aryloxyamines, alkoxylamines and the like) in protic solvents such as alcohols with heating to give a mixture of isomers with the isomer shown in (2) predominating. Compounds of formula (2) can be treated with a suitable organometallic agents such as, but not limited to, Grignard reagents such as methylmagnesium bromide, allylmagnesium bromide, benzylmagnesium chloride and the like, allylic indium reagents, cinnamyl indium reagent, benzyl indium reagent and benzyl titanium reagent, in a suitable solvent such as, but not limited to, water, alcohols, N,N-dimethylformamide, tetrahydrofuran, dioxane, or mixture thereof, to afford an adduct of formula (3) wherein $R^2$ is allyl, alkyl, benzyl or cinnamyl. The amine function can be reacted with an aldehyde of formula $R^{102}CHO$ wherein $R^{102}$ is alkyl or aryl, or ketone of formula $R^{102}C(O)R^{103}$ wherein $R^{102}$ and $R^{103}$ are alkyl, under acidic conditions to give a cyclic protected derivative having formula (4) wherein $R^{102}$ is alkyl or aryl, and $R^{103}$ is hydrogen or alkyl. Compounds of formula (4) wherein $R^2$ is allyl can be treated with other olefinic materials under metathesis conditions and an appropriate catalyst such as, but not limited to, Grubb's catalysts or Hoveyda's catalysts, to give compounds of formula (4) wherein $R^2$ is 2-isopentenyl. Reaction of compounds of formula (4) wherein $R^2$ is alkenyl with hydrogen gas using catalysts such as palladium on carbon (Pd/C), palladium on barium sulfate (Pd/BaSO$_4$), tris(triphenylphosphine) rodium chloride (Wilkinson's catalyst), palladium hydroxide on carbon, or platinum on carbon, in a suitable solvent such as methanol, ethanol, tetrahydrofuran, dioxane or ethyl acetate provides compounds of formula (4) wherein $R^2$ is alkyl. Alternatively, the conversion can be achieved by using ammonium formate in the presence of palladium/carbon. Compounds of formula (5) can be obtained from compounds of formula (4) by (a) treatment with a mild acid; and (b) reaction of the product from step (a) with 1-12 equivalents of tris(methylthio)carbenium methylsulfate in the presence of 2 equivalents of a base such as, but not limited to, pyridine, picoline and collidine, in a solvent such as, but not limited to, dioxane or tetrahydrofuran at reflux for several hours. Examples of the mild acid that can be employed in step (a) include, but not limited to, protic acid such as trifluoroacetic acid, hydrochloric acid, sulfuric acid, nitric acid, perchloric acid, acetic acid and the like, and Lewis acids such as, but not limited to, aluminum chloride, zinc chloride, boron trifluoride etherate and the like.

The ketene dithioacetal having formula (5), can be treated with an o-aminobenzenesulfonamide of formula (6) in a solvent such as, but not limited to, dioxane, xylene, toluene, and the like, or mixtures thereof, at the refluxing temperature of the solvent used, to afford compounds of formula (7). Alternatively, compounds of formula ((3) can be directly converted to the compounds of formula (5) by treatment with tris(methylthio)carbenium methylsulfate using the reaction conditions as described above.

Scheme 2

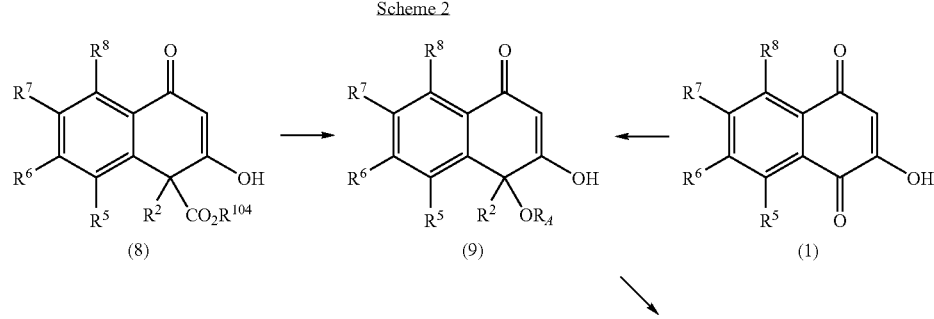

-continued

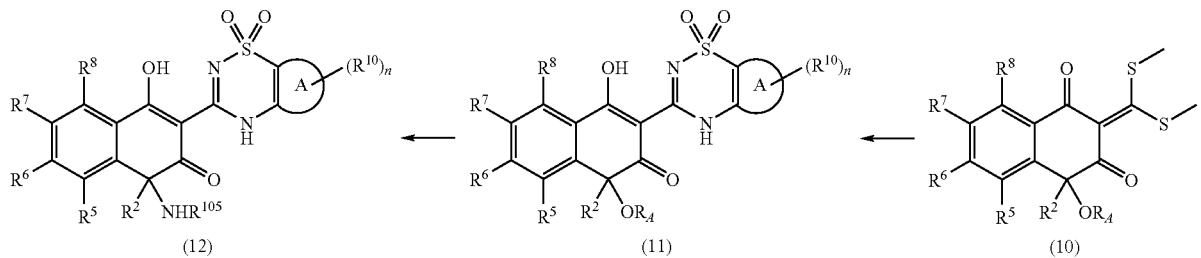

Compounds of formula (12) wherein $R^{105}$ is $R_A$, —C(O)Y or —S(O)$_2$Z, and $R_A$, Y, Z, $R^5$, $R^6$, $R^7$, $R^8$, A, n and $R^{10}$ are as defined in formula (I), can be prepared from either 2-hydroxy-1,4-naphthoquinone of formula (1) or from esters of formula (8) as depicted in Scheme 2.

Treatment of esters of formula (8) wherein $R^{104}$ is alkyl, with aqueous base such as, but not limited to, sodium hydroxide or sodium methoxide at elevated temperatures affords compounds of formula (9) wherein $R_A$ is hydrogen. Alternatively, compounds of formula (9) wherein $R_A$ is hydrogen, can be prepared from compounds of formula (1) through the addition of organometallic agents such as indium (for the case where $R^2$ is allyl) or titanium (for the case where $R^2$ is benzyl) in a solvent such as, but not limited to water or alcohols in the former case, or tetrahydrofuran or dioxane in the latter case. Compounds of formula (9) wherein $R_A$ is hydrogen can be converted to compounds of formula (11) wherein $R_A$ is hydrogen by (a) treatment with 1-12 equivalents of tris(methylthio) carbenium methylsulfate in the presence of 2 equivalents of a base such as, but not limited to, pyridine, picoline and collidine; and (b) treatment of the product of step (a) with an o-aminobenzenesulfonamide of formula (6); using the conditions employed for the transformation of compounds of formula (4) to compounds of formula (7) as described in Scheme 1. Compounds of formula (11) can be treated with nitriles such as acetonitril, benzonitrile, chloroacetonitrile, and the like, in the presence of concentrated sulfuric acid with heating to provide compounds of formula (12) wherein $R^{105}$ is —C(O)$R_A$ and $R_A$ is aryl, alkyl or haloalkyl. Compounds of formula (12) wherein $R^{105}$ is hydrogen can be obtained by acidic hydrolysis of compounds of formula (12) wherein $R^{105}$ is —C(O)$R_A$ and $R_A$ is aryl or alkyl with 4M HCl at reflux. Compounds of formula (12) wherein $R^{105}$ is —S(O)$_2$Z wherein Z is as defined in formula (I) can be obtained from compounds of formula (12) wherein $R^{105}$ is hydrogen using sulfonation reaction conditions well known in the art. Similaryl, compounds of formula (12) wherein $R^{105}$ is —C(O)Y or $R_A$ wherein Y and $R_A$ are as defined in formula (I) can be obtained from compounds of formula (I) wherein $R^{105}$ is hydrogen through methodologies such as, but not limited to, acylation, carbamylation and reductive amination well known to one skilled in the art.

Scheme 3

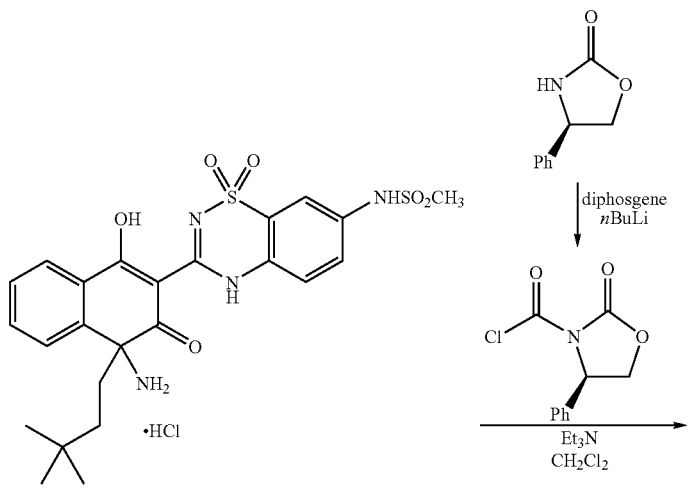

-continued
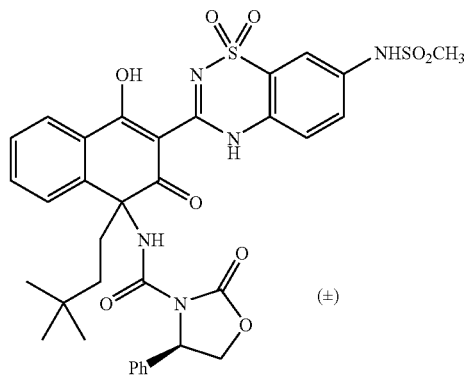
Biotage
Flash 65
step gradient
(0.5% to 5% MeOH/CH$_2$Cl$_2$)
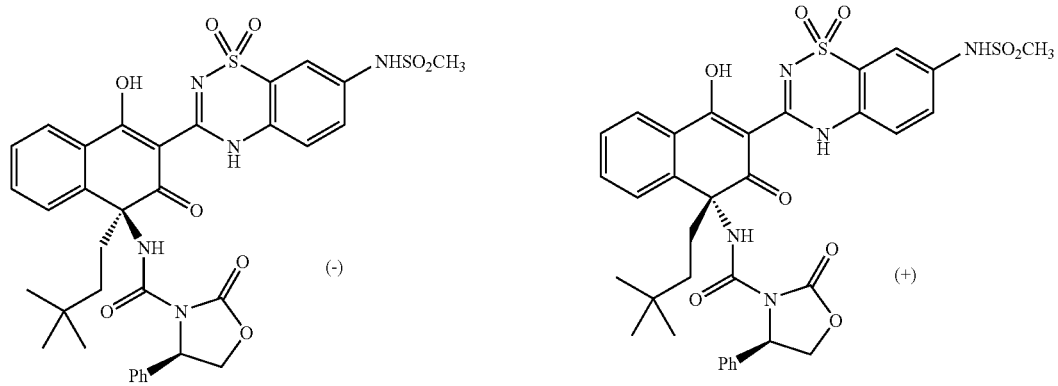
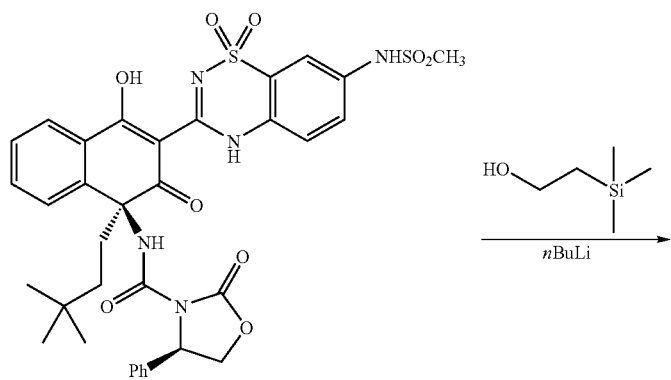

-continued

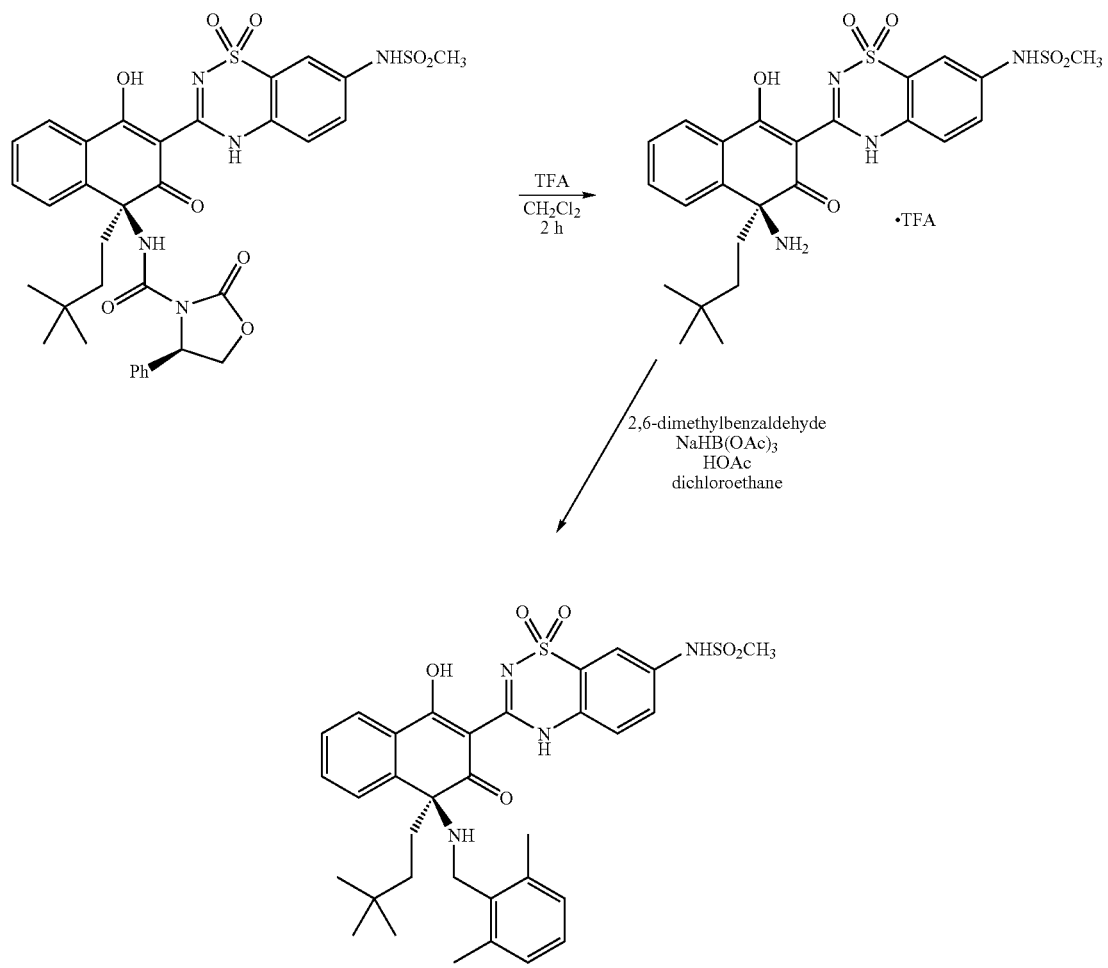

Scheme 3 shows how one skilled in the arts can resolve chiral compounds. Scheme 3 is not intended to be limited to the specific compounds disclosed in the Scheme.

The present invention will now be described in connection with certain preferred embodiments which are not intended to limit its scope. On the contrary, the present invention covers all alternatives, modifications, and equivalents as can be included within the scope of the claims. Routine experimentation, including appropriate manipulation and protection of any chemical functionality, synthesis of the compounds of formula (I) or (II) may be aaccomplished by methods analogous to those described above and in the following examples. Thus, the following examples, which include preferred embodiments, will illustrate the preferred practice of the present invention, it being understood that the examples are for the purpose of illustration of certain preferred embodiments and are presented to provide what is believed to be the most useful and readily understood description of its procedures and conceptual aspects.

Compounds of the invention were named by ACD/ChemSketch version 5.06 (developed by Advanced Chemistry Development, Inc., Toronto, ON, Canada) or were given names consistent with ACD nomenclature.

EXAMPLE 1

N-[3-(4-butyl-1,4-dihydroxy-3-oxo-3,4-dihydronaphthalen-2-yl)-1,1-dioxido-4H-1,2,4-benzothiadiazin-7-yl]methanesulfonamide

EXAMPLE 1A methyl 1-butyl-2-methoxy-1,4-dihydronaphthalene-1-carboxylate

To a stirred solution of methyl 2-methoxynaphthoate (3.25 g, 15 mmol) and tert-butyl alcohol (1.48 ml, 15 mmol) in tetrahydrofuran (10 mL) at −78° C. was added liquid ammonia (60 mL). Potassium metal (2.9 g, 75 mmol) was added in small pieces until the solution stayed dark blue for 30 min. Butyl iodide (5.47 mL, 48 mmol) was added dropwise (the blue coloration disappeared about half-way through addition) and stirring was continued for 1 hour at −78° C. The solution was allowed to warm to room temperature and purged with nitrogen to remove excess ammonia. To the resulting slurry a solution of saturated sodium bicarbonate (100 mL) was added, and the solution was extracted with ether (3×50 mL). The combined organic phases were washed with 10% $Na_2S_2O_3$ (aq), dried ($Na_2SO_4$), and concentrated in vacuo.

Column chromatography on silica (20% ethyl acetate/hexane) gave the title compound as a light yellow oil. This oil was triturated with hexane to afford a white solid (3.2 g, 77.6%).
$^1$H NMR (300 MHz, CDCl$_3$) δ ppm 0.63 (m, 1H), 0.76 (t, J=7.35 Hz, 3H), 0.99 (m, 1H), 1.18 (m, 2H), 2.04 (m, 1H), 2.26 (m, 1H), 3.55 (d, J=3.68 Hz, 2H), 3.61 (s, 3H), 3.63 (s, 3H), 5.05 (t, J=3.68 Hz, 1H), 7.16 (m, 4H); MS (ESI) m/z 275.1 (M+H)$^+$.

EXAMPLE 1B methyl 1-butyl-2-methoxy-4-oxo-1,4-dihydronaphthalene-1-carboxylate A mixture of Example 1A (1.7 g, 6.2 mmol) and pyridinium dichromate (6.8g, 15.5 mmol) in chloroform (60 mL) was heated at reflux with a Dean-Stark trap for 18 h. The reaction mixture was cooled to room temperature and filtered through celite. The filtrate was concentrated in vacuo. Column chromatography on silica (20% ethyl acetate/hexane) afforded the title compound as a white solid (1.1 g, 61.6%). $^1$H NMR (300 MHz, CDCl$_3$) δ ppm 0.52 (m, 1H), 0.73 (t, J=7.35 Hz, 3H), 0.83 (dd, J=12.13, 6.62 Hz, 1H), 1.15 (m, 2H), 2.36 (m, 2H), 3.61 (s, 3H), 3.83 (s, 3H), 5.96 (s, 1H), 7.39 (d, J=7.72 Hz, 1H), 7.44 (t, J=7.35 Hz, 1H), 7.55 (m, 1H), 8.19 (d, J=8.09 Hz, 1H); MS(ESI) m/z 289.0 (M+H)$^+$.

EXAMPLE 1C methyl 1-butyl-2,4-dioxo-1,2,3,4-tetrahydronaphtalene-1-carboxylate To a solution of Example 1B (1 g, 3.5 mmol) in acetonitrile (5 mL) was added iodotrimethylsilane (TMSI) (0.7 mL, 5.2 mmol). The reaction solution was stirred at room temperature for 1 h. The reaction mixture was concentrated in vacuo. Column chromatography on silica (ethyl acetate) afforded the title compound as a white solid (0.88 g, 92%). $^1$H NMR (300 MHz, DMSO-d$_6$) δ ppm 0.47 (m, 1H), 0.68 (t, J=7.35 Hz, 3H), 0.85 (dd, J=12.32, 7.17 Hz, 1H), 1.11 (m, 2H), 2.14 (m, 1H), 2.29 (m, 1H), 3.51 (s, 3H), 5.74 (m, 1H), 7.31 (m, 1H), 7.49 (m, 1H), 7.58 (t, J=7.17 Hz, 1H), 7.93 (d, J=7.35 Hz, 1H), 12.11 (s, 1H); MS(ESI) m/z 275.0 (M+H)$^+$.

EXAMPLE 1D

[bis(methylsulfanyl)methylene](methyl)sulfonium methyl sulfate

Dimethyl trithiocarbonate (2.76 g, 20 mmol) was treated with dimethyl sulfate (2.5 g, 20 mmol) and stirred at 90° C. for 1 h, and cooled to 25° C. The solid was broken up under ether, collected by filtration, and washed with ether to give the title compound (5.1 g, 91%).

EXAMPLE 1E methyl 3-[bis(methylthio)methylene]-1-butyl-2,4-dioxo-1,2,3,4-tetrahydronaphthalene-1-carboxylate To a solution of Example 1C (0.88 g, 3.2 mmol) in dioxane (10 mL) was added Example 1D (2.76 g, 11.2 mmol) followed by pyridine (1.29 mL, 16 mmol). The heterogeneous solution was heated at 55° C. for 3 h. The solution was cooled to room temperature and concentrated in vacuo. Column chromatography on silica (30% ethyl acetate/hexane) afforded the title compound as an orange oil (1.08 g, 90%). $^1$H NMR (300 MHz, DMSO-d$_6$) δ ppm 0.59 (m, 1H), 0.68 (t, J=7.17 Hz, 3H), 0.80 (m, 1H), 1.12 (m, 2H), 2.13 (m, 1H), 2.35 (m, 1H), 2.61 (m, 3H), 3.55 (m, 3H), 7.25 (d, J=6.99 Hz, 1H), 7.51 (t, J=6.99 Hz, 1H), 7.65 (m, 1H)); MS(ESI) m/z 379.1 (M+H)$^+$.

EXAMPLE 1F 2-amino-4-[(methylsulfonyl)amino]-benzenesulfonamide 2,5-Diamino-benzenesulfonamide (288 mg, 1.5 mol, prepared according to the procedure as described in Goldfarb A. R. et. al., *J. Amer. Chem. Soc.* 1943, 65, 738) in dichloromethane (5 mL) and pyridine (5 mL) at 0° C. was treated dropwise with methanesulfonyl chloride (119 μL, 1.5 mmol) over 3 minutes. The reaction mixture was warmed to 25° C. and stirred for 18 hours and concentrated under reduced pressure. The residue was chromatographed on silica gel, eluting with methanol in dichloromethane to yield the title compound (68% yield). $^1$H NMR (300 MHz, DMSO-d$_6$): δ 9.21 (m, 1H), 7.45 (d, J=2.57 Hz, 1H), 7.29 (s, 2H), 7.13 (dd, J=8.64, 2.39 Hz, 1H), 6.78 (d, J=8.82 Hz, 1H), 5.80 (s, 1H), 3.39 (s, 1H), 2.87 (s, 3H).

EXAMPLE 1G methyl 1-butyl-4-hydroxy-3-{7-[(methylsulfonyl)amino]-1,1-dioxido-4H-1,2,4-benzothiadiazin-3-yl}-2-oxo-1,2-dihydronaphthalene-1-carboxylate A mixture of Example 1E (1 g, 2.64 mmol) and Example 1F (0.596 g, 2.24 mmol) in dioxane (12 mL) was heated at 85° C. for 18 h. The solution was cooled to room temperature and concentrated in vacuo. The resulting oil was triturated with hexane, filtered, washed with diethyl ether to afford a white solid (0.99 g, 81%). $^1$H NMR (300 MHz, DMSO-d$_6$) δ ppm 0.54 (m, 1H), 0.68 (t, J=7.17 Hz, 3H), 0.98 (m, 1H), 1.09 (m, 2H), 2.14 (m, 1H), 2.41 (m, 1H), 3.04 (s, 3H), 3.55 (m, 3H), 7.26 (d, J=7.72 Hz, 1H), 7.51 (m, 4H), 7.60 (m, 1H), 8.13 (m, 1H), 10.09 (s, 1H), 14.07 (s, 1H); MS(ESI) m/z 548.1 (M+H)$^+$.

EXAMPLE 1H

N-[3-(4-butyl-1,4-dihydroxy-3-oxo-3,4-dihydronaphthalen-2-yl)-1,1-dioxido-4H-1,2,4-benzothiadiazin-7-yl]methanesulfonamide A mixture of Example 1G (0.3 g, 0.55 mmol) in 30% weight sodium methoxide in methanol (3 mL) was stirred at 25° C. for 24 h. The solution was quenched with saturated NH$_4$Cl, and extracted with ethyl acetate. The organic extract was concentrated in vacuo, extracted with ethyl acetate, and the organic layer was concentrated in vacuo. Column chromatography on silica (4% methanol/ethyl acetate) afforded the title compound as a white solid (0.095 g, 28.8%). $^1$H NMR (300 MHz, DMSO-d$_6$) δ ppm 0.72 (m, 3H), 0.95-1.29 (m, 5H), 1.63 (m, 2H), 2.99 (s, 3H), 4.95 (s, 1H), 7.17-7.59 (m, 8H), 7.93 (d, J=7.35 Hz, 1H), 9.89 (s, 1H); MS(ESI) m/z 504.1 (M+H)$^+$.

EXAMPLE 2

N-{3-[1,4-dihydroxy-4-(3-methylbutyl)-3-oxo-3,4-dihydronaphthalen-2-yl]-1,1-dioxido-4H-1,2,4-benzothiadiazin-7-yl}methanesulfonamide

EXAMPLE 2A methyl 2-methoxy-1-(3-methylbutyl)-1,4-dihydronaphthalene-1-carboxylate To a stirred solution of methyl 2-methoxynaphthoate (1.0 g, 4.6 mmol) and tert-butyl alcohol (0.44 ml, 4.6 mmol) at −78° C. was added liquid ammonia (20 mL). Potassium metal was added in small pieces until the solution stayed dark blue for 30 min. Isoamyl iodide (1.9 mL, 14.8 mmol) was added dropwise (the blue coloration disappeared about half-way through addition) and stirring was continued for 1 hour at −78° C. The solution was allowed to warm to room temperature and purged with nitrogen to remove excess ammonia. To the resulting slurry a solution of saturated sodium bicarbonate (100 mL) was added, and the solution was extracted with ether (3×50 mL). The combined organic phases were washed with 10% $Na_2S_2O_3$ (aq), dried ($Na_2SO_4$), and concentrated in vacuo. Column chromatography on silica (5%→15% ethyl acetate/hexane) afforded the title compound as a light yellow oil (1.1 g, 85%). $^1$H NMR (300 MHz, $CDCl_3$) δ ppm 0.55 (m, 1H), 0.75 (dd, J=14.71, 6.62 Hz, 6H), 0.88 (m, 1H), 1.39 (m, 1H), 2.06 (m, 1H), 2.27 (m, 1H), 3.55 (d, J=3.31 Hz, 2H), 3.60 (s, 3H), 3.61 (s, 3H), 5.05 (t, J=3.68 Hz, 1H), 7.16 (m, 4H); MS m/z 289.0 $(M+H)^+$.

EXAMPLE 2B methyl 2-methoxy-1-(3-methylbutyl)-4-oxo-1,4-dihydronaphthalene-1-carboxylate A mixture of Example 2A (0.3g, 1.0 mmol) and pyridinium dichromate (0.98 g, 2.6 mmol) in chloroform (20 mL) was heated at reflux with a Dean-Stark trap for 18 h. The reaction mixture was cooled to room temperature and filtered through celite. The filtrate was concentrated in vacuo. Column chromatography on silica (5% →15% ethyl acetate/hexane) afforded the title compound as a white solid (0.18 g, 58%). $^1$H NMR (300 MHz, $CDCl_3$) δ ppm 0.40(m, 1H), 0.72 (m, 7H), 1.37(m, 1H), 2.36(m, 2H), 3.61 (s, 3H), 3.83(s, 3H), 5.96 (s, 1H), 7.42 (m, 2H), 7.56 (m, 1H), 8.19 (d, J=7.72 Hz, 1H); MS m/z 303.1 $(M+H)^+$.

EXAMPLE 2C methyl 1-(3-methylbutyl)-2,4-dioxo-1,2,3,4-tetrahydronaphthalene-1-carboxylate To a solution of Example 2B (0.18g, 6 mmol) in acetonitrile (2 mL) was added iodotrimethylsilane (TMSI) (0.13 mL, 0.9 mmol). The reaction solution was stirred at room temperature for 3 h. Afterwhich, additional 1.5 equivalents of TMSI (0.13 mL) were added and stirring was continued for 2 h. The solution was quenched with water (5 mL) and extracted with ethyl acetate (2×5 mL). The combined organic extracts were dried ($Na_2SO_4$) and concentrated in vacuo. Column chromatography on silica (40% →80% ethyl acetate/hexane) afforded the title compound as a white solid (0.11 g, 65%). $^1$H NMR (300 MHz, $CDCl_3$) δ ppm 0.46 (m, 1H), 0.79 (m, 7H), 1.41 (m, 1H), 2.29 (m, 1H), 2.53 (m, 1H), 3.60 (s, 3H), 3.83 (m, 1H), 6.11 (s, 1H), 7.52 (m, 3H), 8.12 (d, J=7.72 Hz, 1H); MS m/z 289.0 $(M+H)^+$.

EXAMPLE 2D 4-hydroxy-4-(3-methylbutyl)naphthalene-1,3(2H,4H)-dione

A solution of Example 2C (1 g, 3.47 mmol) in 1 N NaOH (20.8 mL) was stirred at 40° C. for 4 days. The solution was neutralized to pH 7 with 1 N HCl, extracted with ethyl acetate, and the organic layer was concentrated in vacuo. Column chromatography on silica (7% methanol/dichloromethane) afforded the title compound as a white solid (0.54 g, 63.2%). $^1$H NMR (300 MHz, DMSO-$d_6$) δ ppm 0.48 (s, 1H), 0.68 (dd, J=11.03, 6.62 Hz, 6H), 0.77-1.03 (m, 1H), 1.12-1.36 (m, 1H), 1.75 (m, 1H), 1.90-2.07 (m, 1H), 5.55 (s, 1H), 5.72 (s, 1H), 7.40 (t, 1H), 7.57 (t, J=7.54 Hz, 1H), 7.65 (d, 1H), 7.82 (d, J=7.72 Hz, 1H), 11.22-11.84 (m, 1H); MS (ESI) m/z 247.0 $(M+H)^+$.

EXAMPLE 2E

2-[bis(methylthio)methylene]-4-hydroxy-4-(3-methylbutyl)naphthalene-1,3(2H,4H)-dione To a solution of Example 2D (0.25 g, 1.01 mmol) in dioxane (3 mL) was added Example 1D (0.875 g, 3.54 mmol) followed by pyridine (0.41 mL, 5.05 mmol). The heterogeneous solution was heated at 55° C. for 2 h. The solution was cooled to room temperature and concentrated in vacuo. Column chromatography on silica (20% ethyl acetate/hexane) afforded the title compound as a yellow oil (0.26 g, 73%). $^1$H NMR (300 MHz, DMSO-$d_6$) δ ppm 0.70 (d, J=6.62 Hz, 6H), 0.85-1.12 (m, 2H), 1.18-1.41 (m, 1H), 1.60-1.87 (m, 2H), 2.54-2.65 (m, 6H), 5.76 (s, 1H), 7.37-7.53 (m, 1H), 7.56-7.76 (m, 2H), 7.96 (d, J=7.72 Hz, 1H); MS (ESI) m/z 350.9 $(M+H)^+$.

EXAMPLE 2F

N-{3-[1,4-dihydroxy-4-(3-methylbutyl)-3-oxo-3,4-dihydronaphthalen-2-yl]-1,1-dioxido-4H-1,2,4-benzothiadiazin-7-yl}methanesulfonamide A mixture of Example 2E (0.26 g, 0.74 mmol) and Example 1F (0.177g, 0.67 mmol) in dioxane (2 mL) was heated at 85° C. for 18 h. The solution was cooled to room temperature and concentrated in vacuo. The resulted oil was triturated with 50% ethyl acetate/hexane and the white solid precipitate was filtered to give the title compound (0.28 g, 84%). $^1$H NMR (300 MHz, DMSO-$d_6$) δ ppm 14.05 (br s, 1H), 10.03 (s, 1H), 7.98 (d, J=8.1 Hz, 1H), 7.38-7.66 (m, 6H), 3.03 (s, 3H), 1.64-1.91 (m, 2H), 1.20-1.39 (m, 1H), 0.94-1.10 (m, 1H), 0.80-0.93 (m, 1H), 0.64-0.78 (m, 6H).

EXAMPLE 3

N-{3-[(4S)-1,4-dihydroxy-4-(3-methylbutyl)-3-oxo-3,4-dihydronaphthalen-2-yl]-1,1-dioxido-4H-1,2,4-benzothiadiazin-7-yl}methanesulfonamide The product from Example 2F (175 mg) was separated by chiral HPLC (Chiralpak AS using hexanes/ethanol/methanol/trifluoroacetic acid =70/15/1510.1%) to give the title compound as a light yellow solid (87 mg): $^1$H NMR (300 MHz, DMSO-$d_6$) δ ppm 13.68 (br s, 1H), 10.09 (s, 1H), 8.00 (d, J=8.5 Hz, 1H), 7.39-7.75 (m, 6H), 3.04 (s, 3H), 1.67-1.97 (m, 2H), 1.20-1.40 (m, 1H), 0.91-1.07 (m, 1H), 0.74-0.87 (m, 1H), 0.66-0.74 (m, 6H).

EXAMPLE 4

N-{3-[(4R)-1,4-dihydroxy-4-(3-methylbutyl)-3-oxo-3,4-dihydronaphthalen-2-yl]-1,1-dioxido-4H-1,2,4-benzothiadiazin-7-yl}methanesulfonamide The product from Example 2F (175 mg) was separated by chiral HPLC (Chiralpak AS using hexanes/ethanol/methanol/trifluoroacetic acid =70/15/15/0.1%) to give the title compound as a light yellow solid (84 mg). $^1$H NMR (300 MHz, DMSO-d$_6$) δ ppm 13.68 (br s, 1H), 10.09 (s, 1H), 8.00 (d, J=8.5 Hz, 1H), 7.39-7.75 (m, 6H), 3.04 (s, 3H), 1.67-1.97 (m, 2H), 1.20-1.40 (m, 1H), 0.91-1.07 (m, 1H), 0.74-0.87 (m, 1H), 0.66-0.74 (m, 6H).

EXAMPLE 5

N-(3-{11,4-dihydroxy-3-oxo-4-[(2E)-3-phenylprop-2-enyl]-3,4-dihydronaphthalen-2-yl}-1,1-dioxido-4H-1,2,4-benzothiadiazin-7-yl)methanesulfonamide

EXAMPLE 5A 1,4-dihydroxy-1-[(2E)-3-phenylprop-2-enyl]naphthalen-2(1H)-one

Cinnamyl bromide (0.43 g, 2.2 mmol) was added to a suspension of indium metal (0.17 g, 1.5 mmol) in N,N-dimethylformamide (1 mL) at 25° C. for 0.5 h causing dissolution of the metal. 2-Hydroxy-1,4-naphthoquinone (0.25 g, 1.5 mmol) was dissolved in N,N-dimethylformamide (1 mL) and added to the mixture. After 0.5 h the mixture was partitioned between 1% HCl and ethyl acetate. The orgamic layer was separated, washed with water, brine, dried over sodium sulfate and the solvents were evaporated. The crude residue was purified using BioTage 12L column and 5% methanol/dichloromethane to give the title compound (40 mg, 10% yield).

EXAMPLE 5B

2-[bis(methylthio)methylene]-4-hydroxy-4-[(2E)-3-phenylprop-2-enyl]naphthalene-1,3(2H,4H)-dione Example 5A (40 mg, 0.137 mmol) was dissolved in dioxane (5 mL) and pyridine (55 uL, 0.69 mmol) and treated with Example 1D (84 mg, 0.41 mmol) at 60° C. for 2 h. The mixture was cooled, the solvents were evaporated, and the crude residue was purified via BioTage 12L using ethyl acetate:hexane (2:3) to give the title compound (30 mg, 55%) as a yellow oil.

EXAMPLE 5C

N-(3-{1,4-dihydroxy-3-oxo-4-[(2E)-3-phenylprop-2-enyl]-3,4-dihydronaphthalen-2-yl}-1,1-dioxido-4H-1,2,4-benzothiadiazin-7-yl)methanesulfonamide Example 5B (0.1 g, 0.25 mmol) was dissolved in dioxane (8 mL) and treated with Example 1F (67 mg, 0.25 mmol) at 100° C. for 5 h. The solvents were evaporated and the crude residue was purified via BioTage 40S using 10% methanol/dichloromethane to give the title compound (65 mg, 46%).

EXAMPLE 6

N-[3-(4-benzyl-1,4-dihydroxy-3-oxo-3,4-dihydronaphthalen-2-yl)-1,1-dioxido-4H-1,2,4-benzothiadiazin-7-yl]methanesulfonamide

EXAMPLE 6A 1-benzyl-1,4-dihydroxynaphthalen-2(1H)-one

A suspension of indium powder (529 mg, 4.60 mmol) in anhydrous N,N-dimethylformamide (4.6 mL) at 25° C. was treated dropwise with benzyl bromide (1.18 g, 820 μL, 6.90 mmol). After addition, the mixture became warm, and after stirring for 2 h, most of the indium was consumed. The solution was cooled to 0° C. and a cold (0° C.) solution of 2-hydroxy-1,4-naphthoquinone (200 mg, 1.15 mmol) in N,N-dimethylformamide (2 mL) was added via cannula. The orange solution was stirred at 0° C. for 3 h, and then allowed to warm to ambient temperature for 18 h. The pale yellow solution was treated with saturated ammonium chloride solution and diluted with ethyl acetate. The mixture was stirred with saturated sodium potassium tartarate solution until most solids had dissolved. The layers were separated and the organic layer was extracted with water (4×) and saturated NaCl solution. Drying (Na$_2$SO$_4$), filtering and concentration in vacuo afforded an oil, which was purified by flash chromatography, eluting with methanol in dichloromethane. These procedures afforded the title compound (181 mg, 68%) as a light yellow oil. $^1$H NMR (300 MHz, CDCl$_3$): δ 8.10-6.75 (m, 9H), 4.70 (s, 2H), 4.15 (s, 1H), 3.85 (d, J=19.12 Hz, 1H), 3.70 (d, J=19.12 Hz, 1H).

EXAMPLE 6B 4-benzyl-2-[bis(methylthio)methylene]-4-hydroxynaphthalen-1,3(2H,4h)-dione A solution of the compound of Example 6A (165 mg, 0.62 mmol) and pyridine (490 mg, 501 μL, 6.20 mmol) in anhydrous dioxane (6 mL) was treated with the Example 1D (655 mg, 2.48 mmol) followed by warming at 1001C for 2 h. The solution was cooled and diluted with ethyl acetate. The solution was extracted with water (2×) and with saturated NaCl solution. Drying (Na$_2$SO$_4$), filtering and concentration in vacuo afforded an orange oil which was purified by flash chromatography eluting with ethyl acetate in hexane. These procedures afforded the title compound (84 mg, 37%) as a yellow solid. $^1$H NMR (300 MHz, CDCl$_3$): δ 8.07 (d, J=7.72 Hz, 1H), 7.48 (m, 3H), 7.14 (m, 3H), 6.73 (d, J=7.72 Hz, 2H), 4.39 (s, 1H), 3.09 (s, 2H), 2.52 (s, 6H).

EXAMPLE 6C

N-[3-(4-benzyl-1,4-dihydroxy-3-oxo-3,4-dihydronaphthalen-2-yl)-1,1-dioxido-4H-1,2,4-benzothiadiazin-7-yl]methanesulfonamide A solution of the compound of Example 6B (77 mg, 0.21 mmol) and the compound of Example 1F (55 mg, 0.21 mmol) in anhydrous dioxane (2 mL) was warmed at reflux for 18 h. The solution was cooled and concentrated in vacuo to afford an orange oil, which was purified by flash chromatography eluting with methanol in dichloromethane. These procedures afforded the title compound (70 mg, 63%) as a light orange solid. $^1$H NMR (300 MHz, CDCl$_3$): δ 14.76 (s, 1H), 9.92 (s, 1H), 7.91 (dd, J=5.88, 2.94 Hz, 1H), 7.22-7.61 (m, 5H), 6.88-7.25 (m, 3H), 6.76 (m, 2H), 3.01 (s, 3H), 2.99 (d, J=12.87 Hz, 1H), 2.93 (d, J=12.87 Hz, 1H).

EXAMPLE 7

N-{3-[4-allyl-1-hydroxy-4-(methoxyamino)-3-oxo-3,4-dihydronaphthalen-2-yl]-1,1-dioxido-4H-1,2,4-benzothiadiazin-7-yl}methanesulfonamide

EXAMPLE 7A 2-hydroxynaphthoquinone 1-(O-methyloxime)

2-Hydroxy-1,4-naphthoquinone (3 g, 17 mmol) was dissolved in ethanol (30 mL) and aqueous sodium hydroxide (1N, 51 mL, 51 mmol) and treated with methoxyamine hydrochloride (2.86 g, 34 mmol) at 80° C. for 5 h. The mixture was cooled, the solvents were evaporated, and the crude mixture was acidified using 10% HCl (20 mL). The solids were filtered, rinsed with water, and dried in the vacuum to give the title compound (3.26 g, 93%).

EXAMPLE 7B 4-allyl-3-hydroxy-4-(methoxyamino)naphthalen-1(4H)-one

To a suspension of indium powder (0.68 g, 5.9 mmol) in anhydrous N,N-dimethylformamide (2 mL) at 0° C. was added allylbromide (0.76 mL, 8.8 mmol) dropwise over 5 min. The cooling bath was removed and the resulting exothermic reaction was allowed to stir for several minutes, during which time the indium metal dissolved. The resulting solution was cooled to 0° C., and a solution of Example 7A (1.00 g, 4.9 mmol) in anhydrous N,N-dimethylformamide (8 mL) was added. The resulting solution was allowed to warm to rt and stirred 1 h. The reaction mixture was partitioned between $H_2O$ (50 mL) and ethyl acetate (3×50 mL), and the combined organic layers were dried over $Na_2SO_4$. The solution was filtered and concentrated, and the product was precipitated from diethyl ether to provide the title compound as a light tan powder (0.99 g, 82%). $^1H$ NMR (300 MHz, DMSO-$d_6$) δ ppm 11.84 (s, 1H), 7.85 (d, J=7.7 Hz, 2H), 7.60 (t, J=7.4 Hz, 1H), 7.32-7.48 (m, 1H), 7.14 (br s, 1H), 5.68 (br s, 1H), 5.09 (m, 1H), 4.64-4.81 (m, 2H), 3.11 (s, 3H), 2.20-2.45 (m, 2H).

EXAMPLE 7C 4-allyl-2-[bis(methylthio)methylene]-4-(methoxyamino)naphthalene-1,3(2H,4H)-dione Example 7B (20 mg, 0.082 mmol) was dissolved in dioxane (4 mL) and pyridine (53 μL, 0.66 mmol) and treated with Example 1D (67 mg, 0.33 mmol) at 60° C. for 2 h. The solvents were evaporated, and the crude residue was purified using preparative plate (0.5 mm) silica gel chromatography using dichloromethane to give the title compound (15.4 mg, 54%).

EXAMPLE 7D

N-{3-[4-allyl-1 hydroxy-4-(methoxyamino)-3-oxo-3,4-dihydronaphthalen-2-yl]-1,1-dioxido-4H-1,2,4-benzothiadiazin-7-yl}methanesulfonamide Example 7C (15 mg, 0.043 mmol) was dissolved in dioxane (4 mL) and treated with Example 1F (10 mg, 0.038 mmol) at 100° C. for 5 h. The solvents were evaporated, and the crude residue was purified via using preparative plate (0.5 mm) silica gel chromatography using 6% methanol/dichloromethane to give the title compound (8 mg, 41%).

EXAMPLE 8

N-{3-[4-(3,3-dimethylbutyl)-1,4-dihydroxy-3-oxo-3,4-dihydronaphthalen-2-yl]-1,1-dioxido-4H-1,2,4-benzothiadiazin-7-yl}methanesulfonamide

EXAMPLE 8A methyl 1-(3,3-dimethylbutyl)-2-methoxy-1,4-dihydronaphthalene-1-carboxylate To a solution of methyl 2-methoxy-naphthoate (1.00 g, 4.6 mmol) and tert-butyl alcohol (0.43 mL, 4.6 mmol) in anhydrous tetrahydrofuran (10 mL) at −78° C. under $N_2$ was added anhydrous ammonia (~20 mL), followed by the portionwise addition of potassium metal until a dark blue solution was maintained for >15 min. To the resulting mixture was added neohexyl iodide (0.5 g, 2.36 mmol), the mixture was stirred at −78° C. for 20 min, and then allowed to slowly warm to rt while evaporating the ammonia with a dry $N_2$ stream. To the resulting suspension was added anhydrous tetrahydrofuran (10 mL), and the mixture was heated at 50° C. under $N_2$ for 16 h. The reaction mixture was partitioned between saturated aq. $NaHCO_3$ (20 mL) and ethyl acetate (3×20 mL), and the combined organic layers were dried over $Na_2SO_4$. The crude product was purified by column chromatography on silica gel using 19:1 hexanes:ethyl acetate to provide the title compound as a colorless gum (0.32 g, 23%). $^1H$ NMR (300 MHz, $CDCl_3$) δ ppm 7.11-7.23 (m, 4H), 5.06 (t, J=3.9 Hz, 1H), 3.61 (s, 3H), 3.60 (s, 3H), 3.54-3.57 (m, 2H), 2.20-2.31 (m, 1H), 2.00-2.11 (m, 1H), 0.82-0.94 (m, 1H), 0.75 (s, 9H), 0.45-0.57 (m, 1H).

EXAMPLE 8B methyl 1-(3,3-dimethylbutyl)-2-methoxy-4-oxo-1,4-dihydronaphthalene-1-carboxylate A suspension of Example 8A (0.45g, 1.48 mmol), pyridinium dichromate (2.4 g, 5.92 mmol), celite (0.53 g), 70% t-BuOOH/water (0.82 mL, 5.92 mmol) in benzene (11 mL) was stirred at 25° C. for 2 h. The benzene layer was separated and the mixture was extracted with ethyl acetate. The combined organic layers were concentrated in vacuo. Column chromatography on silica (5%→15% ethyl acetate/hexane) afforded the title compound (0.32 g, 67%). $^1H$ NMR (300 MHz, DMSO-$d_6$) δ ppm 0.17-0.41 (m, 1H), 0.60-0.81 (m, 10H), 2.16-2.36 (m, 2H), 3.56 (s, 3H), 3.84 (s, 3H), 6.04 (s, 1H), 7.41 (d, J=7.72 Hz, 1H), 7.51 (t, J=6.99 Hz, 1H), 7.60-7.75 (m, 1H), 7.89-8.09 (m, 1H)); MS (ESI) m/z 316.9 $(M+H)^+$.

EXAMPLE 8C methyl 1-(3,3-dimethylbutyl)-2,4-dioxo-1,2,3,4-tetrahydronaphthalene-1-carboxylate To a solution of Example 8B (0.31g, 0.98 mmol) in acetonitrile (0.2 mL) was added iodotrimethylsilane (TMSI) (1 mL, 6.86 mmol). The reaction solution was stirred at room temperature for 4 h. The solution was concentrated in vacuo. Column chromatography on silica (50% ethyl acetate/hexane) afforded the title compound as a white solid (0.28g, 95%).

¹H NMR (300 MHz, DMSO-d₆) δ ppm 0.20-0.46 (m, 1H), 0.54-0.99 (m, 10H), 2.02-2.39 (m, 2H), 3.51 (s, 3H), 5.76 (s, 1H), 7.32 (s, 1H), 7.46 (t, J=7.54 Hz, 1H), 7.58 (s, 1H), 7.92 (s, 1H), 12.12 (s, 1H); MS (ESI) m/z 302.9 (M+H)⁺.

EXAMPLE 8D 4-(3,3-dimethylbutyl)-4-hydroxynaphthalene-1,3 (2H,4H)-dione

A solution of Example 8C (0.28 g, 0.93 mmol) in 1 N NaOH (11.2 mL) was stirred at 45° C. for 2 days. The solution was neutralized to PH 3 with 1 N HCl, extracted with ethyl acetate, and the organic layer was concentrated in vacuo. Column chromatography on silica (7% methanol/dichloromethane) afforded the title compound as a white solid (0.135 g, 56%).
¹H NMR (300 MHz, DMSO-d₆) δ ppm 0.47 (m, 1H), 0.68 (s, 9H), 0.74-0.98 (m, 1H), 1.60-2.07 (m, 2H), 4.08 (s, 1H), 5.47 (s, 1H), 7.37 (t, J=7.54 Hz, 1H), 7.54 (t, J=6.80 Hz, 1H), 7.62 (d, 1H), 7.73-7.87 (d, 1H); MS (ESI) m/z 260.8 (M+H)⁺.

EXAMPLE 8E

2-[bis(methylthio)methylene]-4-(3,3-dimethylbutyl)-4-hydroxynaphthalene-1,3(2H,4H)-dione To a solution of Example 8D (0.13 g, 0.5 mmol) in dioxane (2 mL) was added Example 1D (0.431 g, 1.75 mmol) followed by pyridine (0.2 mL, 2.5 mmol). The heterogeneous solution was heated at 55° C. for 2 h. The solution was cooled to room temperature and concentrated in vacuo. Column chromatography on silica (15% ethyl acetate/hexane) afforded the title compound as a yellow oil (0.178 g, 98%). ¹H NMR (300 MHz, DMSO-d₆) δ ppm 0.69 (s, 9H), 0.83-0.98 (m, 1H), 0.98-1.21 (m, 1H), 1.53-1.89 (m, 2H), 2.59 (s, 6H), 5.77 (s, 1H), 7.38-7.58 (m, 1H), 7.56-7.77 (m, 2H), 7.96 (d, J=7.35 Hz, 1H), MS (ESI) m/z 365.1 (M+H)⁺.

EXAMPLE 8F

N-{3-[4-(3,3-dimethylbutyl)-1,4-dihydroxy-3-oxo-3,4-dihydronaphthalen-2-yl]-1,1-dioxido-4H-1,2,4-benzothiadiazin-7-yl}methanesulfonamide A mixture of Example 8E (0.178 g, 0.49 mmol) and Example 1F (0.116g, 0.4 mmol) in dioxane (2 mL) was heated at 85° C. for 16 h. The solution was cooled to room temperature and concentrated in vacuo. The resulted oil was triturated with ethyl acetate and the white solid precipitate was filtered to give the title compound (0.14 g, 60%). ¹H NMR (300 MHz, DMSO-d₆) δ ppm 0.51-0.89 (m, 10H), 0.83-1.20 (m, 1H), 1.47-2.08 (m, 2H), 3.05 (s, 3H), 7.38-7.79 (m, 6H), 8.02 (d, J=7.72 Hz, 1H), 10.13 (s, 1H), 13.48 (s, 1H), MS (ESI) m/z 534.2 (M+H)⁺.

EXAMPLE 9

N-{3-[1-hydroxy-4-(methoxyamino)-3-oxo-4-propyl-3,4-dihydronaphthalen-2-yl]-1,1-dioxido-4H-1,2,4-benzothiadiazin-7-yl}methanesulfonamide To a solution of Example 7 (20 mg, 0.039 mmol) in methanol (1 mL) was added 10% palladium on carbon (5 mg). This solution was stirred under a balloon of H₂ gas for 16 hours. The solution was filtered through Celite, the filter cake washed with 5 mL of methanol and the filtrate removed in vacuo to give a crude product which was purified on a silica gel cartridge (5% methanol/chloroform) to give the title compound as a colorless solid (20 mg, yield quantitative): ¹H NMR (d₆-DMSO) δ 15.20 (s, 1H), 9.86 (s, 1H), 8.05, 8.03 (d, 1H), 7.75, 7.73 (d, 1H), 7.56-7.28 (m, 6H), 7.05 (s, 1H), 3.14 (s, 3H), 3.00 (s, 3H), 1.60-1.48 (m, 1H), 1.44-1.33 (m, 1H), 1.03-0.90 (m, 1H), 0.73-0.56 (m, 4H); MS (ESI) m/z 521 (M+H⁺).

EXAMPLE 10

N-(4-hydroxy-3-{7-[(methylsulfonyl)amino]-1,1-dioxido-4H-1,2,4-benzothiadiazin-3-yl}-2-oxo-1-propyl-1,2-dihydronaphthalen-1-yl)-N-methoxyacetamide To a solution of Example 9 (15 mg, 0.029 mmol) in tetrahydrofuran (200 μL) was added N,N-diisopropylethylamine (11 μL, 0.062 mmol) and acetyl chloride (5 μL, 0.070 mmol) and stirring was continued overnight. The solution was concentrated and taken up in H₂O (1 mL) and 1N NaOH (0.5 mL). This solution was stirred at room temperature for 2 hours and 1N HCl was added slowly until the solution became acidic. This aqueous solution was extracted with ethyl acetate (3×2 mL), the organic extracts combined, dried over Na₂SO₄, the drying agent filtered off, the solvent removed in vacuo, and the crude product was purified by column chromatography on silica gel (5% methanol/chloroform) to give the title compound as a colorless solid: ¹H NMR (d₆-DMSO) δ 13.81 (s, 1H), 10.18 (s, 1H), 8.10, 8.07 (d, 1H), 7.71-7.45 (m, 7H), 4.07 (s, 3H), 3.06 (s, 3H), 2.03 (br s, 3H), 1.30-1.05 (br s, 1H), 1.24 (br s, 2H), 0.75-0.50 (br s, 1H), 0.74-0.65 (t, 3H); MS (ESI) m/z 563 (M+H⁺).

EXAMPLE 11

N-{3-[1-hydroxy-4-methoxy-4-(3-methylbutyl)-3-oxo-3,4-dihydronaphthalen-2-yl]-1,1-dioxido-4H-1,2,4-benzothiadiazin-7-yl}methanesulfonamide

EXAMPLE 11A 1-hydroxy-4-methoxy-1-(3-methylbutyl)naphthalen-2(1H)-one

To a solution of Example 2D (0.43g, 1.7 mmol) in methanol (2 mL) heated at 60° C. was added boron trifluoride diethyl etherate (0.135 mL, 1.0 mmol). The reaction solution was stirred at 60° C. for 5 h. The solution was quenched with saturated NH₄Cl and extracted with ethyl acetate. The organic extract was concentrated in vacuo. Column chromatography on silica (2.5% methanol/dichloromethane) afforded the title compound as a white solid (0.17 g, 37.4%). ¹H NMR (300 MHz, DMSO-d₆) δ ppm 0.70 (dd, J=6.43, 2.39 Hz, 6H), 0.74-0.88 (m, 1H), 0.88-1.06 (m, 1H), 1.16-1.38 (m, 1H), 1.51-1.88 (m, 2H), 3.93 (s, 3H), 5.56 (s, 1H), 5.64 (s, 1H), 7.39 (t, J=7.54 Hz, 1H), 7.52 (t, J=7.54 Hz, 1H), 7.62 (d, 1H), 7.73 (d, J=7.72 Hz, 1H); MS m/z 260.9 (M+H)⁺.

EXAMPLE 11B 1,4-dimethoxy-1-(3-methylbutyl)naphthalen-2(1H)-one

To a solution of Example 11A (40 mg, 0.154 mmol) in N,N-dimethylformamide (1 mL) at 0° C. was added 60% wt sodium hydride (24.6 mg, 0.616 mmol). The reaction solution was stirred for 0.5 h and methyliodide (0.038 mL, 0.616 mmol) was added. The solution was stirred 16 h at room temperature, quenched with saturated NH$_4$Cl, and extracted with ethyl acetate. The organic extract was concentrated in vacuo. Column chromatography on silica (20% ethyl acetate/hexane) afforded the title compound as a white solid (35.4 mg, 84%). $^1$H NMR (300 MHz, DMSO-d$_6$) δ ppm 0.55-0.65 (m, 1H), 0.68 (dd, J=6.80 Hz, 6H), 0.85-1.00 (m, 1H), 1.20-1.33 (m, 1H), 1.56-1.96 (m, 2H), 2.76-2.86 (s, 3H), 3.96-4.02 (s, 3H), 5.48-5.84 (s, 1H), 7.25-7.70 (m, 3H), 7.82 (d, J=7.72 Hz, 1H); MS m/z 274.9 (M+H)$^+$.

EXAMPLE 11C 4-methoxy-4-(3-methylbutyl)naphthalene-1,3(2H,4H)-dione

A solution of Example 11B (35 mg, 0.127 mmol) in methanol (0.25 mL) and 1 N NaOH (0.25 mL) was stirred at 40° C. for 6 hours. The solution was concentrated in vacuo. Column chromatography on silica (7% methanol/dichloromethane) afforded the title compound (30 mg, 90%). $^1$H NMR (300 MHz, DMSO-d$_6$) δ ppm 0.30-0.47 (m, 1H), 0.67 (dd, J=13.97, 6.62 Hz, 6H), 0.75-0.93 (m, 1H), 1.10-1.37 (m, 1H), 1.70-1.95 (m, 1H), 1.98-2.21 (m, 1H), 2.81 (s, 3H), 5.70-5.83 (m, 1H), 7.47 (t, 1H), 7.60 (d, 1H), 7.65 (t, 1H), 7.90 (d, J=7.72 Hz, 1H); MS (ESI) m/z 260.9 (M+H)$^+$.

EXAMPLE 11D

2-[bis(methylthio)methylene]-4-methoxy-4-(3-methylbutyl)naphthalene-1,3(2H,4H)-dione To a solution of Example 11C (27 mg, 0.1 mmol) in dioxane (1 mL) was added Example 1D (89 mg, 0.35 mmol) followed by pyridine (0.042 mL, 0.5 mmol). The heterogeneous solution was heated at 55° C. for 5 h. The solution was cooled to room temperature and concentrated in vacuo. Column chromatography on silica (25% ethyl acetate/hexane) afforded the title compound as a yellow oil (33 mg, 87%). $^1$H NMR (300 MHz, DMSO-d$_6$) δ ppm 0.68 (dd, 6H), 0.71-0.83 (m, 1H), 0.88-1.03 (m, 1H), 1.18-1.33 (m, 1H), 1.66-1.99 (m, 2H), 2.58 (s, 6H), 2.97 (s, 3H), 7.44-7.63 (m, 2H), 7.73 (t, 1H), 8.07 (d, 1H); MS (ESI) m/z 387.0 (M+Na)$^+$.

EXAMPLE 11E

N-{3-[1-hydroxy-4-methoxy-4-(3-methylbutyl)-3-oxo-3,4-dihydronaphthalen-2-yl]-1,1-dioxido-4H-1,2,4-benzothiadiazin-7-yl}methanesulfonamide A mixture of Example 11D (33 mg, 0.09 mmol) and Example 1F (21.6 mg, 0.081 mmol) in dioxane (2 mL) was heated at 85° C. for 16 h. The solution was cooled to room temperature and concentrated in vacuo. Column chromatography on silica (3% methanol/ethyl acetate) afforded the title compound as a light yellow solid (27 mg, 61%). $^1$H NMR (300 MHz, DMSO-d$_6$) δ ppm 0.51-0.68 (m, 1H,) 0.67 (dd, 6H), 0.88-1.01 (m, 1H), 1.19-1.36 (m, 1H), 1.74 (m, 1H), 1.90-2.04 (m, 1H), 2.87 (s, 3H), 3.01 (s, 3H), 7.29-7.69 (m, 6H), 8.04 (d, J=7.72 Hz, 1H), 9.96 (s, 1H), 14.61 (s, 1H); MS m/z 534.0 (M+H)$^+$.

EXAMPLE 12

N-{3-[4-(benzyloxy)-1-hydroxy-4-(3-methylbutyl)-3-oxo-3,4-dihydronaphthalen-2-yl]-1,1-dioxido-4H-1,2,4-benzothiadiazin-7-yl}methanesulfonamide

EXAMPLE 12A 1-(benzyloxy)-4-methoxy-1-(3-methylbutyl)naphthalen-2(1H)-one

To a solution of Example 11A (25 mg, 0.094 mmol) in N,N-dimethylformamide (1 mL) at 0° C. was added 60% wt sodium hydride (15.4 mg, 0.384 mmol). The reaction solution was stirred for 0.5 h and benzylbromide (0.046 mL, 0.384 mmol) was added. The solution was stirred 16 h at room temperature, quenched with saturated NH$_4$Cl, and extracted with ethyl acetate. The organic extract was concentrated in vacuo. Column chromatography on silica (20% ethyl acetate/hexane) afforded the title compound as an oil (29 mg, 86%). $^1$H NMR (300 MHz, DMSO-d$_6$) δ ppm 0.71 (dd, 6H), 0.80-1.03 (m, 2H), 1.19-1.38 (m, 1H), 1.69-2.04 (m, 2H), 3.85 (d, J=10.66 Hz, 1H), 3.98 (s, 3H), 4.04 (d, J=11.03 Hz, 1H), 5.84 (s, 1H) 7.19-7.39 (m, 5H), 7.40-7.57 (m, 1H), 7.58-7.71 (m, 2H), 7.85 (d, J=7.72 Hz, 1H); MS m/z 351.1 (M+H)$^+$.

EXAMPLE 12B 4-(benzyloxy)-4-(3-methylbutyl)naphthalene-1,3(2H,4H)-dione

A solution of Example 12A (26 mg, 0.074 mmol) in methanol (0.25 mL) and 1 N NaOH (0.25 mL) was stirred at 40° C. for 6 hours. The solution was concentrated in vacuo. Column chromatography on silica (7% methanol/dichloromethane) afforded the title compound (23 mg, 91%). $^1$H NMR (300 MHz, DMSO-d$_6$) δ ppm 0.29-0.46 (m, 1H), 0.69 (dd, J=13.97, 6.62 Hz, 6H), 0.80-0.95 (m, 1H), 1.25-1.41 (m, 1H), 1.97 (m, 1H), 2.27 (m, 1H), 3.83 (d, J=10.66 Hz, 1H), 4.04-4.20 (m, 1H), 5.89 (s, 1H), 7.18-7.42 (m, 5H), 7.44-7.59 (m, 1H), 7.71 (br. s, 2H) 7.94 (br. s, 1H), 11.76 (s, 1H); MS (ESI) m/z 337.1 (M+H)$^+$.

EXAMPLE 12C 4-(benzyloxy)-2-[bis(methylthio)methylene]-4-(3-methylbutyl)naphthalene-1,3(2H,4H)-dione To a solution of Example 12B (17 mg, 0.05 mmol) in dioxane (1 mL) was added Example 1D (43 mg, 0.178 mmol) followed by pyridine (0.02 mL, 0.255 mmol). The heterogeneous solution was heated at 60° C. for 6h. The solution was cooled to room temperature and concentrated in vacuo. Column chromatography on silica (25% ethyl acetate/hexane) afforded Compound 10 as a yellow oil (15 mg, 67%). $^1$H NMR (300 MHz, DMSO-d$_6$) δ ppm 0.69 (dd, 6H), 0.77-0.89 (m, 1H), 0.95-1.11 (m, 1H), 1.22-1.36 (m, 1H), 1.77-2.05 (m, 2H), 2.60 (s, 6H), 4.04 (d, 1H), 4.24 (d, J=11.03 Hz, 1H), 7.21-7.41 (m, 5H), 7.48-7.61 (m, 1H), 7.60-7.69 (m, 1H), 7.69-7.82 (m, 1H), 8.06-8.17 (m, 1H); MS (ESI) m/z 441.1 (M+H)$^+$.

EXAMPLE 12D

N-{3-[4-(benzyloxy)-1-hydroxy-4-(3-methylbutyl)-3-oxo-3,4-dihydronaphthalen-2-yl]-1,1-dioxido-4H-1,2,4-benzothiadiazin-7-yl}methanesulfonamide A mixture of Example 12D (14 mg, 0.032 mmol) and Example 1F (7.6 mg, 0.029 mmol) in dioxane (2 mL) was heated at 85° C. for 16 h. The solution was cooled to room temperature and concentrated in vacuo. Column chromatography on silica (10% methanol/dichloromethane) afforded the title compound as a light yellow solid (14.6 mg, 84%). $^1$H NMR (300 MHz, DMSO-$d_6$) δ ppm 0.55-0.62 (m, 1H), 0.70 (dd, 6H), 0.91-1.10 (m, 1H), 1.18-1.39 (m, 1H), 1.72-1.92 (m, 1H), 1.97-2.14 (m, 1H), 3.01 (s, 3H), 3.88 (d, J=11.40 Hz, 1H), 4.21 (d, J=11.03 Hz, 1H), 7.09-7.53 (m, 6H), 7.49-7.69 (m, 2H), 8.07 (d, J=7.72 Hz, 1H), 9.93 (s, 1H), 14.89 (s, 1H); MS m/z 610.2 $(M+H)^+$.

EXAMPLE 13

N-[3-(4-amino-1-hydroxy-3-oxo-4-propyl-3,4-dihydronaphthalen-2-yl)-1,1-dioxido-4H-1,2,4-benzothiadiazin-7-yl]methanesulfonamide To a solution of the product of Example 9 (20 mg, 0.038 mmol) in CH$_3$CN (1.5 mL) was added H$_2$O (100 uL) and molybdenum hexacarbonyl (7 mg, 0.027 mmol) and the solution was refluxed for 2 hours. After cooling to room temperature the solvent was removed in vacuo and the crude product was purified by column chromatography on C-1 8 silica gel (70:30:0.1 methanol:H$_2$O:trifluoroacetic acid) to give the title compound as a colorless solid (13 mg, 69%): $^1$H NMR ($d_6$-DMSO) δ 14.47 (s, 1H), 9.94 (s, 1H), 8.61 (s, 2H), 8.14, 8.11 (d, 1H), 7.70-7.42 (m, 5H), 7.37, 7.34 (d, 1H), 3.01 (s, 3H), 2.03-1.93 (m, 1H), 1.87-1.75 (m, 1H), 1.29-1.14 (m, 1H), 0.96-0.83 (m, 1H), 0.76-0.67 (t, 3H); MS (ESI) m/z 491 $(M+H^+)$.

EXAMPLE 14

N-{3-[1-hydroxy-4-(methoxyamino)-4-(3-methylbut-2-enyl)-3-oxo-3,4-dihydronaphthalen-2-yl]-1,1-dioxido-4H-1,2,4-benzothiadiazin-7-yl}methanesulfonamide

EXAMPLE 14A 2-isopropyl-1-methoxy-9b-(3-methylbut-2-enyl)-1,9b-dihydronaphtho[1,2-d][1,3]oxazol-5(2H)-one To a solution of Example 7B (800 mg, 3.3 mmol) in 1,2-dichloroethane (25 mL) was added isobutyraldehyde (1.8 mL, 19.6 mmol), acetic acid (0.37 mL, 6.5 mmol) and magnesium sulfate (2.5 g). The solution was stirred at room temperature overnight, filtered, and the filtrate washed with 10% NaHCO$_3$ (2×20 mL) and brine (1×20 mL) and the resulting solution dried (MgSO$_4$), the drying agent filtered off and the solvent removed in vacuo to give a crude residue which was purified by column chromatography on silica gel (20% ethyl acetate/hexane) to give the title compound as a colorless solid (710 mg, 73%). $^1$H NMR ($d_6$-DMSO) δ 7.94, 7.91 (d, 1H), 7.75-7.63 (m, 2H), 7.51-7.43 (m, 1H), 5.62, 5.56 (d, 1H), 5.17-5.04 (m, 1H), 4.89, 4.85 (d, 1H), 4.80, 4.74 (d, 1H), 3.48 (s, 3H), 2.76-2.66 (m, 1H), 2.64-2.53 (m, 1H), 2.44-2.30 (m, 1H), 1.22-1.08 (m, 6H); MS (ESI) m/z 300 $(M+H^+)$.

2-isopropyl-1-methoxy-9b-(3-methylbut-2-enyl)-1,9b-dihydronaphtho[1,2-d][1,3]oxazol-5(2h)-one (Example 14B) and 9b-but-2-enyl-2-isopropyl-1-methoxy-1,9b-dihydronaphtho[1,2-d][1,3]oxazol-5(2H)-one (Example 14C)

To a 100 mL pressure vessel containing a solution of Example 14A (1.1 g, 3.7 mmol) in de-gassed, anhydrous dichloromethane (40 mL) was added 2-methyl-2-butene (20 mL) and Hoveda's-Grubbs $2^{nd}$ generation catalyst (100 mg). The tube was sealed and heated at 70-80° C. for 48 hours. More catalyst (50 mg) was added and heating was continued an additional 18 hours. The solution was cooled to room temperature, solvent was removed in vacuo and the crude residue was purified by column chromatography on silica gel (5% ethyl acetate/hexane) to give a colorless solid as a mixture of title compounds (0.52 g, 43%): $^1$H NMR ($d_6$-DMSO) δ 7.94-7.87 (m, 1H), 7.77-7.58 (m, 2H), 7.52-7.39 (m, 1H), 5.74, 5.72 (d, 1H), 5.13-5.05, 4.76-4.67 (dm, 1H), 3.50 (s, 3H), 2.70-2.43 (m, 3H), 2.43-2.26 (m, 1H), 1.49-1.33 (m, 3H), 1.25-1.02 (m, 9H); MS (ESI) m/z 328 $(M+H^+)$. In other runs, only 14B was produced, and no 14C could be isolated.

EXAMPLE 14D 3-hydroxy-4-(methoxyamino)-4-(3-methylbut-2-enyl)naphthalen-1 (4H)-one A solution of Example 14B (16 mg, 49 μmol) in 2:1 tetrahydrofuran:2N aq. HCl (0.9 mL) was stirred at rt 6 h. The solvent was evaporated and the crude product was purified by column chromatography on silica gel using 2:1 ethyl acetate:hexanes to give the title compound as a colorless solid (10 mg, 75%). $^1$H NMR (300 MHz, DMSO-$d_6$) δ ppm 11.76 (br s, 1H), 7.85 (t, J=7.7 Hz, 2H), 7.49-7.68 (m, 1H), 7.40 (t, J=7.7 Hz, 1H), 7.13 (br s, 1H), 5.65 (s, 1H), 4.46 (m, 1H), 3.10 (s, 3H), 1.42-1.66 (m, 1H), 1.31-1.47 (s, 3H), 1.24 (s, 3H), 0.77-0.96 (m, 1H).

EXAMPLE 14E

N-{3-[1-hydroxy-4-(methoxyamino)-4-(3-methylbut-2-enyl)-3-oxo-3,4-dihydronaphthalen-2-yl]-1,1-dioxido-4H-1,2,4-benzothiadiazin-7-yl}methanesulfonamide To a solution of the product from Example 14D (8 mg, 29 μmol) in anhydrous 1,4-dioxane (0.3 mL) was added Example 1D (40 mg, 151 μmol) and pyridine (12 μL, 149 μmol). The resulting mixture was heated at 60° C. for 90 min, the solvent was evaporated, and the crude product was purified by column chromatography on silica gel using 1:1 ethyl acetate:hexanes. The resulting yellow solid was dissolved in anhydrous 1,4-dioxane (0.2 mL) and treated with Example 1F (8 mg, 30 μmol), and the resulting solution was heated at 85° C. for 16 h. The solvent was evaporated, and the crude product was purified by column chromatography on silica gel using 19:1 chloroform:methanol. The title compound was obtained as a light yellow solid (9 mg, 56%). $^1$H NMR (300 MHz, DMSO-$d_6$) δ ppm 13.72 (s, 1H), 10.20 (s, 1H), 8.09 (d, J=7.7 Hz, 1H), 7.95 (d, J=7.7 Hz, 1H), 7.72 (t, J=7.5 Hz, 1H), 7.46-7.64 (m, 4H), 4.47-4.66 (m, 1H), 3.22 (s, 3H), 3.07 (s, 3H), 2.27-2.49 (m, 2H), 1.31-1.41 (m, 1H), 1.09-1.31 (m, 6H), 0.75-0.93 (m, 1H).

EXAMPLE 15

N-{3-[1-hydroxy-4-(methoxyamino)-4-(3-methylbutyl)-3-oxo-3,4-dihydronaphthalen-2-yl]-1,1-dioxido-4H-1,2,4-benzothiadiazin-7-yl}methanesulfonamide

EXAMPLE 15A 3-hydroxy-4-(methoxyamino)-4-(3-methylbutyl)naphthalen-1(4H)-one To a solution of the product from Example 14B (100 mg, 0.3 1 mol) in ethyl acetate (3 mL) was added Adam's catalyst (PtO$_2$.H$_2$O, 7 mg), and the resulting mixture was placed under 1 atm H$_2$ and stirred for 5 h. The catalyst was filtered off, and the solvent was evaporated to give an oil, which was dissolved in 2:1 tetrahydrofuran:2N aq. HCl (3 mL). The resulting solution was stirred at rt 2h, and concentrated in vacuo. The crude product was purified by column chromatography on silica gel using 3% methanol in chloroform to give the title compound as a light tan amorphous solid (82 mg, 98%). $^1$H NMR (300 MHz, DMSO-d$_6$) δ ppm 7.84 (dd, J=10.8, 7.9 Hz, 2H), 7.60 (t, J=7.4 Hz, 1H), 7.42 (t, J=7.5 Hz, 1H), 5.73 (s, 1H), 3.09 (s, 3H), 1.75-1.90 (m, 1H), 1.48-1.62 (m, 1H), 1.15-1.33 (m, 1H), 0.80-0.92 (m, 1H), 0.57-0.72 (m, 6H), 0.30-0.50 (m, 1H).

EXAMPLE 15B

N-{3-[1-hydroxy-4-(methoxyamino)-4-(3-methylbutyl)-3-oxo-3,4-dihydronaphthalen-2-yl]-1,1-dioxido-4H-1,2,4-benzothiadiazin-7-yl}methanesulfonamide The product from Example 15A (82 mg, 0.30 mmol) was subjected to the conditions described in Example 14E. The title compound was obtained as a light yellow solid (0.123 g, 75%): $^1$H NMR (300 MHz, DMSO-d$_6$) δ ppm 13.83 (s, 1H), 10.16 (s, 1H), 8.11 (d, J=7.7 Hz, 1H), 7.88 (d, J=7.7 Hz, 1H), 7.72 (t, J=7.5 Hz, 1H), 7.46-7.62 (m, 4H), 3.16 (s, 3H), 3.06 (s, 3H), 1.72-1.89 (m, 1H), 1.53-1.72 (m, 1H), 1.13-1.33 (m, 1H), 0.77-0.95 (m, 1H), 0.56-0.73 (m, 6H), 0.37-0.56 (m, 1H).

EXAMPLE 16

N-{3-[4-amino-1-hydroxy-4-(3-methylbutyl)-3-oxo-3,4-dihydronaphthalen-2-yl]-1,1-dioxido-4H-1,2,4-benzothiadiazin-7-yl}methanesulfonamide To a solution of the product from Example 15B (40 mg, 73 μmol) in acetonitrile (3 mL) was added molybdenum hexacarbonyl (14 mg, 53 μmol) and H$_2$O (0.2 mL). The resulting mixture was stirred at reflux for 2 h and concentrated in vacuo. The crude product was purified by column chromatography on C-18 reverse-phase silica gel using 3:2:0.1 methanol:H$_2$O:trifluoroacetic acid to give the title compound as a colorless solid (6 mg, 16%).
$^1$H NMR (300 MHz, DMSO-d$_6$) δ ppm 14.46 (s, 1H), 9.94 (s, 1H), 8.60 (s, 2H), 8.12 (d, J=7.4 Hz, 1H), 7.59-7.78 (m, 1H), 7.42-7.56 (m, 4H), 7.30-7.42 (m, 1H), 3.01 (s, 3H), 1.93-2.13 (m, 1H), 1.78-1.95 (m, 1H), 1.22-1.41 (m, 1H), 1.01-1.16 (m, 1H), 0.62-0.84 (m, 7H).

EXAMPLE 17

N-{3-[4-[(benzyloxy)amino]-1-hydroxy-4-(3-methylbutyl)-3-oxo-3,4-dihydronaphthalen-2-yl]-1,1-dioxido-4H-1,2,4-benzothiadiazin-7-yl}methanesulfonamide

EXAMPLE 17A 2-hydroxynaphthoquinone 1-(O-benzyloxime)

To a suspension of 2-hydroxynapthoquinone (18.5 g, 105 mmol) in 50% ethanol/H$_2$O (1.2 L) was added 1N NaOH (46 mL). The suspension was heated to dissolved at 65° C., cooled to 45° C. and added a solution of benzylhydroxyamine hydrochloride (17.11 g, 107 mmol) with 1N NaOH (107 mL) in ethanol (60 mL). The solution was maintained at 45° C. for 2 days, concentrated to half the volume, and the resulted yellow precipitate was filtered and washed with 4% methanol/dichloromethane (20 mL). The filtered solid was dried in vacuo to afforded the title compound (26.5 g, 98%) and used for the next step without further purification. $^1$H NMR (300 MHz, DMSO-d$_6$) δ ppm 5.55 (s, 2H), 5.92 (s, 1H), 7.29-7.45 (m, 3H), 7.49-7.58 (m, 2H), 7.57-7.78 (m, 2H), 7.93-8.14 (m, 1H), 8.78 (d, J=7.35 Hz, 1H), 11.09 (br. s, 1H); MS m/z 280.0 (M+H)$^+$.

EXAMPLE 17B 4-allyl-4-[(benzyloxy)amino]-3-hydroxynaphthalen-1(4H)-one

A 2.4 M solution of the allylindium reagent was prepared by suspending indium powder (5 g, 43.5 mmol) in N,N-dimethylformamide (12.5 mL) was added dropwise allyl bromide (5.65 mL, 65.3 mmol). The reaction mixture was stirred at 25° C. for 1 h. A solution of Example 17A (10.8 g, 38.7 mmol) in N,N-dimethylformamide (20 mL) was added the above 2.4 M solution of allylindium reagent (18 mL, 43.3 mmol). The solution was stirred 1 h at room temperature, quenched with 10% citric acid, and extracted with ethyl acetate. The organic extract was concentrated in vacuo. Column chromatography on silica (3% methanol/dichloromethane) afforded the title compound (11 g, 88%) as a yellow solid. $^1$H NMR (300 MHz, DMSO-d$_6$) δ ppm 2.29-2.43 (m, 2H), 4.27 (d, 1H), 4.38 (d, 1H), 4.66-4.87 (m, 2H), 5.03-5.15 (m, 1H), 5.68 (s, 1H), 6.90 (dd, J=6.62, 2.94 Hz, 2H), 7.08-7.16 (br. s, 1H), 7.20 (q, J=3.68 Hz, 3H), 7.44 (t, J=7.91 Hz, 1H), 7.60 (t, J=7.72 Hz, 1H), 7.80-8.01 (m, 2H), 11.84 (br. s, 1H); MS m/z 322.0 (M+H)$^+$.

EXAMPLE 17C 9b-allyl-1-(benzyloxy)-2-isopropyl-1,9b-dihydronaphtho[1,2-d][1,3]oxazol-5(2H)-one A suspension of Example 17B (3.1 g, 9.66 mmol), isopropionaldehyde (1.6 mL, 17.38 mmol), acetic acid (0.56 mL, 9.66 mmol), magnesium sulfate (5.8 g, 48.3 mmol) in dichloromethane (30 mL) was stirred at 25° C. for 16 h. The reaction mixture was filterd and the filtrate was concentrated in vacuo. The resulting oil was taking up in ethyl acetate, washed with 1N NaHCO$_3$, dried (MgSO$_4$), and concentrated in vacuo. The resulted oil was triturated with methanol and the white solid precipitate was filtered to give the title compound (2.28 g, 63%). $^1$H NMR (300 MHz, DMSO-d$_6$) δ ppm 1.13-1.21 (m, 3H), 1.25 (d, J=6.25 Hz, 3H), 2.37-2.46 (m, 1H), 2.68 (dd, 1H), 2.78 (dd, 1H), 4.71-4.93 (m, 4H), 5.07-5.22 (m, 1H), 5.66 (d, J=9.19 Hz, 1H), 5.76 (s, 1H), 6.62 (d, J=6.62 Hz, 2H), 7.01-7.23 (m, 3H), 7.52 (t, J=7.54 Hz, 1H), 7.66-7.73 (m, 1H), 7.89 (d, J=7.35 Hz, 1H), 7.96 (d, J=6.99 Hz, 1H); MS m/z 376.1 (M+H)$^+$.

EXAMPLE 17D 1-(benzyloxy)-2-isopropyl-9b-(3-methylbut-2-enyl)-1,9b-dihydronaphtho[1,2-d][1,3]oxazol-5(2H)-one A mixture of Example 17C (2.28 g, 6.08 mmol), 2-methyl 2-butene (12 mL, 113 mmol), and Hoveda-Grubbs II catalyst (120 mg, 0.19 mmol) in dichloromethane (12 mL) was heated at 65° C. for 24 h in a seal tube. The solution was cooled to room temperature and concentrated in vacuo. Column chromatography on silica (20% ethyl acetate/hexane) afforded the title compound as an oil (1.78 g, 73%). $^1$H NMR (300 MHz, DMSO-d$_6$) δ ppm 1.16 (s, 3H), 1.17 (d, J=6.62 Hz, 3H), 1.26 (d, J=6.62 Hz, 3H), 1.43 (s, 3H), 2.34-2.46 (m, 1H), 2.66 (d, J=7.35 Hz, 2H), 4.45-4.55 (m, 1H), 4.75 (d, J=9.56 Hz, 1H), 4.88 (d, J=9.56 Hz, 1H), 5.71 (s, 1H), 5.75 (d, 1H), 6.64 (d, J=6.99 Hz, 2H), 7.03-7.18 (m, 3H), 7.49 (t, J=7.54 Hz, 1H), 7.65 (t, J=6.80 Hz, 1H), 7.89 (d, J=7.72 Hz, 1H), 7.94 (d, J=7.72 Hz, 1H); MS m/z 434.1 (M+methanol-H)$^-$.

EXAMPLE 17E 1-(benzyloxy)-2-isopropyl-9b-(3-methylbutyl)-1,9b-dihydronaphtho[1,2-d][1,3]oxazol-5(2H)-one A mixture of Example 17D (1.78 g, 4.44 mmol) and PtO$_2$ (120 mg, 0.53 mmol) in ethyl acetate (50 mL) was hydrogenated at 1 atm for 2 h. The solution was filtered and the filtrate was concentrated in vacuo. Column chromatography on silica (5% ethyl acetate/hexane) afforded the title compound (1.36 g, 76%). $^1$H NMR (300 MHz, DMSO-d$_6$) δ ppm 0.67 (d, 3H), 0.69 (d, 3H), 1.16 (d, J=6.62 Hz, 3H), 1.25 (d, J=6.25 Hz, 3H), 1.89-2.02 (m, 1H), 2.34-2.42 (m, 1H), 4.23 (d, 1H), 4.35 (d, 1H), 4.73 (d, 1H), 4.84 (d, 1H), 5.65 (d, J=9.19 Hz, 1H), 5.77 (s, 1H), 6.60 (d, J=6.99 Hz, 2H), 7.02-7.13 (m, 3H), 7.60 (t, 1H), 7.70 (t, 1H), 7.83 (d, 1H), 7.91 (d, 1H); MS m/z 406.1 (M+H)$^+$.

EXAMPLE 17F

4-[(benzyloxy)amino]-3-hydroxy-4-(3-methylbutyl) naphthalen-1(4H)-one

A solution of Example 17E (1.36 g, 3.35 mmol) in tetrahydrofuran (12 mL) and 2N HCl (6 mL) was stirred at 25° C. for 2 hours. The mixture was concentrated in vacuo and the resulting oil was triturated with ethyl acetate. The white hydrochloride salt was filtered, suspended in ethyl acetate, and basified to pH 10 with 1N NaHCO$_3$. The ethyl acetate layer was dried (Na$_2$SO$_4$), filtered, and concentrated in vacuo to afforded the title compound as an amber oil (1 g, 84.8%) and used for the next step without further purification. $^1$H NMR (300 MHz, DMSO-d$_6$) δ ppm 0.34-0.51 (m, 1H), 0.63 (d, J=6.62 Hz, 3H), 0.69 (d, J=6.62 Hz, 3H), 0.72-0.89 (m, 1H), 0.92-1.09 (m, 1H), 1.16-1.31 (m, 1H), 1.46-1.77 (m, 2H), 4.23 (d, 1H), 4.30-4.40 (m, 1H), 5.71 (s, 1H), 6.84-6.95 (m, 2H), 7.06 (s, 1H), 7.19 (q, J=3.55 Hz, 3H), 7.45 (t, J=6.99 Hz, 1H), 7.61 (t, J=7.17 Hz, 1H), 7.84 (d, J=7.72 Hz, 1H), 7.87 (d, 1H), 11.78 (br.s, 1H); MS (ESI) m/z 352.0 (M+H)$^+$.

EXAMPLE 17G

4-[(benzyloxy)amino]-2-[bis(methylthio)methylene]-4-(3-methylbutyl)naphthalene-1,3(2H,4H)-dione To a solution of Example 17F (0.3 g, 0.85 mmol) in dioxane (2 mL) was added Example 1D (0.74 g, 2.99 mmol) followed by pyridine (0.41 mL, 5.1 mmol). The heterogeneous solution was heated at 55° C. for 3h. The solution was cooled to room temperature and concentrated in vacuo. Column chromatography on silica (15% ethyl acetate/hexane) afforded the title compound as a yellow oil (0.31 g, 80%). $^1$H NMR (300 MHz, DMSO-d$_6$) δ ppm 0.47-0.60 (m, 1H), 0.56-0.71 (m, 6H), 0.66-0.77 (m, 1H), 1.19-1.31 (m, 1H), 1.50-1.65 (m, 1H), 1.70-1.86 (m, 1H), 2.50 (s, 6H), 4.24-4.33 (d, 1H), 4.35-4.45 (m, 1H), 6.89 (dd, J=6.62, 2.94 Hz, 2H), 7.16-7.25 (m, 3H), 7.30 (s, 1H), 7.52 (t, J=7.17 Hz, 1H), 7.70 (t, J=6.99 Hz, 1H), 7.87 (d, J=7.72 Hz, 1H), 8.08 (d, J=6.62 Hz, 1H); MS (ESI) m/z 456.0 (M+H)$^+$.

EXAMPLE 17H

N-{3-[4-[(benzyloxy)amino]-1-hydroxy-4-(3-methylbutyl)-3-oxo-3,4-dihydronaphthalen-2-yl]-1,1-dioxido-4H-1,2,4-benzothiadiazin-7-yl}methanesulfonamide A mixture of Example 17G (0.31 g, 0.68 mmol) and Example 1F (0.177 g, 0.67 mmol) in dioxane (2 mL) was heated at 85° C. for 16 h. The solution was cooled to room temperature and concentrated in vacuo. Column chromatography on silica (5% methanol/dichloromethane) afforded the title compound (0.316 g, 76%). $^1$H NMR (300 MHz, DMSO-d$_6$) δ ppm 0.39-0.56 (m, 1H), 0.64 (dd, J=10.11, 6.43 Hz, 6H), 0.76-0.94 (m, 1H), 1.16-1.30 (m, 1H), 1.50-1.68 (m, J=4.41 Hz, 1H), 1.65-1.84 (m, 1H), 3.04 (s, 3H), 4.36 (dd, 2H), 6.84-7.05 (m, 2H), 7.13-7.32 (m, 3H), 7.42-7.58 (m, 4H), 7.67 (t, J=7.35 Hz, 1H), 7.85 (d, J=7.72 Hz, 1H), 8.13 (d, J=7.35 Hz, 1H), 10.08 (s, 1H), 14.26 (br. s, 1H); MS m/z 625.1 (M+H)$^+$.

EXAMPLE 18

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)acetamide

EXAMPLE 18A tert-butyl 4-amino-3-(aminosulfonyl)phenylcarbamate

A mixture of 2,5-diaminobenzenesulfonamide (prepared according to the procedure as described in Goldfarb A. R. et. al., J. Amer. Chem. Soc. 1943, 65, 738) (0.168 g, 0.896 mmol) and di-tert-butyl dicarbonate (0.196 g, 0.896 mmol) in tetrahydrofuran (10 mL) was stirred at rt for 16 h. The solvent was then evaporated under reduced pressure and the residue purified by chromatography on silica gel, eluting with 3:2 hexane/ethyl acetate, to provide the title compound (0.202 g, 78% yield) as a beige powder. $^1$H NMR (300 MHz, DMSO-d$_6$) δ 1.45 (s, 9H) 5.53 (s, 2H) 6.70 (d, J=8.46 Hz, 1H) 7.20 (m, 3H) 7.77 (s, 1H) 9.06 (s, 1H).

EXAMPLE 18B tert-butyl 3-[1-hydroxy-4-(methoxyamino)-4-(3-methylbutyl)-3-oxo-3,4-dihydronaphthalen-2-yl]-1,1-dioxido-4H-1,2,4-benzothiadiazin-7-ylcarbamate Example 15B was dissolved in dioxane (10 mL) and Example 18A (286 mg, 1 mmol) was added and the solution was refluxed for 2 hours. The solution was cooled to room temperature and the solvent was removed in vacuo to yield a crude solid which was purified by column chromatography on silica gel (10% ethyl acetate/hexane) to give the title compound as a colorless solid (211 mg, 37%). $^1$H NMR (d$_6$-DMSO) δ 13.55 (s, 1H), 9.87 (s, 1H), 8.15, 8.12 (d, 2H), 7.93, 7.90 (d, 1H), 7.81-7.74 (t, 1H), 7.69-7.53 (m, 3H), 3.14 (s, 3H), 1.89-1.78 (m, 1H), 1.72-1.61 (m, 1H), 1.51 (s, 9H), 1.31-1.19 (m, 1H), 0.94-0.79 (m, 1H), 0.72-0.60 (m, 6H), 0.52-0.39 (m, 1H); MS (ESI) m/z 571 (M+H$^+$).

EXAMPLE 18C tert-butyl 3-[4-amino-1-hydroxy-4-(3-methylbutyl)-3-oxo-3,4-dihydronaphthalen-2-yl]-1,1-dioxido-4H-1,2,4-benzothiadiazin-7-ylcarbamate To a solution of Example 18B (205 mg, 0.36 mol) in $CH_3CN$ (16 mL) was added $H_2O$ (1.1 mL) and molybdenum hexacarbonyl (66 mg, 0.25 mol) and the solution was refluxed for 2 hours. After cooling to room temperature the solvent was removed in vacuo and the crude product was purified by column chromatography on silica gel (3% methanol/chloroform) to give the title compound as a colorless solid (163 mg, 81%): $^1$H NMR ($d_6$-dmso) δ 14.34 (s, 1H), 9.64 (s, 1H), 8.59 (br s, 2H), 8.13, 8.11 (d, 1H), 7.94 (s, 1H), 7.71-7.49 (m, 4H), 7.27, 7.24 (d, 1H), 2.06-1.96 (m, 1H), 1.91-1.81 (m, 1H), 1.50 (s, 9H), 1.42-1.18 (m, 1H), 1.18-0.94 (m, 1H), 0.75-0.66 (m, 6H), 0.66-0.59 (m, 1H); MS (ESI) m/z 541 (M+H$^+$).

EXAMPLE 18D

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)acetamide To a solution of Example 18C (30 mg, 0.05 mmol) in dichloromethane (150 µL) was added triethylamine (150 µL, 0.11 mmol) and acetic anhydride (6 µL, 0.06 mmol) and the mixture stirred at room temperature for 16 hours. Solvent was removed in vacuo and the crude residue was dissolved in dichloromethane (0.5 mL) and trifluoroacetic acid (0.5 mL) and the mixture was stirred at room temperature for 2 hours. Solvent was removed in vacuo and the crude residue was dissolved in dichloromethane (0.5 mL) and triethylamine (150 µL, 0.11 mmol) was added followed by methanesulfonyl chloride (10 µL, 0.11 mmol). The mixture was stirred at room temperature for 1.5 hours and the solvent was removed in vacuo and the crude residue was dissolved in ethyl acetate (0.5 mL) and 1N NaOH (0.5 mL) and the solution stirred at room temperature for 16 hours. 1N HCl was added dropwise until acidic pH, then the mixture was extracted with ethyl acetate (3×5 mL) and the organic extracts were combined and dried ($MgSO_4$). The drying agent was filtered off and the solvent was removed in vacuo to give a crude residue which was purified by column chromatography on silica gel (5% methanol/chloroform) to give the title compound as a colorless solid. MS (ESI) m/z 561 (M+H$^+$). $^1$H NMR ($d_6$-DMSO) δ 10.03 (s, 1H), 8.04, 8.02 (d, 1H), 7.55-7.25 (m, 6H), 3.07, 3.06 (d, 3H), 2.01-1.59 (m, 2H), 1.82 (s, 3H), 1.31-1.08 (m, 2H), 1.01-0.84 (m, 1H), 0.71-0.62 (m, 6H).

EXAMPLE 19 methyl 4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-ylcarbamate Follow same procedure as Example 18D treating Example 18C with methyl chloroformate (5.1 µL, 0.06 mmol) in place of acetic anhydride. $^1$H NMR ($d_6$-DMSO) δ 13.79 (s, 1H), 10.21 (s, 1H), 8.45 (s, 1H), 8.12, 8.09 (d, 1H), 7.74-7.45 (m, 6H), 3.43 (s, 3H), 3.07 (s, 3H), 2.01-1.90 (m, 1H), 1.84-1.73 (m, 1H), 1.31-1.15 (m, 2H), 0.99-0.86 (m, 1H), 0.70-0.60 (m, 6H); MS (ESI) m/z 577 (M+H$^+$).

EXAMPLE 20

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)benzamide Follow same procedure as Example 18D treating Example 18C with benzoyl chloride (8.6 uL, 0.07 mmol) in place of acetic anhydride. $^1$H NMR ($d_6$-DMSO) δ 13.69 (s, 1H), 10.26 (s, 1H), 9.52 (s, 1H), 8.17, 8.14 (d, 1H), 7.91, 7.88 (d, 2H), 7.77-7.44 (m, 9H), 3.08 (s, 3H), 2.21-2.01 (m, 2H), 1.37-0.94 (m, 4H), 0.75-0.65 (m, 6H); MS (ESI) m/z 623 (M+H$^+$).

EXAMPLE 21

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)methanesulfonamide Follow same procedure as Example 18D treating Example 18C with methanesulfonyl chloride (4.7 uL, 0.06 mmol) in place of acetic anhydride. $^1$H NMR ($d_6$-DMSO) δ 15.25 (s, 1H), 9.89 (s, 1H), 8.01, 7.98 (d, 1H), 7.67-7.29 (m, 7H), 2.99 (s, 3H), 2.88 (s, 3H), 2.02-1.90 (m, 1H), 1.71-1.57 (m, 1H), 1.33-1.13 (m, 2H), 0.89-0.81 (m, 1H), 0.69-0.60 (m, 6H); MS (ESI) m/z 597 (M+H$^+$).

EXAMPLE 22

N-{3-[(4R)-1-hydroxy-4-(methoxyamino)-4-(3-methylbutyl)-3-oxo-3,4-dihydronaphthalen-2-yl]-1,1-dioxido-4H-1,2,4-benzothiadiazin-7-yl}methanesulfonamide

EXAMPLE 22A (2S,9bR)-9b-allyl-2-(2,2-dimethyl-1,3-dioxolan-4-yl)-1-methoxy-1,9b-dihydronaphtho[1,2-d][1,3]oxazol-5(2H)-one To a solution of the product from Example 7B (1.00 g, 4.1 mmol) in dichloromethane (20 mL) was added isopropylidine-D-glyceraldehyde (1.0 g, 7.7 mmol), AcOH (0.25 mL, 4.1 mmol) and $MgSO_4$ (~2 g), and the resulting mixture was stirred at rt 16 h. The drying agent was filtered off, and the solution was partitioned between saturated aq. $NaHCO_3$ (10 mL) and dichloromethane (3×20 mL). The combined organic layers were dried over $Na_2SO_4$, filtered and concentrated to give a crude mixture of diastereomers, which were separated by column chromatography on silica gel using a solvent gradient of 10-25% ethyl acetate in hexanes. The title compound was isolated as the least polar component, and was obtained as a colorless crystalline solid (0.54 g, 74%). $^1$H NMR (300 MHz, DMSO-$d_6$) δ ppm 7.92 (d, J=8.1 Hz, 1H), 7.62-7.78 (m, 2H), 7.42-7.54 (m, 1H), 5.95 (d, J=6.3 Hz, 1H), 5.83 (s, 1H), 4.99-5.21 (m, 1H), 4.88 (dd, J=9.9, 2.2 Hz, 1H), 4.79 (dd, J=16.7, 2.0 Hz, 1H), 4.55-4.67 (m, 1H), 4.09-4.22 (m, 1H), 3.98-4.10 (m, 1H), 3.51 (s, 3H), 2.60-2.81 (m, 2H), 1.46 (s, 3H), 1.37 (s, 3H).

EXAMPLE 22B (2S,9bR)-2-(2,2-dimethyl-1,3-dioxolan-4-yl)-1-methoxy-9b-(3-methylbut-2-enyl)-1,9b-dihydronaphtho[1,2-d][1,3]oxazol-5(2H)-one The product from Example 22A (0.10 g, 0.28 mmol) was subjected to the procedure described in Example 14B,C. The crude product was purified by column chromatography on silica gel using a solvent gradient of 10-25% ethyl acetate in hexanes to give the title compound as a colorless oil (84 mg, 78%). $^1$H NMR (300 MHz, DMSO-$d_6$) δ ppm 7.90 (d, J=7.7 Hz, 1H), 7.67-7.76 (m, 1H), 7.59-7.68 (m, 1H), 7.46 (t, J=7.5 Hz, 1H), 6.01 (d, J=6.3 Hz, 1H), 5.78 (s, 1H), 4.56-4.68 (m, 1H), 4.37-4.51 (m, 1H), 4.09-4.23 (m, 1H), 3.96-4.10 (m, 1H), 3.52 (s, 3H), 2.52-2.73 (m, 2H), 1.31-1.54 (m, 9H), 1.10 (s, 3H).

EXAMPLE 22C (2S,9bR)-2-(2,2-dimethyl-1,3-dioxolan-4-yl)-1-methoxy-9b-(3-methylbutyl)-1,9b-dihydronaphtho[1,2-d][1,3]oxazol-5(2H)-one The product from Example 22B (82 mg, 0.21 mmol) and PtO$_2$ (Adam's catalyst, 5 mg) in ethyl acetate (2 mL) was stirred at rt under 1 atm H$_2$ for 90 min. The catalyst was filtered off, the solvent was evaporated and the crude product was purified by column chromatography on silica gel using a solvent gradient of 10-25% ethyl acetate in hexanes to provide the title compound as a colorless gum (63 mg, 77%): $^1$H NMR (300 MHz, DMSO-$d_6$) δ ppm 7.95 (d, J=7.4 Hz, 1H), 7.63-7.79 (m, 2H), 7.42-7.56 (m, 1H), 5.91 (d, J=5.5 Hz, 1H), 5.84 (s, 1H), 4.53-4.67 (m, 1H), 4.09-4.22 (m, 1H), 3.98-4.09 (m, 1H), 3.49 (s, 3H), 1.80-1.97 (m, 2H), 1.45 (s, 3H), 1.36 (s, 3H), 1.21-1.34 (m, 1H), 0.82-1.01 (m, 1H), 0.57-0.74 (m, 6H), 0.32-0.52 (m, 1H).

EXAMPLE 22D (4R)-3-hydroxy-4-(methoxyamino)-4-(3-methylbutyl)naphthalen-1(4H)-one hydrochloride The product from Example 22C (60 mg, 0.15 mmol) in a 2:1 mixture of tetrahydrofuran:2N aq. HCl (0.9 mL) was stirred at rt for 3 h and concentrated in vacuo. The crude product was purified by column chromatography on silica gel using 2:1 ethyl acetate:hexanes to give the hydrochloride salt of the title compound as a colorless amorphous solid (42 mg, 87%): $[α]_D$=+152° (c 1.4, methanol).

EXAMPLE 22E

N-{3-[(4R)-1-hydroxy-4-(methoxyamino)-4-(3-methylbutyl)-3-oxo-3,4-dihydronaphthalen-2-yl]-1,1-dioxido-4H-1,2,4-benzothiadiazin-7-yl}methanesulfonamide The product from Example 22D (39 mg, 0.13 mmol) was subjected to the conditions described in Example 14E. The title compound was obtained as a light yellow solid (33 mg, 48%): $^1$H NMR (300 MHz, DMSO-$d_6$) δ ppm 13.92 (br s, 1H), 10.15 (s, 1H), 8.11 (d, J=7.4 Hz, 1H), 7.88 (d, J=7.7 Hz, 1H), 7.71 (t, J=7.0 Hz, 1H), 7.43-7.67 (m, 4H), 3.16 (s, 3H), 3.06 (s, 3H), 1.71-1.89 (m, 1H), 1.53-1.71 (m, 1H), 1.12-1.39 (m, 1H), 0.77-0.94 (m, 1H), 0.56-0.74 (m, 6H), 0.35-0.58 (m, 1H); $[α]_D$=+89° (c 0.7, methanol).

EXAMPLE 23

N-{3-[(4S)-1-hydroxy-4-(methoxyamino)-4-(3-methylbutyl)-3-oxo-3,4-dihydronaphthalen-2-yl]-1,1-dioxido-4H-1,2,4-benzothiadiazin-7-yl}methanesulfonamide

EXAMPLE 23A (4S)-3-hydroxy-4-(methoxyamino)-4-(3-methylbutyl)naphthalen-1(4H)-one hydrochloride The hydrochloride salt of the title compound was prepared using the procedures described for Example 22D, substituting isopropylidine-L-glyceraldehyde for isopropylidine-D-glyceraldehyde, and was isolated as a colorless, amorphous solid: $[α]_D$=−169° (c 1.0, methanol).

EXAMPLE 23B

N-{3-[(4S)-1-hydroxy-4-(methoxyamino)-4-(3-methylbutyl)-3-oxo-3,4-dihydronaphthalen-2-yl]-1,1-dioxido-4H-1,2,4-benzothiadiazin-7-yl}methanesulfonamide The product from Example 23A (58 mg, 0.19 mmol) was subjected to the conditions described in Example 14E. The title compound was obtained as a light yellow solid (72 mg, 71%): $[α]_D$=−109° (c 1.0, methanol).

EXAMPLE 24

N-hydroxy-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)acetamide

EXAMPLE 24A

N-{3-[4-[acetyl(benzyloxy)amino]-1-hydroxy-4-(3-methylbutyl)-3-oxo-3,4-dihydronaphthalen-2-yl]-1,1-dioxido-4H-1,2,4-benzothiadiazin-7-yl}-N-(methylsulfonyl)acetamide A solution of Example 17 (20 mg, 0.032 mmol), pyridine (26µL, 0.32 mmol), acetic anhydride (16 µL, 0.16 mmol) in dichloroethane (0.5 mL) was heated at 70° C. for 3 h. The solution was cooled to room temperature and concentrated in vacuo. Column chromatography on silica (5% methanol/dichloromethane) afforded the title compound (16 mg, 70%). $^1$H NMR (300 MHz, DMSO-$d_6$) δ ppm 0.45 (s, 1H), 0.57-0.71 (dd, 6H), 1.04 (s, 3H), 1.04 (m, 1H), 1.12-1.38 (m, 2H), 1.19-1.36 (m, 1H), 1.95 (s, 3H), 3.57 (s, 3H), 5.13-5.53 (m, 2H), 7.10-7.75 (m, 9H), 7.92 (s, 1H), 8.05 (d, J=7.72 Hz, 1H), 8.52-8.79 (m, 1H), 15.04 (br. s, 1H); MS m/z 709.4 (M+H)$^+$.

EXAMPLE 24B

N-(benzyloxy)-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)acetamide A solution of Example 24A (16 mg, 0.023 mmol) in methanol (0.4 mL) and 1N NaHCO$_3$ (0.12 mL) was stirred at 25° C. for 1 h. The solution was concentrated in vacuo. Column chromatography on silica (5% methanol/dichloromethane)

afforded the title compound (12 mg, 80%). $^1$H NMR (300 MHz, DMSO-$d_6$) δ ppm 0.31-0.55 (m, 1H), 0.64 (dd, J=15.07, 6.62 Hz, 6H), 0.93-1.10 (m, 1H), 1.22-1.37 (m, 1H), 2.08 (s, 3H) 2.18-2.42 (m, 2H), 3.04 (s, 3H), 5.16-5.41 (m, 2H), 7.26-7.65 (m, 11H), 8.06 (d, 1H), 10.11 (s, 1H), 14.24 (br. s, 1H); MS m/z 666.4 (M+H)$^+$.

EXAMPLE 24C

N-hydroxy-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)acetamide A mixture of Example 24B (12 mg, 0.018 mmol) and 10% Pd/C (2 mg) in methanol (1 mL) was hydrogenated at 1 atm for 1 h. The solution was filtered and the filtrate was concentrated in vacuo. Column chromatography on silica (7% methanol/dichloromethane) afforded the title compound (6 mg, 58%). $^1$H NMR (300 MHz, DMSO-$d_6$) δ ppm 0.50-0.62 (m, 1H), 0.67 (dd, J=9.93, 6.62 Hz, 6H), 0.84-1.06 (m, 1H), 1.22-1.33 (m, 1H), 1.96 (s, 3H), 2.01-2.08 (m, 1H), 2.06-2.21 (m, 1H), 3.03 (s, 3H), 7.51 (m, 6H), 8.03 (d, J=8.09 Hz, 1H), 10.04 (s, 1H), 10.22 (s, 1H), 14.45-14.74 (br. s, 1H)); MS m/z 576.4 (M+H)$^+$.

EXAMPLE 25

N-{3-[4-butyl-1-hydroxy-4-(methoxyamino)-3-oxo-3,4-dihydronaphthalen-2-yl]-1,1-dioxido-4H-1,2,4-benzothiadiazin-7-yl}methanesulfonamide

EXAMPLE 25A

4-butyl-3-hydroxy-4-(methoxyamino)naphthalen-1(4H)-one

A mixture of Example 14B and Example 14C (0.52 g, 1.6 mmol) in ethyl acetate (10 mL) was added platinum oxide (36 mg, 0.16 mmol) and the solution was stirred under a balloon of hydrogen gas for 2 hours. The resulting solution was filtered through Celite and the solvent removed in vacuo. The crude residue was dissolved in tetrahydrofuran (8 mL) and 2N HCl (4 mL) was added. The resulting solution was stirred at room temperature for 2 hours and the solvent was removed in vacuo, the crude residue distributed between H$_2$O (10 mL) and ethyl acetate (10 mL) and the aqueous layer extracted with ethyl acetate (3×10 mL). The combined extracts were washed with brine (1×10 mL) and the organic phase was dried over Na$_2$SO$_4$, the drying agent filtered off and the solvent removed in vacuo to give a crude residue which was purified by column chromatography on a C18 silica gel cartridge (0-100% methanol/H$_2$O over 40 minutes) to isolate the title compound as a colorless solid (90 mg, 20%). The corresponding 3-methylbutyl isomer was not isolated from this mixture; $^1$H NMR ($d_6$-dmso) δ 7.85, 7.82 (d, 1H), 7.63, 7.60 (d, 1H), 7.34-7.25 (t, 1H), 7.25-7.17 (t, 1H), 6.82 (s, 1H), 3.07 (s, 3H), 1.48-1.37 (m, 1H), 1.34-1.20 (m, 1H), 1.03-0.84 (m, 3H), 0.68-0.58 (m, 3H), 0.51-0.39 (m, 1H).

EXAMPLE 25B

N-{3-[4-butyl-1-hydroxy-4-(methoxyamino)-3-oxo-3,4-dihydronaphthalen-2-yl]-1,1-dioxido-4H-1,2,4-benzothiadiazin-7-yl}methanesulfonamide To a solution of Example 25A (90 mg, 0.34 mmol) in dioxane (5 mL) was added pyridine (279 uL, 3.4 mmol) and Example 1D (546 mg, 2.1 mmol) and the mixture heated at 60° C. for 2 hours. The mixture was cooled to room temperature, the solvent removed in vacuo and the crude residue was purified by column chromatography on silica gel (20% ethyl acetate/hexane) to give a light yellow solid which was dissolved in dioxane (5 mL) and Example 1F (101 mg, 0.38 mmol) was added and the solution heated at 70° C. for 64 hours. The solution was cooled to room temperature and solvent was removed in vacuo to yield a crude residue which was purified by column chromatography on silica gel (5% methanol/chloroform) to give the title compound as a colorless solid (128 mg, 70%); $^1$H NMR ($d_6$-DMSO) δ 14.95 (s, 1H), 9.94 (s, 1H), 8.06, 8.04 (d, 1H), 7.78, 7.75 (d, 2H), 7.59-7.29 (m, 4H), 3.14 (s, 3H), 3.01 (s, 3H), 1.74-1.38 (m, 4H), 1.10-0.93 (m, 2H), 0.69-0.59 (m, 3H), MS (ESI) m/z 535 (M+H$^+$).

EXAMPLE 26

N-[3-(4-amino-4-butyl-1-hydroxy-3-oxo-3,4-dihydronaphthalen-2-yl)-1,1-dioxido-4H-1,2,4-benzothiadiazin-7-yl]methanesulfonamide To a solution of Example 25 (98 mg, 0.18 mmol) in CH$_3$CN (16 mL) and H$_2$O (1.1 mL) add molybdenum hexacarbonyl (34 mg, 0.13 mmol) and heat at reflux for 2 hours. The solution was cooled to room temperature, solvent removed in vacuo and the crude residue purified by column chromatography on silica gel (5% methanol/chloroform) to give the title compound as a colorless solid (67 mg, 73%); $^1$H NMR ($d_6$-DMSO) δ 14.47 (s, 1H), 9.95 (s, 1H), 8.60 (s, 2H), 8.14, 8.11 (d, 1H), 7.69-7.41 (m, 5H), 7.37, 7.34 (d, 1H), 3.01 (s, 3H), 2.06-1.95 (m, 1H), 1.90-1.79 (m, 1H), 1.29-1.03 (m, 3H), 0.92-0.78 (m, 1H), 0.78-0.64 (t, 3H); MS (ESI) m/z 505 (M+H$^+$).

EXAMPLE 27 benzyl 4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-ylcarbamate To a solution of Example 16 (20 mg, 0.04 mmol) in tetrahydrofuran (0.5 mL) was added triethylamine (11 μL, 0.08 mmol) and benzyl chloroformate (6 μL, 0.04 mmol) and the mixture was stirred at room temperature for 1 hour. Another 11 μL of triethylamine and 6 μL of benzyl chloroformate were added and the solution stirred at room temperature for 16 hours. Solvent was removed in vacuo and the crude residue was purified by column chromatography on silica gel (4% methanol/chloroform) to give the title compound as a colorless solid (9 mg, 36%). $^1$H NMR ($d_6$-DMSO) δ 14.20 (br s, 1H), 10.13 (s, 1H), 8.40 (br s, 1H), 8.10, 8.07 (d, 1H), 7.73-7.21 (m, 11H), 4.90 (s, 2H), 3.06 (s, 3H), 2.00-1.87 (m, 1H), 1.83-1.70 (m, 1H), 1.31-1.13 (m, 2H), 1.00-0.84 (m, 1H), 0.69-0.59 (t, 6H); MS (ESI) m/z 653 (M+H$^+$).

EXAMPLE 28

2-methoxyethyl 4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-ylcarbamate Same procedure as for Example 27 using 2-methoxyethyl chloroformate (9 μL, 0.08 mmol) to give the title compound

EXAMPLE 29

4-{[(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)amino]sulfonyl}benzoic acid Same procedure as for Example 27 using 4-(chlorosulfonyl)benzoic acid (17 mg, 0.08 mmol) to give the title compound as a colorless solid. $^1$H NMR (d$_6$-DMSO) δ 10.31 (s, 1H), 9.46 (s, 1H), 8.14, 8.12 (d, 1H), 7.87, 7.84 (d, 2H), 7.78-7.45 (m, 8H), 3.06 (s, 3H), 2.24-1.99 (m, 2H), 1.38-1.18 (m, 2H), 1.15-0.95 (m, 1H), 0.75-0.63 (q, 6H); MS (ESI) m/z 703 (M+H$^+$).

EXAMPLE 30

N-(1-butyl-4-hydroxy-3-{7-[(methylsulfonyl)amino]-1,1-dioxido-4H-1,2,4-benzothiadiazin-3-yl}-2-oxo-1,2-dihydronaphthalen-1-yl)acetamide To a solution of Example 26 (20 mg, 0.04 mmol) in dichloromethane (0.5 mL) was added triethylamine (17 μL, 0.12 mmol) and acetic anhydride (7 μL, 0.08 mmol) and the solution was stirred at room temperature for 16 hours. Solvent was removed in vacuo to yield bis-substituted material which is dissolved in methanol (2 mL) and solid K$_2$CO$_3$ (excess) was added and the solution stirred at room temperature for 1 hour. H$_2$O (5 mL) was added and the solution extracted with ethyl acetate (3×5 mL). The combined extracts were washed with brine (1×5 mL), dried (Na$_2$SO$_4$), the drying agent filtered and the solvent removed in vacuo to give a crude residue which was purified by column chromatography on silica gel (3% methanol/chloroform) to give the title compound as a colorless solid. $^1$H NMR (d$_6$-DMSO) δ 10.00 (s, 1H), 8.04, 8.01 (d, 1H), 7.57-7.33 (m, 6H), 3.02 (s, 3H), 1.91-1.79 (m, 1H), 1.82 (s, 3H), 1.72-1.62 (m, 1H), 1.31-1.13 (m, 2H), 0.89-0.63 (m, 2H), 0.72-0.63 (m, 3H). MS (ESI) m/z 547 (M+H$^+$).

EXAMPLE 31

N-(1-butyl-4-hydroxy-3-{7-[(methylsulfonyl)amino]-1,1-dioxido-4H-1,2,4-benzothiadiazin-3-yl}-2-oxo-1,2-dihydronaphthalen-1-yl)methanesulfonamide Same procedure as for Example 30 treating Example 26 with methanesulfonyl chloride (6 uL, 0.08 mmol) in place of acetic anhydride to give a colorless solid. $^1$H NMR (d$_6$-DMSO) δ 15.18 (s, 1H), 9.91 (s, 1H), 8.02, 7.99 (d, 1H), 7.68 (s, 1H), 7.61, 7.58 (d, 1H), 7.54-7.30 (m, 5H), 3.00 (s, 3H), 2.89 (s, 3H), 2.00-1.88 (m, 1H), 1.69-1.58 (m, 1H), 1.27-1.21 (br s, 1H), 1.12-0.94 (m, 3H), 0.70-0.62 (t, 3H); MS (ESI) m/z 583 (M+H$^+$).

as a colorless solid; $^1$H NMR (d$_6$-DMSO) δ 13.65 (s, 1H), 10.24 (s, 1H), 8.13, 8.10 (d, 1H), 7.77-7.68 (t, 2H), 7.65-7.48 (m, 4H), 3.43 (s, 3H), 3.24 (s, 2H), 3.08 (s, 3H), 2.02-1.90 (m, 1H), 1.87-1.75 (m, 1H), 1.38-1.10 (m, 2H), 1.10-0.77 (m, 2H), 0.71-0.60 (t, 6H), 0.77-0.48 (br s, 1H); MS (ESI) m/z 621 (M+H$^+$).

EXAMPLE 32

N-{3-[4-(tert-butoxyamino)-1-hydroxy-3-oxo-4-propyl-3,4-dihydronaphthalen-2-yl]-1,1-dioxido-4H-1,2,4-benzothiadiazin-7-yl}methanesulfonamide

EXAMPLE 32A 2-hydroxynaphthoquinone 1-[O-(tert-butyl)oxime]

To a suspension of 2-hydroxynapthoquinone (0.4 g, 2.3 mmol) in 60% ethanol/H$_2$O (13 mL) was added 1N NaOH (1 mL). The suspension was heated to dissolved at 65° C., cooled to 45° C. and added a solution of t-butylhydroxyamine hydrochloride (0.3 g, 2.4 mmol) in 1N NaOH (2.5 mL). The solution was maintained at 45° C. for 2 days, cooled to 0° C., and the resulted yellow precipitate was filtered. The filtered solid was dried in vacuo to afford the title compound (0.312 g, 56%) and used for the next step without further purification. $^1$H NMR (300 MHz, DMSO-d$_6$) δ ppm 1.48 (s, 9H), 5.93 (s, 1H), 7.54-7.82 (m, 2H), 8.06 (d, J=7.35 Hz, 1H), 8.86 (d, J=7.72 Hz, 1H), 10.66 (br.s, 1H); MS m/z 246.0 (M+H)$^+$.

EXAMPLE 32B 4-allyl-4-(tert-butoxyamino)-3-hydroxynaphthalen-1 (4H)-one

A 2.4 M solution of the allylindium reagent was prepared by suspending indium powder (5 g, 43.5 mmol) in N,N-dimethylformamide (12.5 mL) was added dropwise allyl bromide (5.65 mL, 65.3 mmol). The reaction mixture was stirred at 25° C. for 1 h and used for the following reaction without further purification. To a solution of Example 32A (0.29 g, 1.2 mmol) in N,N-dimethylformamide (1 mL) was added the above 2.4 M solution of allylindium reagent (0.6 mL, 1.4 mmol). The solution was stirred 1 h at room temperature, quenched with 10% citric acid, and extracted with ethyl acetate. The organic extract was concentrated in vacuo. Column chromatography on silica (4% methanol/dichloromethane) afforded the title compound (0.3 g, 88%) as a yellow solid $^1$H NMR (300 MHz, DMSO-d$_6$) δ ppm 0.76-0.94 (m, 9H), 4.67-4.84 (m, 2H), 4.98-5.16 (m, 1H), 5.67 (s, 1H), 6.32 (s, 1H), 7.38 (t, J=6.99 Hz, 1H), 7.54 (t, 1H), 7.75 (d, J=7.72 Hz, 1H), 7.81 (d, J=8.09 Hz, 1H), 11.73 (br.s, 1H); MS m/z 287.8 (M+H)$^+$.

EXAMPLE 32C 4-(tert-butoxyamino)-3-hydroxy-4-propylnaphthalen-1 (4H)-one

A mixture of Example 32B (0.28 g, 0.98 mmol) and 10% Pd/C (18 mg) in methanol (3 mL) was hydrogenated at 1 atm for 2 h. The solution was filtered and the filtrate was concentrated in vacuo. Column chromatography on silica (40% ethyl acetate/hexane) afforded the title compound (0.21 mg, 75%). $^1$H NMR (300 MHz, DMSO-d$_6$) δ ppm 0.39-0.57 (m, 1H), 0.65 (t, 3H), 0.82 (s, 9H), 0.87-1.02 (m, 1H), 1.50-1.85 (m, 2H), 5.59-5.84 (m, 1H), 6.22 (s, 1H), 7.28-7.46 (m, 1H), 7.55 (t, J=7.54 Hz, 1H), 7.71 (d, J=7.72 Hz, 1H), 7.85 (d, 1H), 11.67 (br.s, 1H); MS m/z 290.1 (M+H)$^+$.

EXAMPLE 32D

2-[bis(methylthio)methylene]-4-(tert-butoxyamino)-4-propylnaphthalene-1,3(2H,4H)-dione To a solution of Example C (0.05 g, 0.17 mmol) in dioxane (1 mL) was added Example 1D (0.15 g, 0.6 mmol) followed by pyridine (0.068 mL, 0.85 mmol). The heterogeneous solution was heated at 55° C. for 16h. The solution was cooled to room temperature and concentrated in vacuo. Column chromatography on silica (20% ethyl acetate/hexane) afforded the title compound as a yellow oil (0.06 g, 88%). $^1$H NMR (300 MHz, DMSO-$d_6$) δ ppm 0.53-0.64 (m, 1H), 0.66 (t, J=4.78 Hz, 3H), 0.71-0.76 (m, 1H), 0.81 (s, 9H), 1.46-1.69 (m, 1H), 1.80-1.96 (m, 1H), 2.56 (s, 6H), 6.43 (s, 1H), 7.45 (t, J=7.54 Hz, 1H), 7.64 (t, J=7.54 Hz, 1H), 7.72 (d, 1H), 8.01 (d, J=7.72 Hz, 1H), MS m/z 416.0 (M+Na)$^+$.

EXAMPLE 32E

A mixture of Example 32D (0.06 g, 0.15 mmol) and Example 1F (0.038 g, 0.14 mmol) in dioxane (2 mL) was heated at 80° C. for 6 h. The solution was cooled to room temperature and concentrated in vacuo. Column chromatography on silica (7% methanol/dichloromethane) afforded the title compound as a yellow solid (0.07 g, 86%). $^1$H NMR (300 MHz, DMSO-$d_6$) δ ppm 0.53-0.63 (m, 1H), 0.66 (t, 3H), 0.86 (s, 9H), 0.86-1.07 (m, 1H) 1.56-1.77 (m, 1H), 1.84-1.96 (m, 1H), 3.06 (s, 3H), 7.44-7.69 (m, 5H), 7.78 (d, J=8.09 Hz, 1H), 8.09 (d, J=6.99 Hz, 1H), 10.14 (s, 1H), 14.10 (br.s, 1H); MS m/z 563.1 (M+H)$^+$.

EXAMPLE 33

N-{3-[(4S)-4-amino-1-hydroxy-4-(3-methylbutyl)-3-oxo-3,4-dihydronaphthalen-2-yl]-1,1-dioxido-4H-1,2,4-benzothiadiazin-7-yl}methanesulfonamide The product from Example 23 (0.131 mg, 0.24 mmol) was subjected to the conditions described in Example 16. The title compound was obtained as a light tan solid (72 mg, 48%): $^1$H NMR (300 MHz, DMSO-$d_6$) δ ppm 14.46 (s, 1H), 9.95 (s, 1H), 8.60 (br s, 2H), 8.12 (d, J=7.0 Hz, 1H), 7.59-7.71 (m, 2H), 7.51-7.58 (m, 1H), 7.48-7.51 (m, 1H), 7.41-7.48 (m, 1H), 7.32-7.39 (m, 1H), 3.01 (s, 3H), 1.95-2.08 (m, 1H), 1.80-1.93 (m, 1H), 1.24-1.40 (m, 1H), 1.02-1.14 (m, 1H), 0.65-0.82 (m, 7H); [α]$_D$=−65° (c 1.0, methanol).

EXAMPLE 34

N-{3-[1-hydroxy-4-(hydroxyamino)-3-oxo-4-propyl-3,4-dihydronaphthalen-2-yl]-1,1-dioxido-4H-1,2,4-benzothiadiazin-7-yl}methanesulfonamide A solution of Example 32 (21 mg, 0.037 mmol) an in conc. H$_2$SO$_4$ (0.2 mL) was stirred at 25° C. for 2 h. The solution was quenched with water, neutralized to pH 7 with 1 $\underline{\text{N}}$ NaHCO$_3$ and extracted with ethyl acetate. The organic extract was concentrated in vacuo. Column chromatography on silica (15% methanol/dichloromethane) afforded the title compound as a yellow solid (9 mg, 47%). $^1$H NMR (300 MHz, DMSO-$d_6$) δ ppm 0.62 (t, J=4.04 Hz, 3H), 0.65-0.74 (m, 1H), 0.90-1.05 (m, 1H), 1.35-1.54 (m, 1H), 1.55-1.71 (m, 1H), 3.00 (s, 3H), 7.25-7.59 (m, 5H), 7.70 (d, J=6.99 Hz, 1H), 8.05 (d, J=7.72 Hz, 1H), 9.91 (s, 1H), 15.09 (br.s, 1H); MS m/z 507.0 (M+H)$^+$.

EXAMPLE 35

N-{3-[1-hydroxy-4-(methoxyamino)-4-(2-methylprop-2-enyl)-3-oxo-3,4-dihydronaphthalen-2-yl]-1,1-dioxido-4H-1,2,4-benzothiadiazin-7-yl}methanesulfonamide

EXAMPLE 35A 3-hydroxy-4-(methoxyamino)-4-(2-methylprop-2-enyl)naphthalen-1(4H)-one The title compound was prepared using the procedures described for Example 14A, substituting 3-bromo-2-methylpropene for allyl bromide. The crude product was purified by column chromatography on silica gel using 5% methanol in chloroform to give the title compound as a light yellow, crystalline solid (94% yield): $^1$H NMR (300 MHz, DMSO-$d_6$) δ ppm 11.82 (br s, 1H), 7.96-7.75 (m, 2H), 7.59 (m, 1H), 7.41 (t, J=7.5 Hz, 1H), 6.97-7.25(m, 1H), 5.50-5.79 (m, 1H), 4.52 (s, 1H), 4.11-4.26 (m, 1H), 3.10 (s, 3H), 2.19-2.41 (m, 2H), 1.08-1.25 (m, 3H).

EXAMPLE 35B

N-{3-[1-hydroxy-4-(methoxyamino)-4-(2-methylprop-2-enyl)-3-oxo-3,4-dihydronaphthalen-2-yl]-1,1-dioxido-4H-1,2,4-benzothiadiazin-7-yl}methanesulfonamide The product from Example 35A (0.10 g, 0.39 mmol) was subjected to the conditions described in Example 14E. The title compound was obtained as a light yellow solid (0.14 g, 68%): $^1$H NMR (300 MHz, DMSO-$d_6$) δ ppm 14.17 (br s, 1H), 10.11 (s, 1H), 8.08 (d, J=6.6 Hz, 1H), 7.91 (d, J=7.7 Hz, 1H), 7.60-7.76 (m, 1H), 7.41-7.63 (m, 4H), 4.55 (s, 1H), 4.17 (s, 1H), 3.17 (s, 3H), 3.05 (s, 3H), 2.44-2.51 (m, 1H), 2.28-2.44 (m, 1H), 1.21 (m, 3H).

EXAMPLE 36

N-{3-[1-hydroxy-4-isobutyl-4-(methoxyamino)-3-oxo-3,4-dihydronaphthalen-2-yl]-1,1-dioxido-4H-1,2,4-benzothiadiazin-7-yl}methanesulfonamide

EXAMPLE 36A 3-hydroxy-4-isobutyl-4-(methoxyamino)naphthalen-1(4H)-one

To a solution of the product from Example 35A (0.50 g, 1.91 mmol) in methanol (10 mL) was added 10% Pd/C (100 mg), and the resulting mixture was stirred at room temperature under 1 atm H$_2$ for 16 h. The catalyst was filtered off, and the solvent was evaporated to give a crude product which was purified by column chromatography on silica gel using 5% methanol in chloroform. The title compound was obtained as an oil (0.18 g, 36%).

EXAMPLE 36B

N-{3-[1-hydroxy-4-isobutyl-4-(methoxyamino)-3-oxo-3,4-dihydronaphthalen-2-yl]-1,1-dioxido-4H-1,2,4-benzothiadiazin-7-yl}methanesulfonamide The product from Example 36A (0.18 g, 0.60 mmol) was subjected to the conditions described in Example 14E. The title compound was obtained as a light yellow solid (0.17 g, 53%): $^1$H NMR (300 MHz, DMSO-$d_6$) δ ppm 13.99 (br s, 1H), 10.14 (s, 1H), 8.12 (d, J=7.7 Hz, 1H), 7.87 (d, J=7.4 Hz, 1H), 7.70 (t, J=7.0 Hz, 1H), 7.43-7.66 (m, 4H), 3.12 (s, 3H), 3.06 (s, 3H), 1.70-1.83 (m, 1H), 1.56-1.68 (m, 1H), 1.13-1.30 (m, 1H), 0.66 (d, J=6.6 Hz, 3H), 0.39 (d, J=6.6 Hz, 3H).

EXAMPLE 37

N-{3-[1-hydroxy-4-(hydroxyamino)-4-(3-methylbutyl)-3-oxo-3,4-dihydronaphthalen-2-yl]-1,1-dioxido-4H-1,2,4-benzothiadiazin-7-yl}methanesulfonamide A solution of Example 17 (70 mg, 0.112 mmol) an in conc. $H_2SO_4$ (0.5 mL) was stirred at 25° C. for 0.5 h. The solution was quenched with water, neutralized to pH 7 with 1 N NaHCO$_3$, and extracted with ethyl acetate. The organic extract was concentrated in vacuo Column chromatography on silica (7% methanol/dichloromethane) afforded the title compound as a solid (38 mg, 64%). $^1$H NMR (300 MHz, DMSO-$d_6$) δ ppm 0.37-0.59 (m, 1H), 0.67 (dd, J=12.50, 6.62 Hz, 6H,) 0.89-1.10 (m, 1H), 1.31 (m, 1H), 1.78 (m, 1H), 1.94-2.11 (m, 1H), 3.02 (s, 3H), 7.32-7.49 (m, 4H), 7.65 (m, 1H), 7.79 (d, J=8.09 Hz, 1H), 8.15 (d, 1H), 9.98 (s, 1H) 10.38-10.60 (br s, 1H) 14.34 (s, 1H); MS m/z 535.1 (M+H)$^+$.

EXAMPLE 38

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-morpholin-4-ylethanesulfonamide

EXAMPLE 38A tert-butyl 3-{1-hydroxy-4-(3-methylbutyl)-3-oxo-4-[(vinylsulfonyl)amino]-3,4-dihydronaphthalen-2-yl}-1,1-dioxido-4H-1,2,4-benzothiadiazin-7-ylcarbamate To a solution of 2-chloro-1-ethanesulfonyl chloride (29 uL, 0.28 mmol) in anhydrous dichloromethane (2 mL) at 0° C. was added Example 18C (100 mg, 0.18 mmol) and triethylamine (54 uL, 0.39 mmol) and the solution was stirred at 0° C. for 1 hour. Triethylamine (39 μL, 0.28 mmol) was added and stirring was continued for 1 hour at 0° C. and then the solution was allowed to warm to room temperature over 16 hours. The solution was diluted with dichloromethane (10 mL) and washed with H$_2$O (10 mL) and brine (10 mL) and the resulting solution dried (Na$_2$SO$_4$), the drying agent filtered off and the solvent removed in vacuo to yield the title compound as a light-yellow oil. $^1$H NMR (d$_6$-DMSO) δ 13.87 (s, 1H), 9.84 (s, 1H), 8.46 (s, 1H), 8.12-8.05 (m, 1H), 7.73-7.47 (m, 5H), 6.57, 6.54, 6.52, 6.49 (q, 1H), 5.65, 5.62, 5.60 (t, 2H), 2.16-2.03 (m, 1H), 1.89-1.77 (m, 1H), 1.51 (s, 9H), 1.33-1.17 (m, 1H), 0.96-0.80 (m, 1H), 0.75-0.59 (m, 6H), 0.55-0.40 (m, 1H); MS (ESI) m/z 631 (M+H$^+$).

EXAMPLE 38B

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)ethylenesulfonamide To Example 38A (0.18 mmol) was added 4M HCl in dioxane (4 mL). The solution was stirred at room temperature for 2 hours and solvent was removed in vacuo. The crude residue was dissolved in dichloromethane (2 mL) and pyridine (75 μl, 0.9 mmol) and methanesulfonyl chloride (29 μL, 0.36 mmol) were added and the solution was allowed to stir for 3 hours at room temperature. The solvent was removed in vacuo and the crude residue was purified by column chromatography on silica gel (2% methanol/chloroform) to give the title compound as a colorless solid. $^1$H NMR (d$_6$-DMSO) δ 15.05 (s, 1H), 9.94 (s, 1H), 8.02, 7.99 (d, 1H), 7.94 (s, 1H), 7.61-7.32 (m, 5H), 6.72, 6.69, 6.66, 6.63 (q, 1H), 5.71, 5.66, 5.63 (t, 2H), 3.01 (s, 3H), 2.07-1.92 (m, 1H), 1.78-1.61 (m, 1H), 1.32-1.11 (m, 2H), 1.02-0.78 (m, 20' 1H), 0.78-0.58 (m, 6H) 0.58-0.51 (m, 1H); MS (ESI) m/z 609 (M+H$^+$).

EXAMPLE 38C

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-morpholin-4-ylethanesulfonamide To a solution of Example 38B (13.3 mg, 0.02 mmol) in tetrahydrofuran (0.5 mL) was added morpholine (4 uL, 0.04 mmol) and the solution was stirred at room temperature for 16 hours, solvent was removed in vacuo and the crude residue was purified by column chromatography on silica gel (1-3% methanol/chloroform) to give the title compound as a colorless solid. $^1$H NMR (d$_6$-DMSO) δ 15.25 (s, 1H), 8.01, 7.99 (d, 1H), 7.61, 7.59 (d, 2H), 7.53-7.28 (m, 5H), 3.70-3.64 (m, 2H), 3.62-3.49 (m, 5H), 3.10-3.01 (m, 1H), 2.99 (s, 3H), 2.85-2.73 (m, 1H), 2.67-2.55 (m, 1H), 2.44-2.32 (m, 2H), 2.03-1.91 (m, 1H), 1.72-1.61 (m, 1H), 0.99-0.83 (m, 1H), 0.70-0.60 (q, 6H), 0.60-0.45 (m, 1H); MS (ESI) m/z 696 (M+H$^+$).

EXAMPLE 39

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-N-methoxyacetamide

EXAMPLE 39A tert-butyl 3-[4-[acetyl(methoxy)amino]-1-hydroxy-4-(3-methylbutyl)-3-oxo-3,4-dihydronaphthalen-2-yl]-1,1-dioxido-4H-1,2,4-benzothiadiazin-7-ylcarbamate To a solution of the product from Example 18B (23 mg, 0.04 mmol) in pyridine (0.5 mL) was added acetic anhydride (38 μL, 0.4 mmol). The reaction solution was stirred at room temperature for 18 h. After which, the solution was concentrated in vacuo. The resulting residue was taken up ethyl acetate (2 mL) and washed with aqueous 1 N HCl (2×1 mL). The organic layer was dried (Na$_2$SO$_4$) and concentrated in vacuo. Column chromatography on silica (1%→3%→5% methanol/dichloromethane) afforded the title compound as a yellow solid (17 mg, 68%). $^1$H NMR (300 MHz, DMSO-$d_6$) δ ppm 0.34-0.52 (m, 1H), 0.58-0.76 (m, 6H), 0.88-1.04 (m, 1H), 1.20-1.37 (m, 2H), 1.50 (s, 9H), 2.04 (s, 3H), 7.53 (t, J=7.54 Hz, 2H), 7.62-7.77 (m, 3H), 8.07-8.17 (m, 2H), 9.89 (s, 1H), 13.49 (s, 1H); MS m/z 613.1 (M+H)$^+$.

EXAMPLE 39B

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-N-methoxyacetamide A mixture of the product of Example 39A (16 mg, 0.026 mmol) and 4 N HCl in dioxane (0.26 mL) was stirred at room temperature for 4 h and then concentrated in vacuo. The resulting residue was taken up in dichloromethane (1 mL) and triethylamine (36 μL, 0.3 mmol) and methanesulfonyl chloride (10μL, 0.13 mmol) were then added. The reaction solution was stirred at room temperature for 2 h. The solution was then washed with aqueous 1 N HCl (2×0.5 mL), dried (Na$_2$SO$_4$), and concentrated in vacuo. The residue was then dissolved in methanol (1 mL) and treated with excess of K$_2$CO$_3$ for 30 min. The mixture was diluted with ethyl acetate (3 mL) and filtered. The filtrate was washed with aqueous 1 N HCl (2×1 mL), dried (Na$_2$SO$_4$), and concentrated in vacuo. Column chromatography on silica (1%→3%→5% methanol/dichloromethane) afforded the title compound as a yellow solid (8 mg, 53%). $^1$H NMR (300 MHz, DMSO-d$_6$) δ ppm 0.38-0.56 (m, 1H), 0.60-0.73 (m, 6H), 0.91-1.09 (m, 1H), 1.17-1.39 (m, 2H), 2.01 (s, 3H), 2.11-2.32 (m, 1H), 3.03 (s, 3H), 4.05 (s, 3H), 7.32-7.62 (m, 7H), 8.05 (d, J=7.72 Hz, 1H), 10.05 (s, 1H), 14.46 (s, 1H); MS m/z 591.1 (M+H)$^+$.

EXAMPLE 40 methyl[(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)oxy]acetate

EXAMPLE 40A ethyl {[4-methoxy-1-(3-methylbutyl)-2-oxo-1,2-dihydronaphthalen-1-yl]oxy}acetate To a solution of Example 11A (100 mg, 0.384 mmol) in N,N-dimethylformamide (1 mL) at 0° C. was added 60% wt sodium hydride (71.4 mg, 1.54 mmol). The reaction solution was stirred for 0.5 h and 2-iodo ethyl acetate (0.14 mL, 1.15 mmol) was added. The solution was stirred 16 h at room temperature, quenched with saturated NH$_4$Cl, and extracted with ethyl acetate. The organic extract was concentrated in vacuo. Column chromatography on silica (30% ethyl acetate/hexane) afforded the title compound (84 mg, 63%). $^1$H NMR (300 MHz, DMSO-d$_6$) δ ppm 0.61-0.74 (m, 1H), 0.72 (dd, 6H), 0.88-1.00 (m, 1H), 1.14 (t, J=6.99 Hz, 3H), 1.23-1.40 (m, 1H), 1.66-2.05 (m, 2H), 3.40 (d, J=15.08 Hz, 1H), 3.75 (d, J=14.71 Hz, 1H), 3.95 (s, 3H), 3.96-4.11 (m, 2H), 5.77 (s, 1H), 7.44-7.55 (m, 1H), 7.60 (d, J=4.04 Hz, 2H), 7.82 (d, J=7.72 Hz, 1H); MS m/z 346.9 (M+H)$^+$.

EXAMPLE 40B

{[1-(3-methylbutyl)-2,4-dioxo-1,2,3,4-tetrahydronaphthalen-1-yl]oxy}acetic acid

A solution of Example 40A (30 mg, 0.087 mmol) in methanol (0.2 mL) and 1 N NaOH (0.2 mL) was stirred at 25° C. for 16 hours. The methanol was evaporated. The resulted solution was acidified with 1N HCl to pH 3, extracted with ethyl acetate, dried (Na$_2$SO$_4$), and filtered. The filtrate was concentrated in vacuo to afforded the title compound (24 mg, 91%) and used for the next step without further purification. $^1$H NMR (300 MHz, DMSO-d$_6$) δ ppm 0.35-0.49 (m, 1H,) 0.69 (dd, J=13.05, 6.43 Hz, 6H), 0.77-0.96 (m, 1H), 1.24-1.36 (m, 1H), 1.83-1.94 (m, 1H), 2.04-2.22 (m, 1H), 3.18 (d, 1H), 3.67 (d, J=15.44 Hz, 1H), 5.76 (s, 1H), 7.45-7.55 (m, 1H), 7.59-7.73 (m, 2H), 7.90 (d, J=7.72 Hz, 1H), 11.83-12.71 (br. s, 1H); MS (ESI) m/z 304.9 (M+H)$^+$.

EXAMPLE 40C methyl{[1-(3-methylbutyl)-2,4-dioxo-1,2,3,4-tetrahydronaphthalen-1-yl]oxy}acetate A solution of Example 40B (20 mg, 0.066 mmol), 1,3-dicyclohexylcarbodiimide (20 mg, 0.1 mmol) in tetrahydrofuran (2 mL) and methanol (0.5 mL) was stirred at 25° C. for 16 hours. The solution was and concentrated in vacuo. Column chromatography on silica (7% methanol/dichloromethane) afforded the title compound (19 mg, 91%). $^1$H NMR (300 MHz, DMSO-d$_6$) δ ppm 0.37-0.47 (m, 1H), 0.68 (dd, J=13.24, 6.62 Hz, 6H), 0.76-0.91 (m, 1H), 1.15-1.34 (m, 1H), 1.81-1.98 (m, 1H), 2.05-2.22 (m, 1H), 3.40 (d, J=15.08 Hz, 1H), 3.57 (s, 3H), 3.76 (d, J=15.07 Hz, 1H), 5.75 (s, 1H), 7.43-7.57 (m, 1H), 7.55-7.70 (m, 2H), 7.89 (d, J=7.72 Hz, 1H), 11.94 (br. s, 1H); MS (ESI) m/z 319.0 (M+H)$^+$.

EXAMPLE 40D methyl{[3-[bis(methylthio)methylene]-1-(3-methylbutyl)-2,4-dioxo-1,2,3,4-tetrahydronaphthalen-1-yl]oxy}acetate To a solution of Example 40C (18 mg, 0.057 mmol) in dioxane (1 mL) was added Example 1D (139 mg, 0.57 mmol) followed by pyridine (0.06 mL, 0.74 mmol). The heterogeneous solution was heated at 60° C. for 16h. The solution was cooled to room temperature and concentrated in vacuo. Column chromatography on silica (30% ethyl acetate/hexane) afforded the title compound as a yellow oil (18 mg, 75%). $^1$H NMR (300 MHz, DMSO-d$_6$) δ ppm 0.69 (dd, J=6.62, 5.15 Hz, 6H), 0.77-0.90 (m, 1H), 1.04 (m, 1H), 1.22-1.41 (m, 1H), 1.70-1.94 (m, 2H), 2.58 (s, 6H), 3.63 (s, 3H), 3.68 (d, J=15.44 Hz, 1H), 4.02 (d, J=15.44 Hz, 1H), 7.49-7.63 (m, 2H), 7.65-7.74 (m, 1H), 8.06 (d, J=7.72 Hz, 1H); MS (ESI) m/z 445.0 (M+Na)$^+$.

EXAMPLE 40E methyl[(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)oxy]acetate A mixture of Example 40D (17 mg, 0.04 mmol) and Example 1F (10.1 mg, 0.036 mmol) in dioxane (1 mL) was heated at 85° C. for 16 h. The solution was cooled to room temperature and concentrated in vacuo. Column chromatography on silica (10% methanol/dichloromethane) afforded the title compound as a light yellow solid (10 mg, 44%). $^1$H NMR (300 MHz, DMSO-d$_6$) δ ppm 0.56-0.64 (m, 1H), 0.69 (t, J=6.99 Hz, 6H), 0.93-1.06 (m, 1H), 1.20-1.35 (m, 1H), 1.75-1.92 (m, 1H), 1.96-2.15 (m, 1H), 3.02 (s, 3H), 3.50 (d, J=15.07 Hz, 1H), 3.60 (s, 3H), 3.92 (d, J=15.07 Hz, 1H), 7.34-7.66 (m, 6H), 8.04 (d, J=6.62 Hz, 1H), 10.00 (s, 1H), 14.31 (br. s, 1H); MS m/z 589.4 (M−H)$^-$.

EXAMPLE 41

2-[(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)oxy]acetamide A solution of Example 40 (5 mg, 0.008 mmol) in methanol (0.1 1 mL) and ammonium hydroxide (0.1 mL) was stirred at 25° C. for 3 h. The solution was concentrated in vacuo. Column chromatography on silica (10% methanol/dichloromethane) afforded the title compound as a white solid (4 mg, 82%). $^1$H NMR (300 MHz, DMSO-$d_6$) δ ppm 0.51-0.68 (m, 1H), 0.69 (t, J=6.99 Hz, 6H), 0.94-1.02 (m, 1H), 1.21-1.32 (m, 1H), 1.70-1.86 (m, 1H), 1.94-2.15 (m, 1H), 3.00 (s, 3H), 3.27 (d, 1H), 3.42 (d, 1H), 7.20-7.55 (m, 6H), 7.55 (d, J=4.41 Hz, 2H), 8.03 (d, J=7.72 Hz, 1H), 9.91 (s, 1H), 14.93 (s, 1H); MS m/z 576.4 (M+H)$^+$.

EXAMPLE 42

N-((1S)-4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)methanesulfonamide To a solution of the product from Example 33 (0.18 g, 0.35 mmol) in anhydrous dichloromethane (4 mL) was added methanesulfonyl chloride (82 μL, 1.06 mmol) and triethylamine (0.20 mL, 1.48 mmol). The resulting mixture was stirred at rt 2 h, and the solvent was removed in vacuo. The resulting residue was dissolved in anhydrous methanol (4 mL) and treated with $K_2CO_3$ (0.2 g, 1.5 mmol), and the resulting mixture was stirred at rt for 16 h. The mixture was poured into 0.5 N aq. HCl (10 mL) and extracted with 3:1 dichloromethane:2-propanol (3×20 mL). The combined organic layers were dried over $Na_2SO_4$, filtered and concentrated, and the crude product was purified by column chromatography on silica gel using 5% methanol in chloroform. The title compound was obtained as a light yellow solid (0.154 g, 74%): $^1$H NMR (300 MHz, DMSO-$d_6$) δ ppm 13.93 (br s, 1H), 10.17 (s, 1H), 8.23 (s, 1H), 8.10 (d, J=7.7 Hz, 1H), 7.69-7.77 (m, 2H), 7.47-7.68 (m, 4H), 3.06 (s, 3H), 2.80 (s, 3H), 1.97-2.15 (m, 1H), 1.70-1.90 (m, 1H), 1.18-1.36 (m, 1H), 0.82-1.03 (m, 1H), 0.58-0.77 (m, 6H), 0.44-0.58 (m, 1H).

EXAMPLE 43

N-{3-[(4S)-4-(3,3-dimethylbutyl)-1,4-dihydroxy-3-oxo-3,4-dihydronaphthalen-2-yl]-1,1-dioxido-4H-1,2,4-benzothiadiazin-7-yl}methanesulfonamide The product from Example 8 was separated by chiral HPLC (Chiralcel OD using hexanes/ethanol/methanol/trifluoroacetic acid =80/5/15/0.1%) to give the title compound as a light yellow solid: $^1$H NMR (300 MHz, DMSO-$d_6$) δ ppm 13.57 (br s, 1H), 10.12 (s, 1H), 8.01 (d, J=7.4 Hz, 1H), 7.61-7.73 (m, 2H), 7.42-7.61 (m, 4H), 3.05 (s, 3H), 1.71-2.02 (m, 2H), 0.89-1.09 (m, 1H), 0.72-0.83 (m, 1H), 0.70 (s, 9H); $[α]_D$=174° (c 1.5, methanol).

EXAMPLE 44

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-(methylamino)ethanesulfonamide Same procedure as for Example 38C treating Example 38B with 2M methylamine in tetrahydrofuran (22 μL, 0.04 mmol) to give the title compound as a colorless solid; $^1$H NMR ($d_6$-DMSO) δ 14.72 (s, 1H), 9.98 (s, 1H), 8.25 (s, 1H), 8.05, 8.02 (d, 1H), 7.63-7.32 (mm 7H), 3.01 (s, 3H), 2.72 (s, 3H), 2.17-2.06 (m, 1H), 1.74-1.63 (mm 1H), 1.30-1.10 (m, 4H), 0.95-0.72 (m, 2H), 0.71-0.58 (q, 6H), 0.54-0.37 (m, 1H); MS (ESI) m/z 640 (M+H$^+$).

EXAMPLE 45 tert-butyl 2-[(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)amino]-2-oxoethylcarbamate A mixture of N-Boc-glycine (7 mg, 0.038 mmol), 3-(diethoxyphosphoryloxy)-1,2,3-benzotriazin-4(3H)-one (11 mg, 0.038 mmol), and triethylamine (11 μL, 0.077 mmol) in N,N-dimethylformamide (0.3 mL) was stirred at room temperature for 30 min. After which, the product of Example 16 (10 mg, 0.019 mmol) was added and stirring was continued for 2 h. The solution was diluted with ethyl acetate (1 mL) and washed with aqueous 1 N HCl (3×0.5 mL). The organic layer was dried ($Na_2SO_4$) and concentrated in vacuo. Column chromatography on silica (5% methanol/dichloromethane) afforded the title compound as a white solid (7 mg, 64%). $^1$H NMR (300 MHz, DMSO-$d_6$) 1 ppm 0.62-0.75 (m, 6H), 0.84-1.01 (m, 1H), 1.15-1.41 (m, 11H), 1.62-1.78 (m, 1H), 1.81-1.99 (m, 1H), 3.01 (s, 3H), 3.54-3.66 (m, 2H), 6.81 (t, J=5.15 Hz, 1H), 7.30-7.54 (m, 5H), 8.02 (d, J=7.35 Hz, 1H), 8.40 (s, 1H), 9.96 (s, 1H), 14.95 (s, 1H); MS m/z 673.3 (M+H)$^+$.

EXAMPLE 46

2-amino-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)acetamide A mixture of the product of Example 45 (4 mg, 0.0059 mmol) and 4 N HCl in dioxane (0.25 mL) was stirred at room temperature for 2 h. After which, the solution was concentrated in vacuo to afford the title compound as a white solid (3.5 mg, 97%). $^1$H NMR (300 MHz, DMSO-$d_6$) δ ppm 0.57-0.74 (m, 6H), 0.79-0.94 (m, 1H), 1.19-1.39 (m, 2H), 1.75-1.90 (m, 1H), 1.92-2.12 (m, 1H), 3.05 (s, 3H), 7.42-7.66 (m, 5H), 7.88-7.97 (m, 2H), 8.10 (d, J=7.72 Hz, 1H), 9.39 (s, 1H), 10.15 (s, 1H), 14.19 (s, 1H); MS m/z 575.7 (M+H)$^+$.

EXAMPLE 47

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-methoxyethanesulfonamide To a solution of Example 38B (24 mg, 0.04 mmol) in methanol (250 μL) in a pressure flask was added 25% sodium methoxide in methanol (90 μL, 0.4 mmol). The tube was sealed and heated at 85° C. for 16 hours, cooled to room temperature and the solvent removed in vacuo. The crude residue was purified by column chromatography on silica gel (2% methanol/chloroform) to give the title compound as a colorless solid. $^1$H NMR ($d_6$-DMSO) δ 15.26 (s, 1H), 9.89 (s, 1H), 8.01. 7.98 (d, 1H), 7.66-7.28 (m, 7H), 3.80-3.61 (m, 2H), 3.45-3.29 (m, 1H), 3.26 (s, 3H), 3.28-3.12 (m, 1H), 3.00 (s, 3H), 2.04-1.90 (m, 1H), 1.71-1.60 (m, 1H), 1.06-0.88 (m, 2H), 0.70-0.60 (q, 6H), 0.62-0.54 (m, 1H); MS (ESI) m/z 641 (M+H$^+$).

EXAMPLE 48

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-[(2-methoxyethyl)amino]ethanesulfonamide To a solution of Example 388B (15 mg, 0.025 mmol) in tetrahydrofuran (0.2 mL) was added methoxyethylamine (4.3 µL, 0.05 mmol) and the solution was stirred at room temperature for 24 hours. An additional amount of methoxyethylamine (4.3 µL, 0.05 mmol) was added and stirring was continued for an additional 24 hours, solvent was removed in vacuo and the crude residue was purified by column chromatography on silica gel (1% methanol/chloroform) to give the title compound as a colorless solid. $^1$H NMR (d$_6$-DMSO) δ 14.68 (s, 1H), 9.97 (s, 1H), 8.92, 8.77 (br d, 1H), 8.22 (s, 1H), 8.05, 8.02 (d, 1H), 7.64-7.35 (m, 6H), 3.77-3.59 (m, 2H), 3.33 (s, 3H), 3.18-2.96 (m, 2H), 3.01 (s, 3H), 2.10-1.99 (m, 1H), 1.75-1.65 (m, 1H), 1.30-1.15 (m, 2H), 0.96-0.83 (m, 1H), 0.74-0.58 (q, 6H); MS (ESI) m/z 684 (M+H$^+$).

EXAMPLE 49

2-(diethylamino)-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)ethanesulfonamide Same procedure as for Example 48 treating Example 38B with diethylamine (5 µL, 0.05 mmol) to give the title compound as a colorless solid; $^1$H NMR (d$_6$-DMSO) δ 14.55 (s, 1H), 9.97 (s, 1H), 8.29 (br s, 1H), 8.04, 8.01 (d, 1H), 7.61-7.34 (m, 6H), 3.57-3.28 (m, 4H), 3.01 (s, 3H), 2.23-2.02 (m, 1H), 1.78-1.60 (m, 1H), 1.40-1.12 (m, 10H), 0.93-0.78 (m, 2H), 0.70-0.59 (q, 6H), 0.58-0.30 (m, 1H); MS (ESI) m/z 682 (M+H$^+$).

EXAMPLE 50

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-{methyl[2-(methylamino)ethyl]amino}ethanesulfonamide Same procedure as for Example 48 treating example 38B with N,N'-dimethyl ethylenediamine (7 µL, 0.05 mmol) to give the title compound as a colorless solid. $^1$H NMR (d$_6$-DMSO) δ 15.22 (s, 1H), 8.05, 8.03 (d, 1H), 7.63-7.30 (m, 6H), 2.98-2.87 (m, 2H), 2.99 (s, 3H), 2.97 (s, 3H), 2.81-2.67 (m, 2H), 2.61 (s, 3H), 2.18 (s, 2H), 1.67-1.59 (m, 2H), 0.88-0.82 (m, 4H), 0.69-0.59 (q, 6H), 0.52-0.39 (m, 1H); MS (ESI) m/z 697 (M+H$^+$).

EXAMPLE 51

N-{3-[1-hydroxy-4-(isobutylamino)-4-(3-methylbutyl)-3-oxo-3,4-dihydronaphthalen-2-yl]-1,1-dioxido-4H-1,2,4-benzothiadiazin-7-yl}methanesulfonamide To a suspension of the product of Example 16 (10 mg, 0.018 mmol) in dichloromethane (0.2 mL) was added N,N-diisopropylethylamine (6 µL, 0.036 mmol). The mixture was stirred at room temperature until homogenous (approx. 5 min). After which, isobutyraldehyde (2 µL, 0.022 mmol) was added and the mixture was stirred at room temperature for 18 h. To the reaction solution was then added sodium triacetoxyborohydride (7 mg, 0.029 mmol) and glacial acetic acid (3 µL, 0.045 mmol), and stirring was continued at room temperature for 18 h. The mixture was diluted with ethyl acetate (1 mL), washed with water (2×2 mL), dried (Na$_2$SO$_4$), and concentrated in vacuo. Column chromatography on silica (5% methanol/dichloromethane) afforded the title compound as a white solid (8 mg, 80%). $^1$H NMR (300 MHz, DMSO-d$_6$) δ ppm 0.39-0.55 (m, 1H), 0.68 (dd, J=12.69, 6.43 Hz, 6H), 0.87 (dd, J=13.24, 6.62 Hz, 6H), 0.95-1.17 (m, 1H), 1.24-1.40 (m, 1H), 1.80-2.18 (m, 3H), 2.19-2.36 (m, 2H), 3.01 (s, 3H), 7.33-7.39 (m, 1H), 7.42-7.53 (m, 2H), 7.58 (t, J=7.54 Hz, 1H), 7.68 (t, J=7.35 Hz, 1H), 7.84 (d, J=7.35 Hz, 1H), 8.17 (d, J=7.35 Hz, 1H), 9.01 (s, 1H), 9.97 (s, 1H), 13.93 (s, 1H); MS m/z 575.1 (M+H)$^+$.

EXAMPLE 52

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-[(2-methoxybenzyl)(methyl)amino]ethanesulfonamide Same procedure as for Example 48 treating example 38B with 2-methoxy-N-methylbenzylamine (7.3 µL, 0.05 mmol) to give the title compound as a colorless solid. $^1$H NMR (d$_6$-DMSO) δ 9.95 (s, 1H), 8.27 (br s, 1H), 8.04, 8.02 (d, 1H), 7.66-7.33 (m, 8H), 7.15-6.98 (m, 2H), 3.85 (s, 3H), 3.00 (s, 3H), 2.82 (br s, 2H), 2.05-1.85 (m, 1H), 1.79-1.62 (m, 1H), 1.55-1.40 (m, 1H), 1.35-1.14 (m, 1H) 1.24 (s, 3H), 0.93-0.83 (m, 2H), 0.80-0.70 (m, 2H), 0.70-0.60 (q, 6H), 0.55-0.34 (m, 1H); MS (ESI) m/z 760 (M+H$^+$).

EXAMPLE 53 ethyl[{3-[1-hydroxy-4-(hydroxyamino)-4-(3-methylbutyl)-3-oxo-3,4-dihydronaphthalen-2-yl]-1,1-dioxido-4H-1,2,4-benzothiadiazin-7-yl}(methylsulfonyl)amino]acetate

EXAMPLE 53A ethyl N-{3-[4-[(benzyloxy)amino]-1-hydroxy-4-(3-methylbutyl)-3-oxo-3,4-dihydronaphthalen-2-yl]-1,1-dioxido-4H-1,2,4-benzothiadiazin-7-yl}-N-(methylsulfonyl)glycinate A solution of Example 17H (50 mg, 0.08 mmol) in N,N-dimethylformamide (0.25 mL) at 25° C. was added powdered NaHCO$_3$ (40 mg, 0.48 mmol). The reaction solution was stirred for 0.15 h and 2-iodo ethyl acetate (29 µL, 0.24 mmol) was added. The solution was stirred 16 h at room temperature, quenched with 10% citric acid, and extracted with ethyl acetate. The organic extract was concentrated in vacuo. Column chromatography on silica (2% methanol/dichloromethane) afforded the title compound as a white solid (40 mg, 70%). $^1$H NMR (300 MHz, DMSO-d$_6$) δ ppm 0.42-0.57 (m, 1H), 0.64 (dd, J=9.93, 6.62 Hz, 6H), 0.95-1.09 (m, 1H), 1.20 (t, 3H), 1.43-1.80 (m, 2H), 3.12 (s, 3H), 4.12 (q, J=7.23 Hz, 2H), 4.28-4.47 (m, 2H), 4.56 (s, 3H), 6.96 (dd, J=6.80, 2.76 Hz, 2H), 7.16-7.26 (m, 3H), 7.38-7.57 (m, 2H), 7.56-7.73 (m, 2H), 7.75-7.91 (m, 2H), 8.02-8.17 (m, 1H), 14.62 (br.s, 1H); MS m/z 709.0 (M–H)$^−$.

EXAMPLE 53B ethyl [{3-[1-hydroxy-4-(hydroxyamino)-4-(3-methylbutyl)-3-oxo-3,4-dihydronaphthalen-2-yl]-1,1-dioxido-4H-1,2,4-benzothiadiazin-7-yl}(methylsulfonyl)amino]acetate A solution of Example 53A (40 mg, 0.056 mmol) an in conc. $H_2SO_4$ (0.25 mL) was stirred at 25° C. for 1.5 h. The solution was quenched with water, neutralized to pH 7 with 1 N $NaHCO_3$, and extracted with ethyl acetate. The organic extract was concentrated in vacuo. Column chromatography on silica (10% methanol/dichloromethane) afforded the title compound as a yellow solid (23 mg, 75%). $^1$H NMR (300 MHz, DMSO-$d_6$) δ ppm 0.40-0.59 (m, 1H), 0.64 (dd, J=1.40, 6.62 Hz, 6H), 0.81-0.92 (m, 1H), 0.92-1.03 (m, 1H), 1.18 (t, J=7.17 Hz, 3H), 1.45-1.67 (m, 1H), 1.64-1.82 (m, 1H), 3.11 (s, 3H), 4.12 (q, J=6.99 Hz, 2H), 4.54 (s, 2H), 7.30-7.47 (m, 2H), 7.47-7.87 (m, 4H), 8.06 (d, 1H), 14.92-15.36 (br.s, 1H); MS m/z 621.0 $(M+H)^+$.

EXAMPLE 54

[{3-[1-hydroxy-4-(hydroxyamino)-4-(3-methylbutyl)-3-oxo-3,4-dihydronaphthalen-2-yl]-1,1-dioxido-4H-1,2,4-benzothiadiazin-7-yl}(methylsulfonyl)amino]acetic acid A solution of Example 53B (15 mg, 0.024 mmol) in tetrahydrofuran (0.3 mL) and 1 N HCl (0.2 mL) was heated at 65° C. for 4 hours. The solution was cooled to room temperature and concentrated in vacuo. The residue was chromatographed on a reverse phase C18 column eluting with 5%-100% acetonitrile in water containing 0.1% trifluoroacetic acid to afforded the title compound as a yellow solid (4 mg, 28%). $^1$H NMR (300 MHz, DMSO-$d_6$) δ ppm 0.46-0.61 (m, 1H), 0.67 (dd, J=12.50, 6.62 Hz, 6H, 0.93-1.05 (m, 1H), 1.16-1.40 (m, 1H), 1.69-1.90 (m, 1H), 1.96-2.16 (m, 1H), 3.11 (s, 3H), 4.46 (s, 2H), 7.43 (d, J=8.46 Hz, 1H), 7.56 (t, J=6.99 Hz, 1H), 7.61-7.73 (m, 2H), 7.73-7.91 (m, 2H), 8.16 (d, J=8.09 Hz, 1H), 10.45-10.75 (br.s, 1H), 12.91-13.14 (br.s, 1H), 14.50 (s, 1H); MS (ESI) m/z 593.0 $(M+H)^+$.

EXAMPLE 55

2-(acetylamino)-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)acetamide To a solution of the product of Example 46 (10 mg, 0.017 mmol) in dichloromethane (0.25 mL) was added acetic anhydride (8 μL, 0.087 mmol) followed by addition of triethylamine (7 μL, 0.052 mmol). The reaction mixture was stirred at room temperature for 18 h. The solution was then diluted with dichloromethane (1 mL) and washed with aqueous 1 N HCl (2×0.5 mL), dried ($Na_2SO_4$), and concentrated in vacuo. The resulting residue was dissolved in methanol (0.5 mL) and treated with excess $K_2CO_3$ for 30 min. The heterogeneous solution was filtered and the filtrate concentrated in vacuo. The residue was then taken up in ethyl acetate (1 mL), washed with aqueous 1 N HCl (2×1 mL), dried ($Na_2SO_4$), and concentrated in vacuo. Column chromatography on silica (10% methanol/dichloromethane) afforded the title compound as a light yellow solid (5 mg, 45%). $^1$H NMR (300 MHz, DMSO-$d_6$) δ ppm 0.61-0.75 (m, 6H), 0.79-0.97 (m, 1H), 1.16-1.35 (m, 2H), 1.56-1.71 (m, 1H), 1.78 (s, 3H), 1.83-1.97 (m, 1H), 2.99 (s, 3H), 3.64-3.88 (m, 2H), 7.26-7.34 (m, 2H), 7.35-7.44 (m, 2H), 7.46 (d, J=2.21 Hz, 1H), 7.91 (t, J=5.52 Hz, 1H), 7.96-8.02 (m, 1H), 8.36 (s, 1H), 9.86 (s, 1H), 15.39 (s, 1H); MS m/z 618.0 $(M+H)^+$.

EXAMPLE 56

2-(dibenzylamino)-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)ethanesulfonamide Same procedure as for Example 48, treating the product of example 38B with dibenzylamine (9.5 μL, 0.05 mmol) to give the title compound as a colorless solid. $^1$H NMR ($d_6$-DMSO) δ 14.76 (s, 1H), 9.94 (s, 1H), 8.04, 8.01 (d, 1H), 7.56-7.33 (m, 16H), 2.99 (s, 3H), 2.12-1.94 (m, 1H), 1.73-1.58 (m, 1H), 1.23 (s, 6H), 0.92-0.80)(m, 2H), 0.69-0.60 (q, 6H), 0.54-0.39 (m, 1H); MS (ESI) m/z 806 $(M+H^+)$.

EXAMPLE 57

N-{3-[4-{[(tert-butylamino)carbonyl]amino}-1-hydroxy-4-(3-methylbutyl)-3-oxo-3,4-dihydronaphthalen-2-yl]-1,1-dioxido-4H-1,2,4-benzothiadiazin-7-yl}methanesulfonamide To a suspension of the product from Example 16 (10 mg, 0.018 mmol) in dichloromethane was added triethylamine (8 μL, 0.054 mmol) followed by addition of t-butyl isocyanate (3 μL, 0.027 mmol). The reaction mixture was stirred at room temperature for 18 h. The solution was then diluted with dichloromethane (1 mL), washed with aqueous HCl (2×0.5 mL), dried ($Na_2SO_4$), and concentrated in vacuo. Column chromatography on silica (10% methanol/dichloromethane) afforded the title compound as a light yellow solid (11 mg, 100%). $^1$H NMR (300 MHz, DMSO-$d_6$) δ ppm 0.67 (dd, J=6.62, 2.94 Hz, 6H), 0.77-0.88 (m, 1H), 1.12 (s, 9H), 1.20-1.33 (m, 2H), 1.49-1.63 (m, 1H), 1.65-1.80 (m, 1H), 3.01 (s, 3H), 5.85 (s, 1H), 6.39 (s, 1H), 7.24-7.59 (m, 7H), 8.02 (d, J=8.09 Hz, 1H), 9.97 (s, 1H); MS m/z 618.1 $(M+H)^+$.

EXAMPLE 58

N-{3-[4-(benzylamino)-1-hydroxy-4-(3-methylbutyl)-3-oxo-3,4-dihydronaphthalen-2-yl]-1,1-dioxido-4H-1,2,4-benzothiadiazin-7-yl}methanesulfonamide The procedure of Example 51 was followed, except substituting benzaldehyde for isobutyraldehyde. The title compound was prepared as a light yellow solid (8 mg, 73%). $^1$H NMR (300 MHz, DMSO-$d_6$) δ ppm 0.40-0.59 (m, 1H), 0.59-0.74 (m, 6H), 0.96-1.13 (m, 1H), 1.21-1.38 (m, 1H), 1.89-2.06 (m, 1H), 2.17-2.37 (m, 1H), 3.02 (s, 3H), 3.40-3.50 (m, 1H), 3.59-3.76 (m, 1H), 7.27-7.56 (m, 8H), 7.57-7.67 (m, 1H), 7.68-7.77 (m, 1H), 7.88-7.99 (m, 1H), 8.20 (d, J=8.09 Hz, 1H), 9.60 (s, 1H), 9.98 (s, 1H), 14.00 (s, 1H); MS m/z 609.1 $(M+H)^+$.

EXAMPLE 59

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-(methoxyamino)ethanesulfonamide Same procedure as for Example 48 treating the product of example 38B with methoxylamine HCl (4.1 mg, 0.05 mmol) to give the title compound as a colorless solid. $^1$H NMR ($d_6$-DMSO) δ 14.26 (s, 1H), 10.09 (s, 1H), 8.19 (s, 1H), 8.09, 8.06 (d, 1H), 7.70-7.38 (m, 7H), 3.48 (s, 3H), 3.27-3.19 (t, 2H), 3.15-3.08 (t, 2H), 3.04 (s, 3H), 2.10-1.97 (m, 1H), 1.83-1.72 (m, 1H), 1.01-0.79 (m, 2H), 0.71-0.61 (q, 6H), 0.58-0.46 (m, 1H); MS (ESI) m/z 656 (M+H$^+$).

EXAMPLE 60

N-(2-{[(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)amino]sulfonyl}ethyl)-N-methylacetamide Same procedure as for Example 48 treating example 38B with 2M methylamine in tetrahydrofuran (49 μL, 0.10 mmol) to give the methylamine which was dissolved in dichloromethane (2 mL) and acetic anhydride (19 μL, 0.05 mmol) and triethylamine (34 μL, 0.05 mmol) were added and the mixture stirred at room temperature for 18 hours. Solvent was removed in vacuo and the crude residue was dissolved in methanol (1 mL) and K$_2$CO$_3$ (50 mg) was added and the solution was stirred at room temperature for 30 minutes. H$_2$O (5 mL) was added and 1N HCl was added until acidic. The solution was extracted with ethyl acetate (3×5 mL), the organic extracts combined, dried (Na$_2$SO$_4$), the drying agent filtered off and the solvent removed in vacuo to yield a crude residue which was purified by column chromatography on silica gel (10% methanol/chloroform) to give the title compound as a colorless solid. $^1$H NMR (d$_6$-DMSO) δ 14.18 (br s, 1H), 10.11, 10.08 (d, 1H), 8.23, 8.16 (d, 1H), 8.09, 8.06 (d, 1H), 7.79-7.42 (m, 6H), 3.05 (s, 3H), 2.98, 2.77 (d, 3H), 2.16-2.04 (m, 1H), 2.03, 1.97 (d, 3H), 1.85-1.70 (m, 1H), 1.31-1.21 (m, 2H), 1.24 (s, 1H), 0.96-0.83 (m, 1H), 0.71-0.62 (q, 6H), 0.57-0.40 (m, 1H); MS (ESI) m/z 682 (M+H$^+$).

EXAMPLE 61

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-[methoxy(methyl)amino]ethanesulfonamide Same procedure as for Example 48 treating the product of example 38B with N,O-dimethyl-hydroxylamine HCl (5 mg, 0.05 mmol) to give the title compound as a colorless solid; $^1$H NMR (d$_6$-dmso) δ 14.99 (s, 1H), 9.95(s, 1H), 8.04, 8.01 (d, 1H), 7.83 (s, 1H), 7.65-7.34 (m, 7H), 3.01 (s, 3H), 2.98-2.91 (m, 2H), 2.03-1.94 (m, 1H), 1.76-1.64 (m, 1H), 1.31-1.17 (m, 2H), 1.24 (s, 6H), 0.86-0.82 (m, 2H), 0.69-0.61 (q, 6H), 0.59-0.45 (m, 1H); MS (ESI) m/z 670 (M+H$^+$).

EXAMPLE 62

2-[(2,2-dimethoxyethyl)(methyl)amino]-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)ethanesulfonamide Same procedure as for Example 48 treating example 38B with methylaminoacetaldehyde dimethyl acetal (8.4 μL, 0.05 mmol) to give the title compound as a colorless solid. $^1$H NMR (d$_6$-DMSO) δ 9.95 (s, 1H), 8.03, 8.01(d, 1H), 7.61-7.30 (m, 6H), 3.33 (s, 9H), 3.01 (s, 3H), 3.10-2.89 (m, 3H), 2.18-2.03 (m, 1H), 1.73-1.62 (m, 1H), 1.32-1.15 (m, 3H), 0.96-0.80 (m, 2H), 0.71-0.59 (q, 6H), 0.53-0.35 (m, 1H); MS (ESI) m/z 728 (M+H$^+$).

EXAMPLE 63

2-[(1,3-dioxolan-2-ylmethyl)(methyl)amino]-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)ethanesulfonamide Same procedure as for Example 48 treating the product of example 38B with 2-methylaminomethyl-1,3-dioxolane (7.5 μL, 0.05 mmol) to give the title compound as a colorless solid. $^1$H NMR (d$_6$-DMSO) δ 14.60 (s, 1H), 9.96 (s, 1H), 8.24 (br s, 1H), 8.04, 8.01 (d, 1H), 7.61-7.34 (m, 6H), 5.44-5.27 (br s, 1H), 4.02, 3.88 (br d, 3H), 3.58-3.26 (m, 6H), 3.01 (s, 3H), 2.15-2.04 (m, 1H), 1.74-1.63 (m, 1H), 1.31-1.14 (m, 4H), 0.94-0.80 (m, 2H), 0.70-0.59 (q, 6H), 0.49-0.35 (m, 1H); MS (ESI) m/z 726 (M+H$^+$).

EXAMPLE 64

N-{3-[1-hydroxy-4-[(3-methoxybenzyl)amino]-4-(3-methylbutyl)-3-oxo-3,4-dihydronaphthalen-2-yl]-1,1-dioxido-4H-1,2,4-benzothiadiazin-7-yl}methanesulfonamide The procedure of Example 51 was followed, except substituting 3-methoxybenzaldehyde for isobutyraldehyde. The title compound was prepared as a light yellow solid (6 mg, 50%). $^1$H NMR (300 MHz, DMSO-d$_6$) δ ppm 0.41-0.59 (m, 1H), 0.60-0.76 (m, 6H), 0.96-1.16 (m, 1H), 1.19-1.36 (m, 1H), 1.86-2.10 (m, 1H), 2.15-2.37 (m, 1H), 3.02 (s, 3H), 3.60-3.73 (m, 1H), 3.76 (s, 3H), 6.81-6.99 (m, 3H), 7.29 (t, J=7.72 Hz, 1H), 7.34-7.41 (m, 1H), 7.42-7.56 (m, 2H), 7.56-7.66 (m, 1H), 7.66-7.76 (m, 1H), 7.91 (d, J=7.35 Hz, 1H), 8.19 (d, J=7.35 Hz, 1H), 9.57 (s, 1H), 9.97 (s, 1H), 13.98 (s, 1H); MS m/z 639.0 (M+H)$^+$.

EXAMPLE 65

N-(1-(3,3-dimethylbutyl)-4-hydroxy-3-{7-[(methylsulfonyl)amino]-1,1-dioxido-4H-1,2,4-benzothiadiazin-3-yl}-2-oxo-1,2-dihydronaphthalen-1-yl)acetamide To a solution of the product from Example 8F (20 mg, 38 μmol) in CH$_3$CN (0.2 mL) at 0° C. was added conc. H$_2$SO$_4$ (0.2 mL) dropwise. The resulting mixture was stirred at room temperature for 3 h and was poured onto ice (~5 mL). The mixture was allowed to warm to room temperature, and the product was collected by filtration to give the title compound as an off-white solid (19 mg, 88%). $^1$H NMR (300 MHz, DMSO-d$_6$) δ ppm 13.65 (br s, 1H), 10.26 (s, 1H), 9.15 (s, 1H), 8.12 (d, J=7.0 Hz, 1H), 7.69-7.79 (m, 2H), 7.47-7.65 (m, 4H), 3.06 (s, 3H), 2.50 (s, 3H), 1.74-2.06 (m, 2H), 0.84-1.00 (m, 1H), 0.66 (s, 9H), 0.39-0.58 (m, 1H).

EXAMPLE 66

N-{3-[4-amino-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide To a solution of the product from Example 65 (62 mg, 0.11 mmol) in 1,4-dioxane (1 mL) was added 4N HCl (aq., 2 mL), and the resulting mixture was heated at 100° C. for 2 days. The cooled mixture was concentrated in vacuo, and was suspended in $H_2O$ to precipitate unreacted starting material. The filtrate was concentrated in vacuo to give the title compound as an off-white solid (27 mg, 44%). $^1$H NMR (300 MHz, DMSO-$d_6$) δ ppm 14.44 (br s, 1H), 9.95 (s, 1H), 8.62 (br s, 2H), 8.13 (d, J=7.7 Hz, 1H), 7.59-7.74 (m, 2H), 7.48-7.59 (m, 2H), 7.42-7.48 (m, 1H), 7.33-7.39 (m, 1H), 3.01 (s, 3H), 1.94-2.12 (m, 1H), 1.76-1.94 (m, 1H), 1.01-1.18 (m, 1H), 0.70-0.80 (m, 1H), 0.69 (s, 9H).

EXAMPLE 67

N-{3-[4-[(cyclopropylmethyl)amino]-1-hydroxy-4-(3-methylbutyl)-3-oxo-3,4-dihydronaphthalen-2-yl]-1,1-dioxido-4H-1,2,4-benzothiadiazin-7-yl}methanesulfonamide The procedure of Example 51 was followed, except substituting cyclopropane carboxaldehyde for isobutyraldehyde. The title compound was prepared as a light yellow solid (6 mg, 60%). $^1$H NMR (500 MHz, DMSO-$d_6$) δ ppm 0.01-0.17 (m, 2H), 0.36-0.56 (m, 3H), 0.67 (dd, J=18.80, 6.59 Hz, 6H), 0.78-1.10 (m, 2H), 1.21-1.35 (m, 1H), 1.69-2.20 (m, 4H), 3.00 (s, 3H), 7.33 (d, J=8.79 Hz, 1H), 7.41-7.55 (m, 3H), 7.55-7.65 (m, 1H), 7.73-7.83 (m, 1H), 8.05-8.18 (m, 1H), 9.91 (s, 1H); MS m/z 573.0 (M+H)$^+$.

EXAMPLE 68

N-{3-[4-[(aminocarbonyl)amino]-1-hydroxy-4-(3-methylbutyl)-3-oxo-3,4-dihydronaphthalen-2-yl]-1,1-dioxido-4H-1,2,4-benzothiadiazin-7-yl}methanesulfonamide To a solution of the product of Example 57 (8 mg, 0.013 mmol) in dichloromethane (0.3 mL) was added trifluoroacetic acid (0.3 mL). The solution was stirred at room temperature for 18 h and then concentrated in vacuo. Column chromatography on silica (5% methanol/dichloromethane) afforded the title compound as an off-white solid (7 mg, 100%). $^1$H NMR (300 MHz, DMSO-$d_6$) δ ppm 0.67 (dd, J=6.43, 3.86 Hz, 6H), 0.83-1.07 (m, 2H), 1.17-1.31 (m, 1H), 1.46-1.62 (m, 1H), 1.66-1.83 (m, 1H), 2.99 (s, 3H), 5.40 (s, 2H), 6.51 (s, 1H), 7.23-7.33 (m, 2H), 7.34-7.43 (m, 3H), 7.46 (d, J=2.21 Hz, 1H), 7.97 (d, J=8.09 Hz, 1H), 9.86 (s, 1H), 15.47 (s, 1H); MS m/z 562.0 (M+H)$^+$.

EXAMPLE 69

N-(1-(3,3-dimethylbutyl)-4-hydroxy-3-{7-[(methylsulfonyl)amino]-1,1-dioxido-4H-1,2,4-benzothiadiazin-3-yl}-2-oxo-1,2-dihydronaphthalen-1-yl)benzamide The title compound was prepared using the procedures described in Example 65, substituting benzonitrile for acetonitrile. The crude product was partitioned between $H_2O$ and diethyl ether (3×), and the diethyl ether was evaporated to give the title compound as colorless crystals (92% yield): $^1$H NMR (300 MHz, DMSO-$d_6$) δ ppm 13.67 (br s, 1H), 10.26 (s, 1H), 9.54 (s, 1H), 8.16 (d, J=7.7 Hz, 1H), 7.40-7.94 (m, 11H), 3.08 (s, 3H), 2.02-2.28 (m, 2H), 0.91-1.07 (m, 1H), 0.68 (s, 9H), 0.42-0.55 (m, 1H).

EXAMPLE 70 ethyl[(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)amino]acetate Follow same procedure as Example 18D, treating the product of Example 18C with ethyl bromoacetate (5.7μL, 0.05 mmol) and $K_2CO_3$ (6.8 mg, 0.05 mmol). $^1$H NMR ($d_6$-DMSO) δ 13.81 (s, 1H), 9.98 (s, 1H), 8.16, 8.13 (d, 1H), 7.85, 7.83 (d, 1H), 7.69-7.43 (m, 4H), 7.38, 7.35 (d, 1H), 4.15-4.00 (q, 2H), 3.44, 3.38, 3.23, 3.17 (dd, 1H), 3.02 (s, 3H), 2.32-2.16 (m, 1H), 2.15-2.01 (m, 1H), 1.38-1.21 (m, 2H) 1.21-1.09 (t, 3H), 1.09-0.93 (m, 1H), 0.73-0.62 (q, 6H), 0.55-0.42 (m, 1H); MS (ESI) m/z 605 (M+H$^+$).

EXAMPLE 71

2-chloro-N-(1-(3,3-dimethylbutyl)-4-hydroxy-3-{7-[(methylsulfonyl)amino]-1,1-dioxido-4H-1,2,4-benzothiadiazin-3-yl}-2-oxo-1,2-dihydronaphthalen-1-yl)acetamide The title compound was prepared using the procedures described in Example 65, substituting chloroacetonitrile for acetonitrile. The title compound was obtained as an off-white solid (79% yield): $^1$H NMR (300 MHz, DMSO-$d_6$) δ ppm 13.73 (br s, 1H), 10.22 (s, 1H), 9.38 (s, 1H), 8.12 (d, J=7.7 Hz, 1H), 7.65-7.81 (m, 2H), 7.43-7.65 (m, 4H), 4.05-4.21 (m, 2H), 3.07 (s, 3H), 1.93-2.10 (m, 1H), 1.78-1.92 (m, 1H), 0.89-1.04 (m, 1H), 0.66 (s, 9H), 0.48-0.61 (m, 1H).

EXAMPLE 72

N-(1-(3,3-dimethylbutyl)-4-hydroxy-3-{7-[(methylsulfonyl)amino]-1,1-dioxido-4H-1,2,4-benzothiadiazin-3-yl}-2-oxo-1,2-dihydronaphthalen-1-yl)methanesulfonamide The product from Example 66 (20 mg, 35 μmol) was subjected to the conditions described in Example 42. The title compound was obtained as a light yellow solid (9 mg, 42%). $^1$H NMR (300 MHz, DMSO-$d_6$) δ ppm 15.14 (br s, 1H), 9.92 (s, 1H), 9.11 (br s, 1H), 8.01 (d, J=7.7 Hz, 1H), 7.70 (br s, 1H), 7.60 (d, J=7.7 Hz, 1H), 7.46-7.55 (m, 2H), 7.39-7.46 (m, 1H), 7.31-7.39 (m, 2H), 3.00 (s, 3H), 2.85 (s, 3H), 1.92-2.05 (m, 1H), 1.59-1.72 (m, 1H), 0.79-0.92 (m, 1H), 0.64 (s, 9H), 0.45-0.58 (m, 1H).

EXAMPLE 73

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2,5-dimethoxybenzenesulfonamide Follow same procedure as Example 18D treating the product of Example 18C with 2,5-dimethoxybenzenesulfonyl chloride (9.6 mg, 0.05 mmol). $^1$H NMR ($d_6$-DMSO) δ 13.45 (s, 1H), 10.30 (s, 1H), 8.69 (s, 1H), 8.03, 8.01 (d, 1H), 7.73, 7.70 (d, 1H), 7.66-7.56 (m, 2H), 7.40-7.33 (t, 1H), 7.28-7.16 (m, 2H), 7.06, 7.03 (d, 1H), 6.93-6.87 (m, 1H), 6.34, 6.33 (d, 1H), 3.95 (s, 3H), 3.41 (s, 3H), 3.10 (s, 3H), 2.37-2.16 (m, 2H), 2.01-1.85 (m, 1H), 1.33-1.14 (m, 2H), 0.68-0.57 (q, 6H); MS (ESI) m/z 719 (M+H$^+$).

EXAMPLE 74

N-{3-[4-(benzylamino)-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide

EXAMPLE 74A 4-(3,3-dimethylbutyl)-4-hydroxynaphthalene-1,3(2H,4H)-dione

To a suspension of magnesium turnings (2.90 g, 0.12 mol) in tetrahydrofuran (150 mL) was added 1-chloro-3,3-dimethylbutane (14.2 g, 0.12 mol). The mixture was cooled to 0° C. and dibromoethane (2.5 mL, 29 mmol) was added portion wise over 15 min. The mixture was allowed to warm to room temperature and stirred for 1 h. After which, an additional equivalent of dibromoethane (2.5 mL, 29 mmol) was added portion wise over 15 min and stirred at room temperature for 72 h. The mixture was diluted with tetrahydrofuran (50 mL) cooled to −78° C., and treated with titanium(IV) isopropoxide (33.9 mL, 0.11 mol). The reaction mixture was stirred at −78° C. for 1 h and a solution of 2-hydroxy-1,4-naphthoquinone (5.0 g, 29 mmol) in tetrahydrofuran (80 mL) pre-cooled to 0° C. was added via a cannula. After addition, the solution was warmed to room temperature and stirred for 18 h. The solution was diluted with ethyl acetate (250 mL) and washed with aqueous 1 N HCl (2×100 mL). The organic layer was dried (Na$_2$SO$_4$) and concentrated in vacuo. Column chromatography on florisil (dichloromethane→1%→3→%5% methanol/dichloromethane) followed by second column chromatography on silica (30%→50% ethyl acetate/hexane) afforded the title compound as an orange amorphous solid (2.06 g, 28%). $^1$H NMR (300 MHz, DMSO-d$_6$), δ ppm 0.33-0.52 (m, 1H), 0.68 (s, 9H), 0.77-0.92 (m, 1H), 1.67-1.84 (m, 1H), 1.88-2.11 (m, 1H), 5.56 (s, 1H), 7.36-7.45 (m, 1H), 7.57 (t, J=6.99 Hz, 1H), 7.62-7.68 (m, 1H), 7.82 (d, J=6.62 Hz, 1H); MS m/z 261.1 (M+H)$^+$.

EXAMPLE 74B

2-[bis(methylthio)methylene]-4-(3,3-dimethylbutyl)-4-hydroxynaphthalene-1,3(2H,4H)-dione To a solution of the product of Example 74A (1.0 g, 3.8 mmol) in dioxane (20 mL) was added Example 1D (4.7 g, 19.2 mmol) followed by pyridine (1.6 mL, 19.2 mmol). The heterogeneous solution was heated at 55° C. for 3h. The solution was cooled to room temperature and concentrated in vacuo. Column chromatography on silica (10% 15% ethyl acetate/hexane) afforded the title compound as an orange oil (1.0 g, 71%). $^1$H NMR (300 MHz, DMSO-d$_6$), δ ppm 0.69 (s, 9H), 0.83-0.98 (m, 1H), 1.02-1.16 (m, 1H), 1.59-1.80 (m, 2H), 2.59 (s, 6H), 7.42-7.52 (m, 1H), 7.61-7.73 (m, 2H), 7.96 (d, J=7.72 Hz, 1H); MS m/z 365.1 (M+H)$^+$.

EXAMPLE 74C tert-butyl 3-[4-(3,3-dimethylbutyl)-1,4-dihydroxy-3-oxo-3,4-dihydronaphthalen-2-yl]-1,1-dioxido-4H-1,2,4-benzothiadiazin-7-ylcarbamate A mixture of the product of Example 74B (1.0 g, 2.74 mmol) and Example 18A (0.79 g, 2.74 mmol) in dioxane (20 mL) was heated at 85° C. for 18 h. The solution was cooled to room temperature and concentrated in vacuo. The resulting residue was triturated with ethyl acetate, and the precipitate was collected by filtration and dried under high vacuum to give the title compound as a light yellow solid (1.08 g, 71%). $^1$H NMR (300 MHz, DMSO-d$_6$), δ ppm 0.69 (s, 9H), 0.82-1.08 (m, 2H), 1.50 (s, 9H), 1.61-1.86 (m, 2H), 7.35 (d, J=8.82 Hz, 2H), 7.39-7.47 (m, 1H), 7.50-7.63 (m, 3H), 7.97 (d, J=7.35 Hz, 2H), 9.70 (s, 1H), 14.08 (s, 1H); MS m/z 556.3 (M+H)$^+$.

EXAMPLE 74D

N-[3-(7-amino-1,1-dioxido-4H-1,2,4-benzothiadiazin-3-yl)-1-(3,3-dimethylbutyl)-4-hydroxy-2-oxo-1,2-dihydronaphthalen-1-yl]acetamide To a suspension of the product of Example 74C (1.0 g, 1.8 mmol) in acetonitrile (16 mL) at 0° C. was added conc. H$_2$SO$_4$ (8 mL). The reaction mixture was warmed to room temperature and stirred for 2 h. The solution was poured unto ice (100 g) and extracted with 3:1 dichloromethane:isopropanol (3×50 mL). The organic extracts were combined, dried (Na$_2$SO$_4$), and concentrated in vacuo. The resulting residue was dried under high vacuum to give the title compound as a yellow solid (0.98g, 92%). $^1$H NMR (300 MHz, DMSO-d$_6$), δ ppm 0.39-0.56 (m, 1H), 0.65 (s, 9H), 0.81-0.98 (m, 1H), 1.77-1.90 (m, 4H), 1.92-2.07 (m, 1H), 6.90-7.04 (m, 2H), 7.39-7.58 (m, 3H), 7.73 (t, J=7.54 Hz, 1H), 8.11 (d, J=7.35 Hz, 1H), 9.16 (s, 1H), 13.38 (s, 1H); MS m/z 497.2 (M+H)$^+$.

EXAMPLE 74E

N-(1-(3,3-dimethylbutyl)-4-hydroxy-3-{7-[(methylsulfonyl)amino]-1,1-dioxido-4H-1,2,4-benzothiadiazin-3-yl}-2-oxo-1,2-dihydronaphthalen-1-yl)acetamide To a solution of product of Example 74D (1.16 g, 2.33 mmol) in dichloromethane (20 mL) was added triethylamine (1.6 mL, 11.7 mmol) followed by dropwise addition of methanesulfonyl chloride (0.45 mL, 5.84 mmol). The reaction mixture was stirred at room temperature for 18 h. The solution was diluted with ethyl acetate (30 mL), washed with aqueous 1 N HCl (2×15 mL), dried (Na$_2$SO$_4$), and concentrated in vacuo. The resulting residue was taken up in methanol (20 mL) and treated with excess K$_2$CO$_3$ for 2 h. The mixture was filtered. The filtrate was concentrated in vacuo and the resulting residue was taken up in 3:1 dichloromethane:isopropanol (15 mL) and washed with aqueous 1 N HCl (2×10 mL), dried (Na$_2$SO$_4$), and concentrated in vacuo to afford the title compound as a light yellow solid (1.1 g, 82%). $^1$H NMR (500 MHz, DMSO-d$_6$), δ ppm 0.44-0.54 (m, 1H), 0.66 (s, 9H), 0.87-0.98 (m, 1H), 1.80-1.89 (m, 4H), 1.95-2.05 (m, 1H), 3.08 (s, 3H), 7.53 (t, J=7.25 Hz, 2H), 7.58 (dd, J=8.69, 2.32 Hz, 1H), 7.64 (d, J=2.32 Hz, 1H), 7.70-7.78 (m, 2H), 8.12 (d, J=7.54 Hz, 1H), 9.14 (s, 1H), 10.24 (s, 1H), 13.61 (s, 1H); MS m/z 575.2 (M+H)$^+$.

EXAMPLE 74F

N-{3-[4-amino-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide To a solution of 74E (0.6 g, 1.91 mmol) in dioxane (36 mL) was added aqueous 4 N HCl (18 mL). The reaction mixture was stirred at 80° C. for 120 h. After cooling to room temperature, the solution was diluted with water (50 mL) and extracted with 3:1 dichloromethane:isopropanol (3×20 mL). The organic extracts were combined, dried (Na$_2$SO$_4$), and concentrated in vacuo to afford the hydrochloride salt of the title compound as a brown amorphous solid (0.42g, 71%). $^1$H NMR (300 MHz, DMSO-d$_6$), δ ppm 0.67-0.80 (m, 10H), 1.02-1.17 (m, 1H), 1.79-1.92 (m, 1H), 1.95-2.08 (m, 1H), 3.01 (s, 3H), 7.32-7.72 (m, 6H), 8.13 (d, J=7.72 Hz, 1H), 8.62 (s, 2H), 9.95 (s, 1H), 14.44 (s, 1H); MS m/z 533.2 (M+H)$^+$.

EXAMPLE 74G

N-{3-[4-(benzylamino)-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide To a suspension of the product of 74F (0.12 g, 0.21 mmol) in dichloroethane (2 mL) was added N,N-diisopropylethylamine (73 μL, 0.42 mmol). The mixture was stirred at room temperature until homogenous (approx. 5 min). After which, benzaldehyde (38 μL, 3.2 mmol) and MgSO$_4$ (25 mg) were added. The reaction mixture was heated at 50° C. for 18 h. After cooling to room temperature, the reaction solution was filtered. To the filtrate was then added sodium triacetoxyborohydride (72 mg, 0.34 mmol) and glacial acetic acid (36 μL, 0.63 mmol). The mixture was stirred at room temperature for 18 h, diluted with dichloromethane (2 mL), washed with water (2×2 mL), dried (Na$_2$SO$_4$), and concentrated in vacuo. Column chromatography on silica (1%→3%→5% methanol/dichloromethane, afforded the title compound as a yellow solid (15 mg, 56%). $^1$H NMR (300 MHz, DMSO-d$_6$), δ ppm 0.33-0.50 (m, 1H), 0.66 (s, 9H), 0.94-1.10 (m, 1H), 1.95-2.12 (m, 1H), 2.20-2.36 (m, 1H), 3.02 (s, 3H), 3.43-3.54 (m, 1H), 3.57-3.69 (m, 1H), 3.72 (s, 3H), 6.87-7.02 (m, 2H), 7.25 (d, J=7.35 Hz, 1H), 7.30-7.41 (m, 2H), 7.43-7.55 (m, 2H), 7.61 (t, J=7.35 Hz, 1H), 7.74 (t, J=7.35 Hz, 1H), 7.92 (d, J=7.72 Hz, 2H), 8.18 (d, J=7.72 Hz, 1H), 9.97 (s, 1H), 14.08 (s, 1H); MS m/z 653.2 (M+H)$^+$.

EXAMPLE 75

N-(3-{4-(3,3-dimethylbutyl)-1-hydroxy-4-[(3-methoxybenzyl)amino]-3-oxo-3,4-dihydronaphthalen-2-yl}-1,1-dioxido-4H-1,2,4-benzothiadiazin-7-yl)methanesulfonamide The procedure of Example 74G was followed, except substituting 3-methoxybenzaldehyde for benzaldehyde. The title compound was prepared as a yellow solid (17 mg, 59%). $^1$H NMR (300 MHz, DMSO-d$_6$), δ ppm 0.39-0.53 (m, 1H), 0.67 (s, 9H), 0.97-1.14 (m, 1H), 1.89-2.06 (m, 1H), 2.20-2.36 (m, 1H), 3.02 (s, 3H), 3.41 (d, J=12.87 Hz, 2H), 3.76 (s, 3H), 6.85 (d, J=7.72 Hz, 1H), 6.89-6.97 (m, 2H), 7.29 (t, J=7.91 Hz, 1H), 7.34-7.40 (m, 1H), 7.45-7.54 (m, 2H), 7.61 (t, J=7.72 Hz, 1H), 7.72 (t, J=6.80 Hz, 1H), 7.92 (d, J=7.72 Hz, 1H), 8.17-8.23 (m, 1H), 9.58 (s, 1H), 9.98 (s, 1H), 13.96 (s, 1H); MS m/z 653.3 (M+H)$^+$.

EXAMPLE 76

N-(3-{4-(3,3-dimethylbutyl)-1-hydroxy-4-[(2-methoxybenzyl)amino]-3-oxo-3,4-dihydronaphthalen-2-yl}-1,1-dioxido-4H-1,2,4-benzothiadiazin-7-yl)methanesulfonamide The procedure of Example 74G was followed, except substituting 2-methoxybenzaldehyde for benzaldehyde. The title compound was prepared as a yellow solid (84 mg, 60%). $^1$H NMR (300 MHz, DMSO-d$_6$), δ ppm 0.39-0.55 (m, 1H), 0.67 (s, 9H), 0.98-1.14 (m, 1H), 1.90-2.05 (m, 1H), 2.20-2.36 (m, 1H), 3.02 (s, 3H), 3.43 (d, J=12.87 Hz, 2H), 7.28-7.43 (m, 6H), 7.45-7.56 (m, 2H), 7.62 (t, J=7.54 Hz, 1H), 7.68-7.77 (m, 1H), 7.94 (d, J=8.09 Hz, 1H), 8.18-8.24 (m, 1H), 9.61 (s, 1H), 9.98 (s, 1H), 13.99 (s, 1H); MS m/z 623.3 (M+H)$^+$.

EXAMPLE 77

N-(3-{4-(3,3-dimethylbutyl)-1-hydroxy-4-[(4-methoxybenzyl)amino]-3-oxo-3,4-dihydronaphthalen-2-yl}-1,1-dioxido-4H-1,2,4-benzothiadiazin-7-yl)methanesulfonamide The procedure of Example 74G was followed, except substituting 4-methoxybenzaldehyde for benzaldehyde. The title compound was prepared as a yellow solid (13 mg, 45%). $^1$H NMR (300 MHz, DMSO-d$_6$) δ ppm 0.37-0.53 (m, 1H), 0.66 (s, 9H), 0.96-1.13 (m, 1H), 1.89-2.04 (m, 1H), 2.17-2.34 (m, 1H), 3.02 (s, 3H), 3.38 (d, J=12.50 Hz, 2H), 3.73 (s, 3H), 6.92 (d, J=8.46 Hz, 2H), 7.20 (d, J=8.82 Hz, 2H), 7.34-7.38 (m, 1H), 7.44-7.54 (m, 2H), 7.62 (t, J=7.72 Hz, 1H), 7.72 (t, J=6.80 Hz, 1H), 7.93 (d, J=7.72 Hz, 1H), 8.20 (d, J=7.72 Hz, 1H), 9.52 (s, 1H), 9.98 (s, 1H), 13.99 (s, 1H); MS m/z 653.3 (M+H)$^+$.

EXAMPLE 78

3-{[(1-(3,3-dimethylbutyl)-4-hydroxy-3-{7-[(methylsulfonyl)amino]-1,1-dioxido-4H-1,2,4-benzothiadiazin-3-yl}-2-oxo-1,2-dihydronaphthalen-1-yl)amino]methyl}phenyl acetate The procedure of Example 74G was followed, except substituting 3-acetoxybenzaldehyde for benzaldehyde. The title compound was prepared as a yellow solid (16 mg, 53%). $^1$H NMR (300 MHz, DMSO-d$_6$) δ ppm 0.39-0.55 (m, 1H), 0.67 (s, 9H), 0.98-1.13 (m, 1H), 1.89-2.06 (m, 1H), 2.21-2.38 (m, 4H), 3.02 (s, 3H), 3.66-3.75 (m, 2H), 7.10-7.26 (m, 3H), 7.34-7.55 (m, 4H), 7.61 (t, J=7.54 Hz, 1H), 7.68-7.76 (m, 1H), 7.91 (d, J=7.72 Hz, 1H), 8.20 (dd, J=7.72, 1.47 Hz, 1H), 9.67 (s, 1H), 9.98 (s, 1H), 13.97 (s, 1H); MS m/z 681.3 (M+H)$^+$.

EXAMPLE 79

N-(3-{4-(3,3-dimethylbutyl)-4-[(2-furylmethyl)amino]-1-hydroxy-3-oxo-3,4-dihydronaphthalen-2-yl}-1,1-dioxido-4H-1,2,4-benzothiadiazin-7-yl)methanesulfonamide The procedure of Example 74G was followed, except substituting 2-furaldehyde for benzaldehyde. The title compound was prepared as a yellow solid (14 mg, 52%). $^1$H NMR (300 MHz, DMSO-d$_6$) δ ppm 0.36-0.51 (m, 1H), 0.66 (s, 9H), 0.96-1.12 (m, 1H), 1.89-2.04 (m, 1H), 2.16-2.31 (m, 1H), 3.02 (s, 3H), 3.50 (d, J=14.34 Hz, 1H), 3.74-3.83 (m, 1H), 6.42 (d, J=1.47 Hz, 2H), 7.33-7.40 (m, 1H), 7.44-7.54 (m, 2H), 7.59 (t, J=7.54 Hz, 1H), 7.65-7.72 (m, 2H), 7.89 (d, J=7.72 Hz, 1H), 8.18 (dd, J=7.72, 1.47 Hz, 1H), 9.75 (s, 1H), 9.98 (s, 1H), 13.98 (s, 1H); MS m/z 613.3 (M+H)$^+$.

EXAMPLE 80

N-{3-[4-[(4-cyanobenzyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide The procedure of Example 74G was followed, except substituting 4-cyanobenzaldehyde for benzaldehyde. The title compound was prepared as a yellow solid (9 mg, 32%). $^1$H NMR (300 MHz, DMSO-$d_6$) δ ppm 0.39-0.55 (m, 1H), 0.67 (s, 9H), 0.97-1.11 (m, 1H), 1.83-2.04 (m, 1H), 2.14-2.35 (m, 1H), 3.02 (s, 3H), 3.49-3.66 (m, 1H), 3.67-3.85 (m, 1H), 7.33-7.39 (m, 1H), 7.44-7.55 (m, 4H), 7.55-7.74 (m, 2H), 7.85 (d, J=7.35 Hz, 3H), 8.18 (d, J=7.35 Hz, 1H), 9.75 (s, 1H), 9.97 (s, 1H), 13.94 (s, 1H); MS m/z 648.3 (M+H)$^+$.

EXAMPLE 81

N-{3-[4-{[4-(benzyloxy)benzyl]amino}-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide The procedure of Example 74G was followed, except substituting 4-benzyloxybenzaldehyde for benzaldehyde. The title compound was prepared as an orange solid (17 mg, 53%). $^1$H NMR (300 MHz, DMSO-$d_6$) δ ppm 0.36-0.54 (m, 1H), 0.66 (s, 9H), 0.96-1.12 (m, 1H), 1.86-2.04 (m, 1H), 2.14-2.33 (m, 1H), 3.01 (s, 3H), 3.55-3.67 (m, 1H), 5.10 (s, 2H), 7.00 (d, J=8.46 Hz, 2H), 7.19 (d, J=8.82 Hz, 2H), 7.27-7.55 (m, 8H), 7.57-7.66 (m, 1H), 7.71 (t, J=7.72 Hz, 1H), 7.91 (d, J=7.35 Hz, 1H), 8.19 (d, J=7.35 Hz, 1H), 9.50 (s, 1H), 9.97 (s, 1H), 14.00 (s, 1H); MS m/z 729.3 (M+H)$^+$.

EXAMPLE 82

N-{3-[4-[(1-benzothien-3-ylmethyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide The procedure of Example 74G was followed, except substituting 1-benzothiophene-3-carboxaldehyde for benzaldehyde. The title compound was prepared as a yellow solid (11 mg, 37%). $^1$H NMR (300 MHz, DMSO-$d_6$) δ ppm 0.37-0.53 (m, 1H), 0.66 (s, 9H), 0.98-1.13 (m, 1H), 1.89-2.05 (m, 1H), 2.21-2.40 (m, 1H), 3.03 (s, 3H), 3.65-3.78 (m, 1H), 3.95 (d, J=14.34 Hz, 1H), 7.34-7.57 (m, 5H), 7.60-7.79 (m, 3H), 7.84 (s, 1H), 7.95-8.05 (m, 2H), 8.23 (d, J=7.72 Hz, 1H), 9.69 (s, 1H), 9.99 (s, 1H), 13.93 (s, 1H); MS m/z 679.3 (M+H)$^+$.

EXAMPLE 83

N-((1S)-4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-morpholin-4-ylethanesulfonamide

EXAMPLE 83A tert-butyl 3-[(4S)-1-hydroxy-4-(methoxyamino)-4-(3-methylbutyl)-3-oxo-3,4-dihydronaphthalen-2-yl]-1,1-dioxido-4H-1,2,4-benzothiadiazin-7-ylcarbamate To a solution of Example 23A (600 mg, 2.2 mmol) in dioxane (9 mL) was added pyridine (1.8 mL, 22 mmol) and Example 1D (2.9 g, 10.9 mmol) and the solution was heated at 60° C. for 2 hours, cooled to room temperature and the solvent removed in vacuo. The crude residue was taken up in 1:1 ethyl acetate:H$_2$O (10 mL), extracted with ethyl acetate (3×10 mL), the extracts combined, solvent removed in vacuo and the crude residue purified by column chromatography on silica gel (20% ethyl acetate/hexane) to yield an off-white solid which was dissolved in dioxane (9 mL) and Example 18A (626 mg, 2.2 mmol) was added. The solution was heated at reflux for 18 hours, cooled to room temperature, the solvent removed in vacuo and the crude residue was purified by column chromatography (2% methanol/chloroform) to yield the title compound as a colorless solid (907 mg, 73%). $^1$H NMR($d_6$-DMSO) δ 13.52 (s, 1H), 9.88 (s, 1H), 8.15, 8.13 (d, 2H), 7.93, 7.91 (d, 1H), 7.81-7.74 (t, 1H), 7.70-7.53 (m, 3H), 3.15 (s, 3H), 1.90-1.78 (m, 1H), 1.73-1.61 (m, 1H), 1.51 (s, 9H), 1.33-1.20 (m, 1H), 0.92-0.79 (m, 1H), 0.74-0.58 (m, 6H), 0.52-0.39 (m, 1H); MS (ESI) m/z 571 (M+H$^+$).

EXAMPLE 83B tert-butyl 3-[(4S)-4-amino-1-hydroxy-4-(3-methylbutyl)-3-oxo-3,4-dihydronaphthalen-2-yl]-1,1-dioxido-4H-1,2,4-benzothiadiazin-7-ylcarbamate To a solution of Example 83A (905 mg, 1.6 mmol) in CH$_3$CN (72 mL) and H$_2$O (5 mL) was added molybdenum hexacarbonyl (293 mg, 1.1 mmol) and the solution was refluxed for 2 hours, cooled to room temperature, solvent removed in vacuo and the crude residue purified by column chromatography on silica gel (2% methanol/chloroform) to give the title compound as a colorless solid (670 mg, 78%): $^1$H NMR ($d_6$-DMSO) δ 14.34 (s, 1H), 9.64 (s, 1H), 8.59 (br s, 2H), 8.13, 8.11 (d, 1H), 7.93 (s, 1H), 7.69-7.45 (m, 4H), 7.27, 7.24 (d, 1H), 2.08-1.95 (m, 1H), 1.92-1.80 (m, 1H), 1.30-0.99 (m, 4H), 0.54-0.46 (m, 1H), 1.50 (s, 9H), 1.45-1.23 (m, 1H), 1.18-0.96 (m, 1H), 0.92-0.62 (m, 7H); MS (ESI) m/z 541 (M+H$^+$).

EXAMPLE 83C

N-((1S)-4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-morpholin-4-ylethanesulfonamide To a solution of Example 83B (50 mg, 0.09 mmol) in dichloromethane (350 μL) at 0° C. was added 2-chloro-1-ethanesulfonyl chloride (15 μL, 0.14 mmol) and triethylamine (27 μL, 0.19 mmol) and stirring was continued at 0° C. for 1 hour. Triethylamine (19 uL, 0.14 mmol) was added and the solution was warmed to room temperature over 1 hour. 2-chloro-1-ethanesulfonyl chloride (15 μL, 0.14 mmol) and triethylamine (19 μL, 0.14 mmol) were added and stirring continued for 30 minutes. The solution was diluted with dichloromethane (5 mL) and the solution washed with brine (1×5 mL), dried (Na$_2$SO$_4$), the drying agent filtered off and the solvent removed in vacuo. The crude residue was dissolved in tetrahydrofuran (350 μL) and morpholine (16 μL, 0.19 mmol) was added, the solution stirred at room temperature for 16 hours and the solvent removed in vacuo. The crude residue was dissolved in 4M HCl in dioxane (4 mL) and the solution stirred at room temperature for 1 hour. Solvent was removed in vacuo and the crude residue was dissolved in dichloromethane (2 mL) and pyridine (111 μL, 1.4 mmol) and methanesulfonyl chloride (15μL, 0.19 mmol) were added and the solution stirred at room temperature for 16 hours. The sovent was removed in vacuo and the crude residue was purified by column chromatography on silica gel (2-10% methanol/chloroform) to yield the title compound as a colorless solid (58 mg, 91%); $^1$H NMR (d$_6$-DMSO) δ 15.25 (s, 1H), 8.01, 7.99 (d, 1H), 7.61, 7.59 (d, 2H), 7.53-7.28 (m, 5H), 3.70-3.64 (m, 2H), 3.62-3.49 (m, 5H), 3.10-3.01 (m, 1H), 2.99 (s, 3H), 2.85-2.73 (m, 1H), 2.67-2.55 (m, 1H), 2.44-2.32 (m, 2H), 2.03-1.91 (m, 1H), 1.72-1.61 (m, 1H), 0.99-0.83 (m, 2H), 0.70-0.60 (q, 6H), 0.60-0.45 (m, 1H); MS (ESI) m/z 696 (M+H$^+$).

EXAMPLE 84

N-{3-[(4S)-4-(benzylamino)-1-hydroxy-4-(3-methylbutyl)-3-oxo-3,4-dihydronaphthalen-2-yl]-1,1-dioxido-4H-1,2,4-benzothiadiazin-7-yl}methanesulfonamide To a solution of Example 83B (100 mg, 0.18 mmol) in dichloromethane (2.5 mL) was added benzaldehyde (23 μL, 0.22 mmol), acetic acid (26 μL, 0.46 mmol) and sodium triacetoxyborohydride (63 mg, 0.30 mmol) and the solution was stirred at room temperature for 16 hours. 10% NaHCO$_3$ (10 mL) was added and the solution stirred for 10 minutes, diluted with H$_2$O (10 mL) and the solution extracted with dichloromethane (3×10 mL). The organic extracts were combined, dried (Na$_2$SO$_4$), the drying agent filtered off and the solvent removed in vacuo to give a crude residue which was purified by column chromatography on silica gel (2% methanol/chloroform). The pure material was dissolved in 4M HCl in dioxane (4 mL) and the solution stirred at room temperature for 3 hours, solvent removed in vacuo and the residue dissolved in dichloromethane (4 mL). To this solution was added pyridine (56 uL, 0.9 mmol) and methanesulfonyl chloride (13 μL, 0.22 mmol) and the solution stirred at room temperature for 48 hours, solvent was removed in vacuo and the crude residue was purified by column chromatography on silica gel 4-6% methanol/chloroform) to give the title compound as a colorless solid (75 mg, 67%); $^1$H NMR (d$_6$-DMSO) δ 14.00 (s, 1H), 9.98 (s, 1H), 8.21, 8.19 (d, 1H), 7.94, 7.92 (d, 1H), 7.77-7.27 (m, 10H), 3.02 (s, 3H), 2.35-2.17 (m, 1H), 2.05-1.89 (m, 1H), 1.36-1.21 (m, 1H), 0.73-0.61 (q, 6H), 0.58-0.45 (m, 1H); MS (ESI) m/z 609 (M+H$^+$).

EXAMPLE 85

N-(3-{4-(3,3-dimethylbutyl)-1-hydroxy-4-[(2-naphthylmethyl)amino]-3-oxo-3,4-dihydronaphthalen-2-yl}-1,1-dioxido-4H-1,2,4-benzothiadiazin-7-yl)methanesulfonamide The procedure of Example 74G was followed, except substituting 2-naphthaldehyde for benzaldehyde. The title compound was prepared as a yellow solid (11 mg, 38%). $^1$H NMR (300 MHz, DMSO-d$_6$) δ ppm 0.42-0.57 (m, 1H), 0.67 (s, 9H), 0.97-1.17 (m, 1H), 1.91-2.07 (m, 1H), 2.19-2.39 (m, 1H), 3.03 (s, 3H), 3.63 (d, J=12.13 Hz, 1H), 3.84 (d, J=11.40 Hz, 1H), 7.33-7.40 (m, 1H), 7.41-7.59 (m, 5H), 7.59-7.68 (m, 1H), 7.74 (t, J=5.88 Hz, 1H), 7.83-8.02 (m, 5H), 8.22 (d, J=8.46 Hz, 1H), 9.72 (s, 1H), 9.98 (s, 1H), 14.00 (s, 1H); MS m/z 673.3 (M+H)$^+$.

EXAMPLE 86

N-(3-{4-(3,3-dimethylbutyl)-1-hydroxy-3-oxo-4-[(1,3-thiazol-2-ylmethyl)amino]-3,4-dihydronaphthalen-2-yl}-1,1-dioxido-4H-1,2,4-benzothiadiazin-7-yl)methanesulfonamide The procedure of Example 74G was followed, except substituting 2-thiazocarboxaldehyde for benzaldehyde. The title compound was prepared as a yellow solid (3 mg, 1 1%). $^1$H NMR (300 MHz, DMSO-d$_6$) δ ppm 0.43-0.59 (m, 1H), 0.66 (s, 9H), 0.89-1.11 (m, 1H), 1.75-1.96 (m, 1H), 1.98-2.20 (m, 1H), 3.01 (s, 3H), 3.95 (d, J=13.97 Hz, 1H), 7.32-7.39 (m, 1H), 7.41-7.55 (m, 3H), 7.55-7.64 (m, 1H), 7.66-7.73 (m, 1H), 7.73-7.80 (m, 1H), 7.84 (d, J=7.35 Hz, 1H), 8.12 (d, J=7.35 Hz, 1H), 9.95 (s, 1H); MS m/z 630.3 (M+H)$^+$.

EXAMPLE 87

N-(3-{4-(3,3-dimethylbutyl)-1-hydroxy-4-[(3-nitrobenzyl)amino]-3-oxo-3,4-dihydronaphthalen-2-yl}-1,1-dioxido-4H-1,2,4-benzothiadiazin-7-yl)methanesulfonamide The procedure of Example 74G was followed, except substituting 3-nitrobenzaldehyde for benzaldehyde. The title compound was prepared as a yellow solid (13 mg, 45%). $^1$H NMR (300 MHz, DMSO-d$_6$) δ ppm 0.42-0.56 (m, 1H), 0.67 (s, 9H), 0.95-1.14 (m, 1H), 1.84-2.03 (m, 1H), 2.14-2.33 (m, 1H), 3.02 (s, 3H), 3.63-3.94 (m, 1H), 7.32-7.39 (m, 1H), 7.43-7.76 (m, 6H), 7.85 (d, J=8.46 Hz, 1H), 8.13-8.30 (m, 3H), 9.81 (s, 1H), 9.97 (s, 1H), 13.97 (s, 1H); MS m/z 668.2 (M+H)$^+$.

EXAMPLE 88

N-{3-[4-{[2-(benzyloxy)benzyl]amino}-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide The procedure of Example 74G was followed, except substituting 2-benzyloxybenzaldehyde for benzaldehyde. The title compound was prepared as a yellow solid (19 mg, 59%). $^1$H NMR (300 MHz, DMSO-d$_6$) δ ppm 0.34-0.49 (m, 1H), 0.66 (s, 9H), 0.96-1.11 (m, 1H), 1.92-2.09 (m, 1H), 2.19-2.38 (m, 1H), 3.02 (s, 3H), 3.56-3.70 (m, 2H), 5.10 (s, 2H), 6.98 (t, J=7.35 Hz, 1H), 7.07 (d, J=8.09 Hz, 1H), 7.26-7.42 (m, 9H), 7.42-7.56 (m, 3H), 7.85 (d, J=8.09 Hz, 1H), 8.15 (d, J=7.72 Hz, 1H), 9.39 (s, 1H), 9.97 (s, 1H), 14.03 (s, 1H); MS m/z 729.3 (M+H)$^+$.

EXAMPLE 89

N-(3-{4-(3,3-dimethylbutyl)-1-hydroxy-3-oxo-4-[(3-vinylbenzyl)amino]-3,4-dihydronaphthalen-2-yl}-1,1-dioxido-4H-1,2,4-benzothiadiazin-7-yl)methanesulfonamide The procedure of Example 74G was followed, except substituting 3-vinylbenzaldehyde for benzaldehyde. The title compound was prepared as a yellow solid (16 mg, 55%). $^1$H NMR (300 MHz, DMSO-d$_6$) δ ppm 0.38-0.55 (m, 1H), 0.67 (s, 9H), 0.97-1.15 (m, 1H), 1.89-2.06 (m, 1H), 2.19-2.37 (m, 1H), 3.02 (s, 3H), 3.44 (d, J=11.03 Hz, 1H), 3.70 (d, J=9.56 Hz, 1H), 5.31 (d, J=10.66 Hz, 1H), 5.86 (d, J=17.65 Hz, 1H), 6.74 (dd, J=17.46, 10.85 Hz, 1H), 7.20 (d, J=7.35 Hz, 1H), 7.31-7.57 (m, 6H), 7.57-7.68 (m, 1H), 7.72 (t, J=5.70 Hz, 1H), 7.93 (d, J=6.99 Hz, 1H), 8.20 (d, J=7.35 Hz, 1H), 9.63 (s, 1H), 9.98 (s, 1H), 13.99 (s, 1H); MS m/z 649.3 (M+H)$^+$.

EXAMPLE 90

N-{3-[4-{[3-(benzyloxy)benzyl]amino}-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide The procedure of Example 74G was followed, except substituting 3-benzyloxybenzaldehyde for benzaldehyde. The title compound was prepared as a yellow solid (19 mg, 59%). $^1$H NMR (300 MHz, DMSO-d$_6$) δ ppm 0.37-0.57 (m, 1H), 0.67 (s, 9H), 0.97-1.15 (m, 1H), 1.88-2.08 (m, 1H), 2.19-2.38 (m, 1H), 2.96-3.06 (m, 3H), 3.44-3.54 (m, 1H), 3.63-3.76 (m, 1H), 5.10 (s, 2H), 6.87 (d, J=7.35 Hz, 1H), 6.96-7.07 (m, 2H), 7.24-7.55 (m, 9H), 7.57-7.66 (m, 1H), 7.67-7.76 (m, 1H), 7.91 (d, J=6.99 Hz, 1H), 8.20 (d, J=7.35 Hz, 1H), 9.59 (s, 1H), 9.97 (s, 1H), 13.97 (s, 1H); MS m/z 729.3 (M+H)$^+$.

EXAMPLE 91

N-(3-{4-(3,3-dimethylbutyl)-1-hydroxy-4-[(4-hydroxybenzyl)amino]-3-oxo-3,4-dihydronaphthalen-2-yl}-1,1-dioxido-4H-1,2,4-benzothiadiazin-7-yl)methanesulfonamide A mixture of the product from Example 81 (13 mg, 0.018 mmol) and 10% Pd/C (3 mg) in methanol (1 mL) was stirred at room temperature under H$_2$ atmosphere for 6 h. The heterogeneous solution was filtered and the filtrate was concentrated in vacuo. Column chromatography on silica (5% methanol/dichloromethane) afforded the title compound as a yellow solid (8 mg, 73%). $^1$H NMR (500 MHz, DMSO-d$_6$) δ ppm 0.59-0.69 (m, 10H), 0.97-1.07 (m, 1H), 1.78-1.90 (m, 1H), 2.00-2.11 (m, 1H), 2.98 (s, 3H), 3.18 (d, J=12.21 Hz, 1H), 3.41 (d, J=12.21 Hz, 1H), 6.69 (d, J=7.93 Hz, 2H), 7.05 (d, J=8.54 Hz, 2H), 7.24 (d, J=8.54 Hz, 1H), 7.40-7.48 (m, 2H), 7.52-7.60 (m, 2H), 7.80 (d, J=7.93 Hz, 1H), 8.15 (d, J=7.32 Hz, 1H), 8.86 (s, 1H), 14.58 (s, 1H); MS m/z 639.3 (M+H)$^+$.

EXAMPLE 92

N-((1S)-4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2,5-dimethoxybenzenesulfonamide To a solution of Example 83B (138 mg, 0.26 mmol) in N,N-dimethylformamide (1 mL) was added potassium carbonate (70 mg, 0.51 mmol) and 3,5-dimethoxybenzenesulfonyl chloride (61 mg, 0.26 mmol) and the solution was stirred at room temperature for 16 hours. The solution was poured into 1N HCl (5 mL) and extracted with ethyl acetate (3×5 mL), the combined organic extracts washed with brine (1×5 mL) and solvent removed in vacuo to yield crude product which was purified by column chromatography on silica gel (2-4% methanol/chloroform). The pure product was dissolved in 4M HCl in dioxane (2 mL) and stirred at room temperature for 3 hours, solvent removed in vacuo and the crude residue dissolved in dichloromethane (1 mL) and pyridine (68 µL, 0.84 mmol) and methanesulfonyl chloride (26 uL, 0.36 mmol) added and the solution stirred at room temperature for 16 hours. Solvent was removed in vacuo and the crude residue was purified by column chromatography on silica gel (2-4% methanol/chloroform) to give the title compound as a colorless solid; $^1$H NMR (d$_6$-dmso) δ 13.69(s, 1H), 10.23 (s, 1H), 8.49 (s, 1H), 8.02, 7.99 (d, 1H), 7.65-7.55 (q, 3H), 7.40-7.30 (t, 1H), 7.25-7.15 (q, 2H), 7.06, 7.03 (d, 1H), 6.90, 6.89, 6.88, 6.86 (dd, 1H), 6.36, 6.34 (d, 1H), 3.95 (s, 3H), 3.41 (s, 3H), 3.08 (s, 3H), 2.31-2.18 (m, 1H), 1.96-1.84 (m, 1H), 1.29-1.17 (m, 1H), 0.83-0.69 (m, 1H), 0.69-0.57 (q, 6H), 0.36-0.23 (m, 1H); MS (ESI) m/z 719 (M+H$^+$).

EXAMPLE 93

N-(3-{4-(3,3-dimethylbutyl)-1-hydroxy-4-[(2-hydroxybenzyl)amino]-3-oxo-3,4-dihydronaphthalen-2-yl}-1,1-dioxido-4H-1,2,4-benzothiadiazin-7-yl)methanesulfonamide The procedure of Example 91 was followed, except substituting the product from Example 81 with the product from Example 88. The title compound was prepared as a light yellow solid (8 mg, 57%). $^1$H NMR (300 MHz, DMSO-d$_6$) δ ppm 0.41-0.59 (m, 1H), 0.66 (s, 9H), 0.91-1.08 (m, 1H), 1.74-2.26 (m, 2H), 3.01 (s, 3H), 6.75 (d, J=5.15 Hz, 2H), 7.13 (d, J=5.88 Hz, 2H), 7.32-7.39 (m, 1H), 7.40-7.55 (m, 3H), 7.55-7.68 (m, 1H), 7.75-7.90 (m, 1H), 8.14 (d, J=6.99 Hz, 1H), 9.94 (s, 1H); MS m/z 639.3 (M+H)$^+$.

EXAMPLE 94

N-(3-{4-(3,3-dimethylbutyl)-1-hydroxy-3-oxo-4-[(pyridin-3-ylmethyl)amino]-3,4-dihydronaphthalen-2-yl}-1,1-dioxido-4H-1,2,4-benzothiadiazin-7-yl)methanesulfonamide The procedure of Example 74G was followed, except substituting 3-pyridinecarboxaldehyde for benzaldehyde. The title compound was prepared as a yellow solid (6.5 mg, 24%). $^1$H NMR (300 MHz, DMSO-d$_6$) δ ppm 0.41-0.58 (m, 1H), 0.66 (s, 9H), 0.94-1.12 (m, 1H), 1.79-2.03 (m, 1H), 2.05-2.31 (m, 1H), 2.97-3.06 (m, 3H), 3.55-3.81 (m, 1H), 7.29-7.79 (m, 7H), 7.81-7.93 (m, 1H), 8.17 (d, J=8.09 Hz, 1H), 8.45 (s, 1H), 8.52 (s, 1H), 9.96 (s, 1H); MS m/z 624.2 (M+H)$^+$.

EXAMPLE 95

N-{3-[4-[(2,5-dimethoxybenzyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide The procedure of Example 74G was followed, except substituting 2,5-dimethoxybenzaldehyde for benzaldehyde. The title compound was prepared as a yellow solid (16 mg, 53%). $^1$H NMR (300 MHz, DMSO-d,) δ ppm 0.30-0.51 (m, 1H), 0.66 (s, 9H), 0.94-1.10 (m, 1H), 1.95-2.12 (m, 1H), 2.18-2.34 (m, 1H), 3.02 (s, 3H), 3.48 (d, J=12.87 Hz, 1H), 3.54-3.60 (m, 1H), 3.65 (s, 3H), 3.70 (s, 3H), 6.89 (s, 3H), 7.32-7.40 (m, 1H), 7.43-7.55 (m, 2H), 7.60 (t, J=7.54 Hz, 1H), 7.73 (t, J=7.17 Hz, 1H), 7.90 (d, J=7.35 Hz, 1H), 8.18 (d, J=7.72 Hz, 1H), 9.12 (s, 1H), 9.55 (s, 1H), 9.97 (s, 1H), 14.06 (s, 1H); MS m/z 683.2 (M+H)$^+$.

EXAMPLE 96

N-(3-{4-(3,3-dimethylbutyl)-1-hydroxy-4-[(2-methoxy-5-nitrobenzyl)amino]-3-oxo-3,4-dihydronaphthalen-2-yl}-1,1-dioxido-4H-1,2,4-benzothiadiazin-7-yl)methanesulfonamide The procedure of Example 74G was followed, except substituting 2-methoxy-5-nitrobenzaldehyde for benzaldehyde. The title compound was prepared as a yellow solid (17 mg, 55%). $^1$H NMR (300 MHz, DMSO-$d_6$) δ ppm 0.33-0.52 (m, 1H), 0.67 (s, 9H), 0.91-1.10 (m, 1H), 1.88-2.13 (m, 1H), 2.14-2.36 (m, 1H), 3.02 (s, 3H), 3.52-3.65 (m, 1H), 3.64-3.80 (m, 1H), 3.84 (s, 3H), 7.12-7.22 (m, 1H), 7.31-7.37 (m, 1H), 7.43-7.56 (m, 2H), 7.56-7.67 (m, 1H), 7.69-7.79 (m, 1H), 7.79-7.88 (m, 1H), 8.09-8.34 (m, 3H), 9.97 (s, 1H), 14.04 (s, 1H); MS m/z 698.3 (M+H)$^+$.

EXAMPLE 97

N-{3-[4-[(1,1'-biphenyl-4-ylmethyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide The procedure of Example 74G was followed, except substituting 4-biphenylcaboxaldehyde for benzaldehyde. The title compound was prepared as a yellow solid (16 mg, 52%). $^1$H NMR (300 MHz, DMSO-$d_6$) δ ppm 0.39-0.55 (m, 1H), 0.67 (s, 9H), 0.98-1.16 (m, 1H), 1.89-2.06 (m, 1H), 2.19-2.36 (m, 1H), 3.02 (s, 3H), 3.49 (d, J=13.97 Hz, 1H), 3.74 (d, J=13.24 Hz, 1H), 7.32-7.78 (m, 14H), 7.94 (d, J=6.62 Hz, 1H), 8.21 (d, J=7.72 Hz, 1H), 9.64 (s, 1H), 9.97 (s, 1H), 14.01 (s, 1H); MS m/z 699.3 (M+H)$^+$.

EXAMPLE 98

N-(3-{4-(3,3-dimethylbutyl)-1-hydroxy-4-[(2-nitrobenzyl)amino]-3-oxo-3,4-dihydronaphthalen-2-yl}-1,1-dioxido-4H-1,2,4-benzothiadiazin-7-yl)methanesulfonamide The procedure of Example 74G was followed, except substituting 2-nitrobenzaldehyde for benzaldehyde. The title compound was prepared as a yellow solid (11 mg, 38%). $^1$H NMR (300 MHz, DMSO-$d_6$) δ ppm 0.33-0.53 (m, 1H), 0.67 (s, 9H), 0.94-1.11 (m, 1H), 1.90-2.07 (m, 1H), 2.19-2.36 (m, 1H), 3.02 (s, 3H), 3.88-4.05 (m, 1H), 7.36 (d, J=8.82 Hz, 1H), 7.45-7.56 (m, 3H), 7.57-7.74 (m, 3H), 7.78 (t, J=7.35 Hz, 1H), 7.84-7.95 (m, 1H), 8.09-8.22 (m, 2H), 9.98 (s, 1H); MS m/z 668.2 (M+H)$^+$.

EXAMPLE 99

N-(3-{4-(3,3-dimethylbutyl)-1-hydroxy-4-[(4-nitrobenzyl)amino]-3-oxo-3,4-dihydronaphthalen-2-yl}-1,1-dioxido-4H-1,2,4-benzothiadiazin-7-yl)methanesulfonamide The procedure of Example 74G was followed, except substituting 4-nitrobenzaldehyde for benzaldehyde. The title compound was prepared as a yellow solid (12 mg, 41%). $^1$H NMR (300 MHz, DMSO-$d_6$) δ ppm 0.40-0.57 (m, 1H), 0.67 (s, 9H), 0.95-1.12 (m, 1H), 1.81-2.03 (m, 1H), 2.13-2.33 (m, 1H), 3.02 (s, 3H), 3.55-3.90 (m, 2H), 7.32-7.39 (m, 1H), 7.42-7.54 (m, 2H), 7.54-7.73 (m, 4H), 7.83-7.90 (m, 1H), 8.14-8.26 (m, 3H), 9.97 (s, 1H), 13.94 (s, 1H); MS m/z 668.3 (M+H)$^+$.

EXAMPLE 100

N-(3-{4-(3,3-dimethylbutyl)-1-hydroxy-3-oxo-4-[(pyridin-2-ylmethyl)amino]-3,4-dihydronaphthalen-2-yl}-1,1-dioxido-4H-1,2,4-benzothiadiazin-7-yl)methanesulfonamide The procedure of Example 74G was followed, except substituting 2-pyridinecarboxaldehyde for benzaldehyde. The title compound was prepared as a yellow solid (9 mg, 33%). $^1$H NMR (500 MHz, DMSO-$d_6$) δ ppm 0.49-0.60 (m, 1H), 0.66 (s, 9H), 0.90-1.00 (m, 1H), 1.62-1.84 (m, 1H), 1.85-2.07 (m, 1H), 3.00 (s, 3H), 3.37-3.58 (m, 1H), 7.17-7.28 (m, 1H), 7.29-7.36 (m, 2H), 7.38-7.51 (m, 3H), 7.51-7.59 (m, 1H), 7.66-7.82 (m, 2H), 8.10 (d, J=6.71 Hz, 1H), 8.49 (s, 1H), 9.87 (s, 1H), 15.26 (s, 1H); MS m/z 624.3 (M+H)$^+$.

EXAMPLE 101

N-[3-(4-(3,3-dimethylbutyl)-1-hydroxy-3-oxo-4-{[2-(trifluoromethyl)benzyl]amino}-3,4-dihydronaphthalen-2-yl)-1,1-dioxido-4H-1,2,4-benzothiadiazin-7-yl]methanesulfonamide The procedure of Example 74G was followed, except substituting 2-trifluoromethylbenzaldehyde for benzaldehyde. The title compound was prepared as a yellow solid (13 mg, 43%). $^1$H NMR (300 MHz, DMSO-$d_6$) δ ppm 0.35-0.54 (m, 1H), 0.68 (s, 9H), 0.97-1.12 (m, 1H), 1.87-2.11 (m, 1H), 2.25-2.43 (m, 1H), 3.02 (s, 3H), 3.54 (d, J=12.13 Hz, 1H), 3.87 (d, J=10.66 Hz, 1H), 7.37 (d, J=8.82 Hz, 1H), 7.44-7.55 (m, 2H), 7.56-7.92 (m, 7H), 8.19 (d, J=6.25 Hz, 1H), 9.98 (s, 1H), 13.87 (s, 1H); MS m/z 691.2 (M+H)$^+$.

EXAMPLE 102

N-{3-[4-[(2,6-dimethylbenzyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide The procedure of Example 74G was followed, except substituting 2,6-dimethylbenzaldehyde for benzaldehyde. The title compound was prepared as a yellow solid (11 mg, 39%). $^1$H NMR (300 MHz, DMSO-$d_6$) δ ppm 0.31-0.50 (m, 1H), 0.67 (s, 9H), 0.97-1.13 (m, 1H), 1.96-2.13 (m, 1H), 2.26 (s, 6H), 2.31-2.40 (m, 1H), 2.99-3.07 (m, 3H), 3.63-3.79 (m, 1H), 7.03-7.11 (m, 2H), 7.13-7.23 (m, 1H), 7.36 (d, J=8.82 Hz, 1H), 7.42-7.58 (m, 2H), 7.64 (t, J=7.72 Hz, 1H), 7.74 (t, J=6.80 Hz, 1H), 8.03 (d, J=7.35 Hz, 1H), 8.23 (d, J=7.35 Hz, 1H), 8.93 (s, 1H), 9.25 (s, 1H), 9.99 (s, 1H), 13.96 (s, 1H); MS m/z 651.3 (M+H)$^+$.

EXAMPLE 103

N-(3-{4-(3,3-dimethylbutyl)-1-hydroxy-4-[(mesitylmethyl)amino]-3-oxo-3,4-dihydronaphthalen-2-yl}-1,1-dioxido-4H-1,2,4-benzothiadiazin-7-yl)methanesulfonamide The procedure of Example 74G was followed, except substituting mesitaldehyde for benzaldehyde. The title compound was prepared as a yellow solid (8 mg, 27%). $^1$H NMR (300 MHz, DMSO-$d_6$) δ ppm 0.32-0.50 (m, 1H), 0.67 (s, 9H), 0.95-1.13 (m, 1H), 1.96-2.13 (m, 1H), 2.21 (s, 9H), 2.27-2.45 (m, 1H), 2.98-3.06 (m, 3H), 3.58-3.76 (m, 1H), 6.88 (s, 2H), 7.36 (d, J=8.82 Hz, 1H), 7.42-7.56 (m, 2H), 7.64 (t, J=7.54

Hz, 1H), 7.69-7.79 (m, 1H), 8.02 (d, J=7.72 Hz, 1H), 8.22 (d, J=7.72 Hz, 1H), 8.87 (s, 1H), 9.21 (s, 1H), 9.98 (s, 1H), 13.95 (s, 1H); MS m/z 665.2 (M+H)+.

EXAMPLE 104

N-[3-(4-(3,3-dimethylbutyl)-1-hydroxy-4-{[(6-methylpyridin-3-yl)methyl]amino}-3-oxo-3,4-dihydronaphthalen-2-yl)-1,1-dioxido-4H-1,2,4-benzothiadiazin-7-yl]methanesulfonamide The procedure of Example 74G was followed, except substituting 6-methylpyridine-3-carboxaldehyde for benzaldehyde. The title compound was prepared as a yellow solid (15 mg, 58%). $^1$H NMR (300 MHz, DMSO-d$_6$) δ ppm 0.48-0.67 (m, 10H), 0.79-0.93 (m, 1H), 1.54-1.70 (m, 1H), 1.76-1.87 (m, 1H), 2.40 (s, 3H), 2.94 (s, 3H), 7.14 (d, J=7.72 Hz, 1H), 7.28 (d, J=8.82 Hz, 1H), 7.31-7.47 (m, 3H), 7.48-7.60 (m, 2H), 7.75 (d, J=8.09 Hz, 1H), 8.06 (d, J=6.62 Hz, 1H), 8.27 (d, J=2.21 Hz, 1H), 15.29 (s, 1H); MS m/z 638.2 (M+H)+.

EXAMPLE 105

N-[3-(4-(3,3-dimethylbutyl)-1-hydroxy-4-{[(2-methylpyridin-3-yl)methyl]amino}-3-oxo-3,4-dihydronaphthalen-2-yl)-1,1-dioxido-4H-1,2,4-benzothiadiazin-7-yl]methanesulfonamide The procedure of Example 74G was followed, except substituting 2-methylpyridine-3-carboxaldehyde for benzaldehyde. The title compound was prepared as a yellow solid (15 mg, 54%). $^1$H NMR (300 MHz, DMSO-d$_6$) δ ppm 0.47-0.74 (m, 10H), 0.78-0.98 (m, 2H), 1.55-1.95 (m, 2H), 2.34 (s, 3H), 3.01 (s, 3H), 7.12-7.23 (m, 1H), 7.25-7.82 (m, 7H), 8.11 (d, J=7.35 Hz, 1H), 8.26-8.36 (m, 1H), 9.92 (s, 1H); MS m/z 638.2 (M+H)+.

EXAMPLE 106

N-[3-(4-(3,3-dimethylbutyl)-1-hydroxy-4-{[(6-methylpyridin-2-yl)methyl]amino}-3-oxo-3,4-dihydronaphthalen-2-yl)-1,1-dioxido-4H-1,2,4-benzothiadiazin-7-yl]methanesulfonamide The procedure of Example 74G was followed, except substituting 6-methylpyridine-2-carboxaldehyde for benzaldehyde. The title compound was prepared as a yellow solid (19 mg, 68%). $^1$H NMR (300 MHz, DMSO-d$_6$) δ ppm 0.45-0.60 (m, 1H), 0.65 (s, 9H), 0.83-0.98 (m, 1H), 1.57-1.74 (m, 1H), 1.80-1.98 (m, 1H), 2.41 (s, 3H), 2.99 (s, 3H), 3.03-3.11 (m, 1H), 3.13-3.25 (m, 1H), 7.00-7.14 (m, 2H), 7.29-7.45 (m, 3H), 7.46-7.61 (m, 3H), 7.69 (d, J=6.99 Hz, 1H), 8.06 (d, J=7.35 Hz, 1H), 9.89 (s, 1H), 15.33 (s, 1H); MS m/z 638.2 (M+H)+.

EXAMPLE 107

N-{3-[4-[(2-aminobenzyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide To a solution of the product of Example 98 (7 mg, 0.01 mmol) in ethyl acetate (0.5 mL) was added 10% Pd/C (2 mg). The mixture was stirred under H$_2$ atmosphere for 1 h and filtered. The filtrate was concentrated in vacuo. Column chromatography on silica (3% methanol/dichloromethane) afforded the title compound as a yellow solid (4 mg, 57%). $^1$H NMR (300 MHz, DMSO-d$_6$) δ ppm 0.38-0.55 (m, 1H), 0.66 (s, 9H), 0.99-1.14 (m, 1H), 1.86-2.03 (m, 1H), 2.17-2.37 (m, 1H), 3.02 (s, 3H), 3.45-3.57 (m, 1H), 6.55 (t, J=6.25 Hz, 1H), 6.72 (d, J=7.72 Hz, 1H), 6.92 (d, J=7.35 Hz, 1H), 7.00-7.77 (m, 6H), 7.90-8.01 (m, 1H), 8.20 (d, J=6.62 Hz, 1H), 9.97 (s, 1H), 13.90 (s, 1H); MS m/z 638.3 (M+H)+.

EXAMPLE 108

N-(3-{4-(3,3-dimethylbutyl)-1-hydroxy-4-[(imidazo[1,5-a]pyridin-3-ylmethyl)amino]-3-oxo-3,4-dihydronaphthalen-2-yl}-1,1-dioxido-4H-1,2,4-benzothiadiazin-7-yl)methanesulfonamide The procedure of Example 74G was followed, except substituting imidazo[1,5-a]pyridine-3-carboxaldehyde for benzaldehyde. The title compound was prepared as a brown solid (16 mg, 55%). $^1$H NMR (300 MHz, DMSO-d,) δ ppm 0.45-0.67 (m, 10H), 0.82-0.98 (m, 1H), 1.59-1.76 (m, 1H), 1.80-1.96 (m, 1H), 3.01 (s, 3H), 3.40-3.53 (m, 1H), 3.60-3.76 (m, 11H), 6.64-6.82 (m, 2H), 7.23 (s, 1H), 7.32-7.52 (m, 5H), 7.57 (t, J=7.35 Hz, 1H), 7.74 (d, J=7.35 Hz, 1H), 8.12 (dd, J=14.71, 6.62 Hz, 2H), 9.91 (s, 1H), 15.22 (s, 1H); MS m/z 663.2 (M+H)+.

EXAMPLE 109

N-{3-[4-[benzyl(methyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide To a solution of the product of Example 74G (10 mg, 0.016 mmol) in dichloroethane (0.1 mL) was added formic acid (1.2 μL, 0.032 mmol) followed by addition of aqueous 37% formaldehyde solution (1.3 μL, 0.018 mmol). The mixture was heated at 50° C. for 2 h. After cooling to room temperature, the solution was diluted with ethyl acetate (1 mL), washed with water (0.5 mL), dried (Na$_2$SO$_4$), and concentrated in vacuo. Column chromatography on silica (2% methanol/dichloromethane) afforded a greenish brown solid (6 mg, 60%). $^1$H NMR (300 MHz, DMSO-d$_6$) δ ppm 0.31-0.50 (m, 1H), 0.73 (s, 9H), 0.90-1.07 (m, 1H), 2.11-2.30 (m, 1H), 2.35-2.48 (m, 1H), 2.71 (s, 3H), 3.00-3.10 (m, 3H), 3.45-3.62 (m, 1H), 4.07 (d, J=12.87 Hz, 1H), 7.26-7.40 (m, 5H), 7.42-7.60 (m, 3H), 7.64 (t, J=7.54 Hz, 1H), 7.71-7.80 (m, 1H), 7.93 (d, J=8.09 Hz, 1H), 8.22 (d, J=6.62 Hz, 1H), 10.06 (s, 1H), 13.53 (s, 1H); MS m/z 637.2 (M+H)+.

EXAMPLE 110

N-benzyl-N-(1-(3,3-dimethylbutyl)-4-hydroxy-3-{7-[(methylsulfonyl)amino]-1,1-dioxido-4H-1,2,4-benzothiadiazin-3-yl}-2-oxo-1,2-dihydronaphthalen-1-yl)acetamide To a solution of the product of Example 74G (20 mg, 0.032 mmol) in dichloroethane (0.5 mL), acetic anhydride (5 μL, 0.048 mmol) and triethylamine (13 μL, 0.096 mmol) were added. The reaction solution was heated at 75° C. for 96 h. After cooling to room temperature, the solution was concentrated in vacuo. The resulting residue was dissolved in methanol (0.5 mL) and treated with excess of K$_2$CO$_3$ for 30 min. The mixture was filtered and the filtrate was concentrated in vacuo. The resulting residue was taken up in ethyl acetate (1 mL), washed with aqueous 1 N HCl, dried (Na$_2$SO$_4$), and concentrated in vacuo. Column chromatography on silica (1%→2%→3% methanol/dichloromethane) afforded the title compound as a brown solid (5 mg, 24%). $^1$H NMR (300 MHz, DMSO-d$_6$) δ ppm 0.25-0.42 (m, 1H), 0.47 (s, 9H), 0.73-0.96 (m, 1H), 1.68-2.05 (m, 5H), 3.02 (s, 3H), 5.06 (d, J=18.02 Hz, 1H), 5.24-5.42 (m, 1H), 7.27-7.61 (m, 10H), 7.83 (d, J=6.99 Hz, 1H), 10.01 (s, 1H); MS m/z 665.2 (M+H)$^+$.

EXAMPLE 111

N-[3-(4-(3,3-dimethylbutyl)-1-hydroxy-4-{[(2-methoxypyridin-3-yl)methyl]amino}-3-oxo-3,4-dihydronaphthalen-2-yl)-1,1-dioxido-4H-1,2,4-benzothiadiazin-7-yl]methanesulfonamide The procedure of Example 74G was followed, except substituting 2-methoxy-3-pyridinecarboxaldehyde for benzaldehyde. The title compound was prepared as a yellow solid (16 mg, 55%). $^1$H NMR (300 MHz, DMSO-d$_6$) δ ppm 0.33-0.53 (m, 1H), 0.66 (s, 9H), 0.94-1.10 (m, 1H), 1.93-2.10 (m, 1H), 2.14-2.34 (m, 1H), 3.02 (s, 3H), 3.39-3.49 (m, 1H), 3.60-3.73 (m, 1H), 3.80 (s, 3H), 6.93-7.04 (m, 1H), 7.31-7.40 (m, 1H), 7.41-7.56 (m, 2H), 7.56-7.82 (m, 3H), 7.83-7.94 (m, 1H), 8.09-8.24 (m, 2H), 9.97 (s, 1H), 14.05 (s, 1H); MS m/z 654.2 (M+H)$^+$.

EXAMPLE 112

N-{3-[4-[(3-acetylbenzyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide The procedure of Example 74G was followed, except substituting 3-acetylbenzaldehyde for benzaldehyde. The title compound was prepared as a yellow solid (19 mg, 66%). $^1$H NMR (300 MHz, DMSO-d$_6$) δ ppm 0.38-0.76 (m, 10H), 0.94-1.11 (m, 1H), 1.82-2.07 (m, 1H), 2.15-2.38 (m, 1H), 2.57 (s, 3H), 3.01 (s, 3H), 3.49-3.66 (m, 1H), 3.69-3.87 (m, 1H), 7.31-8.25 (m, 11H), 9.70 (s, 1H), 9.96 (s, 1H), 13.98 (s, 1H); MS m/z 665.2 (M+H)$^+$.

EXAMPLE 113

N-(3-{4-(3,3-dimethylbutyl)-1-hydroxy-4-[(1-methyl-1H-benzoimidazol-2-ylmethyl)amino]-3-oxo-3,4-dihydronaphthalen-2-yl}-1,1-dioxido-4H-1,2,4-benzothiadiazin-7-yl)methanesulfonamide The procedure of Example 74G was followed, except substituting 1-methyl-2-formylbenzimidazole for benzaldehyde. The title compound was prepared as a yellow solid (8 mg, 27%). $^1$H NMR (300 MHz, DMSO-D6) δ ppm 15.28 (s, 1H), 9.90 (s, 1H), 8.10 (d, J=6.62 Hz, 1H), 7.75 (d, J=6.99 Hz, 1H), 7.30-7.60 (m, 7H), 7.11-7.23 (m, 2H), 3.65 (s, 3H), 3.37-3.54 (m, 2H), 3.00 (s, 3H), 1.81-1.97 (m, 1H), 1.67 (s, 1H), 0.79-1.00 (m, J=12.50 Hz, 1H), 0.47-0.72 (m, 10H); MS m/z 677.2 (M+H)$^+$.

EXAMPLE 114

N-(3-{4-(3,3-dimethylbutyl)-1-hydroxy-4-[(1-methyl-1H-imidazol-2-ylmethyl)amino]-3-oxo-3,4-dihydronaphthalen-2-yl}-1,1-dioxido-4H-1,2,4-benzothiadiazin-7-yl)methanesulfonamide The procedure of Example 74G was followed, except substituting 1-methylimidazole-2-carbaldehyde for benzaldehyde. The title compound was prepared as a white solid (3 mg, 11%). $^1$H NMR (300 MHz, DMSO-D6) δ ppm 15.27 (s, 1H), 9.90 (s, 1H), 8.07 (d, J=6.99 Hz, 1H), 7.72 (d, J=7.35 Hz, 1H), 7.29-7.60 (m, 5H), 6.99 (s, 1H), 6.73 (s, 1H), 3.48 (s, 3H), 3.22 (d, J=12.13 Hz, 1H), 2.89-3.09 (m, 4H), 1.75-1.93 (m, 1H), 1.51-1.70 (m, J=3.68 Hz, 1H), 0.80-0.98 (m, 1H), 0.63 (s, 9H), 0.45-0.58 (m, 1H); MS m/z 627.2 (M+H)$^+$.

EXAMPLE 115

N-(3-{4-(3,3-dimethylbutyl)-4-[(2,5-dimethyl-2H-pyrazol-3-ylmethyl)amino]-1-hydroxy-3-oxo-3,4-dihydronaphthalen-2-yl}-1,1-dioxido-4H-1,2,4-benzothiadiazin-7-yl)methanesulfonamide The procedure of Example 74G was followed, except substituting 1,3-dimethyl-1-pyrazol-5-carbaldehyde for benzaldehyde. The title compound was prepared as a light brown solid (50 mg, 29%). $^1$H NMR (300 MHz, DMSO-D6) δ ppm 15.30 (s, 1H), 9.90 (s, 1H), 8.07 (d, J=7.72 Hz, 1H), 7.70 (d, J=7.35 Hz, 1H), 7.29-7.59 (m, 5H), 5.85 (s, 1H), 3.57 (s, 3H), 3.27 (d, J=4.41 Hz, 1H), 3.17 (d, J=5.15 Hz, 1H), 2.97-3.04 (m, 3H), 2.05 (s, 3H), 1.72-1.88 (m, 1H), 1.50-1.70 (m, 1H), 0.80-0.98 (m, 1H), 0.45-0.74 (m, 10H); MS m/z 641.3 (M+H)$^+$.

EXAMPLE 116

N-{3-[4-[(2-chloro-6-fluoro-benzyl)amino)]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide The procedure of Example 74G was followed, except substituting 2-chloro-6-fluorobenzaldehyde for benzaldehyde. The title compound was prepared as a yellow solid (17 mg, 57%). $^1$H NMR (300 MHz, DMSO-D6) δ ppm 14.13 (s, 1H), 9.98 (s, 1H), 9.60 (s, 1H), 8.20 (d, J=6.62 Hz, 1H), 7.95 (d, J=7.72 Hz, 1H), 7.70 (t, J=7.17 Hz, 1H), 7.61 (t, J=7.35 Hz, 1H), 7.43-7.55 (m, 3H), 7.26-7.43 (m, 3H), 3.87 (d, J=12.50 Hz, 1H), 3.51 (d, J=11.40 Hz, 1H), 3.02 (s, 3H), 2.22-2.39 (m, 1H), 1.90-2.07 (m, 1H), 0.94-1.11 (m, 1H), 0.67 (s, 9H), 0.34-0.50 (m, 1H); MS m/z 675.3 (M+H)$^+$.

EXAMPLE 117

2-Oxo-4-(R)-phenyl-oxazolidin-3-carbonyl chloride

To a solution of (R)-(−)-4-phenyl-2-oxazolidinone in THF (200 mL) at 0° C. was slowly added a 2.5 M solution of butyllithium in hexane (19 mL, 0.03 mol). The mixture was stirred at 0° C. for 30 min and then cooled to −78° C. Trichloromethyl chloroformate (7.8 mL, 0.03 mol) was added quickly in one portion and the reaction solution was stirred at −78° C. for 30 min. The resulting mixture was allowed to warm to room temperature, and was subsequently concentrated in vacuo. The resulting residue was taken up in CH$_2$Cl$_2$ (200 mL) and filtered, and the filtrate was concentrated in vacuo to afford the title compound as an off-white solid (4.5 g, 65%).

EXAMPLE 118

2-oxo-4-(R)-phenyl-oxazolidine-3-carboxylic acid [1-(S)-(3,3-dimethylbutyl)-4-hydroxy-3-(7-methanesulfonylamino-1,1-dioxido-4H-1,2,4-benzothiadiazin-3-yl)-2-oxo-1,2-dihydronaphthalen-1-yl]amide To a solution of the product of 74F (3.0 g, 5.3 mmol) in $CH_2Cl_2$ (50 mL) was added triethylamine (2.2 mL, 15.8 mmol) followed by the product of Example 117 (1.25 g, 5.5 mmol). The reaction solution was stirred at room temperature for 3 h, after which it was diluted with $CH_2Cl_2$ (100 mL) and washed with 0.1 N aqueous HCl (3×50 mL). The combined organic layers were dried ($Na_2SO_4$) and concentrated in vacuo. Column chromatography on silica (0.5% to 7% $MeOH/CH_2Cl_2$ gradient) afforded the title compound as a yellow solid (1.35 g, 71%). $^1H$ NMR (300 MHz, DMSO-D6) δ ppm 13.60 (s, 1H), 10.20 (s, 1H), 8.77 (s, 1H), 8.09 (d, J=6.62 Hz, 1H), 7.46-7.74 (m, 6H), 7.37 (t, J=7.17 Hz, 2H), 7.18-7.31 (m, 3H), 5.30 (dd, J=8.27, 3.13 Hz, 1H), 4.72-4.85 (m, 1H), 4.17 (dd, J=8.64, 3.13 Hz, 1H), 3.07 (s, 3H), 1.90-2.01 (m, 2H), 0.98-1.13 (m, 1H), 0.66-0.94 (m, 10H); MS m/z 722.2 $(M+H)^+$.

EXAMPLE 119

N-{3-[4-(S)-amino-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide trifluoroacetic acid salt A solution of 2-(trimethylsilyl)ethanol (1.5 mL, 18 mmol) in THF (10 mL) was cooled to 0° C. and a 2.5 M solution of butyllithium in hexane (7.2 mL, 18 mmol) was added dropwise. The reaction mixture was stirred at 0° C. for 30 min. before a solution of the product of Example 118 (1.3 g, 1.8 mmol) in THF (10 mL) was added dropwise. The reaction was allowed to warm to room temperature and was stirred at room temperature for 16 h. The solution was diluted with EtOAc (100 mL) and washed with 0.1 N aqueous HCl (50 mL) and $H_2O$ (50 mL). The organic layer was dried ($Na_2SO_4$) and concentrated in vacuo. Column chromatography on silica (10% to 20% $EtOAc/CH_2Cl_2$ gradient) afforded an orange solid (0.80 g, 66%). This solid was dissolved in $CH_2Cl_2$ (5 mL) and the solution was cooled to 0° C. before trifluoroacetic acid (2.5 mL) was added dropwise. The reaction mixture was stirred at 0° C. for 1 h, and was then allowed to warm to room temperature and was stirred for 1 h. The solution was concentrated in vacuo to afford the title compound as a yellow solid (0.51 g, 68%). $^1H$ NMR (300 MHz, DMSO-D6) δ ppm 14.45 (s, 1H), 9.95 (s, 1H), 8.60 (s, 2H), 8.13 (d, J=7.35 Hz, 1H), 7.28-7.72 (m, 6H), 3.01 (s, 3H), 1.95-2.10 (m, 1H), 1.78-1.94 (m, 1H), 0.99-1.17 (m, 1H), 0.65-0.92 (m, 10H); MS m/z 533.2 $(M+H)^+$.

EXAMPLE 120

N-{3-[4-(S)-[(2,6-dimethylbenzyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide To a suspension of the product of Example 119 (0.4 g, 0.62 mmol) in dichloroethane (6 mL) was added N,N-diisopropylethylamine (0.22 mL, 1.23 mmol). The mixture was stirred at room temperature until homogenous before 2,6-dimethylbenzaldehyde (0.17 g, 1.23 mmol) and $MgSO_4$ (0.15 g) were added. The reaction mixture was heated at 50° C. for 18 h, cooled to room temperature and filtered. To the filtrate was added sodium triacetoxyborohydride (0.21 g, 0.99 mmol) and glacial acetic acid (0.11 mL, 1.86 mmol), and the resulting mixture was stirred at room temperature for 18 h. The reaction mixture was diluted with $CH_2Cl_2$ (25 mL) and washed with distilled $H_2O$ (2×10 mL), dried ($Na_2SO_4$) and concentrated in vacuo. Column chromatography on silica (1% to 3% $MeOH/CH_2Cl_2$ gradient) afforded the title compound as a light orange solid (0.22 g, 40%). $^1H$ NMR (300 MHz, DMSO-D6) δ ppm 13.96 (s, 1H), 9.98 (s, 1H), 8.23 (d, J=7.72 Hz, 1H), 8.03 (d, J=7.72 Hz, 1H), 7.70-7.79 (m, 1H), 7.64 (t, J=7.35 Hz, 1H), 7.45-7.55 (m, 2H), 7.32-7.42 (m, 1H), 7.14-7.22 (m, 1H), 7.04-7.10 (m, 2H), 3.64-3.79 (m, 1H), 3.38-3.43 (m, 1H), 3.02 (s, 3H), 2.31-2.43 (m, 1H), 2.27 (s, 6H), 1.99-2.12 (m, 1H), 0.94-1.12 (m, 1H), 0.68 (s, 9H), 0.32-0.48 (m, 1H); MS m/z 651.3 $(M+H)^+$.

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

SEQUENCE LISTING

```
<160> NUMBER OF SEQ ID NOS: 1

<210> SEQ ID NO 1
<211> LENGTH: 171
<212> TYPE: RNA
<213> ORGANISM: Hepatits C Virus

<400> SEQUENCE: 1
gggcgaauug ggcccucuag augcaugcuc gagcggccgc cagugugaug gauaucugca      60
gaauucgccc uugguggcuc caucuuagcc cuagucacgg cuagcuguga aaggccgug     120 agccgcuuga cugcagagag ugcugauacu ggccucucug cagaucaagu c

What is claimed is:

1. A compound, a stereoisomer of the compound, a tautomer of the compound, a pharmaceutically acceptable salt of the compound, stereoisomer, or tautomer, or a combination thereof, wherein:

the compound corresponds to formula (I):

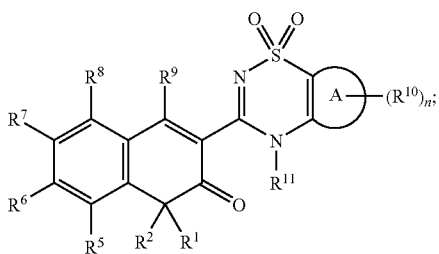

A is phenyl;

$R^1$ is selected fro the group consisting of —$OR_A$, —O-alkyl-C(O)Y, —$NR_AR_B$, —$N(R_C)(—N(R_C)(R_A))$, —$N(R_B)L^1(O)Y$, and —$N(R_B)S(O)_2Z$;

X at each occurrence, is independently selected from the group consisting of $R_A$, —$OR_A$ and —$NR_AR_B$;

$L^1$ is selected from the group consisting of a bond or lower alkyl;

Y is selected from the group consisting of $R_A$, —$OR_A$, —$NR_AR_B$, —O-alkyl-$OR_A$, —O-alkyl-$NR_AR_B$, —$N(R_C)$-alkyl-$NR_AR_B$, —$(CR^3R^4)$—$N(R_C)C(O)X$; —$(CR^3R^4)$—$NR_AR_B$, and heterocycle;

Z is selected from the group consisting of $R_A$, —$OR_A$, —$NR_AR_B$, -alkyl-$OR_A$, -alkyl-$NR_AR_B$, -alkyl-$N(R_C)$C(O)X, -alkyl-O-alkyl-$OR_A$, -alkyl-O-alkyl-$NR_AR_B$ and -alkyl-$N(R_C)$-alkyl-$NR_AR_B$;

$R^3$ and $R^4$ are independently selected from the group consisting of hydrogen, alkyl, alkenyl and arylalkyl wherein:

the aryl moiety of the arylalkyl is substituted with 0, 1, 2, 3, 4 or 5 substituents independently selected from the group consisting of alkyl, alkenyl, alkynyl, formyl, halo, nitro, cyano, alkoxy, —OH, —OC(O)(alkyl), —SH, —S(alkyl), —S(O)alkyl, —S(O)$_2$(alkyl), —NH$_2$, —N(H)(alkyl), —N(alkyl)$_2$, —C(O)alkyl, —C(O)OH, —C(O)(—Oalkyl), —C(O)NH$_2$, —C(O)N(H)(alkyl), —C(O)N(alkyl)$_2$ and haloalkyl;

$R_A$ at each occurrence is independently selected from the group consisting of hydrogen, alkyl, alkenyl, haloalkyl, haloalkenyl, $R_a$ and -alkyl$R_a$;

$R_B$ at each occurrence is independently selected from the group consisting of hydrogen, alkyl, haloalkyl, $R_a$, -alkyl$R_a$, —OH, alkoxy, hydroxyalkyl, alkoxyalkyl, —$OR_a$, and —O-alkyl$R_a$;

$R_C$ at each occurrence is independently selected from the group consisting of hydrogen and lower alkyl;

$R_a$ at each occurrence is independently selected from the group consisting of cycloalkyl, cycloalkenyl, heterocycle, aryl and heteroaryl, wherein:

each such substituent is substituted with 0, 1, 2, 3, 4 or 5 substituents independently selected from the group consisting of alkyl, alkenyl, alkynyl, formyl, halo, nitro, cyano, alkoxy, —OH, —O-alkyl-$R_b$, —OC(O)(alkyl), —SH, —S(alkyl), —S(O)alkyl, —S(O)$_2$(alkyl), —NH$_2$, —N(H)(alkyl), —N(alkyl)$_2$, —C(O)alkyl, —C(O)OH, —C(O)(—Oalkyl), —C(O)NH$_2$, —C(O)N(H)(alkyl), —C(O)N(alkyl)$_2$, haloalkyl, $R_b$ and -alkyl-$R_b$;

$R_b$ at each occurrence is independently selected from the group consisting of cycloalkyl, cycloalkenyl, heterocycle, aryl and heteroaryl, wherein:

each such substituent is substituted with 0, 1, 2, 3, 4 or 5 substituents independently selected from the group consisting of alkyl, alkenyl, alkynyl, formyl, halo, nitro, cyano, alkoxy, —OH, —OC(O)(alkyl), —SH, —S(alkyl), —S(O)alkyl, —S(O)$_2$(alkyl), —NH$_2$, —N(H)(alkyl), —N(alkyl)$_2$, —C(O)alkyl, —C(O)OH, —C(O)(—Oalkyl), —C(O)NH$_2$, —C(O)N(H)(alkyl), —C(O)N(alkyl)$_2$ and haloalkyl;

$R^2$ is selected from the group consisting of hydrogen, alkyl, alkenyl, alkynyl, $R_a$, -alkyl-$R_a$, -alkenyl-$R_a$, -alkynyl-$R_a$, haloalkyl, hydroxyalkyl, formylalkyl, cyanoalkyl, -alkyl-$OR_A$, and -alkyl-$NR_AR_B$;

$R^5$, $R^6$, $R^7$, and $R^8$ are each independently selected from the group consisting of hydrogen, alkyl, alkenyl, alkynyl, cyano, formyl, halo, nitro, —$OR_A$, —$OC(O)R_A$, —$OC(O)OR_A$, —$OC(O)NR_AR_B$, —$OS(O)_2R_A$, —$SR_A$, —$S(O)R_A$, —$S(O)_2R_A$, —$S(O)_2(OR_A)$, —$S(O)_2NR_AR_B$, —$NR_AR_B$, —$N(R_C)C(O)R_A$, —$N(R_C)C(O)NR_AR_B$, —$N(R_C)C(O)OR_A$, —$N(R_C)S(O)_2R_A$, —$N(R_C)S(O)_2NR_AR_B$, —$N(R_C)S(O)_2N(R_C)C(O)OR_A$, —$C(O)R_A$, —$C(O)OR_A$, —$C(O)NR_AR_B$, haloalkyl, cyanoalkyl, -alkyl$OR_A$, -alkyl-OC(O)$R_A$, -alkyl-OC(O)$OR_A$, -alkyl-OC(O)$NR_AR_B$, -alkyl-OS(O)$_2R_A$, -alkyl-$SR_A$, -alkyl-S(O)$R_A$, -alkyl-S(O)$_2R_A$, -alkyl-S(O)$_2$(OR$_A$), -alkyl-S(O)$_2NR_AR_B$, -alkyl-$NR_AR_B$, -alkyl-N(R$_C$)C(O)$R_A$, -alkyl-N(R$_C$)C(O)$NR_AR_B$, -alkyl-N(R$_C$)C(O)$OR_A$, -alkyl-N(R$_C$)S(O)$_2R_A$, -alkyl-N(R$_C$)S(O)$_2NR_AR_B$, -alkyl-N(R$_C$)S(O)$_2N(R_C)C(O)OR_A$, -alkyl-C(O)$R_A$, -alkyl-C(O)(OR$_A$) and -alkyl-C(O)$NR_AR_B$;

$R^9$ is selected from the group consisting of —$OR_A$, —$SR_A$, —$NR_AR_B$, —$N(R_C)C(O)R_A$, —$N(R_C)C(O)OR_A$, —$N(R_C)S(O)_2R_A$, and —$N(R_C)S(O)_2NR_AR_B$;

n is 0, 1, 2, 3 or 4;

$R^{10}$ at each occurrence is independently selected from the group consisting of alkyl, alkenyl, alkynyl, cyano, formyl, nitro, halo, $R_a$, —$OR_A$, —OC(O)X, —OS(O)$_2R_A$, —O-alkyl-$G^1$, —$SR_A$, —S(O)$R_A$, —S(O)$_2$X, —$NR_AR_B$, —N(R$_B$)C(O)X, —N(R$_B$)C(O)(-alkyl-$G^1$), —N(R$_B$)S(O)$_2$X, —N(R$_B$)S(O)$_2$(-alkyl-$G^1$), —C(O)X, —C(O)N(R$_B$)(-alkyl-$G^1$), haloalkyl, cyanoalkyl, nitroalkyl, -alkyl-$R_a$, —N(-alkyl-C(O)X)(S(O)$_2$X,) and -alkyl-$G^1$;

$G^1$ at each occurence is independently selected from the group consisting of —$OR_A$, —$NR_AR_B$, —N(R$_C$)(—NR$_AR_B$), —N(R$_C$)S(O)$_2$X, —N(R$_C$)C(O)X, —C(O)X, —OC(O)X, and —S(O)$_2$X; and $R^{11}$ is selected from the group consisting of hydrogen, alkyl, alkenyl and arylalkyl, wherein:

the aryl moiety of the arylalkyl is substituted with 0, 1, 2, 3, 4 or 5 substituents independently selected from the group consisting of alkyl, alkenyl, alkynyl, formyl, halo, nitro, cyano, haloalkyl, —OH, alkoxy, —OC(O)(alkyl), —NH$_2$, —N(H)(alkyl), —N(alkyl)$_2$, —C(O)OH, —C(O)(—Oalkyl), —C(O)alkyl, —C(O)NH$_2$, —C(O)N(H)(alkyl), and —C(O)N(alkyl)$_2$.

2. The compound, stereoisomer, tautomer, salt, or combination of claim 1, wherein:

$R^9$ is —$OR_A$; and $R_A$ is hydrogen.

3. The compound, stereoisomer, tautomer, salt, or combination of claim 1, wherein:

Y is selected from the group consisting of $R_A$, —$OR_A$, $NR_AR_B$, —O-alkyl-$OR_A$, —O-alkyl-$NR_AR_B$, —N($R_C$)-alkyl-$NR_AR_B$, —($CR^3R^4$)—N($R_C$)C(O)X and —($CR^3R^4$)—$NR_AR_B$, and 2-oxo-4-(R)-phenyl-oxazolidine.

4. The compound, stereoisomer, tautomer, salt, or combination of claim 1, wherein the compound is selected from the group consisting of N-[3-(4-butyl-1,4-dihydroxy-3-oxo-3,4-dihydronaphthalen-2-yl)-1,1-dioxido-4H-1,2,4-benzothiadiazin-7-yl]methanesulfonamide;

N-{3-[1,4-dihydroxy-4-(3-methylbutyl)-3-oxo-3,4-dihydronaphthalen-2-yl]-1,1-dioxido-4H-1,2,4-benzothiadiazin-7-yl}methanesulfonamide;

N-{3-[(4S)-1,4-dihydroxy-4-(3-methylbutyl)-3-oxo-3,4-dihydronaphthalen-2-yl]-1,1-dioxido-4H-1,2,4-benzothiadiazin-7-yl}methanesulfonamide;

N-{3-[(4R)-1,4-dihydroxy-4-(3-methylbutyl)-3-oxo-3,4-dihydronaphthalen-2-yl]-1,1-dioxido-4H-1,2,4-benzothiadiazin-7-yl}methanesulfonamide;

N-(3-{1,4-dihydroxy-3-oxo-4-[(2E)-3-phenylprop-2-enyl]-3,4-dihydronaphthalen-2-yl}-1,1-dioxido-4H-1,2,4-benzothiadiazin-7-yl)methanesulfonamide;

N-[3-(4-benzyl-1,4-dihydroxy-3-oxo-3,4-dihydronaphthalen-2-yl)-1,1-dioxido-4H-1,2,4-benzothiadiazin-7-yl]methanesulfonamide;

N-{3-[4-allyl-1-hydroxy-4-(methoxyamino)-3-oxo-3,4-dihydronaphthalen-2-yl]-1,1-dioxido-4H-1,2,4-benzothiadiazin-7-yl}methanesulfonamide;

N-{3-[4-(3,3-dimethylbutyl)-1,4-dihydroxy-3-oxo-3,4-dihydronaphthalen-2-yl]-1,1-dioxido-4H-1,2,4-benzothiadiazin-7-yl}methanesulfonamide;

N-{3-[1-hydroxy-4-(methoxyamino)-3-oxo-4-propyl-3,4-dihydronaphthalen-2-yl]-1,1-dioxido-4H-1,2,4-benzothiadiazin-7-yl}methanesulfonamide;

N-(4-hydroxy-3-{7-[(methylsulfonyl)amino]-1,1-dioxido-4H-1,2,4-benzothiadiazin-3-yl}-2-oxo-1-propyl-1,2-dihydronaphthalen-1-yl)-N-methoxyacetamide;

N-{3-[1-hydroxy-4-methoxy-4-(3-methylbutyl)-3-oxo-3,4-dihydronaphthalen-2-yl]-1,1-dioxido-4H-1,2,4-benzothiadiazin-7-yl}methanesulfonamide;

N-{3-[4-(benzyloxy)-1-hydroxy-4-(3-methylbutyl)-3-oxo-3,4-dihydronaphthalen-2-yl]-1,1-dioxido-4H-1,2,4-benzothiadiazin-7-yl}methanesulfonamide;

N-[3-(4-amino-1-hydroxy-3-oxo-4-propyl-3,4-dihydronaphthalen-2-yl)-1,1-dioxido-4H-1,2,4-benzothiadiazin-7-yl]methanesulfonamide;

N-{3-[1-hydroxy-4-(methoxyamino)-4-(3-methylbut-2-enyl)-3-oxo-3,4-dihydronaphthalen-2-yl]-1,1-dioxido-4H-1,2,4-benzothiadiazin-7-yl}methanesulfonamide;

N-{3-[1-hydroxy-4-(methoxyamino)-4-(3-methylbutyl)-3-oxo-3,4-dihydronaphthalen-2-yl]-1,1-dioxido-4H-1,2,4-benzothiadiazin-7-yl}methanesulfonamide;

N-{3-[4-amino-1-hydroxy-4-(3-methylbutyl)-3-oxo-3,4-dihydronaphthalen-2-yl]-1,1-dioxido-4H-1,2,4-benzothiadiazin-7-yl}methanesulfonamide;

N-{3-[4-[(benzyloxy)amino]-1-hydroxy-4-(3-methylbutyl)-3-oxo-3,4-dihydronaphthalen-2-yl]-1,1-dioxido-4H-1,2,4-benzothiadiazin-7-yl}methanesulfonamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)acetamide;

methyl 4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-ylcarbamate;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)benzamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)methanesulfonamide;

N-{3-[(4R)-1-hydroxy-4-(methoxyamino)-4-(3-methylbutyl)-3-oxo-3,4-dihydronaphthalen-2-yl]-1,1-dioxido-4H-1,2,4-benzothiadiazin-7-yl}methanesulfonamide;

N-{3-[(4S)-1-hydroxy-4-(methoxyamino)-4-(3-methylbutyl)-3-oxo-3,4-dihydronaphthalen-2-yl]-1,1-dioxido-4H-1,2,4-benzothiadiazin-7-yl}methanesulfonamide;

N-hydroxy-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)acetamide;

N-{3-[4-butyl-1-hydroxy-4-(methoxyamino)-3-oxo-3,4-dihydronaphthalen-2-yl]-1,1-dioxido-4H-1,2,4-benzothiadiazin-7-yl}methanesulfonamide;

N-[3-(4-amino-4-butyl-1-hydroxy-3-oxo-3,4-dihydronaphthalen-2-yl)-1,1-dioxido-4H-1,2,4-benzothiadiazin-7-yl]methanesulfonamide;

benzyl 4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-ylcarbamate;

2-methoxyethyl 4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-ylcarbamate;

4-{[(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)amino]sulfonyl}benzoic acid;

N-(1-butyl-4-hydroxy-3-{7-[(methylsulfonyl)amino]-1,1-dioxido-4H-1,2,4-benzothiadiazin-3-yl}-2-oxo-1,2-dihydronaphthalen-1-yl)acetamide;

N-(1-butyl-4-hydroxy-3-{7-[(methylsulfonyl)amino]-1,1-dioxido-4H-1,2,4-benzothiadiazin-3-yl}-2-oxo-1,2-dihydronaphthalen-1-yl)methanesulfonamide;

N-{3-[4-(tert-butoxyamino)-1-hydroxy-3-oxo-4-propyl-3,4-dihydronaphthalen-2-yl]-1,1-dioxido-4H-1,2,4-benzothiadiazin-7-yl}methanesulfonamide;

N-{3-[(4S)-4-amino-1-hydroxy-4-(3-methylbutyl)-3-oxo-3,4-dihydronaphthalen-2-yl]-1,1-dioxido-4H-1,2,4-benzothiadiazin-7-yl}methanesulfonamide;

N-{3-[1-hydroxy-4-(hydroxyamino)-3-oxo-4-propyl-3,4-dihydronaphthalen-2-yl]-1,1-dioxido-4H-1,2,4-benzothiadiazin-7-yl}methanesulfonamide;

N-{3-[1-hydroxy-4-(methoxyamino)-4-(2-methylprop-2-enyl)-3-oxo-3,4-dihydronaphthalen-2-yl]-1,1-dioxido-4H-1,2,4-benzothiadiazin-7-yl}methanesulfonamide;

N-{3-[1-hydroxy-4-isobutyl-4-(methoxyamino)-3-oxo-3,4-dihydronaphthalen-2-yl]-1,1-dioxido-4H-1,2,4-benzothiadiazin-7-yl}methanesulfonamide;

N-{3-[1-hydroxy-4-(hydroxyamino)-4-(3-methylbutyl)-3-oxo-3,4-dihydronaphthalen-2-yl]-1,1-dioxido-4H-1,2,4-benzothiadiazin-7-yl}methanesulfonamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-morpholin-4-ylethanesulfonamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-N-methoxyacetamide;

methyl[(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)oxy]acetate;

2-[(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)oxy]acetamide;

N-((1S)-4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)methanesulfonamide;

N-{3-[(4S)-4-(3,3-dimethylbutyl)-1,4-dihydroxy-3-oxo-3,4-dihydronaphthalen-2-yl]-1,1-dioxido-4H-1,2,4-benzothiadiazin-7-yl}methanesulfonamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-(methylamino)ethanesulfonamide;

tert-butyl 2-[(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)amino]-2-oxoethylcarbamate;

2-amino-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)acetamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-methoxyethanesulfonamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-[(2-methoxyethyl)amino]ethanesulfonamide;

2-(diethylamino)-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)ethanesulfonamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-{methyl[2-(methylamino)ethyl]amino}ethanesulfonamide;

N-{3-[1-hydroxy-4-(isobutylamino)-4-(3-methylbutyl)-3-oxo-3,4-dihydronaphthalen-2-yl]-1,1-dioxido-4H-1,2,4-benzothiadiazin-7-yl}methanesulfonamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-[(2-methoxybenzyl)(methyl)amino]ethanesulfonamide;

ethyl[{3-[1-hydroxy-4-(hydroxyamino)-4-(3-methylbutyl)-3-oxo-3,4-dihydronaphthalen-2-yl]-1,1-dioxido-4H-1,2,4-benzothiadiazin-7-yl}(methylsulfonyl)amino]acetate;

[{3-[1-hydroxy-4-(hydroxyamino)-4-(3-methylbutyl)-3-oxo-3,4-dihydronaphthalen-2-yl]-1,1-dioxido-4H-1,2,4-benzothiadiazin-7-yl}(methylsulfonyl)amino]acetic acid;

2-(acetylamino)-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)acetamide;

2-(dibenzylamino)-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)ethanesulfonamide;

N-{3-[4-{[(tert-butylamino)carbonyl]amino}-1-hydroxy-4-(3-methylbutyl)-3-oxo-3,4-dihydronaphthalen-2-yl]-1,1-dioxido-4H-1,2,4-benzothiadiazin-7-yl}methanesulfonamide;

N-{3-[4-(benzylamino)-1-hydroxy-4-(3-methylbutyl)-3-oxo-3,4-dihydronaphthalen-2-yl]-1,1-dioxido-4H-1,2,4-benzothiadiazin-7-yl}methanesulfonamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-(methoxyamino)ethanesulfonamide;

N-(2-{[(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)amino]sulfonyl}ethyl)-N-methylacetamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-[methoxy(methyl)amino]ethanesulfonamide;

2-[(2,2-dimethoxyethyl)(methyl)amino]-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)ethanesulfonamide;

2-[(1,3-dioxolan-2-ylmethyl)(methyl)amino]-N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)ethanesulfonamide;

N-{3-[1-hydroxy-4-[(3-methoxybenzyl)amino]-4-(3-methylbutyl)-3-oxo-3,4-dihydronaphthalen-2-yl]-1,1-dioxido-4H-1,2,4-benzothiadiazin-7-yl}methanesulfonamide;

N-(1-(3,3-dimethylbutyl)-4-hydroxy-3-{7-[(methylsulfonyl)amino]-1,1-dioxido-4H-1,2,4-benzothiadiazin-3-yl}-2-oxo-1,2-dihydronaphthalen-1-yl)acetamide;

N-{3-[4-amino-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-{3-[4-[(cyclopropylmethyl)amino]-1-hydroxy-4-(3-methylbutyl)-3-oxo-3,4-dihydronaphthalen-2-yl]-1,1-dioxido-4H-1,2,4-benzothiadiazin-7-yl}methanesulfonamide;

N-{3-[4-[(aminocarbonyl)amino]-1-hydroxy-4-(3-methylbutyl)-3-oxo-3,4-dihydronaphthalen-2-yl]-1,1-dioxido-4H-1,2,4-benzothiadiazin-7-yl}methanesulfonamide;

N-(1-(3,3-dimethylbutyl)-4-hydroxy-3-{7-[(methylsulfonyl)amino]-1,1-dioxido-4H-1,2,4-benzothiadiazin-3-yl}-2-oxo-1,2-dihydronaphthalen-1-yl)benzamide;

ethyl[(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)amino]acetate;

2-chloro-N-(1-(3,3-dimethylbutyl)-4-hydroxy-3-{7-[(methylsulfonyl)amino]-1,1-dioxido-4H-1,2,4-benzothiadiazin-3-yl}-2-oxo-1,2-dihydronaphthalen-1-yl)acetamide;

N-(1-(3,3-dimethylbutyl)-4-hydroxy-3-{7-[(methylsulfonyl)amino]-1,1-dioxido-4H-1,2,4-benzothiadiazin-3-yl}-2-oxo-1,2-dihydronaphthalen-1-yl)methanesulfonamide;

N-(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2,5-dimethoxybenzenesulfonamide;

N-{3-[4-(benzylamino)-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-(3-{4-(3,3-dimethylbutyl)-1-hydroxy-4-[(3-methoxybenzyl)amino]-3-oxo-3,4-dihydronaphthalen-2-yl}-1,1-dioxido-4H-1,2,4-benzothiadiazin-7-yl)methanesulfonamide;

N-(3-{4-(3,3-dimethylbutyl)-1-hydroxy-4-[(2-methoxybenzyl)amino]-3-oxo-3,4-dihydronaphthalen-2-yl}-1,1-dioxido-4H-1,2,4-benzothiadiazin-7-yl)methanesulfonamide;

N-(3-{4-(3,3-dimethylbutyl)-1-hydroxy-4-[(4-methoxybenzyl)amino]-3-oxo-3,4-dihydronaphthalen-2-yl}-1,1-dioxido-4H-1,2,4-benzothiadiazin-7-yl)methanesulfonamide;

3-{[(1-(3,3-dimethylbutyl)-4-hydroxy-3-{7-[(methylsulfonyl)amino]-1,1-dioxido-4H-1,2,4-benzothiadiazin-3-yl}-2-oxo-1,2-dihydronaphthalen-1-yl)amino]methyl}phenyl acetate;

N-(3-{4-(3,3-dimethylbutyl)-4-[(2-furylmethyl)amino]-1-hydroxy-3-oxo-3,4-dihydronaphthalen-2-yl}-1,1-dioxido-4H-1,2,4-benzothiadiazin-7-yl)methanesulfonamide;

N-{3-[4-[(4-cyanobenzyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-{3-[4-{[4-(benzyloxy)benzyl]amino}-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-{3-[4-[(1-benzothien-3-ylmethyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-((1S)-4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2-morpholin-4-ylethanesulfonamide;

N-{3-[(4S)-4-(benzylamino)-1-hydroxy-4-(3-methylbutyl)-3-oxo-3,4-dihydronaphthalen-2-yl]-1,1-dioxido-4H-1,2,4-benzothiadiazin-7-yl}methanesulfonamide;

N-(3-{4-(3,3-dimethylbutyl)-1-hydroxy-4-[(2-naphthylmethyl)amino]-3-oxo-3,4-dihydronaphthalen-2-yl}-1,1-dioxido-4H-1,2,4-benzothiadiazin-7-yl)methanesulfonamide;

N-(3-{4-(3,3-dimethylbutyl)-1-hydroxy-3-oxo-4-[(1,3-thiazol-2-ylmethyl)amino]-3,4-dihydronaphthalen-2-yl}-1,1-dioxido-4H-1,2,4-benzothiadiazin-7-yl)methanesulfonamide;

N-(3-{4-(3,3-dimethylbutyl)-1-hydroxy-4-[(3-nitrobenzyl)amino]-3-oxo-3,4-dihydronaphthalen-2-yl}-1,1-dioxido-4H-1,2,4-benzothiadiazin-7-yl)methanesulfonamide;

N-{3-[4-{[2-(benzyloxy)benzyl]amino}-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-(3-{4-(3,3-dimethylbutyl)-1-hydroxy-3-oxo-4-[(3-vinylbenzyl)amino]-3,4-dihydronaphthalen-2-yl}-1,1-dioxido-4H-1,2,4-benzothiadiazin-7-yl)methanesulfonamide;

N-{3-[4-{[3-(benzyloxy)benzyl]amino}-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-(3-{4-(3,3-dimethylbutyl)-1-hydroxy-4-[(4-hydroxybenzyl)amino]-3-oxo-3,4-dihydronaphthalen-2-yl}-1,1-dioxido-4H-1,2,4-benzothiadiazin-7-yl)methanesulfonamide;

N-((1S)-4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)-2,5-dimethoxybenzenesulfonamide;

N-(3-{4-(3,3-dimethylbutyl)-1-hydroxy-4-[(2-hydroxybenzyl)amino]-3-oxo-3,4-dihydronaphthalen-2-yl}-1,1-dioxido-4H-1,2,4-benzothiadiazin-7-yl)methanesulfonamide;

N-(3-{4-(3,3-dimethylbutyl)-1-hydroxy-3-oxo-4-[(pyridin-3-ylmethyl)amino]-3,4-dihydronaphthalen-2-yl}-1,1-dioxido-4H-1,2,4-benzothiadiazin-7-yl)methanesulfonamide;

N-{3-[4-[(2,5-dimethoxybenzyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-(3-{4-(3,3-dimethylbutyl)-1-hydroxy-4-[(2-methoxy-5-nitrobenzyl)amino]-3-oxo-3,4-dihydronaphthalen-2-yl}-1,1-dioxido-4H-1,2,4-benzothiadiazin-7-yl)methanesulfonamide;

N-{3-[4-[(1,1'-biphenyl-4-ylmethyl)amino]-4-(3,3-dimethylbutyl)-1-hydroxy-3-oxo-3,4-dihydronaphthalen-2-yl]1,1-dioxido-4H-1,2,4-benzothiadiazin-7-yl}methanesulfonamide;

N-(3-{4-(3,3-dimethylbutyl)-1-hydroxy-4-[(2-nitrobenzyl)amino]-3-oxo-3,4-dihydronaphthalen-2-yl}-1,1-dioxido-4H-1,2,4-benzothiadiazin-7-yl)methanesulfonamide;

N-(3-{4-(3,3-dimethylbutyl)-1-hydroxy-4-[(4-nitrobenzyl)amino]-3-oxo-3,4-dihydronaphthalen-2-yl}-1,1-dioxido-4H-1,2,4-benzothiadiazin-7-yl)methanesulfonamide;

N-(3-{4-(3,3-dimethylbutyl)-1-hydroxy-3-oxo-4-[(pyridin-2-ylmethyl)amino]-3,4-dihydronaphthalen-2-yl}-1,1-dioxido-4H-1,2,4-benzothiadiazin-7-yl)methanesulfonamide;

N-[3-(4-(3,3-dimethylbutyl)-1-hydroxy-3-oxo-4-{[2-(trifluoromethyl)benzyl]amino}-3,4-dihydronaphthalen-2-yl)-1,1-dioxido-4H-1,2,4-benzothiadiazin-7-yl]methanesulfonamide;

N-{3-[4-[(2,6-dimethylbenzyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-(3-{4-(3,3-dimethylbutyl)-1-hydroxy-4-[(mesitylmethyl)amino]-3-oxo-3,4-dihydronaphthalen-2-yl}-1,1-dioxido-4H-1,2,4-benzothiadiazin-7-yl)methanesulfonamide;

N-[3-(4-(3,3-dimethylbutyl)-1-hydroxy-4-{[(6-methylpyridin-3-yl)methyl]amino}-3-oxo-3,4-dihydronaphthalen-2-yl)-1,1-dioxido-4H-1,2,4-benzothiadiazin-7-yl]methanesulfonamide;

N-[3-(4-(3,3-dimethylbutyl)-1-hydroxy-4-{[(2-methylpyridin-3-yl)methyl]amino}-3-oxo-3,4-dihydronaphthalen-2-yl)-1,1-dioxido-4H-1,2,4-benzothiadiazin-7-yl]methanesulfonamide;

N-[3-(4-(3,3-dimethylbutyl)-1-hydroxy-4-{[(6-methylpyridin-2-yl)methyl]amino}-3-oxo-3,4-dihydronaphthalen-2-yl)-1,1-dioxido-4H-1,2,4-benzothiadiazin-7-yl]methanesulfonamide;

N-{3-[4-[(2-aminobenzyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-(3-{4-(3,3-dimethylbutyl)-1-hydroxy-4-[(imidazo[1,5-a]pyridin-3-ylmethyl)amino]-3-oxo-3,4-dihydronaphthalen-2-yl}-1,1-dioxido-4H-1,2,4-benzothiadiazin-7-yl)methanesulfonamide;

N-{3-[4-[benzyl(methyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide;

N-benzyl-N-(1-(3,3-dimethylbutyl)-4-hydroxy-3-{7-[(methylsulfonyl)amino]-1,1-dioxido-4H-1,2,4-benzothiadiazin-3-yl}-2-oxo-1,2-dihydronaphthalen-1-yl)acetamide;

N-[3-(4-(3,3-dimethylbutyl)-1-hydroxy-4-{[(2-methoxypyridin-3-yl)methyl]amino}-3-oxo-3,4-dihydronaphthalen-2-yl)-1,1-dioxido-4H-1,2,4-benzothiadiazin-7-yl]methanesulfonamide; and N-{3-[4-[(3-acetylbenzyl)amino]-4-(3,3-dimethylbutyl)-1-hydroxy-3-oxo-3,4-dihydronaphthalen-2-yl]-1,1-dioxido-4H-1,2,4-benzothiadiazin-7-yl}methanesulfonamide.

5. The compound, stereoisomer, tautomer, salt or combination of claim 1, wherein:
the compound corresponds to formula (II):

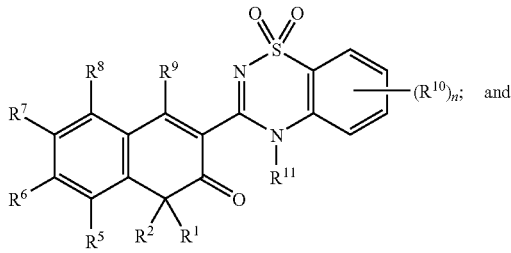

(II)

Y is selected from the group consisting of $R_A$, —$OR_A$, —$NR_AR_B$, —O-alkyl-$OR_A$, —O-alkyl-$NR_AR_B$, —N($R_C$)-alkyl-$NR_AR_B$, —$(CR^3R^4)$—N($R_C$)C(O)X and —$(CR^3R^4)$—$NR_AR_B$.

6. The compound, stereoisomer, tautomer, salt or combination of claim 1, wherein:
$R^9$ is $OR_a$; and
$R_A$ is hydrogen 7. The compound, stereoisomer, tautomer, salt, or combination of claim 5, wherein:
$R^2$ is selected from the group consisting of alkyl, alkenyl, -alkyl-$R_a$, and -alkenyl-$R_a$; and
$R^9$ is $OR_A$, wherein $R_A$ is hydrogen.

8. The compound, stereoisomer, tautomer, salt, or combination of claim 5, wherein:
$R^2$ is selected from the group consisting of alkyl, alkenyl, -alkyl-$R_a$, and -alkenyl-$R_a$;
R9 is $OR_A$, wherein $R_A$ is hydrogen; and
$R^{11}$ is hydrogen.

9. The compound, stereoisomer, prodrug, salt, or combination of claim 5, wherein:
$R^2$ is selected from the group consisting of alkyl, alkenyl, -alkyl-$R_a$, and -alkenyl-$R_a$;
$R^9$ is $OR_A$, wherein $R_A$ is hydrogen;
$R^{11}$ is hydrogen; and $R^1$ is —$NR_AR_B$, wherein:
$R_A$ is selected from the group consisting of hydrogen and alkyl, and
$R_B$ is selected from the group consisting of hydrogen, alkyl, -alkyl$R_a$, —OH, and alkoxy.

10. The compound, stereoisomer, tautomer, salt, or combination of claim 5, wherein:
$R^2$ is selected from the group consisting of alkyl, alkenyl -alkyl-$R_a$ and -alkenyl-$R_a$ wherein:
$R_a$ is aryl, unsubstituted or substituted with 1, 2, 3, 4, or 5 substituents independently selected from the group consisting of alkyl, alkenyl, alkynyl, formyl, halo, nitro, cyano, alkoxy, —OH, —O-alkyl-$R_b$, —OC(O)(alkyl), —SH, —S(alkyl), —S(O)alkyl, —S(O)$_2$(alkyl), —NH$_2$, —N(H)(alkyl), —N(alkyl)$_2$, —C(O)alkyl, —C(O)OH, —C(O)(-Oalkyl), —C(O)NH$_2$, —C(O)N(H)(alkyl), -C(O)N(alkyl)$_2$, haloalkyl, $R_b$, and -alkyl-$R_b$;
$R^9$ is $OR_A$, wherein $R_A$ is hydrogen;
$R^1$ is $NR_AR_B$, wherein:
$R_A$ is selected from the group consisting of hydrogen and alkyl, and
$R_B$ is selected from the group consisting of hydrogen, alkyl, -alkyl$R_a$, —OH, and alkoxy, wherein:
$R_a$ is selected from the group consisting of aryl, $C_3$-$C_6$ cycloalkyl, and heteroaryl, wherein each such substituent is independently unsubstituted or substituted with 1, 2, 3, 4, or 5 substituents independently selected from the group consisting of alkyl, alkenyl, alkynyl, formyl, halo, nitro, cyano, alkoxy, —OH, —O-alkyl-$R_b$, —OC(O)(alkyl), —SH, —S(alkyl), —S(O)alkyl, —S(O)$_2$(alkyl), 'NH2, —N(H)(alkyl), —N(alkyl)$_2$, —C(O)alkyl, —C(O)OH, —C(O)(-Oalkyl), —C(O)NH$_2$, —C(O)N(H)(alkyl), —C(O)N(alkyl)$_2$, haloalkyl, and -alkyl-$R_b$; and
$R^{11}$ is hydrogen.

11. The compound, stereoisomer, tautomer, salt, or combination of claim 5, wherein:
$R^2$ is selected from the group consisting of alkyl, alkenyl, -alkyl-$R_a$, and -alkenyl-$R_a$, wherein:
$R_a$ is aryl, unsubstituted or substituted with 1, 2, 3, 4, or 5 substituents independently selected from the group consisting of alkyl, alkenyl, alkynyl, formyl, halo, nitro, cyano, alkoxy, —OH, —O-alkyl-$R_b$, —OC(O)(alkyl), —SH, —S(alkyl), —S(O)alkyl, —S(O)$_2$(alkyl), —NH$_2$, —N(H)(alkyl), —N(alkyl)$_2$, —C(O)alkyl, —C(O)OH, —C(O)(-Oalkyl), —C(O)NH$_2$, —C(O)N(H)(alkyl), -C(O)N(alkyl)$_2$, haloalkyl, $R_b$, and -alkyl-$R_b$;
$R^9$ is $OR_A$, wherein $R_A$ is hydrogen;
$R^1$ is $NR_AR_B$, wherein:
$R_A$ is selected from the group consisting of hydrogen and alkyl, and
$R_B$ is selected from the group consisting of hydrogen, alkyl, -alkyl$R_a$, —OH, and alkoxy, wherein:
$R_a$ is selected from the group consisting of aryl, $C_3$-$C_6$ cycloalkyl, and heteroaryl, wherein each such substituent is independently unsubstituted or substituted with 1, 2, 3, 4, or 5 substituents independently selected from the group consisting of alkyl, alkenyl, alkynyl, formyl, halo, nitro, cyano, alkoxy, —OH, —O-alkyl-$R_b$, —OC(O)(alkyl), —SH, —S(alkyl), —S(O)alkyl, —S(O)$_2$(alkyl), 'NH2, —N(H)(alkyl), —N(alkyl)$_2$, —C(O)alkyl, —C(O)

OH, —C(O)(-Oalkyl), —C(O)NH$_2$, —C(O)N(H)(alkyl), —C(O)N(alkyl)$_2$, haloalkyl, R$_b$, and -alkyl-R$_b$; and R$^{11}$ is hydrogen;

n is 1; and

R$^{10}$ is selected from the group consisting of —N(R$_B$)SO$_2$X and —N(-alkyl-C(O)X)(S(O)$_2$X).

12. The compound, stereolsomer, tautomer, salt, or combination of claim 5, wherein:

R$^2$ is selected from the group consisting of alkyl, alkenyl -alkyl-R$_a$ and -alkenyl-R$_a$ wherein:

R$_a$ is aryl, unsubstituted or substituted with 1, 2, 3, 4, or 5 substituents independently selected from the group consisting of alkyl, alkenyl, alkynyl, formyl, halo, nitro, cyano, alkoxy, —OH, —O-alkyl-R$_b$, —OC(O)(alkyl), —SH, —S(alkyl), —S(O)alkyl, —S(O)$_2$(alkyl), —NH$_2$, —N(H)(alkyl), —N(alkyl)$_2$, —C(O)alkyl, —C(O)OH, —C(O)(-Oalkyl), —C(O)NH$_2$, —C(O)N(H)(alkyl), -C(O)N(alkyl)$_2$, haloalkyl, R$_b$, and -alkyl-R$_b$;

R$^9$ is OR$_A$, wherein R$_A$ is hydrogen;

R$^1$ is NR$_A$R$_B$, wherein:

R$_A$ is selected from the group consisting of hydrogen and alkyl, and

R$_B$ is selected from the group consisting of hydrogen, alkyl, -alkylR$_a$, —OH, and alkoxy, wherein:

R$_a$ is selected from the group consisting of aryl, C$_3$-C$_6$ cycloalkyl, and heteroaryl, wherein each such substituent is independently unsubstituted or substituted with 1, 2, 3, 4, or 5 substituents independently selected from the group consisting of alkyl, alkenyl, alkynyl, formyl, halo, nitro, cyano, alkoxy, —OH, —O-alkyl-R$_b$, —OC(O)(alkyl), —SH, —S(alkyl), —S(O)alkyl, —S(O)$_2$(alkyl), 'NH2, —N(H)(alkyl), —N(alkyl)$_2$, —C(O)alkyl, —C(O)OH, —C(O)(-Oalkyl), —C(O)NH$_2$, —C(O)N(H)(alkyl), —C(O)N(alkyl)$_2$, haloalkyl, R$_b$, and -alkyl-R$_b$; and R$^{11}$ is hydrogen.

n is 1;

R$^{10}$ is —N(R$_B$)SO$_2$X, wherein R$_B$ is selected from the group consisting of hydrogen and alkyl, and X is alkyl; and R$^5$, R$_6$, R$^7$, and R$^8$ are each independently selected from the group consisting of hydrogen, alkyl, alkenyl, alkynyl, cyano, halo, nitro, —OR$_A$, —OC(O)R$_A$, —OC(O)OR$_A$, —OC(O)NR$_A$R$_B$, —OS(O)$_2$R$_A$, —SR$_A$, —S(O)R$_A$, —S(O)$_2$R$_A$, S(O)$_2$NR$_A$R$_B$, —NR$_A$R$_B$, —N(R$_C$)C(O)R$_A$, —C(O)R$_A$, —C(O)OR$_A$, —C(O)NR$_A$R$_B$, haloalkyl, and -alkylOR$_A$, wherein:

R$_A$ and R$_B$ are independently selected from the group consisting of hydrogen and alkyl, and R$_C$ is selected from the group consisting of hydrogen and lower alkyl.

13. The compound, stereoisomer, tautomer, salt, or combination of claim 5, wherein:

R$^2$ is selected from the group consisting of alkyl, alkenyl -alkyl-R$_a$ and -alkenyl-R$_a$ wherein:

R$_a$ is aryl, unsubstituted or substituted with 1, 2, 3, 4, or 5 substituents independently selected from the group consisting of alkyl, alkenyl, alkynyl, formyl, halo, nitro, cyano, alkoxy, —OH, —O-alkyl-R$_b$, —OC(O)(alkyl), —SH, —S(alkyl), —S(O)alkyl, —S(O)$_2$(alkyl), —NH$_2$, —N(H)(alkyl), —N(alkyl)$_2$, —C(O)alkyl, —C(O)OH, —C(O)(-Oalkyl), —C(O)NH$_2$, —C(O)N(H)(alkyl), -C(O)N(alkyl)$_2$, haloalkyl, R$_b$, and -alkyl-R$_b$;

R$^9$ is OR$_A$, wherein R$_A$ is hydrogen;

R$^1$ is OR$_A$, wherein:

R$_A$ is selected from the group consisting of hydrogen and alkyl, and-alkyl-R$_a$, wherein:

R$_a$ is selected from the group consisting of cycloalkyl, cycloalkenyl, heterocycle, aryl and heteroaryl, wherein:

each such substituent is substituted with 0, 1, 2, 3, 4, or 5 substituents independently selected from the group consisting of alkyl, alkenyl, alkynyl, formyl, halo, nitro, cyano, alkoxy, —OH, —O-alkyl-R$_b$, —OC(O)(alkyl), —SH, —S(alkyl), —S(O)alkyl, —S(O)$_2$(alkyl), 'NH2, —N(H)(alkyl), —N(alkyl)$_2$, —C(O)alkyl, —C(O)OH, —C(O)(-Oalkyl), —C(O)NH$_2$, —C(O)N(H)(alkyl), —C(O)N(alkyl)$_2$, haloalkyl, R$_b$, and -alkyl-R$_b$;

R$^{11}$ is hydrogen;

n is 1;

R$^{10}$ is —N(R$_B$)SO$_2$X, wherein:

R$_B$ is selected from the group consisting of hydrogen and alkyl, and

X is alkyl; and

R$^5$, R$_6$, R$^7$, and R$^8$ are each independently selected from the group consisting of hydrogen, alkyl, alkenyl, alkynyl, cyano, halo, nitro, —OR$_A$, —OC(O)R$_A$, —OC(O)OR$_A$, —OC(O)NR$_A$R$_B$, —OS(O)$_2$R$_A$, —SR$_A$, —S(O)R$_A$, —S(O)$_2$R$_A$, S(O)$_2$NR$_A$R$_B$, —NR$_A$R$_B$, —N(R$_C$)C(O)R$_A$, —C(O)R$_A$, —C(O)OR$_A$, —C(O)NR$_A$R$_B$, haloalkyl, and -alkylOR$_A$, wherein:

R$_A$ and R$_B$ are independently selected from the group consisting of hydrogen and alkyl, and R$_C$ is selected from the group consisting of hydrogen and lower alkyl.

14. The compound, stereoisomer, tautomer, salt, or combination of claim 5, wherein:

R$^2$ is selected from the group consisting of alkyl, alkenyl -alkyl-R$_a$ and -alkenyl-R$_a$ wherein:

R$_a$ is aryl, unsubstituted or substituted with 1, 2, 3, 4, or 5 substituents independently selected from the group consisting of alkyl, alkenyl, alkynyl, formyl, halo, nitro, cyano, alkoxy, —OH, —O-alkyl-R$_b$, —OC(O)(alkyl), —SH, —S(alkyl), —S(O)alkyl, —S(O)$_2$(alkyl), —NH$_2$, —N(H)(alkyl), —N(alkyl)$_2$, —C(O)alkyl, —C(O)OH, —C(O)(-Oalkyl), —C(O)NH$_2$, —C(O)N(H)(alkyl), -C(O)N(alkyl)$_2$, haloalkyl, R$_b$, and -alkyl-R$_b$;

R$^9$ is OR$_A$, wherein R$_A$ is hydrogen;

R$^1$ is —O-alkyl-C(O)Y, wherein:

Y is selected from the group consisting of —OR$_A$ and —NR$_A$R$_B$, and

R$_A$ and R$_B$ are independently selected from the group consisting of hydrogen and alkyl;

R$^{11}$ is hydrogen;

n is 1;

R$^{10}$ is —N(R$_B$)SO$_2$X, wherein:

R$_B$ is selected from the group consisting of hydrogen and alkyl, and

X is alkyl; and

R$^5$, R$_6$, R$^7$, and R$^8$ are each independently selected from the group consisting of hydrogen, alkyl, alkenyl, alkynyl, cyano, halo, nitro, —OR$_A$, —OC(O)R$_A$, —OC(O)OR$_A$, —OC(O)NR$_A$R$_B$, —OS(O)$_2$R$_A$, —SR$_A$, —S(O)R$_A$, —S(O)$_2$R$_A$, S(O)$_2$NR$_A$R$_B$, —NR$_A$R$_B$, —N(R$_C$)C(O)R$_A$, —C(O)R$_A$, —C(O)OR$_A$, —C(O)NR$_A$R$_B$, haloalkyl, and -alkylOR$_A$, wherein:

R$_A$ and R$_B$ are independently selected from the group consisting of hydrogen and alkyl, and R$_C$ is selected from the group consisting of hydrogen and lower alkyl.

15. The compound, stereoisomer, tautomer, salt, or combination of claim 1, wherein:

R$^2$ is selected from the group consisting of alkyl, alkenyl -alkyl-R$_a$ and -alkenyl-R$_a$ wherein:

R$_a$ is aryl, unsubstituted or substituted with 1, 2, 3, 4, or 5 substituents independently selected from the group consisting of alkyl, alkenyl, alkynyl, formyl, halo, nitro, cyano, alkoxy, —OH, —O-alkyl-R$_b$, —OC(O)(alkyl), —SH, —S(alkyl), —S(O)alkyl, —S(O)$_2$(alkyl), —NH$_2$, —N(H)(alkyl), —N(alkyl)$_2$, —C(O)alkyl, —C(O)OH, —C(O)(-Oalkyl), —C(O)NH$_2$, —C(O)N(H)(alkyl), -C(O)N(alkyl)$_2$, haloalkyl, R$_b$, and -alkyl-R$_b$;

R$^9$ is OR$_A$, wherein R$_A$ is hydrogen;

R$^1$ is —N(R$_a$)L$^1$C(O)Y, wherein:

L$^1$ is a bond or alkyl,

R$_B$ is selected from the group consisting of hydrogen, —OH, —alkylR$_a$ and alkoxy, wherein:

R$_a$ is aryl, unsubstituted or substituted with 1, 2, 3, 4, or 5 substituents independently selected from the group consisting of alkyl, alkenyl, alkynyl, formyl, halo, nitro, cyano, alkoxy, —OH, —O-alkyl-R$_b$, —OC(O)(alkyl), —SH, —S(alkyl), —S(O)alkyl, —S(O)$_2$(alkyl), —NH$_2$, —N(H)(alkyl), —N(alkyl)$_2$, —C(O)alkyl, —C(O)OH, —C(O)(-Oalkyl), —C(O)NH$_2$, —C(O)N(H)(alkyl), -C(O)N(alkyl)$_2$, haloalkyl, R$_b$, and -alkyl-R$_b$, and Y is selected from the group consisting of R$_A$, —NR$_A$R$_B$, OR$_A$, —O-alkyl-OR$_A$, CR$^3$R$^4$—N(R$_C$)C(O)X, and —CR$^3$R$^4$—NR$_A$R$_B$;

R$^{11}$ is hydrogen;

n is 1;

R$^{10}$ is —N(R$_B$)SO$_2$X, wherein:

R$_B$ is hydrogen or alkyl, and

X is alkyl; and

R$^5$, R$_6$, R$^7$, and R$^8$ are each independently selected from the group consisting of hydrogen, alkyl, alkenyl, alkynyl, cyano, halo, nitro, —OR$_A$, —OC(O)R$_A$, —OC(O)OR$_A$, —OC(O)NR$_A$R$_B$, —OS(O)$_2$R$_A$, —SR$_A$, —S(O)R$_A$, —S(O)$_2$R$_A$, S(O)$_2$NR$_A$R$_B$, —NR$_A$R$_B$, —N(R$_C$)C(O)R$_A$, —C(O)R$_A$, —C(O)OR$_A$, —C(O)NR$_A$R$_B$, haloalkyl, and -alkylOR$_A$, wherein:

R$_A$ and R$_B$ are independently selected from the group consisting of hydrogen and alkyl, and R$_C$ is selected from the group consisting of hydrogen and lower alkyl.

16. The compound, stereoisomer, tautomer, salt, or combination of claim 1, wherein:

R$_a$ is aryl, unsubstituted or substituted with 1, 2, 3, 4, or 5 substituents independently selected from the group consisting of alkyl, alkenyl, alkynyl, formyl, halo, nitro, cyano, alkoxy, —OH, —O-alkyl-R$_b$, —OC(O)(alkyl), —SH, —S(alkyl), —S(O)alkyl, —S(O)$_2$(alkyl), —NH$_2$, —N(H)(alkyl), —N(alkyl)$_2$, —C(O)alkyl, —C(O)OH, —C(O)(-Oalkyl), —C(O)NH$_2$, —C(O)N(H)(alkyl), -C(O)N(alkyl)$_2$, haloalkyl, R$_b$, and -alkyl-R$_b$;

R$^9$ is OR$_A$, wherein R$_A$ is hydrogen;

R$_1$ is —N(R$_B$)S(O)$_2$Z, wherein:

R$_B$ is hydrogen or alkyl, and

Z is selected from the group consisting of R$_A$, -alkyl-NR$_A$R$_B$, -alkyl-OR$_A$ -alkyl-N(R$_C$)-alkyl-NR$_A$R$_B$, and -alkyl-N(R$_C$)C(O)X;

R$^{11}$ is hydrogen;

n is 1;

R$^{10}$ is —N(R$_b$)SO$_2$X, wherein:

R$_B$ is selected from the group consisting of hydrogen and alkyl, and

X is alkyl; and

R$^5$, R$_6$, R$^7$, and R$^8$ are each independently selected from the group consisting of hydrogen, alkyl, alkenyl, alkynyl, cyano, halo, nitro, —OR$_A$, —OC(O)R$_A$, —OC(O)OR$_A$, —OC(O)NR$_A$R$_B$, —OS(O)$_2$R$_A$, —SR$_A$, —S(O)R$_A$, —S(O)$_2$R$_A$, S(O)$_2$NR$_A$R$_B$, —NR$_A$R$_B$, —N(R$_C$)C(O)R$_A$, —C(O)R$_A$, —C(O)OR$_A$, —C(O)NR$_A$R$_B$, haloalkyl, and -alkylOR$_A$, wherein:

R$_A$ and R$_B$ are independently selected from the group consisting of hydrogen and alkyl, and R$_C$ is selected from the group consisting of hydrogen and lower alkyl.

17. A pharmaceutical composition comprising:

one or more compounds, stereoisomers, tautomers, or salts of claim 1 or a combination thereof, and a pharmaceutically acceptable carrier.

18. A method of inhibiting the replication of a hepatitis C virus in vitro comprising contacting the virus with a therapeutically effective amount of one or more compounds, stereolsomers, tautomers, or salts of claim 1, or a combination thereof.

19. A method of treating hepatitis C virus infection comprising administering to a patient in need of such treatment a therapeutically effective amount of one or more compounds, stereoisomers, tautomers, or salts of claim 1, or a combination thereof.

* * * * *